US008697709B2

(12) United States Patent
Dar et al.

(10) Patent No.: US 8,697,709 B2
(45) Date of Patent: Apr. 15, 2014

(54) FUSED RING HETEROARYL KINASE INHIBITORS

(75) Inventors: Arvin Dar, San Francisco, CA (US); Kevan M Shokat, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 33 days.

(21) Appl. No.: 13/124,657

(22) PCT Filed: Oct. 16, 2009

(86) PCT No.: PCT/US2009/060985
§ 371 (c)(1),
(2), (4) Date: Jul. 27, 2011

(87) PCT Pub. No.: WO2010/045542
PCT Pub. Date: Apr. 22, 2010

(65) Prior Publication Data
US 2011/0275651 A1 Nov. 10, 2011

Related U.S. Application Data

(60) Provisional application No. 61/106,137, filed on Oct. 16, 2008, provisional application No. 61/106,453, filed on Oct. 17, 2008.

(51) Int. Cl.
*A61K 31/519* (2006.01)
*A61P 43/00* (2006.01)
*C12N 9/99* (2006.01)

(52) U.S. Cl.
USPC .................................................. 514/262.1

(58) Field of Classification Search
USPC .................................................. 514/262.1
See application file for complete search history.

(56) References Cited

U.S. PATENT DOCUMENTS

| 4,704,381 A | 11/1987 | Schaumann et al. |
| 5,240,941 A | 8/1993 | Bruneau |
| 5,310,731 A | 5/1994 | Olsson et al. |
| 5,364,862 A | 11/1994 | Spada et al. |
| 5,420,419 A | 5/1995 | Wood |
| 5,428,125 A | 6/1995 | Hefner, Jr. et al. |
| 5,442,039 A | 8/1995 | Hefner, Jr. et al. |
| 5,506,347 A | 4/1996 | Erion et al. |
| 5,561,134 A | 10/1996 | Spada et al. |
| 5,563,257 A | 10/1996 | Zilch et al. |
| 5,593,997 A | 1/1997 | Dow et al. |
| 5,646,128 A | 7/1997 | Firestein et al. |
| 5,652,366 A | 7/1997 | Spada et al. |
| 5,654,307 A | 8/1997 | Bridges et al. |
| 5,665,721 A | 9/1997 | Bhagwat et al. |
| 5,674,998 A | 10/1997 | Boyer et al. |
| 5,686,455 A | 11/1997 | Adams et al. |
| 5,736,554 A | 4/1998 | Spada et al. |
| 5,747,235 A | 5/1998 | Farid et al. |
| 5,756,711 A | 5/1998 | Zilch et al. |
| 5,763,596 A | 6/1998 | Boyer et al. |
| 5,763,597 A | 6/1998 | Ugarkar et al. |
| 5,763,885 A | 6/1998 | Murphy et al. |
| 5,795,977 A | 8/1998 | Ugarkar et al. |
| 5,824,492 A | 10/1998 | Hiles et al. |
| 5,858,753 A | 1/1999 | Chantry et al. |
| 5,914,488 A | 6/1999 | Sone |
| 5,919,808 A | 7/1999 | Petrie et al. |
| 5,922,753 A | 7/1999 | Petrie et al. |
| 5,948,776 A | 9/1999 | Petrie et al. |
| 5,965,573 A | 10/1999 | Petrie et al. |
| 5,977,061 A | 11/1999 | Holy et al. |
| 5,981,533 A | 11/1999 | Traxler et al. |
| 5,985,589 A | 11/1999 | Chantry et al. |
| 5,990,169 A | 11/1999 | Petrie et al. |
| 5,994,358 A | 11/1999 | Petrie et al. |
| 6,001,839 A | 12/1999 | Calderwood et al. |
| 6,057,305 A | 5/2000 | Holy et al. |
| 6,084,095 A | 7/2000 | Bridges et al. |
| 6,093,737 A | 7/2000 | Anthony et al. |
| 6,127,121 A | 10/2000 | Meyer, Jr. et al. |
| 6,153,631 A | 11/2000 | Petrie et al. |
| 6,191,170 B1 | 2/2001 | Medina |
| 6,251,901 B1 | 6/2001 | Petrie et al. |
| 6,265,410 B1 | 7/2001 | Bridges et al. |
| 6,268,370 B1 | 7/2001 | Adams et al. |
| 6,312,894 B1 | 11/2001 | Hedgpeth et al. |
| 6,323,201 B1 | 11/2001 | Carson et al. |

(Continued)

FOREIGN PATENT DOCUMENTS

| CA | 1338379 | 6/1996 |
| CN | 101602768 | 12/2009 |

(Continued)

OTHER PUBLICATIONS

Korean Intellectual Property Office, PCT/US2009/060985 International Search Report and Written Opinion, Issued Jun. 28, 2010, 14 pages.
U.S. Appl. No. 13/016,957, filed Jan. 28, 2011, Tanaka et al.
U.S. Appl. No. 13/112,611, filed May 20, 2011, Ren et al.
U.S. Appl. No. 13/289,540, filed Nov. 4, 2011, Ren et al.
Ames et al., "Heterocyclic Synthesis from o-Halogen-acids. Part II. Thienopyridinones and Thienopyranones from 3- bromothiophene -2- and 4-Bromothiophene-3-Carboxylic Acids", Journal of the Chemical Society, Perkin Transactions 1, Jan., 14:1390-1395 (1975).
BASOTEST®, "Test Kit for the Quantitative Determination of the Degranulation of Basophilic Granulocytes in Heparinized Human Whole Blood", [www.biocarta.com/TDS/10-0500.pdf], Retrieved from the Internet Nov. 29, 2011, 10 pages.

(Continued)

*Primary Examiner* — Jeffrey S. Lundgren
*Assistant Examiner* — Zenab Olabowale
(74) *Attorney, Agent, or Firm* — Kilpatrick Townsend & Stockton LLP

(57) ABSTRACT

Provided herein are fused ring heteroaryl compounds useful in a variety of methods, including reducing the activity of certain kinases and treating certain disease states.

10 Claims, 11 Drawing Sheets

(56) References Cited

U.S. PATENT DOCUMENTS

| | | |
|---|---|---|
| 6,342,514 B1 | 1/2002 | Petrie et al. |
| 6,350,741 B1 | 2/2002 | Golec et al. |
| 6,383,790 B1 | 5/2002 | Shokat |
| 6,384,039 B1 | 5/2002 | Fossa |
| 6,387,894 B1 | 5/2002 | Fossa |
| 6,390,821 B1 | 5/2002 | Shokat |
| 6,455,534 B2 | 9/2002 | Bridges et al. |
| 6,472,153 B1 | 10/2002 | Dempcy et al. |
| 6,482,623 B1 | 11/2002 | Vanhaesebroeck et al. |
| 6,485,906 B2 | 11/2002 | Meyer, Jr. et al. |
| 6,492,346 B1 | 12/2002 | Hedgpeth et al. |
| 6,506,769 B2 | 1/2003 | Snow et al. |
| 6,518,277 B1 | 2/2003 | Sadhu et al. |
| 6,521,417 B1 | 2/2003 | Shokat |
| 6,521,620 B1 | 2/2003 | Bridges et al. |
| 6,531,491 B1 | 3/2003 | Kania et al. |
| 6,534,524 B1 | 3/2003 | Kania et al. |
| 6,545,005 B1 | 4/2003 | Baxter et al. |
| 6,552,192 B1 | 4/2003 | Hanus et al. |
| 6,562,819 B2 | 5/2003 | Carson et al. |
| 6,583,161 B1 | 6/2003 | Medina |
| 6,613,798 B1 | 9/2003 | Porter et al. |
| 6,630,495 B1 | 10/2003 | Cooke et al. |
| 6,632,789 B1 | 10/2003 | June |
| 6,645,989 B2 | 11/2003 | Adams et al. |
| 6,649,631 B1 | 11/2003 | Orme et al. |
| 6,653,296 B1 | 11/2003 | Holy et al. |
| 6,653,306 B1 | 11/2003 | Alexander et al. |
| 6,660,744 B1 | 12/2003 | Hirst et al. |
| 6,660,845 B1 | 12/2003 | Gall et al. |
| 6,664,269 B2 | 12/2003 | Martin et al. |
| 6,667,300 B2 | 12/2003 | Sadhu et al. |
| 6,690,583 B1 | 2/2004 | Bergstedt et al. |
| 6,713,484 B2 | 3/2004 | Bridges et al. |
| 6,720,344 B2 | 4/2004 | Kerwin et al. |
| 6,734,187 B1 | 5/2004 | Tanaka et al. |
| 6,770,639 B2 | 8/2004 | Snow et al. |
| 6,777,425 B2 | 8/2004 | Burli et al. |
| 6,777,439 B2 | 8/2004 | Durden |
| 6,790,844 B2 | 9/2004 | Ueno et al. |
| 6,800,620 B2 | 10/2004 | Sadhu et al. |
| 6,849,420 B2 | 2/2005 | Vanhasebroeck et al. |
| 6,849,713 B2 | 2/2005 | Zhang et al. |
| 6,852,727 B2 | 2/2005 | Goulet et al. |
| 6,906,103 B2 | 6/2005 | Zhang et al. |
| 6,919,332 B2 | 7/2005 | Noe et al. |
| 6,921,763 B2 | 7/2005 | Hirst et al. |
| 6,949,535 B2 | 9/2005 | Sadhu et al. |
| 7,026,461 B1 | 4/2006 | Shokat |
| 7,041,676 B2 | 5/2006 | McDonald et al. |
| 7,049,116 B2 | 5/2006 | Shokat |
| 7,049,312 B1 | 5/2006 | Rafferty et al. |
| 7,064,218 B2 | 6/2006 | Dyatkina et al. |
| 7,071,355 B2 | 7/2006 | Leban et al. |
| 7,115,627 B2 | 10/2006 | Pinto et al. |
| 7,115,653 B2 | 10/2006 | Baxter et al. |
| 7,144,903 B2 | 12/2006 | Collins et al. |
| 7,157,487 B2 | 1/2007 | Nakayama et al. |
| 7,166,293 B2 | 1/2007 | Teng et al. |
| 7,208,601 B2 | 4/2007 | Mjalli et al. |
| 7,217,794 B2 | 5/2007 | Abdel-Meguid et al. |
| 7,244,741 B2 | 7/2007 | Simon et al. |
| 7,247,736 B2 | 7/2007 | Leban et al. |
| 7,262,204 B2 | 8/2007 | Collins et al. |
| 7,265,111 B2 | 9/2007 | Bigot et al. |
| 7,265,131 B2 | 9/2007 | Johnson et al. |
| 7,329,765 B2 | 2/2008 | Burli et al. |
| 7,332,497 B2 | 2/2008 | Hirst et al. |
| 7,348,427 B2 | 3/2008 | Burli et al. |
| 7,365,094 B2 | 4/2008 | Leban et al. |
| 7,384,967 B2 | 6/2008 | Polisetti et al. |
| 7,396,836 B2 | 7/2008 | Harada et al. |
| 7,414,036 B2 | 8/2008 | Sevillano et al. |
| 7,429,596 B2 | 9/2008 | Tanaka et al. |
| 7,439,254 B2 | 10/2008 | Bergnes |
| 7,459,462 B2 | 12/2008 | Simon et al. |
| 7,459,472 B2 | 12/2008 | Mjalli et al. |
| 7,470,721 B2 | 12/2008 | Durden |
| 7,501,538 B2 | 3/2009 | Mjalli et al. |
| 7,534,797 B2 | 5/2009 | Arnold et al. |
| 7,541,373 B2 | 6/2009 | Polisetti et al. |
| 7,569,571 B2 | 8/2009 | Dong et al. |
| 7,572,913 B2 | 8/2009 | McKerracher et al. |
| 7,579,348 B2 | 8/2009 | Wang et al. |
| 7,585,868 B2 | 9/2009 | Knight et al. |
| 7,608,594 B2 | 10/2009 | Blagg et al. |
| 7,615,552 B2 | 11/2009 | Ono et al. |
| 7,622,451 B2 | 11/2009 | Blagg et al. |
| 7,678,803 B2 | 3/2010 | Huang et al. |
| 7,700,607 B2 | 4/2010 | Hu et al. |
| 7,745,485 B2 | 6/2010 | Durden |
| 7,932,260 B2 | 4/2011 | Fowler et al. |
| 2001/0019829 A1 | 9/2001 | Nelson et al. |
| 2001/0027197 A1 | 10/2001 | Bridges et al. |
| 2002/0016460 A1 | 2/2002 | Snow et al. |
| 2002/0016976 A1 | 2/2002 | Shokat |
| 2002/0037856 A1 | 3/2002 | Zhang et al. |
| 2002/0102590 A1 | 8/2002 | Taing et al. |
| 2002/0146690 A1 | 10/2002 | Meyer et al. |
| 2002/0147160 A1 | 10/2002 | Bhat et al. |
| 2002/0156081 A1* | 10/2002 | Hirst et al. ............... 514/247 |
| 2002/0161014 A1 | 10/2002 | Sadhu et al. |
| 2002/0173524 A1 | 11/2002 | Collins et al. |
| 2003/0001141 A1 | 1/2003 | Sun et al. |
| 2003/0008896 A1 | 1/2003 | Martin et al. |
| 2003/0018022 A1 | 1/2003 | Collins et al. |
| 2003/0022344 A1 | 1/2003 | Williams et al. |
| 2003/0064997 A1 | 4/2003 | Adams et al. |
| 2003/0073218 A1 | 4/2003 | Shokat et al. |
| 2003/0083268 A1 | 5/2003 | Burli et al. |
| 2003/0109248 A1 | 6/2003 | Lewis |
| 2003/0113765 A1 | 6/2003 | Dempcy et al. |
| 2003/0119479 A1 | 6/2003 | Arima et al. |
| 2003/0119791 A1 | 6/2003 | Kerwin et al. |
| 2003/0139427 A1 | 7/2003 | Castelhano et al. |
| 2003/0143602 A1 | 7/2003 | Meyer, Jr. et al. |
| 2003/0166929 A1 | 9/2003 | Snow et al. |
| 2003/0180924 A1 | 9/2003 | Desimone et al. |
| 2003/0186987 A1 | 10/2003 | Bridges et al. |
| 2003/0187001 A1 | 10/2003 | Calderwood et al. |
| 2003/0195211 A1 | 10/2003 | Sadhu et al. |
| 2003/0199516 A1 | 10/2003 | Moser et al. |
| 2003/0208800 A1 | 11/2003 | Eby et al. |
| 2003/0212113 A1 | 11/2003 | Dyatkina et al. |
| 2003/0232849 A1 | 12/2003 | Noe et al. |
| 2003/0235822 A1 | 12/2003 | Lokhov et al. |
| 2004/0039035 A1 | 2/2004 | Collins et al. |
| 2004/0043983 A1 | 3/2004 | Li |
| 2004/0067901 A1 | 4/2004 | Bhat et al. |
| 2004/0067915 A1 | 4/2004 | McMahon et al. |
| 2004/0072766 A1 | 4/2004 | June |
| 2004/0072788 A1 | 4/2004 | Bhat et al. |
| 2004/0102423 A1 | 5/2004 | MacLaughlan et al. |
| 2004/0102437 A1 | 5/2004 | Takami et al. |
| 2004/0110717 A1 | 6/2004 | Bhat et al. |
| 2004/0110945 A1 | 6/2004 | Nakayama et al. |
| 2004/0116689 A1 | 6/2004 | Gall et al. |
| 2004/0122235 A1 | 6/2004 | Polisetti et al. |
| 2004/0127434 A1 | 7/2004 | Bigot et al. |
| 2004/0176458 A1 | 9/2004 | Leban et al. |
| 2004/0176601 A1 | 9/2004 | Goulet et al. |
| 2004/0192758 A1 | 9/2004 | Leban et al. |
| 2004/0266780 A1 | 12/2004 | Sadhu et al. |
| 2005/0004149 A1 | 1/2005 | Harada et al. |
| 2005/0043239 A1 | 2/2005 | Douangpanya et al. |
| 2005/0049310 A1 | 3/2005 | Mjalli et al. |
| 2005/0054614 A1 | 3/2005 | Diacovo et al. |
| 2005/0059713 A1 | 3/2005 | Mjalli et al. |
| 2005/0085472 A1 | 4/2005 | Tanaka et al. |
| 2005/0101551 A1 | 5/2005 | Sevillano et al. |
| 2005/0124637 A1 | 6/2005 | Cheng et al. |
| 2005/0143317 A1 | 6/2005 | Abdel-Meguid et al. |
| 2005/0153997 A1 | 7/2005 | Simon et al. |
| 2005/0171148 A1 | 8/2005 | Mjalli et al. |

(56) References Cited

U.S. PATENT DOCUMENTS

| | | |
|---|---|---|
| 2005/0182045 A1 | 8/2005 | Nagase et al. |
| 2005/0187418 A1 | 8/2005 | Small et al. |
| 2005/0197340 A1 | 9/2005 | Arora et al. |
| 2005/0215579 A1 | 9/2005 | Simon et al. |
| 2005/0239809 A1 | 10/2005 | Watts et al. |
| 2005/0250770 A1 | 11/2005 | Ono et al. |
| 2005/0256066 A1 | 11/2005 | Abel et al. |
| 2005/0261317 A1 | 11/2005 | Sadhu et al. |
| 2005/0272751 A1 | 12/2005 | McKerracher et al. |
| 2006/0019988 A1 | 1/2006 | McDonald et al. |
| 2006/0069034 A1 | 3/2006 | Burli et al. |
| 2006/0079538 A1 | 4/2006 | Hallahan et al. |
| 2006/0106038 A1 | 5/2006 | Bouscary et al. |
| 2006/0116326 A1 | 6/2006 | Burli et al. |
| 2006/0135790 A1 | 6/2006 | Hyett et al. |
| 2006/0156485 A1 | 7/2006 | Lim |
| 2006/0183783 A1 | 8/2006 | Polisetti et al. |
| 2006/0199776 A1 | 9/2006 | Blagg et al. |
| 2006/0235031 A1 | 10/2006 | Arnold et al. |
| 2006/0276470 A1 | 12/2006 | Jackson et al. |
| 2006/0287295 A1 | 12/2006 | Barlaam et al. |
| 2007/0015773 A1 | 1/2007 | Bergeron et al. |
| 2007/0027193 A1 | 2/2007 | Leban et al. |
| 2007/0032640 A1 | 2/2007 | Varghese et al. |
| 2007/0054915 A1 | 3/2007 | Arora et al. |
| 2007/0072897 A1 | 3/2007 | Mahaney et al. |
| 2007/0099871 A1 | 5/2007 | Davis et al. |
| 2007/0142405 A1 | 6/2007 | Dong et al. |
| 2007/0224672 A1 | 9/2007 | Leban et al. |
| 2007/0249598 A1 | 10/2007 | Wang et al. |
| 2007/0270452 A1 | 11/2007 | Blagg et al. |
| 2008/0032960 A1 | 2/2008 | Knight et al. |
| 2008/0058521 A1 | 3/2008 | Krishnan et al. |
| 2008/0070935 A1 | 3/2008 | Huang et al. |
| 2008/0119454 A1 | 5/2008 | Polisetti et al. |
| 2008/0119455 A1 | 5/2008 | Polisetti et al. |
| 2008/0119461 A1 | 5/2008 | Sin et al. |
| 2008/0200465 A1 | 8/2008 | Burli et al. |
| 2008/0249090 A1 | 10/2008 | Hu et al. |
| 2008/0261956 A1 | 10/2008 | Choi et al. |
| 2008/0287469 A1 | 11/2008 | Diacovo et al. |
| 2008/0292626 A1 | 11/2008 | Wang et al. |
| 2008/0293674 A1 | 11/2008 | Schwarz et al. |
| 2008/0306053 A1 | 12/2008 | Tachdjian et al. |
| 2008/0306093 A1 | 12/2008 | Servant et al. |
| 2008/0312180 A1 | 12/2008 | Liang et al. |
| 2008/0318942 A1 | 12/2008 | Simon et al. |
| 2009/0030023 A1 | 1/2009 | Harada et al. |
| 2009/0053192 A1 | 2/2009 | Millan et al. |
| 2009/0088452 A1 | 4/2009 | Coleman et al. |
| 2009/0099214 A1 | 4/2009 | Fairhurst et al. |
| 2009/0105233 A1 | 4/2009 | Chua et al. |
| 2009/0118283 A1 | 5/2009 | Defert et al. |
| 2009/0124638 A1 | 5/2009 | Shokat et al. |
| 2009/0124654 A1 | 5/2009 | Mjalli et al. |
| 2009/0163481 A1 | 6/2009 | Murphy et al. |
| 2009/0163709 A1 | 6/2009 | Blagg |
| 2009/0170879 A1 | 7/2009 | Szucova et al. |
| 2009/0181920 A1 | 7/2009 | Watkins et al. |
| 2009/0181988 A1 | 7/2009 | Tanaka et al. |
| 2009/0187014 A1 | 7/2009 | Blagg |
| 2009/0203689 A1 | 8/2009 | Dhalla et al. |
| 2009/0232768 A1 | 9/2009 | Birkus et al. |
| 2009/0247513 A1 | 10/2009 | Burli et al. |
| 2009/0253694 A1 | 10/2009 | Ono et al. |
| 2009/0264409 A1 | 10/2009 | Dong et al. |
| 2009/0264423 A2 | 10/2009 | Chua et al. |
| 2009/0270567 A1 | 10/2009 | Small et al. |
| 2009/0312319 A1 | 12/2009 | Ren et al. |
| 2009/0312406 A1 | 12/2009 | Hsieh et al. |
| 2009/0325967 A1 | 12/2009 | Fairhurst et al. |
| 2010/0009963 A1 | 1/2010 | Knight et al. |
| 2010/0022585 A1 | 1/2010 | Delong et al. |
| 2010/0029658 A1 | 2/2010 | Gavish et al. |
| 2010/0029693 A1 | 2/2010 | Douangpanya et al. |
| 2010/0048540 A1 | 2/2010 | Boyle et al. |
| 2010/0048882 A1 | 2/2010 | Blagg et al. |
| 2010/0056494 A1 | 3/2010 | Winzeler et al. |
| 2010/0105630 A1 | 4/2010 | Blagg |
| 2010/0190749 A1 | 7/2010 | Ren et al. |
| 2011/0046165 A1 | 2/2011 | Ren et al. |
| 2011/0124641 A1 | 5/2011 | Ren et al. |
| 2011/0144134 A1 | 6/2011 | Shokat et al. |
| 2011/0172228 A1 | 7/2011 | Ren et al. |
| 2011/0224223 A1 | 9/2011 | Shokat et al. |
| 2011/0269779 A1 | 11/2011 | Wilson et al. |
| 2011/0281866 A1 | 11/2011 | Ren et al. |
| 2011/0301144 A1 | 12/2011 | Knight et al. |
| 2012/0322814 A1* | 12/2012 | Korennykh et al. ....... 514/262.1 |

FOREIGN PATENT DOCUMENTS

| | | |
|---|---|---|
| EP | 773023 A1 | 5/1997 |
| EP | 1020445 B1 | 8/2008 |
| GB | 812366 | 4/1959 |
| GB | 937725 | 9/1963 |
| JP | 61109797 | 5/1986 |
| JP | 5256693 | 10/1993 |
| JP | 8295667 A | 12/1996 |
| JP | 9143163 A | 6/1997 |
| JP | 10206995 A | 8/1998 |
| JP | 2000072773 A | 3/2000 |
| JP | 2002131859 A2 | 5/2002 |
| JP | 2003073357 A2 | 3/2003 |
| JP | 2004161716 A | 6/2004 |
| WO | WO83/01446 A1 | 4/1983 |
| WO | WO91/17161 A1 | 11/1991 |
| WO | WO92/14733 A1 | 9/1992 |
| WO | WO93/16091 A1 | 8/1993 |
| WO | WO93/16092 A1 | 8/1993 |
| WO | WO93/18035 A1 | 9/1993 |
| WO | WO93/22443 A1 | 11/1993 |
| WO | WO 94-13677 A1 | 6/1994 |
| WO | WO94/17803 A1 | 8/1994 |
| WO | WO95/12588 A1 | 5/1995 |
| WO | WO95/29673 A1 | 11/1995 |
| WO | WO95/32984 A1 | 12/1995 |
| WO | WO96/40706 A1 | 12/1996 |
| WO | WO97/28133 A1 | 8/1997 |
| WO | WO97/28161 A1 | 8/1997 |
| WO | WO98/41525 A1 | 9/1998 |
| WO | WO98/52611 A1 | 11/1998 |
| WO | WO98/57952 A1 | 12/1998 |
| WO | WO00/17202 A1 | 3/2000 |
| WO | WO01/02369 A2 | 1/2001 |
| WO | WO01/16114 A2 | 3/2001 |
| WO | WO01/19829 A2 | 3/2001 |
| WO | WO01/25238 A2 | 4/2001 |
| WO | WO01/31063 A1 | 5/2001 |
| WO | WO01/38584 A2 | 5/2001 |
| WO | WO01/16114 A3 | 8/2001 |
| WO | WO01/55140 A1 | 8/2001 |
| WO | WO01/56988 A1 | 8/2001 |
| WO | WO01/19829 A3 | 9/2001 |
| WO | WO01/25238 A3 | 10/2001 |
| WO | WO01/38584 A3 | 10/2001 |
| WO | WO01/81346 A2 | 11/2001 |
| WO | WO02/06192 A1 | 1/2002 |
| WO | WO01/81346 A3 | 3/2002 |
| WO | WO01/02369 A3 | 4/2002 |
| WO | WO02/30944 A2 | 4/2002 |
| WO | WO02/057425 A2 | 7/2002 |
| WO | WO02/076986 A1 | 10/2002 |
| WO | WO02/080926 A1 | 10/2002 |
| WO | WO02/083143 A1 | 10/2002 |
| WO | WO02/088025 A1 | 11/2002 |
| WO | WO02/090334 A1 | 11/2002 |
| WO | WO02/30944 A3 | 1/2003 |
| WO | WO03/000187 A2 | 1/2003 |
| WO | WO03/016275 A1 | 2/2003 |
| WO | WO03/020880 A2 | 3/2003 |
| WO | WO03/024969 A1 | 3/2003 |
| WO | WO03/035075 A1 | 5/2003 |
| WO | WO03/059884 A1 | 7/2003 |

(56) References Cited

FOREIGN PATENT DOCUMENTS

| WO | WO03/020880 A3 | 10/2003 |
|---|---|---|
| WO | WO03/082341 A1 | 10/2003 |
| WO | WO03/106426 A1 | 12/2003 |
| WO | WO2004/006906 A2 | 1/2004 |
| WO | WO2004/006906 A3 | 3/2004 |
| WO | WO2004/031177 A1 | 4/2004 |
| WO | WO2004/018058 A2 | 5/2004 |
| WO | WO2004/039774 A2 | 5/2004 |
| WO | WO2004/018058 A3 | 7/2004 |
| WO | WO2004/039774 A3 | 7/2004 |
| WO | WO03/000187 A3 | 8/2004 |
| WO | WO2004/087053 A2 | 10/2004 |
| WO | WO2004/111014 A1 | 12/2004 |
| WO | WO2005/002585 A1 | 1/2005 |
| WO | WO2005/012323 A2 | 2/2005 |
| WO | WO2005/016348 A1 | 2/2005 |
| WO | WO2005/016349 A1 | 2/2005 |
| WO | WO2005/016528 A2 | 2/2005 |
| WO | WO2005/021533 A1 | 3/2005 |
| WO | WO02/57425 A3 | 4/2005 |
| WO | WO2005/007085 A | 5/2005 |
| WO | WO2005/012323 A3 | 5/2005 |
| WO | WO2005/016528 A3 | 5/2005 |
| WO | WO2005/044181 A2 | 5/2005 |
| WO | WO2005/047289 A1 | 5/2005 |
| WO | WO2005/061460 A1 | 7/2005 |
| WO | WO2005/063258 A1 | 7/2005 |
| WO | WO2005/067901 A2 | 7/2005 |
| WO | WO2005/074603 A2 | 8/2005 |
| WO | WO2005/007085 A3 | 9/2005 |
| WO | WO2005/097800 A1 | 10/2005 |
| WO | WO2005/105760 A1 | 11/2005 |
| WO | WO2005/067901 A3 | 12/2005 |
| WO | WO2005/112935 A1 | 12/2005 |
| WO | WO2005/113556 A1 | 12/2005 |
| WO | WO2005/117889 A1 | 12/2005 |
| WO | WO2005/120511 A1 | 12/2005 |
| WO | WO2005/044181 A3 | 3/2006 |
| WO | WO2006/030032 A1 | 3/2006 |
| WO | WO2006/038865 A1 | 4/2006 |
| WO | WO2006/050501 A2 | 5/2006 |
| WO | WO 2006-050946 A1 | 5/2006 |
| WO | WO2006/068760 A2 | 6/2006 |
| WO | WO2004/087053 A3 | 8/2006 |
| WO | WO2006/089106 A2 | 8/2006 |
| WO | WO2006/108107 A1 | 10/2006 |
| WO | WO2006/112666 A1 | 10/2006 |
| WO | WO2005/074603 A3 | 11/2006 |
| WO | WO2006/114064 A2 | 11/2006 |
| WO | WO2006/114065 | 11/2006 |
| WO | WO2006/068760 A3 | 12/2006 |
| WO | WO2006/089106 A3 | 12/2006 |
| WO | WO2007/002293 A2 | 1/2007 |
| WO | WO2007/006547 A1 | 1/2007 |
| WO | WO2007/020046 A1 | 2/2007 |
| WO | WO2007/002293 A3 | 3/2007 |
| WO | WO2007/025090 A2 | 3/2007 |
| WO | WO2006/050501 A3 | 5/2007 |
| WO | WO2007/061737 A2 | 5/2007 |
| WO | WO2006/114064 A3 | 6/2007 |
| WO | WO2006/114065 A3 | 6/2007 |
| WO | WO2007/025090 A3 | 6/2007 |
| WO | WO2007/075554 A2 | 7/2007 |
| WO | WO2007/079164 A2 | 7/2007 |
| WO | 2007/106503 A2 | 9/2007 |
| WO | WO2007/075554 A3 | 9/2007 |
| WO | WO2007/079164 A3 | 9/2007 |
| WO | WO2007/103308 A2 | 9/2007 |
| WO | WO2007/112005 A2 | 10/2007 |
| WO | WO2007/114926 A2 | 10/2007 |
| WO | WO2007/121453 A2 | 10/2007 |
| WO | WO2007/121920 A2 | 11/2007 |
| WO | WO2007/121924 A2 | 11/2007 |
| WO | WO2007/124854 A1 | 11/2007 |
| WO | WO2007/125310 A2 | 11/2007 |
| WO | WO2007/125315 A2 | 11/2007 |
| WO | WO2007/126841 A2 | 11/2007 |
| WO | WO2007/134828 A1 | 11/2007 |
| WO | WO2007/135380 A2 | 11/2007 |
| WO | WO2007/135398 A1 | 11/2007 |
| WO | WO2007/061737 A3 | 12/2007 |
| WO | WO2007/125315 A3 | 12/2007 |
| WO | WO2007/121920 A3 | 1/2008 |
| WO | WO2007/103308 A3 | 2/2008 |
| WO | WO2007/112005 A3 | 2/2008 |
| WO | WO2007/125310 A3 | 3/2008 |
| WO | WO2008/025755 A1 | 3/2008 |
| WO | WO2008/047821 A1 | 4/2008 |
| WO | WO2008/063625 A2 | 5/2008 |
| WO | WO2008/064018 A1 | 5/2008 |
| WO | WO2007/121453 A3 | 7/2008 |
| WO | WO2007/135380 A3 | 7/2008 |
| WO | WO2008/063625 A3 | 7/2008 |
| WO | WO2008/079028 A1 | 7/2008 |
| WO | WO2008/082487 A2 | 7/2008 |
| WO | WO2008/094737 A2 | 8/2008 |
| WO | WO2007/121924 A3 | 9/2008 |
| WO | WO2008/112715 A2 | 9/2008 |
| WO | WO2007/114926 A3 | 10/2008 |
| WO | WO2008/118454 A2 | 10/2008 |
| WO | WO2008/118455 A1 | 10/2008 |
| WO | WO2008/118468 A1 | 10/2008 |
| WO | WO2008/125014 A1 | 10/2008 |
| WO | WO2008/125207 A1 | 10/2008 |
| WO | WO2008/127226 A2 | 10/2008 |
| WO | WO2007/126841 A3 | 11/2008 |
| WO | WO2008/112715 A3 | 11/2008 |
| WO | WO2008/118454 A3 | 11/2008 |
| WO | WO2008/136457 A1 | 11/2008 |
| WO | WO2008/082487 A3 | 12/2008 |
| WO | WO2008/136457 A3 | 12/2008 |
| WO | WO2009/000412 A1 | 12/2008 |
| WO | WO2009/004621 A1 | 1/2009 |
| WO | WO2009/010925 A2 | 1/2009 |
| WO | WO2009/023718 A2 | 2/2009 |
| WO | WO2008/094737 A3 | 3/2009 |
| WO | WO2009/023718 A3 | 4/2009 |
| WO | WO2009/044707 A1 | 4/2009 |
| WO | WO2009/050506 A2 | 4/2009 |
| WO | WO2009/064802 A2 | 5/2009 |
| WO | WO2009/010925 A3 | 7/2009 |
| WO | WO2009/064802 A3 | 7/2009 |
| WO | WO2009/088986 A1 | 7/2009 |
| WO | WO2009/088990 A1 | 7/2009 |
| WO | WO2009/100406 A2 | 8/2009 |
| WO | WO2009/117157 A1 | 9/2009 |
| WO | WO2009/050506 A3 | 11/2009 |
| WO | WO2009/100406 A3 | 11/2009 |
| WO | WO2010/009207 A1 | 1/2010 |
| WO | WO2010/019210 A2 | 2/2010 |
| WO | WO2010/036380 A1 | 4/2010 |
| WO | WO2010/039534 A2 | 4/2010 |
| WO | WO2010/019210 A3 | 5/2010 |
| WO | 2010/039534 A3 | 8/2010 |

OTHER PUBLICATIONS

Cámpora, et al. Binuclear complexes of nickel bridged by hydrocarbon ligands. Isocyanide insertion chemistry and amide formation by intramolecular coupling of acyl and imidoyl functionalities. Organometallics. Jan. 1992;11(1):11-13.

Cámpora, et al. Isocyanide insertion chemistry. Synthesis and structural characterization of bridging imidoyl complexes of nickel and amide formation by intramolecular coupling of acyl and imidoyl functionalities. Organometallics. Oct. 1993;12(10):4025-31.

Chaisuparat, et al. Dual Inhibition of PI3K(alpha) and mTOR as an Alternative Treatment for Kaposi's Sarcoma. Cancer Research. 2008;68:8361.

Chappelow, et al. Neovascular Age-Related Macular Degeneration: Potential Therapies. Drugs. 2008;68(8):1029-1036.

Davis, et al. The Preparation of Substituted 1(2H)-Isoquinolinones from Dilithiated 2-Methyl-N-arylbenzamides, 2-Methyl-N-(arylmethyl)-benzamides, or 2-Methylbenzoic Acid, 2,2-Dimethylhydrazide. Synthetic Communications. Sep. 1997;27(17):2961-9.

(56) References Cited

OTHER PUBLICATIONS

Dijksman, et al. 271. 1 : 2-Dihydro-2-thianaphthalene derivatives. Part I. Preparation and reactions of 1 : 2-dihydro-1-keto-2-thianaphthalenes. J. Chem. Soc. 1951:1213-18.
Donati. Emerging Therapies for Neovascular Age-Related Macular Degeneration: State of the Art. Ophthalmologica. 2007;221:366-377.
European search report and search opinion dated Oct. 26, 2011 for Application No. 9700424.6, 5 pages.
European Search Report dated Mar. 1, 2010 for EP Application No. 07873406.8, 5 pages.
Extended European Search Report from corresponding European Application No. 09700784.3 dated Oct. 28, 2011, 6 pages.
Graupera, et al. Angiogenesis selectively requires the p110 isoform of PI3K to control endothelial cell migration. Nature. 2008;453:662-666.
Hellwinkel, et al. Heterocyclensynthesen mit Mf/A1203-Basensystemen: 2-Arylbenzofurane and 2,3-Diarylisochinolin-1(2H)-one. Synthesis. 1995(9):1135-41.
International Preliminary Report on Patentability from International Application No. PCT/US2009/000042 issued Jul. 6, 2010, 9 pages.
International search report and written opinion dated Aug. 22, 2011 for PCT/US2011/037412, 2 pages.
International search report and written opinion dated Nov. 20, 2009 for PCT/US2009/005380, 9 pages.
International search report dated Nov. 2, 2010 for PCT Application No. PCT/US10/02020, 8 pages.
International search report dated Mar. 11, 2009 for PCT Application No. PCT/US2009/00038, 1 page.
International search report dated Mar. 23, 2009 for PCT Application No. PCT/US2009/00042, 2 pages.
Kajita, et al. Nickel-catalyzed decarbonylative addition of phthalimides to alkynes. J Am Chem Soc. May 14, 2008;130(19):6058-9.
Kost et al., "Recyclization of 3-Alkyl- and 1,3-Dialkylisoquinolinium Salts to Naphthylamines", Chemistry of Heterocyclic Compounds, Jan., 16(9):965-970 (1981).
Kumar et al., "Keten Dithioacetals. Part II. Reaction of 3-Cyano-4-Methylthio-2(1H)-pyridones with Hydazine and Guanidine: Synthesis of Novel Substituted and Fused Pyrazolo[4,3-c]pyridone and Pyrido[4,3-d]pyrimidine Derivatives", Journal of the Chemical Society, Perkin Transactions 1, Chemical Society, Letchworth, Jan., 8:857-862 (1978).
Kundu, et al. Palladium-Catalysed Heteroannulation with Terminal Alkynes: a Highly Regio- and Stereoselective Synthesis of (Z)-3-Aryl(alkyl)idene Isoindolin-1-ones1. Tetrahedron. Jun. 30, 2000;56(27):4777-92.
Lee, et al. All roads lead to mTOR: integrating inflammation and tumor angiogenesis.. Cell Cycle. 2007;6(24):3011-3014.
Majumder, et al. mTOR inhibition reverses Akt-dependent prostate intraepithelial neoplasia through regulation of apoptotic and HIF-1-dependent pathways. Nature Medicine. 2004;10:594-601.
Mellinghoff, et al. TORward AKTually useful mouse models. Nature Medicine. 2004;10:579-580.
Modi, et at. Isoquinolones: Part IV—Synthesis of 3-Methyl, 3-Formyl & Other 3-Substituted N-Arylisoquinolones, Indian J. Chem. 1979; 18B:304-306.
Nemazanyi, et al. 3-Amino-4-aryl-1(2H)-isoquinolones. Chemistry of Heterocyclic Compounds. Mar. 1991;27(3):307-8.
Oda, et al. PIK3CA Cooperates with Other Phosphatidylinositol 3'-Kinase Pathway Mutations to Effect Oncogenic Transformation. Cancer Research. 2008;68:8127.
Ozaki, et al. Studies on 4 (1H)-Quinazolinones. IV. Convenient Syntheses of 12-Methyl-6H-isoquino [2,1-a] quinazolin-6-one and 6-Methyl-13H-quinazolino [3,4-a] quinazolin-13-one. Chem. Pharm. Bull. Jun. 25, 1984;32(6):2160-4.
Ozol, et al. Autoxidative transformations of 2-substituted 3-alkyl-4-hydroxy-1-oxo-1, 2-dihydroisoquinolines. Chemistry of Heterocyclic Compounds. Jun. 1978;14(6):644-8.
Patel, et al. Immunopathological aspects of age-related macular degeneration. Seminars in Immunopathology. 2008;30(2):97-110.
Stanoeva et al. Homophthalic anhydrides and their application to the synthesis of heterocyclic compounds (review). Chemistry of Heterocyclic Compounds. Dec. 1984;20(12);1305-15.
Supplementary European Examination Report dated Sep. 20, 2011 for EP Application No. 07754845.1, 4 pages.
Vasilevsky et al., "Study of the Heterocyclization of vic-Substituted Hydrazides of Acetylenylpyrazolecarboxylic Acids into N-Amino Pyrazolopyridinones", Journal of Heterocyclic Chemistry, Nov., 39(6):1229-1233 (2002).
Vasilevsky et al., "Unexpected results in the heterocyclization of 5-acetylenylpyrazole4-carboxylic acid hydrazides under the influence of CuCl: formatin of a diazepinone and dehydrodimerization into the corresponding bis(pyrazolo [4,3-d] [1,2] diazepinone)", Tetrahedron Letters, Jan., 46(26): 4457-4459 (2005).
Yaguchi, et al. Antitumor activity of ZSTK474, a new phosphatidylinositol 3-kinase inhibitor. J. Natl. Cancer. Inst. 2006; 98(8): 545-556. Abstract only.
"Report of the Expert Committee on the Diagnosis and Classification of Diabetes Mellitus", *Diabetes Care* (1992) 2(Suppl 1):S5-S19.
Abdel-Mohsen, S.A., "Synthesis, reactions and antimicrobial activity of 2-amino-4-(8-quinolinol-5-yl)-1-(p-tolyl)-pyrrole-3-carbonitrile", Bull. Korean Chem. Soc. 2005 26(5):719-728.
Andrews, R.C., et al. "Effects of the 11β-Hydroxysteroid Dehydrogenase Inhibitor Carbenoxolone on Insulin Sensitivity in Men with Type 2 Diabetes", *J. Clin. Endocrinol. Metab.* (2003) 88(1):285-291.
Arnold, et al. "Pyrrolo[2,3-*d*]pyrimidines containing an extended 5-substituent as potent and selective inhibitors of lck I", *Bioorg. & Med. Chem. Lett* (2000) 10:2167-70.
Banker, G.S., et al. *Modern Pharmaceutics*, 3ed, Marcel Dekker, New York, 1996, pp. 451-596.
Barf, T. et al. "Arylsulfonamidothiazoles as a New Class of Potential Antidiabetic Drugs. Discovery of Potent and Selective Inhibitors of the 11β-Hydroxysteroid Dehydrogenase Type 1", *J. Med. Chem.* (2002) 45(18):3813-3815.
Barnes, P.J., et al. "Efficacy and Safety of Inhaled Corticosteroids in Asthma", *Am. Rev. Respir. Dis.* (1993) 148:S1-26.
Beeram, M. et al., "Akt-induced endocrine therapy resistance is reversed by inhibition of mTOR signaling", Annals of Oncology 18:1323-1328, 2007.
Bell, G., et al. "Glucokinase Mutations Insulin Secretion, and Diabetes Mellitus", *Annu. Rev. Physiol.*, (1996) 58:171-186.
Bhat, G. A., et al., "Pyrazolopyrimidine nucleosides. 12. Synthesis and biological activity of certain pyrazolo[3,4-d]pyrimidine nucleosides related to adenosine," J. Med. Chem. vol. 24, No. 10, (1981), pp. 1165-1172.
Bishop, A.C. et al. "Generation of monospecific nanomolar tyrosine kinase inhibitors via a chemical genetic approach", Journal of the American Chemical Society, American Chemical Society, Washington, DC, US, vol. 121, No. 4, 1999, pp. 627-631.
Bohren, K.M., et al. "Expression, Crystallization and Preliminary Crystallographic Analysis of Human Carbonyl Reductase", *J. Mol. Biol.* (1994) 224:659-664.
Cox, B., et al. "Human Colorectal Cancer Cells Efficiently Conjugate the Cyclopentenone Prostaglandin, Prostaglandin $J_2$ to Glutathione", *Biochim. Biophys. Acta* (2002) 1584:37-45.
Diederich, S., et al. "In the Search for Specific Inhibitors of Human 11β-HydroxysteroidDehydrogenases (11β-HSDs): Chenodeoxycholic Acid Selectively Inhibits 11β-HSD-I", *Eur. J. Endocrinol.* (2000) 142:200-207.
Ding, S., et al. "A Combinatorial Scaffold Approach Toward Kinase-Directed Heterocycle Libraries", *J. Am. Chem. Soc.* (2002) 124(8):1594-1596.
Ding, S., et al. "A Concise and Traceless Linker Strategy Toward Combinatorial Libraries of 2,6,9-Substituted Purines",*J. Org. Chem.* (2001) 66:8273-8276.
Ding, S., et al. "Resin-Capture and Release Strategy Toward Combinatorial Libraries of 2,6,9-Substituted Purines", *J. Comb. Chem.*(2002) 4:183-186.
European Examination Report dated Sep. 14, 2011 for EP Application No. 07873406.8, 4 pages.
European Search Report Dated Feb. 4, 2011 for EP Application No. 05857011.0, 5 pages.

(56) References Cited

OTHER PUBLICATIONS

Examination Report for GB Application No. GB0819947.3 dated Oct. 27, 2010, 2 pages.
Fajans, S., et al."Maturity Onset Diabetes of the Young (MODY)", *Diabet. Med.* (1996) 13:S90-S95.
Feinstein, M.B., et al. "Regulation of the Action of Hydrocotisone in Airway Epithelial Cells by 11β-Hydroxysteroid Dehydrogenase", *Am. J. Respir. Cell. Mol. Biol.* (1999) 21:403-408.
Feldman, M.E. et al. , "Active site inhibitors of mTOR target rapamycin-resistant outputs of mTORC1 and mTORC2", Plos Biology 7(2):371-383, Feb. 2009.
Fingl, E., et al. "General Principles", *The Pharmacological Basis of Therapeutics*, Fifth Edition (1975), Ch. 1, 1-46.
Forrest, G.L., et al. "Carbonyl Reductase", *Chem. Biol. Interact.* (2000) 129:21-40.
Forrest, G.L., et al. "Induction of a Human Carbonyl Reductase Gene Located on Chromosome 21", *Biochim. Biophys. Acta.* (1990) 1048:149-155.
Franzen, R. "The Suzuki, the Heck, and the Stille reaction—three versative methods for the introduction of new C—C bonds on solid support", *Can J. Chem.* (2000) 78:957-962.
Funder, J.W., et al. "Mineralocorticoid Action: Target Tissue Specificity is Enzyme, Not Receptor, Mediated", *Science* (1998) 242:583-585.
Garber, M.E., et al. "Diversity of Gene Expression in Adenocarcinoma of the Lung", *Proc. Nat. Acad. Sci. USA* (2001) 98(24):13784-13789.
Gonzalez, B., et al. "Protection against Daunorubicin Cytotoxicity by Expression of a Cloned Human Carbonyl Reductase cDNA in K562 Leukemia Cells", *Cancer Res.* (1995) 55:4646-4650.
Haase, A.,et al. "Detection of Viral Nucleic Acids by in Situ Hybridization", *Methods in Virology* (1984) VII:189-226.
Hanefeld, U., et al. "One-pot Synthesis of Tetrasubstituted Pyrazoles Proof of Regiochemistry", *J. Chem. Soc. Perkin Trans.* (1996) 1:1545-1552.
International Preliminary Report on Patentability and Written Opinion dated Apr. 19, 2011 for International Application No. PCT/US2009/060985, 6 pages.
International Preliminary Report on Patentability and Written Opinion dated Jan. 1, 2011 for International Application No. PCT/US2009/049969, 7 pages.
International Preliminary Report on Patentability and Written Opinion dated May 22, 2007 for International Application No. PCT/US2005/042524, 12 pages.
International Preliminary Report on Patentability and Written Opinion dated Nov. 4, 2008 for International Application No. PCT/US2007/008355, 7 pages.
International Preliminary Report on Patentability and Written Opinion dated Oct. 8, 2008 for International Application No. PCT/US2007/008395, 6 pages.
International Search Report Dated Apr. 5, 2006 for international Application No. PCT/FR2005/051073, 3 pages.
International Search Report dated Aug. 27, 2008 for International Application No. PCT/US07/08395, 4 pages.
International Search Report dated Mar. 15, 2010 for International Application No. PCT/US2009/049969, 4 pages.
International Search Report dated Oct. 2, 2006 for International Application No. PCT/US05/042524, 7 pages.
International Search Report dated Sep. 25, 2008 for International Application No. PCT/US07/08355, 1 page.
Ishiyama, T., et al. "A Stoichiometric Aromatic C-H Borylation Catalyzed by Iridium(I)/2,2'-Bipyridine Complexes at Room Temperature", *Angew. Chem. Int. Ed.* (2002) 41(16):3056-3058.
Ishiyama, T., et al. "Mild Iridium-Catalyzed Borylation of Arenes. High Turnover Numbers, Room Temperature Reactions, and Isolation of a Potential Intermediate", *J. Am. Chem. Soc.* (2002) 124(3):390-391.

Kallberg, Y., et al. "Short-Chain Dehydrogenase/Reductase (SDR) Relationships: a Large Family with Eight Clusters Common to Human, Animal, and Plant Genomes", *Protein Sci.* (2002) 11:636-641.
Kallberg, Y., et al. "Short-Chain Dehydrogenases/Reductases (SDRs)", *Eur. J. Biochem.* (2002) 269:4409-4417.
Kim, M. et al. , "Activation and function of the mTORC1 pathway in mast cells", The Journal of Immunology 180:4586-4595, Apr. 2008.
Knight, et al. "A Pharmacological Map of the P13-K Family Defines a Role for p110α in Insulin Signaling", *Cell* (2006) 125:733-747.
Kraybill, B.C. et al. "Inhibitor scaffolds as new allele specific kinase substrates", Journal of the American Chemical Society, American Chemical Society, Washington, DC, US, vol. 124, No. 41, Oct. 16, 2002, pp. 12118-12128.
Kreutzberger, A. et al. , "5-substituierte 4-aminopyrimidine durch aminomethinylierung von acetonitrilen", Justus Liebigs Annalen der Chemie 4:537-544, 1977.
Kwok, B.H., et al. "The Anti-Inflammatory Natural Product Parthenolide from the Medicinal Herb Feverfew Directly Binds to and Inhibits IkB Kinase", *Chem. Biol.* (2001) 8:759-766.
Mayer, T.U., et al. "Small Molecule Inhibitor of Mitotic Spindle Bipolarity Identified in a Pheontype-Based Screen", *Science* (1999) 286:971-974.
Miyaura, N., et al., "Palladium-Catalyzed Cross-Coupling Reactions of Organoboron Compounds," *Chem. Rev.* (1995) 95(7):2457-2483.
Moon, H.S., et al. "A Novel Microtubule Destabilizing Entity from Orthogonal Synthesis of Triazine Library and Zebrafish Embryo Screening", *J. Am. Chem. Soc.* (2002) 124:11608-11609.
Nakanishi, M., et al. "Cloning and Sequence Analysis of a cDNA Encoding Tetrameric Carbonyl Reductase of Pig Lung", *Biochem. Biophys. Acta* (1993) 194(3):1311-1316.
Niswender, C.M., et al. "Protein Engineering of Protein Kinase A Catalytic Subunits Results in the Acquisition of Novel Inhibitor Sensitivity", *The Journal of Biological Chemistry* (2002) 277(32):28916-28922.
Nobel, C.S.I., et al. "Purification of Full-Length Recombinant Human and Rat Type 1 11β-hydroxysteroid Dehydrogenases with Retained Oxidoreductase Activities", *Protein Expr. Purif.* (2002) 26:349-356.
Oppermann, U.C., et al. "Forms and Functions of Human SDR Enzymes", *Chem. Biol. Interact.* (2001) 130-132(1-3):699-705.
Persson, C.G. "Glucocorticoids for Asthma—Early Contributions", *Pulm. Pharmacol.* (1989) 2:163-166.
Pietrie et al., "novel biotinylated adenylate analogue derived from pyrazolo[3,4-d]pyrimidine for labeling DNA probes," *Bioconj. Chem.* vol. 2, No. 6, (1991), pp. 441-446.
Pudlo, J.S., et al. "Synthesis, Antiproliferative, and Antiviral Activity of Certain 4-Substituted and 4,5 Disubstituted 7-[1,3-Dihydroxy-2-propoxy)methyl]pyrrolo[2,3-d]pyrimidines", *J. Med. Chem.* (1990) 33:1984-1992.
Robertson, R.P. "Eicosandoids and Human Disease", *Harrison's Principles of Internal Medicine*, Isselbacher K.J., et al. (eds.), McGraw-Hill, New York City (1994) 1:431-435.
Romero, D.G., et al. "Cloning and Expression of the Bovine 11β—hydroxysteroid Dehydrogenase Type-2", *J. Steroid Biochm. Mol. Biol.* (2000) 72:231-237.
Singer, R.H., et al. "Optimization of in situ Hybridization Using Isotopic and Non-Isotopic Detection Methods", *Biotechniques* (1986) 4(3):230-250.
Soldan, M., et al. "Induction of Daunorubicin Carbonyl Reducing Enzymes by Daunorubicin in Sensitive and Resistant Pancreas Carcinoma Cells", *Biochem. Pharmacol.* (1996) 51:117-123.
Supplementary European Search Report dated Feb. 16, 2010 for EP Application No. 07754845.1, 4 pages.
Supplementary European Search Report dated Feb. 24, 2010 for EP Application No. 07754845, 4 pages.
Supplementary European Search Report dated Sep. 20, 2011 for EP Application No. 07754845.1, 4 pages.
Takeuchi, H. et al. , "Synergistic augmentation of reapamycin-induced autophagy in malignant glioma cells by phosphatidylinositol 3-kinase/protein kinase B inhibitors", Cancer Research 65(8):3336-3346, Apr. 15, 2005.

(56) References Cited

OTHER PUBLICATIONS

Tanaka, M., et al. "An Unbiased Cell Morphology-Based Screen for New, Biologically Active Small Molecules", *PLoS Biology* (2005) 3(5):0764-0776.

Ugarkar, B.G., et al. "Adenosine Kinase Inhibitors. 2. Synthesis, Enzyme Inhibition, and Antiseizure Activity of Diaryltubercidin Analogues",*J. Med. Chem.* (2000) 43:2894-2905.

White, P.C., et al. "11β—Hydroxysteroid Dehydrogenase and the Syndrome of Apparent Mineralocorticoid Excess", *Endocr. Rev.* (1997) 18(1):135-156.

Widler, L., et al. "7-Alkyl- and 7-Cycloalkyl-5-aryl-pyrrolo [2,3-*d*]pyrimidines-Potent Inhibitors of the Tyrosine Kinase c-Src," *Bioorganic & Medicinal Chemistry Letters* (2001) 11(6):849-852.

Wolff, M. E. *Burger's Medicinal Chemistry*, 5ed, Part 1, John Wiley & Sons, 1995, pp. 975-977.

\* cited by examiner

Type I Inhibition

FUSED RING HETEROARYL KINASE INHIBITORS

CROSS-REFERENCES TO RELATED APPLICATIONS

This present application is a U.S. National Phase Application under 35 U.S.C. §371 of International Application No. PCT/US2009/060985, filed Oct. 16, 2009, which claims the benefit of U.S. Provisional Application No. 61/106,137, filed Oct. 16, 2008 and U.S. Provisional Application No. 61/106,453, filed Oct. 17, 2008, all of which are expressly incorporated herein by reference in their entireties and for all purposes.

STATEMENT AS TO RIGHTS TO INVENTIONS MADE UNDER FEDERALLY SPONSORED RESEARCH AND DEVELOPMENT

This invention was made with government support under grant number W81XWH-06-1-0727 awarded by the Department of Defense. The Government has certain rights in the invention.

BACKGROUND OF THE INVENTION

Protein kinases represent one of the largest super-families of drug targets across all therapeutic areas. The central challenge in the development of kinase inhibitor drug candidates is in targeting the disregulated kinase while avoiding inhibition of non-disease related kinases containing closely related ATP binding pockets. Imatinib, the first clinically approved kinase inhibitor provided a remarkable example of a highly selective inhibitor of the translocation product Bcr-Abl (SEQ ID NO:1) (Capdeville et al., 2002, *Nat Rev Drug Discov* 1:493-502; Sawyers, 2002, *Cancer Cell* 1:13-15). Imatinib potently inhibits Bcr-Abl, the oncogene which drives chronic myelogenous leukaemia, but does not inhibit the cytoplasmic tyrosine kinase, c-Src (SEQ ID NO:2), despite the fact that the two kinases share almost completely identical amino acids lining the ATP binding pocket which Imatinib contacts (FIG. 1A; Schindler et al., 2000, *Science* 289:1938-1942; Seeliger et al., 2007, *Structure* 15:299-311). Significant medicinal chemistry, structural biology, and computational modelling efforts have focussed on understanding the differential selectivity of Imatinib for Bcr-Abl and c-Src.

The first insight into the basis for selectivity of Imatinib was revealed when Kuriyan and co-workers solved the Imatinib-Abl co-crystal structure (Nagar et al., 2002, *Cancer Research* 62:4236-4243; Schindler et al., 2000, Id.). This structure revealed a not-previously observed kinase conformation indicating that Imatinib binds Abl in a catalytically inactive conformation defined by a crank shaft-like displacement of the N-terminal region of the activation loop of the kinase effecting a dramatic change in the conformation of the Asp-Phe-Gly (DFG) triad. This conformational change has been subsequently observed in other protein kinase-drug co-crystal structures (Irk, Kit, Flt3, p38 Mapk and B-Raf; Griffith et al., 2004, *Mol Cell* 13:169-178; Hubbard et al., 1994, *Nature* 372:746-754; Mol et al., 2004, *J Biol Chem* 279:31655-31663; Pargellis et al., 2002, *Nat Struct Biol* 9:268-272; Wan et al., 2004, *Cell* 116:855-867) and has been termed the "type-II" or "DFG-out" conformation. ATP competitive inhibitors which bind to kinases in the active conformation are termed "type-I" or "DFG-in" binders; FIGS. 1B and C; Liu and Gray, 2006, *Nat Chem Biol* 2:358-364). The identification of an inactive conformation of Abl bound by the highly selective inhibitor Imatinib has guided many successful medicinal chemistry campaigns in search of selective kinase inhibitors (Angell et al., 2008, *Bioorg Med Chem Lett* 18:4433-4437; Cumming et al., 2004, *Bioorg Med Chem Lett* 14:5389-5394; Gill et al., 2005, *J Med Chem* 48:414-426; Heron et al., 2006, *Bioorg Med Chem Lett* 16:1320-1323; Okram et al., 2006, *Chem Biol* 13:779-786).

A wealth of data currently supports the view that the Imatinib bound conformation (DFG-out) of Abl is thermodynamically stable in complex with Imatinib, but that such conformations require energetically unfavourable interactions in c-Src complexes (Levinson et al., 2006, *PLoS Biol* 4:e144; Nagar et al., 2002, Id.; Seeliger et al., 2007, Id.; Vajpai et al., 2008, *J Biol Chem* 283:18292-18302). Imatinib has been crystallized in both its potent target Abl (Nagar et al., 2002, Id.; Schindler et al., 2000, Id.), as well as the poorly inhibited target, c-Src (Seeliger et al., 2007, Id.). Surprisingly, the Imatinib/co-crystal structures are virtually identical despite the significantly different affinities of Imatinib for the two protein kinases. Efforts to construct mutant forms of c-Src with the ability to be potently inhibited by Imatinib were only partially successful, which led Kuriyan and co-workers to suggest a distributed thermodynamic penalty for c-Src to adopt the DFG-out conformation (Seeliger et al., 2007, Id.). The importance of kinase conformational preference over precise amino acid identity is highlighted by studies with the Imatinib target receptor kinase, c-Kit (SEQ ID NO:3). Although c-Kit is more closely related to c-Src than Abl (SEQ ID NO:11) in the amino acids lining the ATP binding pocket, c-Kit is more potently inhibited by Imatinib (Deininger et al., 2005, *Blood* 105:2640-2653). Structural studies of c-Kit in the absence of ligand (ATP or Imatinib) show the kinase adopts the DFG-out conformation, suggesting the Imatinib bound conformation is stable and pre-formed in the absence of Imatinib, thereby explaining its Imatinib sensitivity (Mol et al., 2004, Id.)

Without wishing to be bound by any theory, it is widely held that the explanation of the discrepancy in affinity of Imatinib despite the close similarity in structure of the two drug-protein complexes is based on the relative propensity of the two kinases to adopt the relevant drug-bound (DFG-out/type II) conformation: Abl is predicted to prefer the DFG out conformation relative to c-Src, and since Imatinib binds to the type-II conformation of the kinase, its affinity is higher to Abl than to c-Src.

BRIEF SUMMARY OF THE INVENTION

Provided herein are new modalities for the inhibition of certain kinases and anti-cancer treatments. In particular, fused ring heteroaryl compounds useful in a variety of methods, including reducing the activity of certain kinases and treating certain disease states are provided.

In one aspect, compounds are provided having the formula:

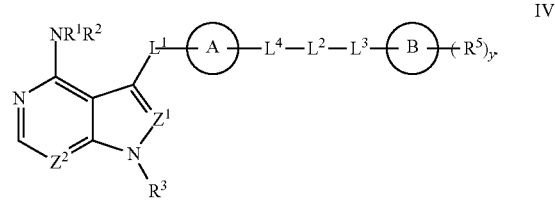

IV

In Formula IV, x is an integer from 0 to 4, y is an integer from 0 to 5. Ring A is arylene or heteroarylene. Ring B is aryl or heteroaryl. $Z^1$ is —N= or —C($R^{22}$)=. $Z^2$ is —N= or —C($R^{23}$)=. $R^1$ and $R^2$ are independently hydrogen, substituted or unsubstituted alkyl, or substituted or unsubstituted heteroalkyl. $R^3$, $R^{22}$ and $R^{23}$ are independently —CN, —$CF_3$, —S(O)$_n R^6$, —N(O)$_m$, —$NR^7 R^8$, —C(O)$R^9$, —$NR^{10}$—C(O) $R^{11}$, —$NR^{12}$—C(O)—$OR^{13}$, —C(O)$NR^{14} R^{15}$, —$NR^{16}$S (O)$_2$ $R^{17}$, —S(O)$_2 NR^{18} R^{18'}$, —$OR^{19}$, halomethyl, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein n is an integer from 0 to 2, and m is an integer from 1 to 2. $R^4$ and $R^5$ are independently halogen, —CN, —$CF_3$, —S(O)$_n R^6$, —N(O)$_m$, —$NR^7 R^8$, —C(O)$R^9$, —$NR^{10}$—C(O) $R^{11}$, —$NR^{12}$—C(O)—$OR^{13}$, —C(O)$NR^{14} R^{15}$, —$NR^{16}$S (O)$_2$ $R^{17}$, —S(O)$_2 NR^{18} R^{18'}$, —$OR^{19}$, halomethyl, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein n is an integer from 0 to 2, and m is an integer from 1 to 2. $L^1$ is a bond, substituted or unsubstituted alkylene or substituted or unsubstituted heteroalkylene. $L^2$ is —S(O)—, —S(O)$_2$— or —C(O)—. $L^3$ is a bond, —N($R^{20}$)—, substituted or unsubstituted alkylene, or substituted or unsubstituted heteroalkylene. $L^4$ is a bond, —NH— or —$CH_2$—. $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{18'}$, $R^{19}$ and $R^{20}$ are independently hydrogen, substituted or unsubstituted alkyl, substituted or unsubstituted heteroalkyl, unsubstituted cycloalkyl, substituted or unsubstituted heterocycloalkyl, substituted or unsubstituted aryl, or substituted or unsubstituted heteroaryl.

In another aspect, compounds are provided having the formula:

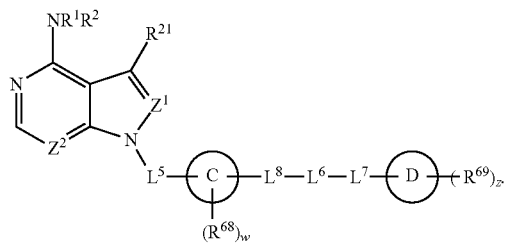

VI

In Formula VI, w is an integer from 0 to 4, and z is an integer from 0 to 5. Ring C is cycloalkylene, heterocycloalkylene, arylene, or heteroarylene. Ring D is aryl or heteroaryl. $Z^1$, $Z^2$, $R^1$, $R^2$, $R^{22}$ and $R^{23}$ are as defined for Formula IV above. $R^{21}$ is —CN, —$CF_3$, —S(O)$_n R^6$, —N(O)$_m$, —$NR^7 R^8$, —C(O) $R^9$, —N=NH, —$NR^{10}$—C(O)$R^{11}$, —$NR^{12}$—C(O)—$OR^{13}$, —C(O)$NR^{14} R^{15}$, —$NR^{16}$S(O)$_2 R^{17}$, —S(O)$_2 NR^{18} R^{18'}$, —$OR^{19}$, substituted or unsubstituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein n, m, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{18'}$, and $R^{19}$ are as defined for Formula IV above. $R^{68}$ and $R^{69}$ are independently halogen, —CN, —$CF_3$, —S(O)$_n$ $R^6$, —N(O)$_m$, —$NR^7 R^8$, —C(O)$R^9$, —N=NH, —$NR^{10}$—C (O)$R^{11}$, —$NR^{12}$—C(O)—$OR^{13}$, —C(O)$NR^{14} R^{15}$, —$NR^{16}$S (O)$_2 R^{17}$, —S(O)$_2 NR^{18} R^{18'}$, —$OR^{19}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein n, m, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{18'}$, and $R^{19}$ are as defined for Formula IV above. $L^5$ is a bond, substituted or unsubstituted alkylene, or substituted or unsubstituted heteroalkylene. $L^6$ is —S(O)—, —S(O)$_2$— or —C(O)—. $L^7$ is a bond, —N($R^{20}$)—, substituted or unsubstituted alkylene, or substituted or unsubstituted heteroalkylene, wherein $R^{20}$ is as defined for Formula IV above. $L^8$ is a bond, —C(O)—, —NH— or —$CH_2$—.

In another aspect, compounds are provided having the formula:

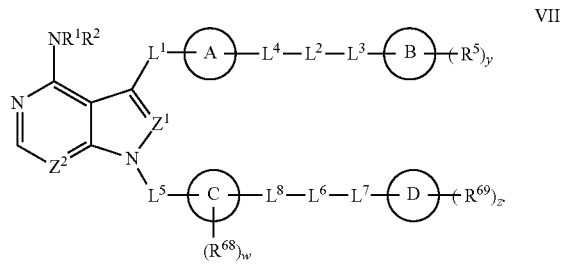

VII

In Formula VII, $Z^1$, $Z^2$, $R^1$, $R^2$, $R^4$, $R^5$, $R^{68}$, $R^{69}$, w, x, y, z, ring A, ring B, ring C, ring D, $L^1$, $L^2$, $L^3$, $L^4$, $L^5$, $L^6$, $L^7$, and $L^8$ are as defined for Formulae V and VI above.

In another aspect, a method is provided for treating liver cancer, colon cancer, breast cancer, melanoma, acute myelogenous leukemia, chronic myelogenous leukemia, non-small-cell lung cancer, a gastrointestinal stromal tumor, Philadelphia chromosome-positive acute lymphoblastic leukemia (Ph+ ALL), renal cell carcinoma, hepatocellular carcinoma, hypereosinophilic syndrome, or dermatofibrosarcoma protuberans. The method includes administering an effective amount of a fused ring heteroaryl inhibitor disclosed herein to a subject in need of treatment for an indication described herein.

In another aspect, a method of reducing the activity of a Src tyrosine kinase is provided. The method includes contacting the Src tyrosine kinase with an effective amount of a fused ring heteroaryl inhibitor disclosed herein.

In another aspect, a method of reducing the activity of an Abl tyrosine kinase is provided. The method includes contacting the Abl tyrosine kinase with an effective amount of a fused ring heteroaryl inhibitor disclosed herein.

In another aspect, a method of reducing the activity of a T315I Bcr-Abl kinase is provided. The method includes contacting the T315I Bcr-Abl Kinase with an effective amount of a fused ring heteroaryl inhibitor disclosed herein.

In another aspect, a method of treating a disease mediated by a T315I Bcr-Abl kinase in a subject in need thereof is provided. The method includes administering to a subject an effective amount of a fused ring heteroaryl inhibitor disclosed herein.

DETAILED DESCRIPTION OF THE INVENTION

I. Definitions

Figure 1A:
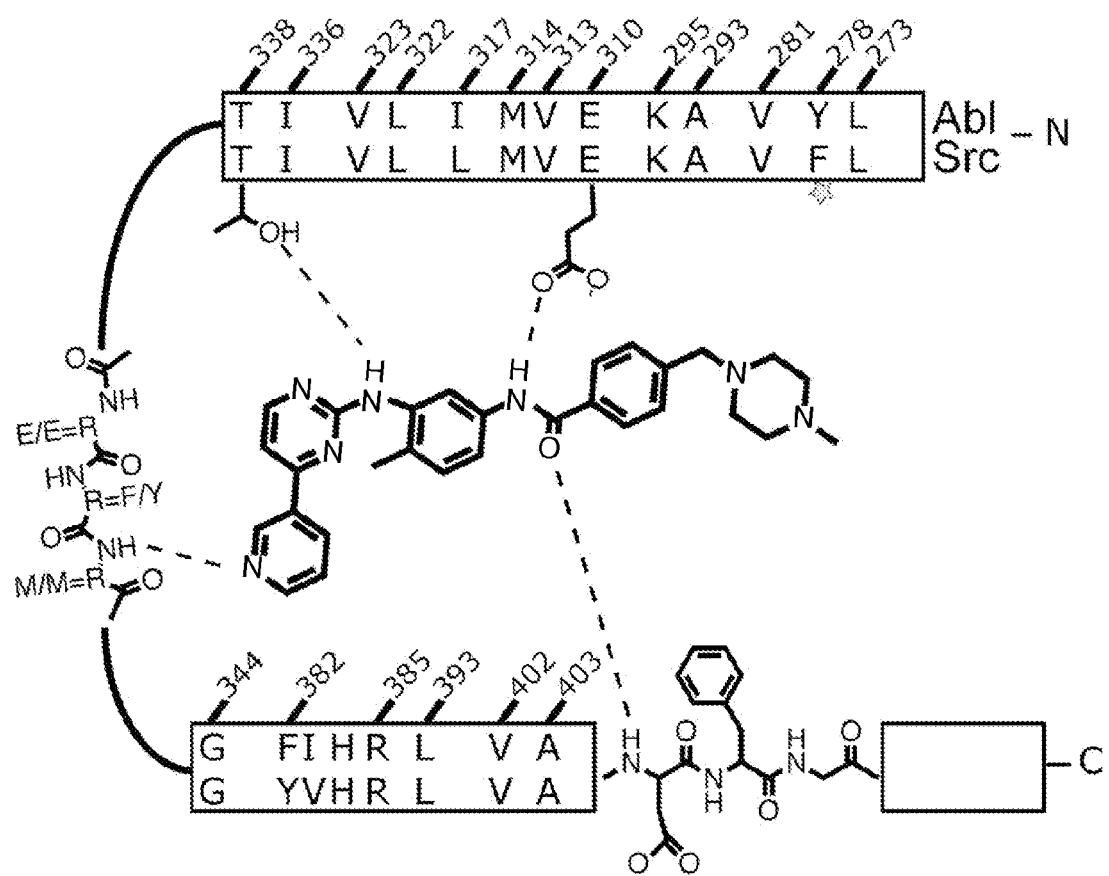
FIG. 1A. A schematic representation of Imatinib contacts identified in its complexes with c-Src (PDB ID 2OIQ) (SEQ ID NO:4) and Abl (PDB ID 1IEP) (SEQ ID NO:5). B. Type I inhibitors, such as PP1 (1-tert-butyl-3-p-tolyl-1H-pyrazolo [3,4-d]pyrimidin-4-amine), occupy the adenosine pocket forming multiple hydrogen bonds with the hinge region of the kinase and threonine gatekeeper. C. Type II inhibitors, such as Imatinib, engage both the hinge binding region and extend into the pocket created by the DFG flip.

The abbreviations used herein have their conventional meaning within the chemical and biological arts.

Where substituent groups are specified by their conventional chemical formulae, written from left to right, they equally encompass the chemically identical substituents that would result from writing the structure from right to left, e.g., —$CH_2O$— is equivalent to —$OCH_2$—.

The term "alkyl," by itself or as part of another substituent, means, unless otherwise stated, a straight (i.e. unbranched) or branched carbon chain, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

The term "alkylene" by itself or as part of another substituent means a divalent radical derived from an alkyl, as exemplified, but not limited, by —$CH_2CH_2CH_2CH_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The term "heteroalkyl," by itself or in combination with another term, means, unless otherwise stated, a stable straight or branched chain, or cyclic hydrocarbon radical, or combinations thereof, consisting of at least one carbon atoms and at least one heteroatom selected from the group consisting of O, N, P, Si and S, and wherein the nitrogen and sulfur atoms may optionally be oxidized and the nitrogen heteroatom may optionally be quaternized. The heteroatom(s) O, N, P and S and Si may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, —CH=CH—N($CH_3$)—$CH_3$, O—$CH_3$, —O—$CH_2$—$CH_3$, and —CN. Up to two heteroatoms may be consecutive, such as, for example, —$CH_2$—NH—$OCH_3$ and —$CH_2$—O—Si($CH_3$)$_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and "heterocycloalkylene" refer to a divalent radical derived from cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, hydrocarbon substituent which can be a single ring or multiple rings (preferably from 1 to 3 rings) which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. "Arylene" and "heteroarylene" refers to a divalent radical derived from a aryl and heteroaryl, respectively. A "fused ring" refers a ring system with two or more rings having at least one bond and two atoms in common. Thus, a "fused ring aryl" and a "fused ring heteroaryl" refer to ring systems having at least one aryl and heteroaryl, respectively, that share at least one bond and two atoms in common with another ring.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

The term "oxo" as used herein means an oxygen that is double bonded to a carbon atom.

The term "alkylsulfonyl" as used herein means a moiety having the formula —S(O$_2$)—R', where R' is an alkyl group as defined above. R' may have a specified number of carbons (e.g. "$C_1$-$C_4$ alkylsulfonyl").

Each of the above terms (e.g., "alkyl," "heteroalkyl," "aryl" and "heteroaryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', halogen, —SiR'R"R"', —OC(O)R', —C(O)R', —CO$_2$R', —CONR'R", —OC(O)NR'R", —NR"C(O)R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R"' and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. When a compound of the invention includes more than one R group, for example, each of the R groups is independently selected as are each R', R", R"' and R"" groups when more than one of these groups is present. When R' and R" are attached to the same nitrogen atom, they can be combined with the nitrogen atom to form a 4-, 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: halogen, —OR', —NR'R", —SR', halogen, —SiR'R"R"', —OC(O)R', —C(O)R', —CO$_2$R', —CONR'R", —OC(O)NR'R", —NR"C(O)R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', —CN and —NO$_2$, —R', —N$_3$, —CH(Ph)$_2$, fluoro($C_1$-$C_4$)alkoxy, and fluoro($C_1$-$C_4$)alkyl, in a number ranging from zero to the total number of open valences on the aromatic ring system; and where R', R", R"' and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the invention includes more than one R group, for example, each of the R groups is independently selected as are each R', R", R"' and R"" groups when more than one of these groups is present.

Two of the substituents on adjacent atoms of the aryl or heteroaryl ring may optionally faun a ring of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"')$_d$—, where s and d are independently integers of from 0 to 3, and X' is —O—, —NR'—, —S—, —S(O)—, —S(O)$_2$—, or —S(O)$_2$NR'—. The substituents R, R', R" and R"' are preferably independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the term "heteroatom" or "ring heteroatom" is meant to include oxygen (O), nitrogen (N), sulfur (S), phosphorus (P), and silicon (Si).

A "substituent group," as used herein, means a group selected from the following moieties:

(A) —OH, —NH$_2$, —SH, —CN, —CF$_3$, —NO$_2$, oxo, halogen, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:

(i) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from:
(a) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and
(b) alkyl, heteroalkyl, cycloalkyl, heterocycloalkyl, aryl, or heteroaryl, substituted with at least one substituent selected from oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein means a group selected from all of the substituents described above for a "substituent group," wherein each substituted or unsubstituted alkyl is a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, and each substituted or unsubstituted heterocycloalkyl is a substituted or unsubstituted 3 to 8 membered heterocycloalkyl.

A "lower substituent" or "lower substituent group," as used herein means a group selected from all of the substituents described above for a "substituent group," wherein each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_3$-C$_8$ cycloalkyl, and each substituted or unsubstituted heterocycloalkyl is a substituted or unsubstituted 3 to 8 membered heterocycloalkyl.

The term "halomethyl" refers halogen substituted methyl, for example monohalomethyl, dihalomethyl or trihalomethyl. The substituting halogens can be homogeneous (e.g., trifluoromethyl) or heterogeneous (e.g., chlorofluoromethyl). Exemplary halomethyl substituents include, but are not limited to, monofluoromethyl, difluoromethyl, trifluoromethyl, monochloromethyl, dichloromethyl, trichloromethyl, chlorofluoromethyl, and the like.

The compounds of the present invention may exist as salts. The present invention includes such salts. Examples of applicable salt forms include hydrochlorides, hydrobromides, sulfates, methanesulfonates, nitrates, maleates, acetates, citrates, fumarates, tartrates (e.g., (+)-tartrates, (−)-tartrates or mixtures thereof including racemic mixtures, succinates, benzoates and salts with amino acids such as glutamic acid. These salts may be prepared by methods known to those skilled in art. Also included are base addition salts such as sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived organic acids like acetic, propionic, isobutyric, maleic, malonic, benzoic, succinic, suberic, fumaric, lactic, mandelic, phthalic, benzenesulfonic, p-tolyl-sulfonic, citric, tartaric, methanesulfonic, and the like. Also included are salts of amino acids such as arginate and the like, and salts of organic acids like glucuronic or galactunoric acids and the like. Certain specific compounds of the present invention contain both basic and acidic functionalities that allow the compounds to be converted into either base or acid addition salts.

The neutral forms of the compounds are preferably regenerated by contacting the salt with a base or acid and isolating the parent compound in the conventional manner. The parent form of the compound differs from the various salt form's in certain physical properties, such as solubility in polar solvents.

Certain compounds of the present invention can exist in unsolvated forms as well as solvated forms, including hydrated fauns. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

The neutral forms of the compounds are preferably regenerated by contacting the salt with a base or acid and isolating the parent compound in the conventional manner. The parent form of the compound differs from the various salt forms in certain physical properties, such as solubility in polar solvents.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, tautomers, geometric isomers and individual isomers are encompassed within the scope of the present invention. The compounds of the present invention do not include those which are known in the art to be too unstable to synthesize and/or isolate.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are encompassed within the scope of the present invention.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted C$_1$-C$_{20}$ alkyl, or unsubstituted 2 to 20 membered heteroalkyl," the group may contain one or more unsubstituted C$_1$-C$_{20}$ alkyls, and/or one or more unsubstituted 2 to 20 membered heteroalkyls.

"Methods of treating a disease," as used herein, refers to methods of treating a disease state, a condition caused by a disease state, or disease symptoms. The term "treating," "treatment" and other conjugations thereof, include prevention of a disease.

An "inhibitor" of a kinase as used herein refers to a compound capable of reducing the enzymatic activity of the kinase. Where a method is provided of "reducing the activity" of a kinase disclosed herein, the method reduces the enzymatic kinase activity of the recited kinase.

An "effective amount" as used herein refers to an amount effective to accomplish the intended purpose of the recited method (e.g. reducing a kinase activity or treating a disease state).

The term "PDB" refers to the Protein Data Bank archive of the Worldwide Protein Data Bank, as known in the art. PDB identification numbers ("PDB ID") refer to unique alphanumeric identifiers for the structural data files forming the PDB.

Specific amino acid substitution in a peptide or protein is indicated, as is customary in the art, by the designator "XNNNY" where "X" is the native single letter amino acid code, "NNN" is the numerical position of the substitution, and "Y" is the single letter amino acid code for the substituting residue. The position of a specific amino acid within a peptide or protein sequence is indicated, as is customary in the art, by either a superscripted numerical position identifier prepended (e.g., "$^{123}$Gly") or postpended (e.g., "Gly123") to the amino acid name.

Fused Ring Heteroaryl Inhibitors

Provided herein are certain fused ring heteroaryls useful in, inter alia, reducing the activity of a Src kinase and/or an Abl kinase (i.e. fused ring heteroaryl inhibitors). In one aspect, a compound is provided having the formula:

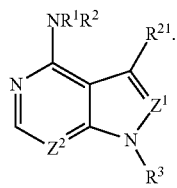

V

In Formula V, $R^1$ and $R^2$ are independently hydrogen, substituted or unsubstituted alkyl, substituted or unsubstituted heteroalkyl. $Z^1$ is —N= or —C($R^{22}$)=. $Z^2$ is —N= or —C($R^{23}$)=. $R^3$, $R^{21}$, $R^{22}$ and $R^{23}$ are independently —CN, —CF$_3$, —S(O)$_n$R$^6$, —N(O)$_m$, —NR$^7$R$^8$, —C(O)R$^9$, —N=NH, —NR$^{10}$—C(O)R$^{11}$, —NR$^{12}$—C(O)—OR$^{13}$, —C(O)NR$^{14}$R$^{15}$, —NR$^{16}$S(O)$_2$R$^{17}$, —S(O)$_2$NR$^{18}$R$^{18'}$, —OR$^{19}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein n is an integer from 0 to 2, and m is an integer from 1 to 2. $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{18'}$, and $R^{19}$ are independently hydrogen, substituted or unsubstituted alkyl, substituted or unsubstituted heteroalkyl, unsubstituted cycloalkyl, substituted or unsubstituted heterocycloalkyl, substituted or unsubstituted aryl, or substituted or unsubstituted heteroaryl.

In some embodiments for compounds having the structure of Formula V, $R^1$ and $R^2$ are independently hydrogen, $R^{24}$-substituted or unsubstituted alkyl, or $R^{24}$-substituted or unsubstituted heteroalkyl. $R^{24}$ is —OH, —NH$_2$, —SH, —CN, —CF$_3$, —NO$_2$, oxo, halogen, $R^{25}$-substituted or unsubstituted alkyl, $R^{25}$-substituted or unsubstituted heteroalkyl, $R^{25}$-substituted or unsubstituted cycloalkyl, $R^{25}$-substituted or unsubstituted heterocycloalkyl, $R^{25}$-substituted or unsubstituted aryl, or $R^{25}$-substituted or unsubstituted heteroaryl.

In some embodiments, $R^3$ is —CN, —CF$_3$, —S(O)$_n$R$^6$, —N(O)$_m$, —NR$^7$R$^8$, —C(O)R$^9$, —N=NH, —NR$^{10}$—C(O)R$^{11}$, —NR$^{12}$—C(O)—OR$^{13}$, —C(O)NR$^{14}$R$^{15}$, —NR$^{16}$S(O)$_2$R$^{17}$, —S(O)$_2$NR$^{18}$R$^{18'}$, —OR$^{19}$, substituted alkyl, substituted heteroalkyl, substituted cycloalkyl, substituted heterocycloalkyl, substituted aryl or substituted heteroaryl, wherein n is an integer from 0 to 2, and m is an integer from 1 to 2. In some embodiments, $R^3$ is —CN, —CF$_3$, —S(O)$_n$R$^6$, —N(O)$_m$, —NR$^7$R$^8$, —C(O)R$^9$, —N=NH, —NR$^{10}$—C(O)R$^{11}$, —NR$^{12}$—C(O)—OR$^{13}$, —C(O)NR$^{14}$R$^{15}$, —NR$^{16}$S(O)$_2$R$^{17}$, —S(O)$_2$NR$^{18}$R$^{18'}$, —OR$^{19}$, $R^{26}$-substituted or unsubstituted alkyl, $R^{26}$-substituted or unsubstituted heteroalkyl, $R^{26}$-substituted or unsubstituted cycloalkyl, $R^{26}$-substituted or unsubstituted heterocycloalkyl, $R^{26}$-substituted or unsubstituted aryl, or $R^{26}$-substituted or unsubstituted heteroaryl. $R^{26}$ is —OH, —NH$_2$, —SH, —CN, —CF$_3$, —NO$_2$, oxo, halogen, —COOH, —COOR$^{27}$, —C(O)NHR$^{27}$, $R^{27}$-substituted or unsubstituted alkyl, $R^{27}$-substituted or unsubstituted heteroalkyl, $R^{27}$-substituted or unsubstituted cycloalkyl, $R^{27}$-substituted or unsubstituted heterocycloalkyl, $R^{27}$-substituted or unsubstituted aryl, or $R^{27}$-substituted or unsubstituted heteroaryl. In some embodiments, $R^3$ is unsubstituted alkyl or unsubstituted heterocycloalkyl.

In some embodiments, $R^6$ is $R^{32}$-substituted or unsubstituted alkyl, $R^{32}$-substituted or unsubstituted heteroalkyl, $R^{32}$-substituted or unsubstituted cycloalkyl, $R^{32}$-substituted or unsubstituted heterocycloalkyl, $R^{32}$-substituted or unsubstituted aryl, or $R^{32}$-substituted or unsubstituted heteroaryl. $R^{32}$ is —OH, —NH$_2$, —SH, —CN, —CF$_3$, —NO$_2$, oxo, halogen, $R^{33}$-substituted or unsubstituted alkyl, $R^{33}$-substituted or unsubstituted heteroalkyl, $R^{33}$-substituted or unsubstituted cycloalkyl, $R^{33}$-substituted or unsubstituted heterocycloalkyl, $R^{33}$-substituted or unsubstituted aryl, or $R^{33}$-substituted or unsubstituted heteroaryl.

In some embodiments, $R^7$ and $R^8$ are independently hydrogen, $R^{34}$-substituted or unsubstituted alkyl, $R^{34}$-substituted or unsubstituted heteroalkyl, $R^{34}$-substituted or unsubstituted cycloalkyl, $R^{34}$-substituted or unsubstituted heterocycloalkyl, $R^{34}$-substituted or unsubstituted aryl, or $R^{34}$-substituted or unsubstituted heteroaryl. $R^{34}$ is —OH, —NH$_2$, —SH, —CN, —CF$_3$, —NO$_2$, oxo, halogen, $R^{35}$-substituted or unsubstituted alkyl, $R^{35}$-substituted or unsubstituted heteroalkyl, $R^{35}$-substituted or unsubstituted cycloalkyl, $R^{35}$-substituted or unsubstituted heterocycloalkyl, $R^{35}$-substituted or unsubstituted aryl, or $R^{35}$-substituted or unsubstituted heteroaryl.

In some embodiments, $R^9$ is hydrogen, $R^{36}$-substituted or unsubstituted alkyl, $R^{36}$-substituted or unsubstituted heteroalkyl, $R^{36}$-substituted or unsubstituted cycloalkyl, $R^{36}$-substituted or unsubstituted heterocycloalkyl, $R^{36}$-substituted or unsubstituted aryl, or $R^{36}$-substituted or unsubstituted heteroaryl. $R^{36}$ is —OH, —NH$_2$, —SH, —CN, —CF$_3$, —NO$_2$, oxo, halogen, $R^{37}$-substituted or unsubstituted alkyl, $R^{37}$-substituted or unsubstituted heteroalkyl, $R^{37}$-substituted or unsubstituted cycloalkyl, $R^{37}$-substituted or unsubstituted heterocycloalkyl, $R^{37}$-substituted or unsubstituted aryl, or $R^{37}$-substituted or unsubstituted heteroaryl.

In some embodiments, $R^{10}$ is hydrogen, $R^{38}$-substituted or unsubstituted alkyl, $R^{38}$-substituted or unsubstituted heteroalkyl, $R^{38}$-substituted or unsubstituted cycloalkyl, $R^{38}$-substituted or unsubstituted heterocycloalkyl, $R^{38}$-substituted or unsubstituted aryl, or $R^{38}$-substituted or unsubstituted heteroaryl. $R^{38}$ is —OH, —NH$_2$, —SH, —CN, —CF$_3$, —NO$_2$, oxo, halogen, $R^{39}$-substituted or unsubstituted alkyl, $R^{39}$-substituted or unsubstituted heteroalkyl, $R^{38}$-substituted or unsubstituted cycloalkyl, $R^{39}$-substituted or unsubstituted heterocycloalkyl, $R^{39}$-substituted or unsubstituted aryl, or $R^{39}$-substituted or unsubstituted heteroaryl.

In some embodiments, $R^{11}$ is hydrogen, $R^{40}$-substituted or unsubstituted alkyl, $R^{40}$-substituted or unsubstituted heteroalkyl, $R^{40}$-substituted or unsubstituted cycloalkyl, $R^{40}$-substituted or unsubstituted heterocycloalkyl, $R^{40}$-substituted or unsubstituted aryl, or $R^{40}$-substituted or unsubstituted heteroaryl. $R^{40}$ is —OH, —NH$_2$, —SH, —CN, —CF$_3$, —NO$_2$, oxo, halogen, $R^{41}$-substituted or unsubstituted alkyl, $R^{41}$-substituted or unsubstituted heteroalkyl, $R^{41}$-substituted or unsubstituted cycloalkyl, $R^{41}$-substituted or unsubstituted heterocycloalkyl, $R^{41}$-substituted or unsubstituted aryl, or $R^{41}$-substituted or unsubstituted heteroaryl.

In some embodiments, $R^{12}$ is hydrogen, $R^{42}$-substituted or unsubstituted alkyl, $R^{42}$-substituted or unsubstituted heteroalkyl, $R^{42}$-substituted or unsubstituted cycloalkyl, $R^{42}$-substituted or unsubstituted heterocycloalkyl, $R^{42}$-substituted or unsubstituted aryl, or $R^{42}$-substituted or unsubstituted heteroaryl. $R^{42}$ is —OH, —NH$_2$, —SH, —CN, —CF$_3$, —NO$_2$, oxo, halogen, $R^{43}$-substituted or unsubstituted alkyl, $R^{43}$-substituted or unsubstituted heteroalkyl, $R^{43}$-substituted or unsubstituted cycloalkyl, $R^{43}$-substituted or unsubstituted heterocycloalkyl, $R^{43}$-substituted or unsubstituted aryl, or $R^{43}$-substituted or unsubstituted heteroaryl.

In some embodiments, $R^{13}$ is hydrogen, $R^{44}$-substituted or unsubstituted alkyl, $R^{44}$-substituted or unsubstituted heteroalkyl, $R^{44}$-substituted or unsubstituted cycloalkyl, $R^{44}$-substituted or unsubstituted heterocycloalkyl, $R^{44}$-substituted or unsubstituted aryl, or $R^{44}$-substituted or unsubstituted heteroaryl. $R^{44}$ is —OH, —NH$_2$, —SH, —CN, —CF$_3$, —NO$_2$, oxo, halogen, $R^{45}$-substituted or unsubstituted alkyl, $R^{45}$-substituted or unsubstituted heteroalkyl, $R^{45}$-substituted or unsubstituted cycloalkyl, $R^{45}$-substituted or unsubstituted heterocycloalkyl, $R^{45}$-substituted or unsubstituted aryl, or $R^{45}$-substituted or unsubstituted heteroaryl.

In some embodiments, $R^{14}$ and $R^{15}$ are independently hydrogen, $R^{46}$-substituted or unsubstituted alkyl, $R^{46}$-substituted or unsubstituted heteroalkyl, $R^{46}$-substituted or unsubstituted cycloalkyl, $R^{46}$-substituted or unsubstituted heterocycloalkyl, $R^{46}$-substituted or unsubstituted aryl, or $R^{46}$-substituted or unsubstituted heteroaryl. $R^{46}$ is —OH, —NH$_2$, —SH, —CN, —CF$_3$, —NO$_2$, oxo, halogen, $R^{47}$-substituted or unsubstituted alkyl, $R^{47}$-substituted or unsubstituted heteroalkyl, $R^{47}$-substituted or unsubstituted cycloalkyl, $R^{47}$-substituted or unsubstituted heterocycloalkyl, $R^{47}$-substituted or unsubstituted aryl, or $R^{47}$-substituted or unsubstituted heteroaryl.

In some embodiments, $R^{16}$ is hydrogen, $R^{48}$-substituted or unsubstituted alkyl, $R^{48}$-substituted or unsubstituted heteroalkyl, $R^{48}$-substituted or unsubstituted cycloalkyl, $R^{48}$-substituted or unsubstituted heterocycloalkyl, $R^{48}$-substituted or unsubstituted aryl, or $R^{48}$-substituted or unsubstituted heteroaryl. $R^{48}$ is —OH, —NH$_2$, —SH, —CN, —CF$_3$, —NO$_2$, oxo, halogen, $R^{49}$-substituted or unsubstituted alkyl, $R^{49}$-substituted or unsubstituted heteroalkyl, $R^{49}$-substituted or unsubstituted cycloalkyl, $R^{49}$-substituted or unsubstituted heterocycloalkyl, $R^{49}$-substituted or unsubstituted aryl, or $R^{49}$-substituted or unsubstituted heteroaryl.

In some embodiments, $R^{17}$ is hydrogen, $R^{50}$-substituted or unsubstituted alkyl, $R^{50}$-substituted or unsubstituted heteroalkyl, $R^{50}$-substituted or unsubstituted cycloalkyl, $R^{50}$-substituted or unsubstituted heterocycloalkyl, $R^{50}$-substituted or unsubstituted aryl, or $R^{50}$-substituted or unsubstituted heteroaryl. $R^{50}$ is —OH, —NH$_2$, —SH, —CN, —CF$_3$, —NO$_2$, oxo, halogen, $R^{51}$-substituted or unsubstituted alkyl, $R^{51}$-substituted or unsubstituted heteroalkyl, $R^{51}$-substituted or unsubstituted cycloalkyl, $R^{51}$-substituted or unsubstituted heterocycloalkyl, $R^{51}$-substituted or unsubstituted aryl, or $R^{51}$-substituted or unsubstituted heteroaryl.

In some embodiments, $R^{18}$ and $R^{18'}$ are independently hydrogen, $R^{52}$-substituted or unsubstituted alkyl, $R^{52}$-substituted or unsubstituted heteroalkyl, $R^{52}$-substituted or unsubstituted cycloalkyl, $R^{52}$-substituted or unsubstituted heterocycloalkyl, $R^{52}$-substituted or unsubstituted aryl, or $R^{52}$-substituted or unsubstituted heteroaryl. $R^{52}$ is —OH, —NH$_2$, —SH, —CN, —CF$_3$, —NO$_2$, oxo, halogen, $R^{53}$-substituted or unsubstituted alkyl, $R^{53}$-substituted or unsubstituted heteroalkyl, $R^{53}$-substituted or unsubstituted cycloalkyl, $R^{53}$-substituted or unsubstituted heterocycloalkyl, $R^{53}$-substituted or unsubstituted aryl, or $R^{53}$-substituted or unsubstituted heteroaryl.

In some embodiments, $R^{19}$ is hydrogen, $R^{54}$-substituted or unsubstituted alkyl, $R^{54}$-substituted or unsubstituted heteroalkyl, $R^{54}$-substituted or unsubstituted cycloalkyl, $R^{54}$-substituted or unsubstituted heterocycloalkyl, $R^{54}$-substituted or unsubstituted aryl, or $R^{54}$-substituted or unsubstituted heteroaryl. $R^{54}$ is —OH, —NH$_2$, —SH, —CN, —CF$_3$, —NO$_2$, oxo, halogen, $R^{55}$-substituted or unsubstituted alkyl, $R^{55}$-substituted or unsubstituted heteroalkyl, $R^{55}$-substituted or unsubstituted cycloalkyl, $R^{55}$-substituted or unsubstituted heterocycloalkyl, $R^{55}$-substituted or unsubstituted aryl, or $R^{55}$-substituted or unsubstituted heteroaryl.

In some embodiments, $R^{21}$ is —CN, —CF$_3$, —S(O)$_n$R$^6$, —N(O)$_m$, —NR$^7$R$^8$, —C(O)R$^9$, —N=NH, —NR$^{10}$—C(O)R$^{11}$, —NR$^{12}$—C(O)—OR$^{13}$, —C(O)NR$^{14}$R$^{15}$, —NR$^{16}$S(O)$_2$R$^{17}$, —S(O)$_2$NR$^{18}$R$^{18'}$, —OR$^{19}$, substituted alkyl, substituted heteroalkyl, substituted cycloalkyl, substituted heterocycloalkyl, substituted aryl substituted heteroaryl. In some embodiments, $R^{21}$ is —CN, —CF$_3$, —S(O)$_n$R$^6$, —N(O)$_m$, —NR$^7$R$^8$, —C(O)R$^9$, —N=NH, —NR$^{10}$—C(O)R$^{11}$, —NR$^{12}$—C(O)—OR$^{13}$, —C(O)NR$^{14}$R$^{15}$, —NR$^{16}$S(O)$_2$R$^{17}$, —S(O)$_2$NR$^{18}$R$^{18'}$, —OR$^{19}$, $R^{56}$-substituted or unsubstituted alkyl, —C(O)NR$^{14}$R$^{15}$, —NR$^{16}$S(O)$_2$R$^{17}$, —S(O)$_2$NR$^{18}$R$^{18'}$, —OR$^{19}$, $R^{56}$-substituted or unsubstituted alkyl, $R^{56}$-substituted or unsubstituted heteroalkyl, $R^{56}$-substituted or unsubstituted cycloalkyl, $R^{56}$-substituted or unsubstituted heterocycloalkyl, $R^{56}$-substituted or unsubstituted aryl, or $R^{56}$-substituted or unsubstituted heteroaryl. $R^{56}$ is —OH, —NH$_2$, —SH, —CN, —CF$_3$, —NO$_2$, oxo, halogen, $R^{57}$-substituted or unsubstituted alkyl, $R^{57}$-substituted or unsubstituted heteroalkyl, $R^{57}$-substituted or unsubstituted cycloalkyl, $R^{57}$-substituted or unsubstituted heterocycloalkyl, $R^{57}$-substituted or unsubstituted aryl, or $R^{57}$-substituted or unsubstituted heteroaryl.

In some embodiments, $R^{22}$ is —CN, —CF$_3$, —S(O)$_n$R$^6$, —N(O)$_m$, —NR$^7$R$^8$, —C(O)R$^9$, —N=NH, —NR$^{10}$—C(O)R$^{11}$, —NR$^{12}$—C(O)—OR$^{13}$, —C(O)NR$^{14}$R$^{15}$, —NR$^{16}$S(O)$_2$R$^{17}$, —S(O)$_2$NR$^{18}$R$^{18'}$, —OR$^{19}$, $R^{60}$-substituted or unsubstituted alkyl, $R^{60}$-substituted or unsubstituted heteroalkyl, $R^{60}$-substituted or unsubstituted cycloalkyl, $R^{60}$-substituted or unsubstituted heterocycloalkyl, $R^{60}$-substituted or unsubstituted aryl, or $R^{60}$-substituted or unsubstituted heteroaryl. $R^{60}$ is —OH, —NH$_2$, —SH, —CN, —CF$_3$, —NO$_2$, oxo, halogen, $R^{61}$-substituted or unsubstituted alkyl, $R^{61}$-substituted or unsubstituted heteroalkyl, $R^{61}$-substituted or unsubstituted cycloalkyl, $R^{61}$-substituted or unsubstituted heterocycloalkyl, $R^{61}$-substituted or unsubstituted aryl, or $R^{61}$-substituted or unsubstituted heteroaryl.

In some embodiments, $R^{23}$ is —CN, —CF$_3$, —S(O)$_n$R$^6$, —N(O)$_m$, —NR$^7$R$^8$, —C(O)R$^9$, —N=NH, —NR$^{10}$—C(O)R$^{11}$, —NR$^{12}$—C(O)—OR$^{13}$, —C(O)NR$^{14}$R$^{15}$, —NR$^{16}$S(O)$_2$R$^{17}$, —S(O)$_2$NR$^{18}$R$^{18'}$, —OR$^{19}$, $R^{62}$-substituted or unsubstituted alkyl, $R^{62}$-substituted or unsubstituted heteroalkyl, $R^{62}$-substituted or unsubstituted cycloalkyl, $R^{62}$- substituted or unsubstituted heterocycloalkyl, $R^{62}$-substituted or unsubstituted aryl, or $R^{62}$-substituted or unsubstituted heteroaryl. $R^{62}$ is —OH, —$NH_2$, —SH, —CN, —$CF_3$, —$NO_2$, oxo, halogen, $R^{63}$-substituted or unsubstituted alkyl, $R^{63}$-substituted or unsubstituted heteroalkyl, $R^{63}$-substituted or unsubstituted cycloalkyl, $R^{63}$-substituted or unsubstituted heterocycloalkyl, $R^{63}$-substituted or unsubstituted aryl, or $R^{63}$-substituted or unsubstituted heteroaryl.

Further to embodiments for the compound having the structure of Formula V, $R^{25}$, $R^{27}$, $R^{33}$, $R^{35}$, $R^{37}$, $R^{39}$, $R^{41}$, $R^{43}$, $R^{45}$, $R^{47}$, $R^{49}$, $R^{51}$, $R^{53}$, $R^{55}$, $R^{57}$, $R^{61}$ and $R^{63}$ are independently —OH, —$NH_2$, —SH, —CN, —$CF_3$, —$NO_2$, oxo, halogen, unsubstituted alkyl, unsubstituted heteroalkyl, unsubstituted cycloalkyl, unsubstituted heterocycloalkyl, unsubstituted aryl, or unsubstituted heteroaryl.

In another aspect, compounds are provided having the structure of Formula III:

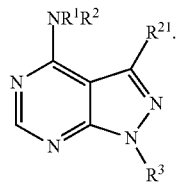

III

In Formula III, $R^1$, $R^2$, $R^3$ and $R^{21}$ are as defined above for Formula V.

In another aspect, compounds are provided having the structure of Formula IV:

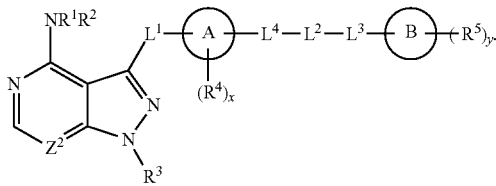

IV

In Formula IV, $Z^1$, $Z^2$, $R^1$, $R^2$, and $R^3$ are as defined for Formula V.

In Formula IV, x is an integer from 0 to 4, and y is an integer from 0 to 5. In some embodiments, x is 0. In some embodiments, y is 0 or 1, In some embodiments, y is 0.

Ring A is arylene or heteroarylene, e.g., phenylene. Ring B is aryl or heteroaryl, e.g., phenyl.

In some embodiments, $R^4$ is halogen, —CN, —$CF_3$, —$S(O)_nR^6$, —$N(O)_m$, —$NR^7R^8$, —$C(O)R^9$, —N=NH, —$NR^{10}$—$C(O)R^{11}$, —$NR^{12}$—C(O)—$OR^{13}$, —C(O)$NR^{14}R^{15}$, —$NR^{16}S(O)_2R^{17}$, —$S(O)_2NR^{18}R^{18'}$, —$OR^{19}$, $R^{28}$-substituted or unsubstituted alkyl, $R^{28}$-substituted or heteroalkyl, $R^{28}$-substituted or unsubstituted cycloalkyl, $R^{28}$-substituted or unsubstituted heterocycloalkyl, $R^{28}$-substituted or unsubstituted aryl, or $R^{28}$-substituted or unsubstituted heteroaryl. $R^{28}$ is —OH, —$NH_2$, —SH, —CN, —$CF_3$, —$NO_2$, oxo, halogen, $R^{29}$-substituted or unsubstituted alkyl, $R^{29}$-substituted or unsubstituted heteroalkyl, $R^{29}$-substituted or unsubstituted cycloalkyl, $R^{29}$-substituted or unsubstituted heterocycloalkyl, $R^{29}$-substituted or unsubstituted aryl, or $R^{29}$-substituted or unsubstituted heteroaryl.

In some embodiments, $R^5$ is halogen, —CN, —$CF_3$, —$S(O)_nR^6$, —$N(O)_m$, —$NR^7R^8$, —$C(O)R^9$, —N=NH, —$NR^{10}$—$C(O)R^{11}$, —$NR^{12}$—C(O)—$OR^{13}$, —C(O)$NR^{14}R^{15}$, —$NR^{16}S(O)_2R^{17}$, —$S(O)_2NR^{18}R^{18'}$, —$OR^{19}$, halomethyl, $R^{30}$-substituted or unsubstituted alkyl, $R^{30}$-substituted or unsubstituted heteroalkyl, $R^{30}$-substituted or unsubstituted cycloalkyl, $R^{30}$-substituted or unsubstituted heterocycloalkyl, $R^{30}$-substituted or unsubstituted aryl, or $R^{30}$-substituted or unsubstituted heteroaryl. $R^{30}$ is —OH, —$NH_2$, —SH, —CN, —$CF_3$, —$NO_2$, oxo, halogen, $R^{31}$-substituted or unsubstituted alkyl, $R^{31}$-substituted or unsubstituted heteroalkyl, $R^{31}$-substituted or unsubstituted cycloalkyl, $R^{31}$-substituted or unsubstituted heterocycloalkyl, $R^{31}$-substituted or unsubstituted aryl, or $R^{31}$-substituted or unsubstituted heteroaryl.

In some embodiments, $L^1$ is a bond, substituted or unsubstituted alkylene or substituted or unsubstituted heteroalkylene. In some embodiments, $L^1$ is a bond, $R^{64}$-substituted or unsubstituted alkylene, or $R^{64}$-substituted or unsubstituted heteroalkylene. $R^{64}$ is —OH, —$NH_2$, —SH, —CN, —$CF_3$, —$NO_2$, oxo, halogen, $R^{65}$-substituted or unsubstituted alkyl, $R^{65}$-substituted or heteroalkyl, $R^{65}$-substituted or unsubstituted cycloalkyl, $R^{65}$-substituted or unsubstituted heterocycloalkyl, $R^{65}$-substituted or unsubstituted aryl, or $R^{65}$-substituted or unsubstituted heteroaryl. In some embodiments, $L^1$ is methylene.

In some embodiments, $L^2$ is —S(O)—, —$S(O)_2$— or —C(O)—. In some embodiments, $L^2$ is —S(O)—. In some embodiments, $L^2$ is —$S(O)_2$—. In some embodiments, $L^2$ is —C(O)—.

In some embodiments, $L^3$ is a bond, —N($R^{20}$)—, substituted or unsubstituted alkylene, or substituted or unsubstituted heteroalkylene. In some embodiments, $L^3$ is a bond, —N($R^{20}$)—, $R^{66}$-substituted or unsubstituted alkylene, or $R^{66}$-substituted or unsubstituted heteroalkylene. $R^{66}$ is —OH, —$NH_2$, —SH, —CN, —$CF_3$, —$NO_2$, oxo, halogen, $R^{67}$-substituted or unsubstituted alkyl, $R^{67}$-substituted or heteroalkyl, $R^{67}$-substituted or unsubstituted cycloalkyl, $R^{67}$-substituted or unsubstituted heterocycloalkyl, $R^{67}$-substituted or unsubstituted aryl, or $R^{67}$-substituted or unsubstituted heteroaryl. In some embodiments, $L^3$ is —N($R^{20}$)—. In some embodiments, $L^3$ is —NH—.

In some embodiments, $R^{20}$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In some embodiments, $R^{20}$ is hydrogen, $R^{58}$-substituted or unsubstituted alkyl, $R^{58}$-substituted or unsubstituted heteroalkyl, $R^{58}$-substituted or unsubstituted cycloalkyl, $R^{58}$-substituted or unsubstituted heterocycloalkyl, $R^{58}$-substituted or unsubstituted aryl, or $R^{58}$-substituted or unsubstituted heteroaryl. $R^{58}$ is —OH, —$NH_2$, —SH, —CN, —$CF_3$, —$NO_2$, oxo, halogen, $R^{59}$-substituted or unsubstituted alkyl, $R^{59}$-substituted or unsubstituted heteroalkyl, $R^{59}$-substituted or unsubstituted cycloalkyl, $R^{59}$-substituted or unsubstituted heterocycloalkyl, $R^{59}$-substituted or unsubstituted aryl, or $R^{59}$-substituted or unsubstituted heteroaryl.

In some embodiments, $R^{29}$, $R^{31}$, $R^{59}$, $R^{65}$ and $R^{67}$ are independently —OH, —$NH_2$, —SH, —CN, —$CF_3$, —$NO_2$, oxo, halogen, unsubstituted alkyl, heteroalkyl, unsubstituted cycloalkyl, unsubstituted heterocycloalkyl, unsubstituted aryl, or unsubstituted heteroaryl.

In some embodiments, $L^4$ is a bond, —NH— or —$CH_2$—. In some embodiments, $L^4$ is a bond. In some embodiments, $L^4$ is —NH—. In some embodiments, $L^4$ is —$CH_2$—.

In another embodiment, compounds are provided having the formula:

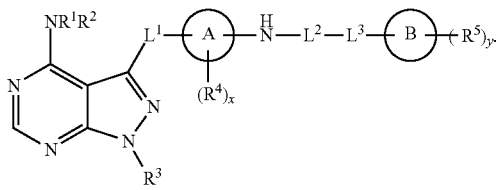

In Formula I, x, y, ring A, ring B, $L^1$, $L^2$, $L^3$, $R^1$, $R^2$, $R^3$, $R^4$, and $R^5$ are as defined for Formula IV above.

In another embodiment, compounds are provided having the formula:

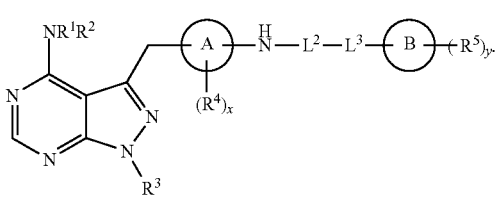

In Formula Ia, x, y, ring A, ring B, $L^2$, $L^3$, $R^1$, $R^2$, $R^3$, $R^4$, and $R^5$ are as defined for Formula IV above.

In some embodiments, a compound is provided having the structure of Formula Ib:

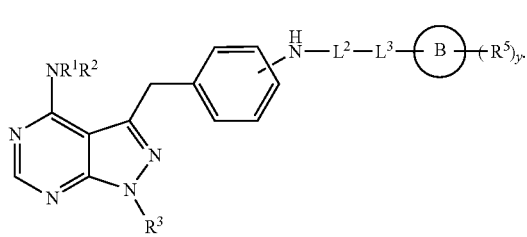

In Formula Ib, y, ring B, $L^2$, $L^3$, $R^1$, $R^2$, $R^3$ and $R^5$ are as defined for Formula IV above. In some embodiments, $R^1$ and $R^2$ are hydrogen. In some embodiments, $R^3$ is unsubstituted alkyl. In some embodiments, $R^3$ is $C_1$-$C_{10}$ alkyl, preferably methyl, ethyl, isopropyl or cyclopentyl. In some embodiments, $R^3$ is substituted $C_1$-$C_{10}$ alkyl. In some embodiments, $R^3$ is substituted alkyl, including but not limited to, benzyl or cyclopropylmethyl. In some embodiments, $R^3$ is substituted or unsubstituted pyrrolidine. In some embodiments, $R^3$ is substituted or unsubstituted tetrahydrofuran.

In some embodiments, a compound is provided having the structure of Formula II:

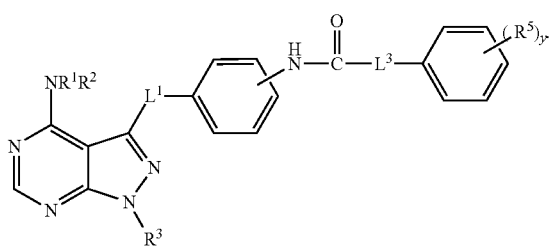

In Formula II, $R^1$, $R^2$, $R^3$ are as defined above in Formulae I, III, IV and/or V; $R^5$ and y are as defined above for Formula V; and $L^1$ and $L^3$ are as defined above in Formula I and/or IV. In some embodiments, $R^1$ and $R^2$ in Formula II are hydrogen, $L^1$ is a bond or methylene, $L^3$ is —N($R^{20}$)—, and y is 1. In some embodiments, $R^1$ and $R^2$ are hydrogen, $L^1$ is methylene, $L^3$ is —N($R^{20}$)—, and y is 1. In some embodiments, $R^1$ and $R^2$ are hydrogen, $L^1$ is methylene, $L^3$ is —NH—, and y is 1.

In some embodiments of Formulae I and/or IV, ring A is arylene, and ring B is aryl. Further, ring A may be phenylene, and ring B may be phenyl.

In some embodiments of Formulae I, II, and/or IV, $L^1$ is substituted or unsubstituted $C_1$-$C_3$ alkylene or substituted or unsubstituted 2 to 4 membered heteroalkylene. In some embodiments, $L^1$ is $R^{64}$-substituted or unsubstituted $C_1$-$C_3$ alkylene or $R^{64}$-substituted or unsubstituted 2 to 4 membered heteroalkylene, where $R^{64}$ is as defined for Formulae I, II and/or IV. $L^1$ may be unsubstituted $C_1$-$C_3$ alkylene or unsubstituted 2 to 4 membered heteroalkylene. $L^1$ may be unsubstituted $C_1$-$C_{10}$ alkylene or unsubstituted 2 to 10 membered heteroalkylene. $L^1$ may further be methylene.

In other embodiments of Formulae I, II, III, IV and/or V, at least one of $R^1$ or $R^2$ may be hydrogen. $R^1$ and $R^2$ may also both be hydrogen simultaneously. $R^3$ may also be substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^3$ may also be substituted or unsubstituted alkyl or substituted or unsubstituted heterocycloalkyl. In some embodiments, $R^3$ is $R^{26}$-substituted or unsubstituted alkyl, $R^{26}$-substituted or unsubstituted heteroalkyl, $R^{26}$-substituted or unsubstituted cycloalkyl, $R^{26}$-substituted or unsubstituted heterocycloalkyl, $R^{26}$-substituted or unsubstituted aryl, or $R^{26}$-substituted or unsubstituted heteroaryl, where $R^{26}$ is as defined for Formulae I, III, IV and/or IV. In some embodiments, $R^3$ is unsubstituted alkyl, unsubstituted heteroalkyl, unsubstituted cycloalkyl, unsubstituted heterocycloalkyl, unsubstituted aryl, or unsubstituted heteroaryl. In some embodiments, $R^3$ is $R^{26}$-substituted or unsubstituted alkyl, or $R^{26}$-substituted or unsubstituted heterocycloalkyl.

$R^3$ may also be substituted or unsubstituted $C_1$-$C_{10}$ alkyl or substituted or unsubstituted 3 to 6 membered heterocycloalkyl. $R^3$ may also be substituted or unsubstituted $C_1$-$C_3$ alkyl. $R^3$ may be methyl, ethyl or isopropyl. $R^3$ may also be an unsubstituted 3 to 6 membered heterocycloalkyl. $R^3$ may be cyclopentyl. In some embodiments, $R^3$ is $R^{26}$-substituted or unsubstituted $C_1$-$C_{10}$ alkyl, or $R^{26}$-substituted or unsubstituted 3 to 8 membered heterocycloalkyl, where $R^{26}$ is as defined for Formulae I, III, IV and/or IV. In some embodiments, $R^3$ is $R^{26}$-substituted or unsubstituted $C_1$-$C_3$ alkyl. In some embodiments, $R^3$ is $R^{26}$-substituted 3 to 6 membered heterocycloalkyl.

In some embodiments of Formulae I, II, and/or IV, $R^5$ is halomethyl. In some embodiments, $R^5$ may be —Br, —Cl, —I, —NO$_2$, —CH$_3$, —C$_2$H$_5$, —SH, —OH, —OCH$_3$, —CN, —SCH$_3$, —NO or —C(O)H. In some embodiments, $R^5$ may be —CF$_3$. In other embodiments, $L^2$ may be a bond or —C(O)-$L^3$-. $L^3$ may be —N($R^{20}$)—. $L^3$ may be —NH—. $L^1$ may be substituted or unsubstituted alkylene or substituted or unsubstituted 2 to 10 membered heteroalkylene. In some embodiments, $L^1$ is $R^{64}$-substituted or unsubstituted $C_1$-$C_{10}$ alkylene or $R^{64}$-substituted or unsubstituted 2 to 10 membered heteroalkylene, where $R^{64}$ is as defined for Formulae I, II and/or IV. The symbol x may be 0 and y may be 1.

In some embodiments, a compound is provided having the structure of Formula IIa:

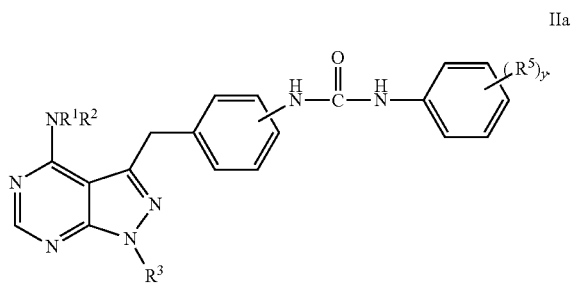

In Formula IIa, $R^1$, $R^2$, $R^3$ are as defined above in Formulae I, III, IV and/or V; $R^5$ and y are as defined above for Formula V. In some embodiments, $R^1$ and $R^2$ in Formula IIa are hydrogen, and y is 1. In some embodiments, $R^3$ is $R^{26}$-substituted or unsubstituted alkyl, $R^{26}$-substituted or unsubstituted heteroalkyl, $R^{26}$-substituted or unsubstituted cycloalkyl, $R^{26}$-substituted or unsubstituted heterocycloalkyl, $R^{26}$-substituted or unsubstituted aryl, or $R^{26}$-substituted or unsubstituted heteroaryl, wherein $R^{26}$ is as defined for Formula IV. In some embodiments, $R^3$ is $R^{26}$-substituted or unsubstituted alkyl, or $R^{26}$-substituted or unsubstituted cycloalkyl. In some embodiments, $R^3$ is $R^{26}$-substituted alkyl. In some embodiments, $R^3$ is benzyl. In some embodiments, $R^3$ is cyclopropylmethyl. In some embodiments, $R^3$ is unsubstituted alkyl or unsubstituted cycloalkyl. In some embodiments, $R^3$ is unsubstituted $C_1$-$C_{10}$ alkyl or unsubstituted $C_3$-$C_8$ cycloalkyl. In some embodiments, $R^3$ is unsubstituted $C_1$-$C_3$ alkyl or unsubstituted $C_3$-$C_6$ cycloalkyl. In some embodiments, $R^3$ is methyl, ethyl, n-propyl, isopropyl, n-butyl, tort-butyl, or cyclopentanyl. In some embodiments, $R^3$ is methyl. In some embodiments, $R^3$ is isopropyl. In some embodiments, $R^3$ is cyclopentanyl. In some embodiments, $R^5$ is $R^{30}$-substituted or unsubstituted alkyl, $R^{30}$-substituted or unsubstituted heteroalkyl, $R^{30}$-substituted or unsubstituted cycloalkyl, $R^{30}$-substituted or unsubstituted heterocycloalkyl, $R^{30}$-substituted or unsubstituted aryl, or $R^{30}$-substituted or unsubstituted heteroaryl, wherein $R^{30}$ is as defined for Formula IV. In some embodiments, $R^5$ is $R^{30}$-substituted or unsubstituted alkyl. In some embodiments, $R^5$ is $R^{30}$-substituted or unsubstituted $C_1$-$C_{10}$ alkyl. In some embodiments, $R^5$ is $R^{30}$-substituted or unsubstituted $C_1$-$C_3$ alkyl. In some embodiments, $R^5$ is $R^{30}$-substituted alkyl. In some embodiments, $R^5$ is halogen substituted methyl, preferably trifluoromethyl.

In some embodiments, a compound is provided having the structure of Formula IIb:

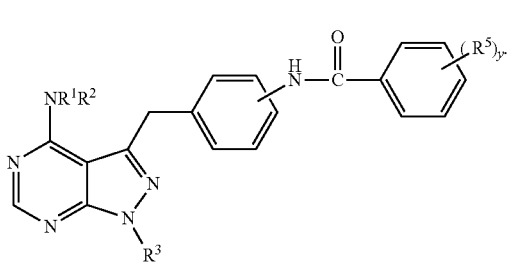

In Formula IIb, $R^1$, $R^2$, $R^3$ are as defined above in Formulae I, III, IV and/or V; $R^5$ and y are as defined above for Formula V. In some embodiments, $R^1$ and $R^2$ in Formula IIa are hydrogen, and y is 1. In some embodiments, $R^3$ is $R^{26}$-substituted or unsubstituted alkyl, $R^{26}$-substituted or unsubstituted heteroalkyl, $R^{26}$-substituted or unsubstituted cycloalkyl, $R^{26}$-substituted or unsubstituted heterocycloalkyl, $R^{26}$-substituted or unsubstituted aryl, or $R^{26}$-substituted or unsubstituted heteroaryl, wherein $R^{26}$ is as defined for Formula IV. In some embodiments, $R^3$ is $R^{26}$-substituted or unsubstituted alkyl, or $R^{26}$-substituted or unsubstituted cycloalkyl. In some embodiments, $R^3$ is $R^{26}$-substituted alkyl. In some embodiments, $R^3$ is benzyl. In some embodiments, $R^3$ is cyclopropylmethyl. In some embodiments, $R^3$ is unsubstituted alkyl or unsubstituted cycloalkyl. In some embodiments, $R^3$ is unsubstituted $C_1$-$C_{10}$ alkyl or unsubstituted $C_3$-$C_8$ cycloalkyl. In some embodiments, $R^3$ is unsubstituted $C_1$-$C_3$ alkyl or unsubstituted $C_3$-$C_6$ cycloalkyl. In some embodiments, $R^3$ is methyl, ethyl, n-propyl, isopropyl, n-butyl, tert-butyl, or cyclopentanyl. In some embodiments, $R^3$ is methyl. In some embodiments, $R^3$ is isopropyl. In some embodiments, $R^3$ is cyclopentanyl. In some embodiments, $R^5$ is $R^{30}$-substituted or unsubstituted alkyl, $R^{30}$-substituted or unsubstituted heteroalkyl, $R^{30}$-substituted or unsubstituted cycloalkyl, $R^{30}$-substituted or unsubstituted heterocycloalkyl, $R^{30}$-substituted or unsubstituted aryl, or $R^{30}$-substituted or unsubstituted heteroaryl, wherein $R^{30}$ is as defined for Formula IV. In some embodiments, $R^5$ is $R^{30}$-substituted or unsubstituted alkyl. In some embodiments, $R^5$ is $R^{30}$-substituted or unsubstituted $C_1$-$C_{10}$ alkyl. In some embodiments, $R^5$ is $R^{30}$-substituted or unsubstituted $C_1$-$C_3$ alkyl. In some embodiments, $R^5$ is $R^{30}$-substituted alkyl. In some embodiments, $R^5$ is halogen substituted methyl, preferably trifluoromethyl.

In some embodiments, a compound is provided having the structure of Formula IIc:

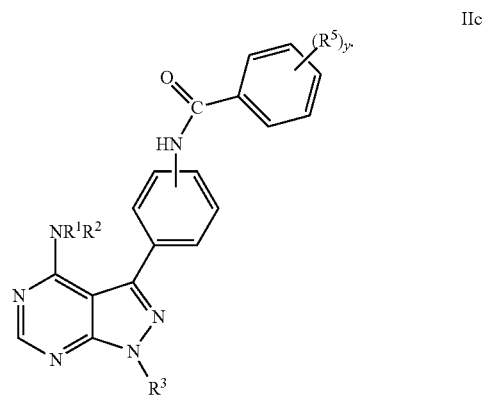

In Formula IIc, $R^1$, $R^2$, $R^3$ are as defined above in Formulae I, III, IV and/or V; $R^5$ and y are as defined above for Formula V. In some embodiments, $R^1$ and $R^2$ in Formula IIa are hydrogen, and y is 1. In some embodiments, $R^3$ is $R^{26}$-substituted or unsubstituted alkyl, $R^{26}$-substituted or unsubstituted heteroalkyl, $R^{26}$-substituted or unsubstituted cycloalkyl, $R^{26}$-substituted or unsubstituted heterocycloalkyl, $R^{26}$-substituted or unsubstituted aryl, or $R^{26}$-substituted or unsubstituted heteroaryl, wherein $R^{26}$ is as defined for Formula IV. In some embodiments, $R^3$ is $R^{26}$-substituted or unsubstituted alkyl, or $R^{26}$-substituted or unsubstituted cycloalkyl. In some embodiments, $R^3$ is $R^{26}$-substituted alkyl. In some embodiments, $R^3$ is benzyl. In some embodiments, $R^3$ is cyclopropylmethyl. In some embodiments, $R^3$ is unsubstituted alkyl or unsubstituted cycloalkyl. In some embodiments, $R^3$ is unsubstituted $C_1$-$C_{10}$ alkyl or unsubstituted $C_3$-$C_8$ cycloalkyl. In some embodiments, $R^3$ is unsubstituted $C_1$-$C_3$ alkyl or unsubstituted $C_3$-$C_6$ cycloalkyl. In some embodiments, $R^3$ is methyl, ethyl, n-propyl, isopropyl, n-butyl, tert-butyl, or cyclopentanyl. In some embodiments, $R^3$ is methyl. In some embodiments, $R^3$ is isopropyl. In some embodiments, $R^3$ is cyclopentanyl. In some embodiments, $R^5$ is $R^{30}$-substituted or unsubstituted alkyl, $R^{30}$-substituted or unsubstituted heteroalkyl, $R^{30}$-substituted or unsubstituted cycloalkyl, $R^{30}$-substituted or unsubstituted heterocycloalkyl, $R^{30}$-substituted or unsubstituted aryl, or $R^{30}$-substituted or unsubstituted heteroaryl, wherein $R^{30}$ is as defined for Formula IV. In some embodiments, $R^5$ is $R^{30}$-substituted or unsubstituted alkyl. In some embodiments, $R^5$ is $R^{30}$-substituted or unsubstituted $C_1$-$C_{10}$ alkyl. In some embodiments, $R^5$ is $R^{30}$-substituted or unsubstituted $C_1$-$C_3$ alkyl. In some embodiments, $R^5$ is $R^{30}$-substituted alkyl. In some embodiments, $R^5$ is halogen substituted methyl, preferably trifluoromethyl.

In some embodiments, a compound is provided having the structure of Formula IId:

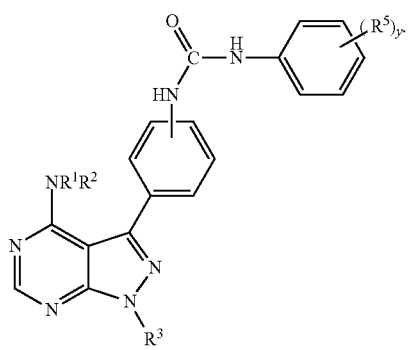

IId

In Formula IId, $R^1$, $R^2$, $R^3$ are as defined above in Formulae I, III, IV and/or V; $R^5$ and y are as defined above for Formula V. In some embodiments, $R^1$ and $R^2$ in Formula IIa are hydrogen, and y is 1. In some embodiments, $R^3$ is $R^{26}$-substituted or unsubstituted alkyl, $R^{26}$-substituted or unsubstituted heteroalkyl, $R^{26}$-substituted or unsubstituted cycloalkyl, $R^{26}$-substituted or unsubstituted heterocycloalkyl, $R^{26}$-substituted or unsubstituted aryl, or $R^{26}$-substituted or unsubstituted heteroaryl, wherein $R^{26}$ is as defined for Formula IV. In some embodiments, $R^3$ is $R^{26}$-substituted or unsubstituted alkyl, or $R^{26}$-substituted or unsubstituted cycloalkyl. In some embodiments, $R^3$ is $R^{26}$-substituted alkyl. In some embodiments, $R^3$ is benzyl. In some embodiments, $R^3$ is cyclopropylmethyl. In some embodiments, $R^3$ is unsubstituted alkyl or cycloalkyl. In some embodiments, $R^3$ is unsubstituted $C_1$-$C_{10}$ alkyl or unsubstituted $C_3$-$C_8$ cycloalkyl. In some embodiments, $R^3$ is unsubstituted $C_1$-$C_3$ alkyl or unsubstituted $C_3$-$C_6$ cycloalkyl. In some embodiments, $R^3$ is methyl, ethyl, n-propyl, isopropyl, n-butyl, tert-butyl, or cyclopentanyl. In some embodiments, $R^3$ is methyl. In some embodiments, $R^3$ is isopropyl. In some embodiments, $R^3$ is cyclopentanyl. In some embodiments, $R^5$ is $R^{30}$-substituted or unsubstituted alkyl, $R^{30}$-substituted or unsubstituted heteroalkyl, $R^{30}$-substituted or unsubstituted cycloalkyl, $R^{30}$-substituted or unsubstituted heterocycloalkyl, $R^{30}$-substituted or unsubstituted aryl, or $R^{30}$-substituted or unsubstituted heteroaryl, wherein $R^{30}$ is as defined for Formula IV. In some embodiments, $R^5$ is $R^{30}$-substituted or unsubstituted alkyl. In some embodiments, $R^5$ is $R^{30}$-substituted or unsubstituted $C_1$-$C_{10}$ alkyl. In some embodiments, $R^5$ is $R^{30}$-substituted or unsubstituted $C_1$-$C_3$ alkyl. In some embodiments, $R^5$ is $R^{30}$-substituted alkyl. In some embodiments, $R^5$ is halogen substituted methyl, preferably trifluoromethyl.

In another aspect, compounds are provided having the formula:

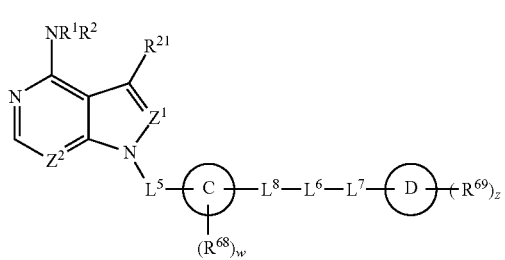

VI wherein $R^1$, $R^2$, $Z^1$, and $Z^2$ are as defined above.

Ring C is cycloalkylene, heterocycloalkylene, arylene, or heteroarylene. Ring D is aryl or heteroaryl. In some embodiments, ring C is heteroarylene or heterocycloalkylene. In some embodiments, ring C is a nitrogen-containing 5-6 membered heterocycloalkylene, e.g., pyrrolidine-diyl. In some embodiment, ring D is aryl or heteroaryl. In one embodiment, ring D is aryl, e.g., phenyl.

In Formula VI, w is an integer from 0 to 4, and z is an integer from 0 to 5. In some embodiments, w is 0. In some embodiments, z is 0 or 1, In some embodiments, z is 0.

In some embodiments, $R^{68}$ is halogen, —CN, —CF$_3$, —S(O)$_n$R$^6$, —N(O)$_m$, —NR$^7$R$^8$, —C(O)R$^9$, —N=NH, —NR$^{10}$—C(O)R$^{11}$, —NR$^{12}$—C(O)—OR$^{13}$, —C(O)NR$^{14}$R$^{15}$, —NR$^{16}$S(O)$_2$R$^{17}$, —S(O)$_2$NR$^{18}$R$^{18'}$, —OR$^{19}$, $R^{70}$-substituted or unsubstituted alkyl, $R^{70}$-substituted or unsubstituted heteroalkyl, $R^{70}$-substituted or unsubstituted cycloalkyl, $R^{70}$-substituted or unsubstituted heterocycloalkyl, $R^{70}$-substituted or unsubstituted aryl, or $R^{70}$-substituted or unsubstituted heteroaryl. $R^{70}$ is —OH, —NH$_2$, —SH, —CN, —CF$_3$, —NO$_2$, oxo, halogen, $R^{71}$-substituted or unsubstituted alkyl, $R^{71}$-substituted or unsubstituted heteroalkyl, $R^{71}$-substituted or unsubstituted cycloalkyl, $R^{71}$-substituted or unsubstituted heterocycloalkyl, $R^{71}$-substituted or unsubstituted aryl, or $R^{71}$-substituted or unsubstituted heteroaryl.

In some embodiments, $R^{69}$ is halogen, —CN, —CF$_3$, —S(O)$_n$R$^6$, —N(O)$_m$, —NR$^7$R$^8$, —C(O)R$^9$, —N=NH, —NR$^{10}$—C(O)R$^{11}$, —NR$^{12}$—C(O)—OR$^{13}$, —C(O)NR$^{14}$R$^{15}$, —NR$^{16}$S(O)$_2$R$^{17}$, —S(O)$_2$NR$^{18}$R$^{18'}$, —OR$^{19}$, halomethyl, $R^{72}$-substituted or unsubstituted alkyl, $R^{72}$-substituted or unsubstituted heteroalkyl, $R^{72}$-substituted or unsubstituted cycloalkyl, $R^{72}$-substituted or unsubstituted heterocycloalkyl, $R^{72}$-substituted or unsubstituted aryl, or $R^{72}$-substituted or unsubstituted heteroaryl. $R^{72}$ is —OH, —NH$_2$, —SH, —CN, —CF$_3$, —NO$_2$, oxo, halogen, $R^{73}$-substituted or unsubstituted alkyl, $R^{73}$-substituted or unsubstituted heteroalkyl, $R^{73}$-substituted or unsubstituted cycloalkyl, $R^{73}$-substituted or unsubstituted heterocycloalkyl, $R^{73}$-substituted or unsubstituted aryl, or $R^{73}$-substituted or unsubstituted heteroaryl.

In some embodiments, $L^5$ is a bond, substituted or unsubstituted alkylene or substituted or unsubstituted heteroalkylene. In some embodiments, $L^5$ is a bond, $R^{74}$-substituted or unsubstituted alkylene, or $R^{74}$-substituted or unsubstituted heteroalkylene. $R^{74}$ is —OH, —NH$_2$, —SH, —CN, —CF$_3$, —NO$_2$, oxo, halogen, $R^{75}$-substituted or unsubstituted alkyl, $R^{75}$-substituted or heteroalkyl, $R^{75}$-substituted or unsubstituted cycloalkyl, $R^{75}$-substituted or unsubstituted heterocycloalkyl, $R^{75}$-substituted or unsubstituted aryl, or $R^{75}$-substituted or unsubstituted heteroaryl. In some embodiments, $L^5$ is a bond. In some embodiments, $L^5$ is a bond, and $R^{21}$ is substituted phenyl, preferably NH$_2$-substituted phenyl.

In some embodiments, $L^6$ is —S(O)—, —S(O)$_2$— or —C(O)—. In some embodiments, $L^6$ is —S(O)—. In some embodiments, $L^6$ is —S(O)$_2$—. In some embodiments, $L^6$ is —C(O)—.

In some embodiments, $L^7$ is a bond, —N(R$^{78}$)—, substituted or unsubstituted alkylene, or substituted or unsubstituted heteroalkylene. In some embodiments, $L^7$ is a bond, —N(R$^{78}$)—, $R^{76}$-substituted or unsubstituted alkylene, or $R^{76}$-substituted or unsubstituted heteroalkylene. $R^{76}$ is —OH, —NH$_2$, —SH, —CN, —CF$_3$, —NO$_2$, oxo, halogen, $R^{77}$-substituted or unsubstituted alkyl, $R^{77}$-substituted or heteroalkyl, $R^{77}$-substituted or unsubstituted cycloalkyl, $R^{77}$-substituted or unsubstituted heterocycloalkyl, $R^{77}$-substituted or unsubstituted aryl, or $R^{77}$-substituted or unsubstituted heteroaryl.

In some embodiments, $R^{78}$ is hydrogen, substituted or unsubstituted alkyl, substituted or unsubstituted heteroalkyl, unsubstituted cycloalkyl, substituted or unsubstituted heterocycloalkyl, substituted or unsubstituted aryl, or substituted or unsubstituted heteroaryl. In some embodiments, $R^{78}$ is hydrogen, $R^{79}$-substituted or unsubstituted alkyl, $R^{79}$-substituted or unsubstituted heteroalkyl, $R^{79}$-substituted or unsubstituted cycloalkyl, $R^{79}$-substituted or unsubstituted heterocycloalkyl, $R^{79}$-substituted or unsubstituted aryl, or $R^{79}$-substituted or unsubstituted heteroaryl. $R^{79}$ is —OH, —NH$_2$, —SH, —CN, —CF$_3$, —NO$_2$, oxo, halogen, $R^{80}$-substituted or unsubstituted alkyl, $R^{80}$-substituted or unsubstituted heteroalkyl, $R^{80}$-substituted or unsubstituted cycloalkyl, $R^{80}$-substituted or unsubstituted heterocycloalkyl, $R^{80}$-substituted or unsubstituted aryl, or $R^{80}$-substituted or unsubstituted heteroaryl.

In some embodiments, $R^{71}$, $R^{73}$, $R^{75}$, $R^{77}$ and $R^{80}$ are independently —OH, —NH$_2$, —SH, —CN, —CF$_3$, —NO$_2$, oxo, halogen, unsubstituted alkyl, heteroalkyl, unsubstituted cycloalkyl, unsubstituted heterocycloalkyl, unsubstituted aryl, or unsubstituted heteroaryl.

In some embodiments, $L^8$ is a bond, —C(O)—, —NH— or —CH$_2$—. In some embodiments, $L^8$ is a bond. In some embodiments, $L^8$ is —C(O)—. In some embodiments, $L^8$ is —NH—. In some embodiments, $L^8$ is —CH$_2$—.

In some embodiments, compounds are provided having the formula

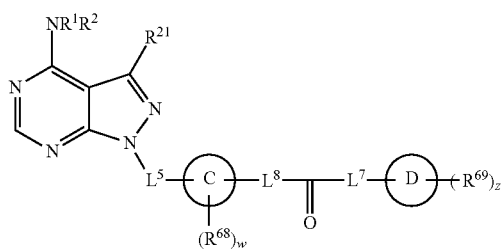

VIa wherein $R^1$, $R^2$, $R^{21}$, $L^5$, $L^7$, $L^8$, ring C, ring D, $R^{68}$, $R^{69}$, w and z are as defined above. In some embodiments, a compound is provided wherein $R^{21}$ is substituted aryl, $L^5$ and $L^8$ are bonds, ring C is heterocycloalkylene, preferably nitrogen containing heterocycloalkylene, $L^7$ is —NH—, ring D is aryl, preferably phenyl, w is 0, and z is 0 or 1. In some embodiments, z is 1, and $R^{69}$ is halomethyl, preferably trifluoromethyl. In some embodiments, $R^{21}$ is NH$_2$-substituted phenyl.

In another aspect, compounds are provided having the formula:

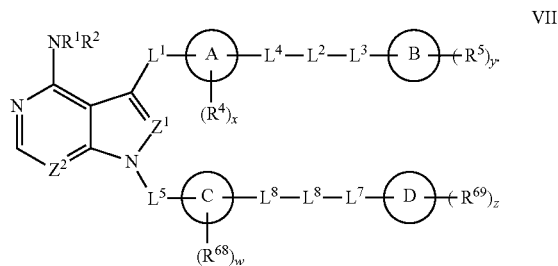

VII wherein $Z^1$, $Z^2$, $R^1$, $R^2$, $R^4$, $R^5$ $R^{68}$, $R^{69}$, w, x, y, z, ring A, ring B, ring C, ring D, $L^1$, $L^2$, $L^3$, $L^4$, $L^5$, $L^6$, $L^7$, and $L^8$ are as defined above. In some embodiments, $R^5$ and $R^{69}$ are independently halomethyl, preferably trifluoromethyl.

In some embodiments, compounds are provided having the formula:

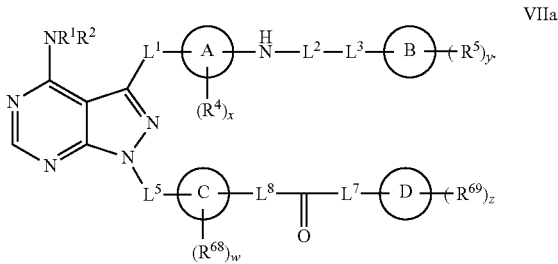

VIIa wherein $R^1$, $R^2$, $R^4$, $R^5$, $L^1$, $L^2$, $L^3$, $L^5$, $L^7$, $L^8$, ring A, ring B, ring C, ring D, $R^{68}$, $R^{69}$, w, x, y and z are as defined above. In some embodiments, $L^1$, $L^5$ and $L^8$ are bonds, $L^2$ is —C(O)—, $L^3$ and $L^7$ are —NH—, ring A is arylene, preferably phenylene, ring B and ring D are independently aryl, preferably phenyl, ring C is heterocycloalkylene, x and w are 0, y and z are 1, and $R^5$ and $R^{69}$ are independently halomethyl, preferably trifluoromethyl.

In some embodiments, one or more substituted groups described in any of the above Formulae is substituted with at least one substituent group. More specifically, in some embodiments, at least one substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, or substituted heteroarylene described in the above Formulae is substituted with at least one substituent group. In other embodiments, at least one or all of these groups are substituted with at least one size-limited substituent group. Alternatively, at least one or all of these groups are substituted with at least one lower substituent group.

In other embodiments of the Formulae, each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_4$-$C_8$ cycloalkyl, each substituted or unsubstituted heterocycloalkyl is a substituted or unsubstituted 4 to 8 membered heterocycloalkyl, each substituted or unsubstituted aryl is a substituted or unsubstituted $C_4$-$C_8$ aryl, each substituted or unsubstituted heteroaryl is a substituted or unsubstituted 4 to 8 membered heteroaryl, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene substituted or unsubstituted $C_4$-$C_8$ cycloalkylene, each substituted or unsubstituted heterocycloalkylene is a substituted or unsubstituted 4 to 8 membered heterocycloalkylene, and each substituted or unsubstituted arylene is a substituted or unsubstituted $C_4$-$C_8$ arylene, each substituted or unsubstituted heteroarylene is a substituted or unsubstituted 4 to 8 membered heteroarylene.

Alternatively, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_5$-$C_7$ cycloalkyl, each substituted or unsubstituted heterocycloalkyl is a substituted or unsubstituted 5 to 7 membered heterocycloalkyl, each substituted or unsubstituted aryl is a substituted or unsubstituted $C_5$-$C_7$ aryl, each substituted or unsubstituted heteroaryl is a substituted or unsubstituted 5 to 7 membered heteroaryl, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene substituted or unsubstituted $C_5$-$C_6$ cycloalkylene, and each substituted or unsubstituted heterocycloalkylene is a substituted or unsubstituted 5 to 7 membered heterocycloalkylene, each substituted or unsubstituted arylene is a substituted or unsubstituted $C_5$-$C_7$ arylene, each substituted or unsubstituted heteroarylene is a substituted or unsubstituted 5 to 7 membered heteroarylene.

In any of the Formulae above, the substituents described herein, including linking moieties (e.g., alkylene or heteroalkylene), can be size-limited substituents or lower substituent groups. For example, any alkyl group can be a $C_1$-$C_{10}$, $C_1$-$C_6$, or $C_1$-$C_4$ alkyl group. Any heteroalkyl group can have 2-10, 2-6, or 2-4 members. Any cycloalkyl group can be a $C_3$-$C_8$, $C_5$-$C_7$, or $C_5$-$C_6$ cycloalkyl group. Any heterocycloalkyl group can have 3-8, 4-7, or 5-6 members. Any aryl group can be a $C_5$-$C_8$ or $C_5$-$C_6$ aryl group. Any heteroaryl group can have 5-8 or 5-6 members.

In some embodiments, the compound is a compound set forth in Table 1a below. In some embodiments, the compound is a compound set forth in Table 1b below.

TABLE 1a

Inhibition data for selected compounds described herein.

| Compound | Name | MW (g/mol) | IC$_{50}$ WT Src | IC$_{50}$ T338G Src | IC$_{50}$ WT Abl | IC$_{50}$ T315A Abl | IC$_{50}$ T315I Abl |
|---|---|---|---|---|---|---|---|
| [structure] | AD7 | 426.14 | ++ | + | | ++ | |
| [structure] | AD8 | 441.15 | ++ | ++ | | ++ | |
| [structure] | AD15 | 424.14 | + | ++ | | +++ | |

TABLE 1a-continued
Inhibition data for selected compounds described herein.
| Compound | Name | MW (g/mol) | IC$_{50}$ WT Src | IC$_{50}$ T338G Src | IC$_{50}$ WT Abl | IC$_{50}$ T315A Abl | IC$_{50}$ T315I Abl |
|---|---|---|---|---|---|---|---|
| 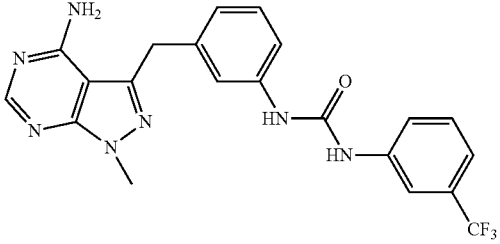 [SMILES: Cn1nc(Cc2cccc(NC(=O)Nc3cccc(C(F)(F)F)c3)c2)c2c(N)ncnc21] | AD16[1] | 441.15 | ++ | +++ | ++ | | ++ |
| 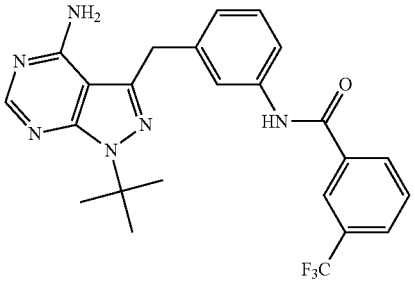 [SMILES: CC(C)(C)n1nc(Cc2cccc(NC(=O)c3cccc(C(F)(F)F)c3)c2)c2c(N)ncnc21] | AD25 | 468.19 | ++ | +++ | | | +++ |
| 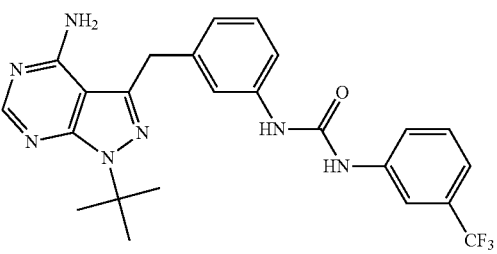 [SMILES: CC(C)(C)n1nc(Cc2cccc(NC(=O)Nc3cccc(C(F)(F)F)c3)c2)c2c(N)ncnc21] | AD26[4] | 483.2 | +++ | +++ | +++ | | +++ |
| 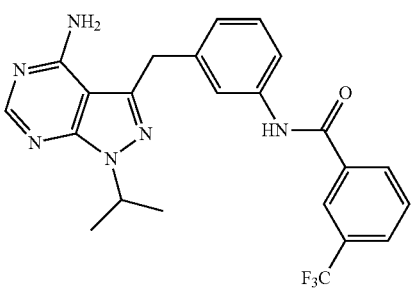 [SMILES: CC(C)n1nc(Cc2cccc(NC(=O)c3cccc(C(F)(F)F)c3)c2)c2c(N)ncnc21] | AD35 | 454.17 | + | ++ | | | +++ |
| 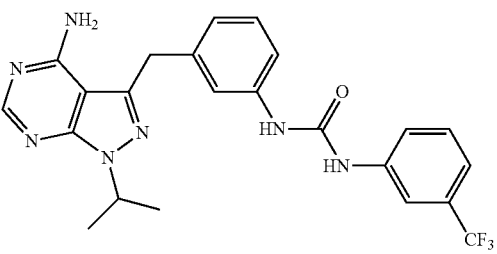 [SMILES: CC(C)n1nc(Cc2cccc(NC(=O)Nc3cccc(C(F)(F)F)c3)c2)c2c(N)ncnc21] | AD36[2] | 469.18 | ++ | +++ | ++ | | +++ |

TABLE 1a-continued

Inhibition data for selected compounds described herein.

| Compound | Name | MW (g/mol) | IC$_{50}$ WT Src | IC$_{50}$ T338G Src | IC$_{50}$ WT Abl | IC$_{50}$ T315A Abl | IC$_{50}$ T315I Abl |
|---|---|---|---|---|---|---|---|
| [structure] | BB5 | 502.17 | ++ | ++ | | ++ | |
| [structure] | BB6 | 517.18 | ++ | ++ | | +++ | |
| [structure] | BB9 | 480.19 | +++ | +++ | | ++ | |
| [structure] | BB10[3] | 495.2 | +++ | +++ | ++ | +++ | |
| [structure] | BB13 | 466.17 | + | +++ | | +++ | |

TABLE 1a-continued

Inhibition data for selected compounds described herein.

| Compound | Name | MW (g/mol) | IC$_{50}$ WT Src | IC$_{50}$ T338G Src | IC$_{50}$ WT Abl | IC$_{50}$ T315A Abl | IC$_{50}$ T315I Abl |
|----------|------|------------|------------------|---------------------|------------------|---------------------|---------------------|
| [structure] | BB14 | 481.18 | +++ | +++ | | +++ | |
| [structure] | AD71a | 482.46 | +++ | | + | | |
| [structure] | AD71c | 669.58 | ++ | | + | | |

TABLE 1a-continued

Inhibition data for selected compounds described herein.

| Compound | Name | MW (g/mol) | IC$_{50}$ WT Src | IC$_{50}$ T338G Src | IC$_{50}$ WT Abl | IC$_{50}$ T315A Abl | IC$_{50}$ T315I Abl |
|---|---|---|---|---|---|---|---|
| | AD73a | 482.46 | | | | | |
| | AD73c | 669.58 | ++ | | + | | |
| | AD78 | 582.58 | +++ | | ++ | | |

TABLE 1a-continued

Inhibition data for selected compounds described herein.

| Compound | Name | MW (g/mol) | IC$_{50}$ WT Src | IC$_{50}$ T338G Src | IC$_{50}$ WT Abl | IC$_{50}$ T315A Abl | IC$_{50}$ T315I Abl |
|---|---|---|---|---|---|---|---|
| 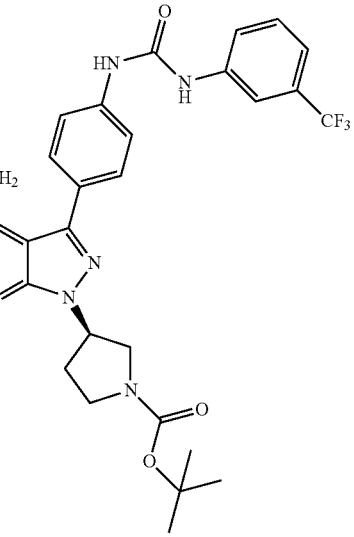 | AD79 | 582.58 | +++ | | ++ | | |

Footnotes:
[1]AD16 is also referred to herein as Cmpd 1;
[2]AD36 is also referred to herein as Cmpd 2;
[3]BB10 is also referred to herein as Cmpd 3;
[4]AD26 is also referred to herein as Cmpd 4;
+++ represents an IC$_{50}$ of less than 1 μM;
++ represents an IC$_{50}$ from 1 μM to 5μM; and
+ represents an IC$_{50}$ of over 5 μM.

TABLE 1b

Inhibition data for selected compounds described herein.

| Compound | Name | MW (g/mol) | IC$_{50}$ WT Src | IC$_{50}$ T338G Src | IC$_{50}$ WT Abl | IC$_{50}$ T315A Abl | IC$_{50}$ T315I Abl |
|---|---|---|---|---|---|---|---|
| 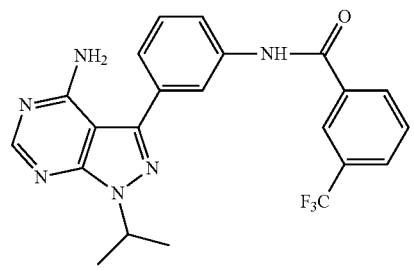 [SMILES: CC(C)n1nc(-c2cccc(NC(=O)c3cccc(C(F)(F)F)c3)c2)c2c(N)ncnc21] | AD52 | 440.16 | ++ | +++ | | | |
| 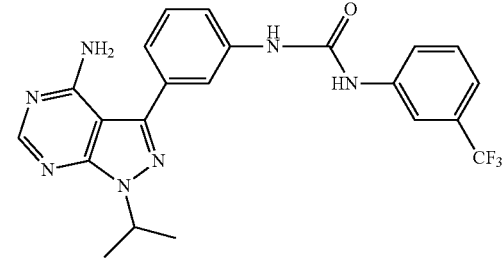 [SMILES: CC(C)n1nc(-c2cccc(NC(=O)Nc3cccc(C(F)(F)F)c3)c2)c2c(N)ncnc21] | AD53 | 455.17 | ++ | +++ | | | |

TABLE 1b-continued

Inhibition data for selected compounds described herein.

| Compound | Name | MW (g/mol) | IC$_{50}$ WT Src | IC$_{50}$ T338G Src | IC$_{50}$ WT Abl | IC$_{50}$ T315A Abl | IC$_{50}$ T315I Abl |
|---|---|---|---|---|---|---|---|
| (structure) | AD56 | 440.16 | ++ | +++ | | | |
| (structure) | AD57[5] | 455.17 | +++ | +++ | +++ | | +++ |
| (structure) | AD58 | 387.44 | +++ | | +++ | | +++ |
| (structure) | AD59 | 427.14 | | | | +++ | +++ |

TABLE 1b-continued

Inhibition data for selected compounds described herein.

| Compound | Name | MW (g/mol) | IC$_{50}$ WT Src | IC$_{50}$ T338G Src | IC$_{50}$ WT Abl | IC$_{50}$ T315A Abl | IC$_{50}$ T315I Abl |
|---|---|---|---|---|---|---|---|
| | AD60 | 481.18 | | | +++ | | +++ |
| | AD61 | 523.51 | +++ | +++ | +++ | +++ | +++ |
| | AD62 | 551.56 | +++ | +++ | +++ | +++ | +++ |
| | AD63 | 615.65 | + | ++ | + | + | +++ |

TABLE 1b-continued

Inhibition data for selected compounds described herein.

| Compound | Name | MW (g/mol) | IC$_{50}$ WT Src | IC$_{50}$ T338G Src | IC$_{50}$ WT Abl | IC$_{50}$ T315A Abl | IC$_{50}$ T315I Abl |
|---|---|---|---|---|---|---|---|
| | AD64 | 471.44 | +++ | | + | | |
| | AD65 | 456.42 | + | | + | | |
| | AD66 | 481.47 | +++ | | +++ | | |

TABLE 1b-continued

Inhibition data for selected compounds described herein.

| Compound | Name | MW (g/mol) | IC$_{50}$ WT Src | IC$_{50}$ T338G Src | IC$_{50}$ WT Abl | IC$_{50}$ T315A Abl | IC$_{50}$ T315I Abl |
|---|---|---|---|---|---|---|---|
| | AD67 | 468.43 | +++ | | ++ | | |
| | AD68 | 468.43 | + | | + | | |
| | AD69 | 483.45 | ++ | | + | | |

TABLE 1b-continued
Inhibition data for selected compounds described herein.
| Compound | Name | MW (g/mol) | IC$_{50}$ WT Src | IC$_{50}$ T338G Src | IC$_{50}$ WT Abl | IC$_{50}$ T315A Abl | IC$_{50}$ T315I Abl |
|---|---|---|---|---|---|---|---|
| 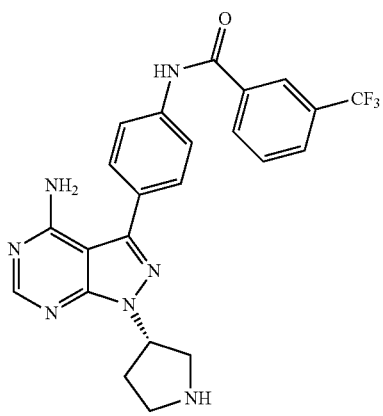 [SMILES: Nc1ncnc2c1c(-c1ccc(NC(=O)c3cccc(C(F)(F)F)c3)cc1)nn2[C@H]1CCNC1] | AD70 | 467.45 | + | | + | | |
| 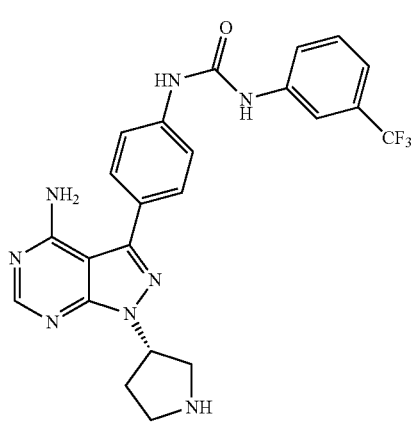 [SMILES: Nc1ncnc2c1c(-c1ccc(NC(=O)Nc3cccc(C(F)(F)F)c3)cc1)nn2[C@H]1CCNC1] | AD71b | 482.46 | +++ | | + | | |
| 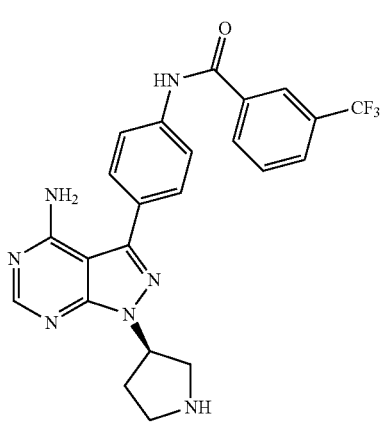 [SMILES: Nc1ncnc2c1c(-c1ccc(NC(=O)c3cccc(C(F)(F)F)c3)cc1)nn2[C@@H]1CCNC1] | AD72 | 467.45 | + | | + | | |

TABLE 1b-continued

Inhibition data for selected compounds described herein.

| Compound | Name | MW (g/mol) | IC$_{50}$ WT Src | IC$_{50}$ T338G Src | IC$_{50}$ WT Abl | IC$_{50}$ T315A Abl | IC$_{50}$ T315I Abl |
|---|---|---|---|---|---|---|---|
| 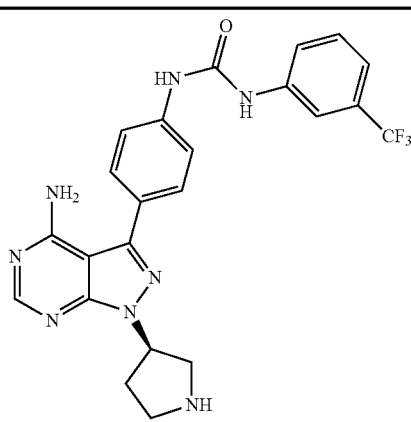 | AD73b | 482.46 | +++ | | +++ | | |

Footnotes:
[5]AD57 is also referred to herein as Cmpd 5;
+++ represents an IC$_{50}$ of less than 1 µM;
++ represents an IC$_{50}$ from 1 µM to 5 µM; and
+ represents an IC$_{50}$ of over 5 µM.

Some methods of synthesizing the fused ring heteroaryl compounds disclosed herein are set forth in the examples section below. One skilled in the art will immediately understand how to synthesize any of the fused ring heteroaryl compounds within the scope of this invention using or elaborating upon the synthesis methods disclosed herein and general principles of chemical synthesis known in the art.

Methods of Reducing Kinase Activity

In another aspect, a method of reducing the activity of a Src tyrosine kinase is provided. The method includes contacting the Src tyrosine kinase with an effective amount of the compound of Formula I, II, III, IV or V. In some embodiments, the compound is the compound of Formula I, II or IV. In other embodiments, the compounds are the compound of Formula I.

A Src tyrosine kinase, as used herein, refers to any one of the family of Src proto-oncogenic tyrosine kinases and oncogene tyrosine kinases. In some embodiments, the Src tyrosine kinase is the cellular Src tyrosine kinase (c-Src), such as the human c-Src (also referred to in the art MGC117393) (SEQ ID NO:6) or oncogenic derivatives thereof. See also Mather et al., *J Biol Chem.* 2008 Aug. 15; 283(33):22709-22.

The contacting may occur in vitro, in situ, or in vivo. For example, the compound may be exposed to a cell containing the Src tyrosine kinase, allowed to enter into the cell, and contact the Src tyrosine kinase thereby reducing the activity of the Src tyrosine kinase. The cell may be any appropriate cell, such as a mammalian cell (e.g. a human cell). The cell may also form part of a tissue, organ or organism.

In some related embodiments, the compound may also be capable of reducing the activity of an Abl tyrosine kinase. An Abl tyrosine kinase refers to any one of the family of Abl proto-oncogenic tyrosine kinases. In some embodiments, the Abl tyrosine kinase is the cellular Abl tyrosine kinase (c-Abl) or oncogenic derivatives thereof such as Bcr-Abl. See, e.g. Shaul Y (2000), *Cell Death Differ.* 7 (1): 10-6; Era T (2002) *Int. J. Hematol.* 76 (1): 35-43; and Pendergast A M (2003) *Adv. Cancer Res.* 85: 51-100. Thus, in some embodiments the Abl kinase is a Bcr-Abl kinase or a T315I Bcr-Abl kinase. The method may further include contacting an Abl tyrosine kinase with the compound thereby reducing the activity of the Abl tyrosine kinase. Where the method further includes contacting an Abl tyrosine kinase with the compound, it is understood that more than one compound is typically required to contact both an Abl and a Src tyrosine kinase. Therefore, a plurality of compounds having the same chemical structure are used.

As described above, the contacting of the Abl and Src tyrosine kinases may occur in vitro, in situ, or in vivo. Thus, in some embodiments, a plurality of the compound is contacted with a cell or vessel containing the Abl and Src tyrosine kinases. Once contacted by the compound, the Abl and Src tyrosine kinase activities are reduced.

In another aspect, a method of reducing the activity of an Abl tyrosine kinase is provided. The method includes contacting the Abl tyrosine kinase with an effective amount of a compound of Formula I, II, III, IV or V. In some embodiments, the compound is the compound of Formula I, II or IV. In other embodiments, the compounds is the compound of Formula I. In some embodiments, the Abl kinase is a Bcr-Abl kinase or a T315I Bcr-Abl kinase. As described above, the contacting of the Abl tyrosine kinases may occur in vitro, in situ, or in vivo. Thus, the compound may be exposed to a cell containing the Abl tyrosine kinase, allowed to enter into the cell, and contact the Abl tyrosine kinase thereby reducing the activity of the Src tyrosine kinase.

In some related embodiments, the compound may also be capable of reducing the activity of a Src kinase. Thus, the method may further include contacting a Src tyrosine kinase with the compound thereby reducing the activity of the Src tyrosine kinase. As explained above, where the method further includes contacting a Src tyrosine kinase with the compound, it is understood that more than one compound is typically required to contact both an Abl and a Src tyrosine kinase. Therefore, a plurality of compounds having the same chemical structure are used. Thus, in some embodiments, a plurality of the compound is contacted with a cell or vessel containing the Abl and Src tyrosine kinases. Once contacted by the compound, the Abl and Src tyrosine kinase activities are reduced.

In another aspect, a method of reducing the activity of a T315I Bcr-Abl kinase is provided. The method includes contacting the T315I Bcr-Abl Kinase with an effective amount of a compound having Formula I, II, III, IV or V. In some embodiments, the compound had the Formula I, II or IV. In another embodiment, the compound had the Formula I.

In some related embodiments, the compound may also be capable of reducing the activity of a Src kinase. Thus, the method may further include contacting a Src tyrosine kinase with the compound thereby reducing the activity of the Src tyrosine kinase. As explained above, where the method further includes contacting a Src tyrosine kinase with the compound, it is understood that more than one compound is typically required to contact both a T315I Bcr-Abl kinase and a Src tyrosine kinase. Therefore, a plurality of compounds having the same chemical structure are used. Thus, in some embodiments, a plurality of the compound is contacted with a cell or vessel containing the T315I Bcr-Abl kinase and Src tyrosine kinases. Once contacted by the compound, the T315I Bcr-Abl kinase and Src tyrosine kinase activities are reduced.

Methods of Treatment

In another aspect, a method of treating a disease mediated by a T315I Bcr-Abl kinase in a subject in need thereof is provided. The method includes administering to a subject an effective amount of a compound of Formula I, II, III, IV or V. In some embodiments, the compound is the compound of Formula I, II or IV. The disease mediated by a T315I Bcr-Abl kinase may be hypereosinophilic syndrome, dermatofibrosarcoma protuberans, chronic myelogenous leukemia, or a gastrointestinal stromal tumor. The compound may also be co-administered with a pharmaceutically acceptable excipient.

In another aspect, a method is provided for treating liver cancer, colon cancer, breast cancer, melanoma, acute myelogenous leukemia, chronic myelogenous leukemia, non-small-cell lung cancer, a gastrointestinal stromal tumor, Philadelphia chromosome-positive acute lymphoblastic leukemia (Ph+ ALL), renal cell carcinoma, hepatocellular carcinoma, hypereosinophilic syndrome, or dermatofibrosarcoma protuberans. The method includes administering an effective amount of the compound of Formula I, II, III, IV or V to a subject in need thereof. In some embodiments, the compound is of Formula I, II or IV. The compound may also be co-administered with a pharmaceutically acceptable excipient.

Thus, the present invention provides methods of reducing Src (e.g. c-Src) and or Abl (e.g. Bcr-Abl or T315I Bcr-Abl) kinase activity in a cell. The method includes contacting the cell with a fused ring heteroaryl inhibitor described above (e.g. a compound of Formula I, II, III, IV or V). The cell may be isolated or form part of an organ or organism.

The inhibitors provided herein find therapeutic utility via reduction of Src (e.g. c-Src) and or Abl (e.g. Bcr-Abl or T315I Bcr-Abl) kinase activity in the treatment of diseases or conditions. The inhibitor may have an $IC_{50}$ or $K_i$ against the Src and/or Abl kinase of less than 10 μM, 5 μM, 1 μM, 500 nM, 100 nM, 50 nM, 25 nM, 10 nM, 5 nM, 1 nM, 0.5 nM, or 0.1 nM.

In therapeutic use for the treatment of disease states recited above, the fused ring heteroaryls utilized in the pharmaceutical method of the invention are administered at the initial dosage of about 0.001 mg/kg to about 1000 mg/kg daily. A daily dose range of about 0.1 mg/kg to about 100 mg/kg is more typical. The dosages, however, may be varied depending upon the requirements of the patient, the severity of the condition being treated, and the modulator being employed. Determination of the proper dosage for a particular situation is within the skill of the practitioner. Generally, treatment is initiated with smaller dosages, which are less than the optimum dose of the modulator. Thereafter, the dosage is increased by small increments until the optimum effect under the circumstances is reached. For convenience, the total daily dosage may be divided and administered in portions during the day.

Pharmaceutical Formulations

In another aspect, the present invention provides a pharmaceutical composition including a compound in admixture with a pharmaceutically acceptable excipient. One of skill in the art will recognize that the pharmaceutical compositions include the pharmaceutically acceptable salts of the compounds of the present invention described above.

In therapeutic and/or diagnostic applications, the compounds of the invention can be formulated for a variety of modes of administration, including systemic and topical or localized administration. Techniques and formulations generally may be found in *Remington: The Science and Practice of Pharmacy* ($20^{th}$ ed.) Lippincott, Williams & Wilkins (2000).

The compounds according to the invention are effective over a wide dosage range. The exact dosage will depend upon the route of administration, the form in which the compound is administered, the subject to be treated, the body weight of the subject to be treated, and the preference and experience of the attending physician.

Pharmaceutically acceptable salts are generally well known to those of ordinary skill in the art, and may include, by way of example but not limitation, acetate, benzenesulfonate, besylate, benzoate, bicarbonate, bitartrate, bromide, calcium edetate, carnsylate, carbonate, citrate, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, mucate, napsylate, nitrate, pamoate (embonate), pantothenate, phosphate/diphosphate, polygalacturonate, salicylate, stearate, subacetate, succinate, sulfate, tannate, tartrate, or teoclate. Other pharmaceutically acceptable salts may be found in, for example, Remington: *The Science and Practice of Pharmacy* ($20^{th}$ ed.) Lippincott, Williams & Wilkins (2000). Preferred pharmaceutically acceptable salts include, for example, acetate, benzoate, bromide, carbonate, citrate, gluconate, hydrobromide, hydrochloride, maleate, mesylate, napsylate, pamoate (embonate), phosphate, salicylate, succinate, sulfate, or tartrate.

Depending on the specific conditions being treated, such agents may be formulated into liquid or solid dosage foams and administered systemically or locally. The agents may be delivered, for example, in a timed- or sustained-low release form as is known to those skilled in the art. Techniques for formulation and administration may be found in Remington: The Science and Practice of Pharmacy ($20^{th}$ ed.) Lippincott, Williams & Wilkins (2000). Suitable routes may include oral, buccal, by inhalation spray, sublingual, rectal, transdermal, vaginal, transmucosal, nasal or intestinal administration; parenteral delivery, including intramuscular, subcutaneous, intramedullary injections, as well as intrathecal, direct intraventricular, intravenous, intra-articullar, intra-sternal, intra-synovial, intra-hepatic, intralesional, intracranial, intraperitoneal, intranasal, or intraocular injections or other modes of delivery.

For injection, the agents of the invention may be formulated and diluted in aqueous solutions, such as in physiologically compatible buffers such as Hank's solution, Ringer's solution, or physiological saline buffer. For such transmucosal administration, penetrants appropriate to the barrier to be permeated are used in the formulation. Such penetrants are generally known in the art.

Use of pharmaceutically acceptable inert carriers to formulate the compounds herein disclosed for the practice of the invention into dosages suitable for systemic administration is within the scope of the invention. With proper choice of carrier and suitable manufacturing practice, the compositions of the present invention, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the invention to be formulated as tablets, pills, capsules, liquids, gels, syrups, slurries, suspensions and the like, for oral ingestion by a subject (e.g. patient) to be treated.

For nasal or inhalation delivery, the agents of the invention may also be formulated by methods known to those of skill in the art, and may include, for example, but not limited to, examples of solubilizing, diluting, or dispersing substances such as, saline, preservatives, such as benzyl alcohol, absorption promoters, and fluorocarbons.

Pharmaceutical compositions suitable for use in the present invention include compositions wherein the active ingredients are contained in an effective amount to achieve its intended purpose. Determination of the effective amounts is well within the capability of those skilled in the art, especially in light of the detailed disclosure provided herein.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

Pharmaceutical preparations for oral use can be obtained by combining the active compounds with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations, for example, maize starch, wheat starch, rice starch, potato starch, gelatin, gum tragacanth, methyl cellulose, hydroxypropylmethyl-cellulose, sodium carboxymethyl-cellulose (CMC), and/or polyvinylpyrrolidone (PVP: povidone). If desired, disintegrating agents may be added, such as the cross-linked polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol (PEG), and/or titanium dioxide, lacquer solutions, and suitable organic solvents or solvent mixtures. Dye-stuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols (PEGs). In addition, stabilizers may be added.

Depending upon the particular condition, or disease state, to be treated or prevented, additional therapeutic agents, which are normally administered to treat or prevent that condition, may be administered together with the inhibitors of this invention. For example, chemotherapeutic agents or other anti-proliferative agents may be combined with the inhibitors of this invention to treat proliferative diseases and cancer. Examples of known chemotherapeutic agents include, but are not limited to, adriamycin, dexamethasone, vincristine, cyclophosphamide, fluorouracil, topotecan, taxol, interferons, and platinum derivatives.

Other examples of agents the compounds of this invention may also be combined with include, without limitation, anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; agents for treating diabetes such as insulin, insulin analogues, alpha glucosidase inhibitors, biguanides, and insulin sensitizers; and agents for treating immunodeficiency disorders such as gamma globulin.

These additional agents may be administered separately, as part of a multiple dosage regimen, from the composition. Alternatively, these agents may be part of a single dosage form, mixed together with the compound in a single composition.

The present invention is not to be limited in scope by the exemplified embodiments, which are intended as illustrations of single aspects of the invention. Indeed, various modifications of the invention in addition to those described herein will become apparent to those having skill in the art from the foregoing description. Such modifications are intended to fall within the scope of the invention. Moreover, any one or more features of any embodiment of the invention may be combined with any one or more other features of any other embodiment of the invention, without departing from the scope of the invention. For example, the compounds of the present invention described above are equally applicable to the methods of treatment and the method of reducing kinase activity described herein. References cited throughout this application are examples of the level of skill in the art and are hereby incorporated by reference herein in their entirety for all purposes, whether previously specifically incorporated or not.

Assays

The activity of Abl or Src kinases can be assessed using a variety of in vitro, in situ, and in vivo assays, e.g., $P^{32}$ assays, fluorescent assays, immunoassays and the like. Furthermore, such assays can be used to test for inhibitors of Abl and Src kinases. One particular assay is disclosed below in the Examples in the section entitled "In vitro Kinase Assays." Abl and Src kinases have been implicated in a number of disorders that are targets for a therapeutic or prophylactic regimen. The inhibitors and methods of the invention are useful to treat these disease states as discussed above. Thus, using methods disclosed herein as well as those generally known in the art, one skilled in the art can easily make and test the fused ring heteroaryl compounds set forth herein to assess the degree to which kinase activities are reduced.

Exemplary Syntheses

The compounds of the invention are synthesized by an appropriate combination of generally well known synthetic methods. Techniques useful in synthesizing the compounds of the invention are both readily apparent and accessible to those of skill in the relevant art. The discussion below is offered to illustrate certain of the diverse methods available for use in assembling the compounds of the invention. However, the discussion is not intended to define the scope of reactions or reaction sequences that are useful in preparing the compounds of the present invention.

For example, Scheme 1 following provides one of a variety of overall synthetic strategies which may be employed in the synthesis of compounds described herein. Substituents in Scheme 1 are as described herein for Formula IV.

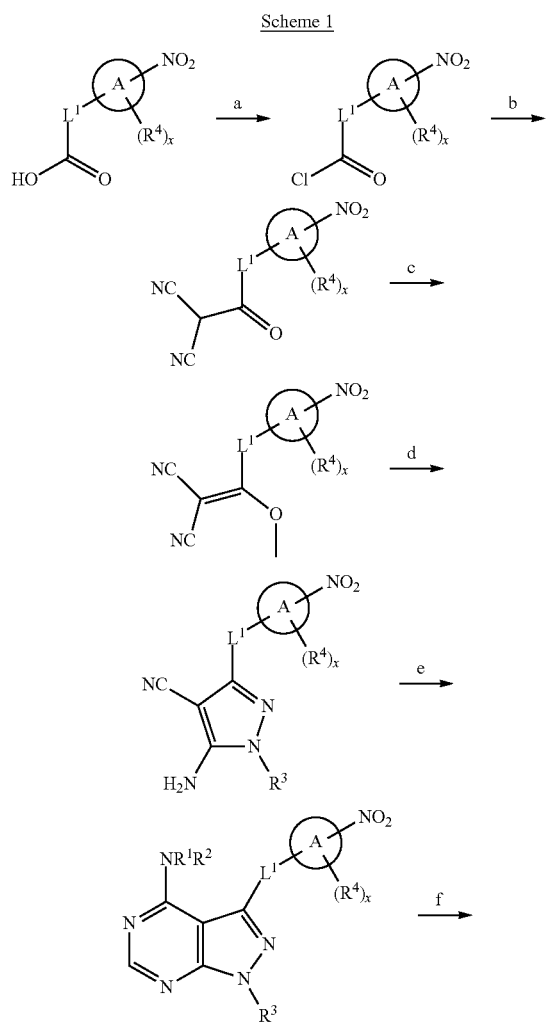

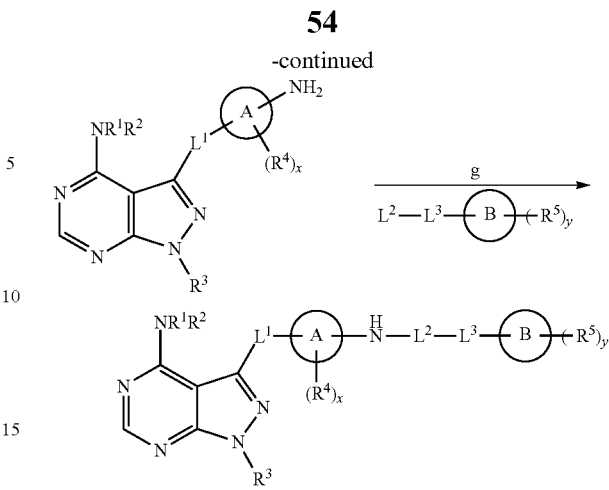

Regarding Scheme 1, in Step a, an acid starting material may be reacted with oxalyl chloride, e.g., in DMF and $CH_2Cl_2$, to afford the acid chloride. In Step b, the acid chloride may be reacted with malononitrile and NaH in, e.g., THF, to afford the substituted malononitrile. In Step c, the compound may be further reacted with dimethyl sulfate and NaHCO3 in, e.g., dioxane and water, to afford the enol ether. In Step d, the enol ether may be reacted with a hydrazine in, e.g., THF, to afford the pyrazole. In Step e, the pyrazole may be further reacted with an amide to afford the pyrazolo[3,4-d]pyrimidine amine. In Step f, the pendant nitrate may be reduced to afford the amine. Finally, in Step g, elaboration at the pendant amine may be employed to afford a compound of the invention.

Optionally, one or more functionalities described herein and in Scheme 1 may be protected during synthesis and subsequently deprotected by methods well known in the art. Exemplary amine protecting groups include, but are not limited to, carbobenzyloxy (Cbx), p-methyoxybenzyl carbonyl (Boz), tert-butyloxycarbonyl (Boc), 9-fluorenylmethyloxy carbonyl (FMoc), benzyl (Bn), p-methoxybenzyl (PMB), 2,3-dimethoxybenzyl (DMPM), p-methoxyphenyl (PMP), tosyl (Ts), allyloxycarbonyl (Alloc), and the like.

Formation of carbon-carbon bonds, for example between aryl functionalities, is available by a variety of routes known in the art. For example, the Suzuki reaction depicted in Scheme 2 is the reaction of an aryl- or vinyl-boronic acid with an aryl- or vinyl-halide, catalyzed by a Pd complex. Exemplary Pd complexes include, but are not limited to, tetrakis(triphenylphosphine)palladium(O), and polymer-bound tetrakis palladium, as known in the art.

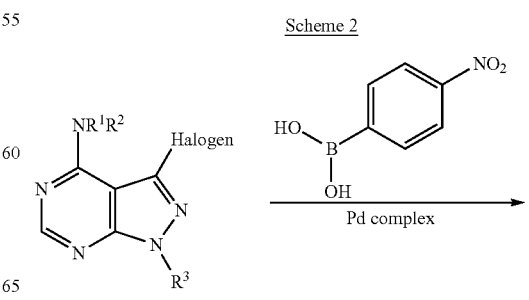

-continued

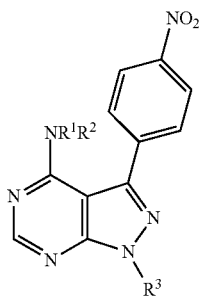

EXAMPLES

Example 1

Protein Expression and Purification

6×HIS (SEQ ID NO:7) fusions of c-Src or Abl were expressed in bacteria in the presence of the YopH phosphatase and GroEL chaperone based on a recently developed strategy (Seeliger et al., 2005, *Protein Sci* 14:3135-3139). Briefly each kinase was purified in batch by Ni-NTA immobilized metal affinity chromatography. The 6×His was removed by TEV cleavage to yield the liberated kinase domain. Following cleavage, ion exchange chromatography was utilized to remove excess TEV and minor contaminants. In the final step the proteins were applied to a gel filtration column in 100 mM NaCl, 20 mM Tris, 5% glycerol, 2 mM DTT. Pooled fractions were concentrated and flash frozen in liquid nitrogen for storage. Proteins were isolated in their unphosphorylated state as revealed by Western blot analysis, as known in the art. Typical yields for either protein construct ranged from 1-10 mg of protein per 1 L of bacterial culture.

Example 2

In Vitro Kinase Assays

Purified c-Src or Abl were diluted in kinase reaction buffer (10 mM HEPES [pH 7.2], 10 mM MgCl2, 0.2 mM DTT) to a concentration of approximately 10 nM and pre-incubated with 1 mg/mL BSA, 2.5% (v/v) DMSO, 133 µM peptide (sequence EAIYAAPFKKK (SEQ ID NO:8) for Abl and EIYGEFKKK (SEQ ID NO:9) for c-Src), and varying concentrations of inhibitor. Kinase reactions were initiated by the addition of 100 mM cold ATP supplemented with 5 mCi $\gamma^{32}$P ATP and allowed to proceed at room temperature (RT). At 10 minutes 1 mL of the reactions were spotted onto phosphocellulose sheets (P81, Whatman) and subsequently soaked in wash buffer (1.0% (v/v) phosphoric acid). The sheets were washed five times in buffer, dried, and transferred radioactivity was measured by phosphorimaging using a Typhoon™ scanner (Molecular Dynamics). Radioactive counts were quantified using ImageQuant™ software, and titration data were fit to a sigmoidal dose response to derive $IC_{50}$ values using the Prism® software package. Dose responses were based on a 12 point inhibitor titration, using ⅓ dilutions starting from 100 mM. Experiments were completed 2-4 times to derive mean values.

Example 3

Crystallization and Structure Determination

Figure 6:
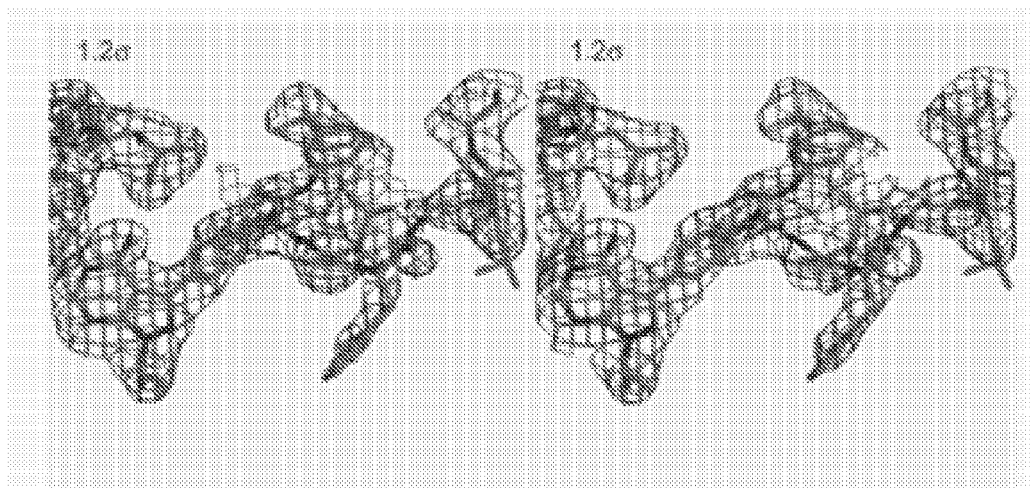
FIG. 6. A composite $|2F_o-F_c|$ simulated annealing omit electron density map (Bhat, 1988, *Journal of Applied Crystallography* 21:279-281) computed at 2.3 Å and contoured at 1.2σ and centered on Cmpd 5.

Prior to crystallization, purified c-Src was applied to a S200 gel filtration column. Pooled fractions were concentrated to 3-10 mg/mL and mixed with equimolar amounts of 3 or 5 in 100 mM NaCl, 10 mM Tris [pH 7.8], 5% glycerol, 2 mM DTT, 4% DMSO. Hanging drops containing 1 µL of complexes were mixed with equal volume of well buffer containing 4% PEG 4K, 16% glycerol, 50 mM NaAc, 100 mM MES [pH 6.5] and grown at 14° C. to yield both the c-Src-3 and c-Src-5 crystals. Crystals were cryoprotected in well buffer supplemented with 20% glycerol and flash frozen. Diffraction data were collected at −170° C. Data processing and reduction was carried out using HKL2000 (Otwinowski and Minor, 1997, *Macromolecular Crystallography, Pt A* 276:307-326) for the c-Src-5 complex and XDS (Kabsch, 1993, *Journal of Applied Crystallography* 26:795-800) for the c-Src-3 complex. Both structures were solved by molecular replacement using the X-ray crystallographic structure of the Src kinase domain (PDB ID:1YOJ) (SEQ ID NO:12) lacking the activation segment, helix aC, and any ligands as the search model in the program PHASER (Mccoy et al., 2007, *Journal of Applied Crystallography* 40:658-674). Molecular replacement solutions were modified and refined with alternate cycles of manual fitting and building into |2Fo−Fc| and composite omit electron density maps using Coot (Emsley and Cowtan, 2004, *Acta Crystallographica Section D-Biological Crystallography* 60:2126-2132). Refinement of the structures was conducted using simulated annealing and maximum likelihood protocols using CNS (Brunger et al., 1998, *Acta Crystallographica Section D-Biological Crystallography* 54:905-921) and REFMAC (Murshudov et al., 1997, *Acta Crystallographica Section D-Biological Crystallography* 53:240-255). Topology and parameter files for the inhibitors were generated using PRODRG (Schuttelkopf and van Aalten, 2004, *Acta Crystallographica Section D-Biological Crystallography* 60:1355-1363). Data collection and refinement statistics are shown in Table 2 below. A representative composite omit simulated annealing electron density (|2F$_o$−F$_c$|) map from the Src-5 complex is shown in FIG. 6. All structural figures were prepared with PYMOL (Delano and Lam, 2005, *Abstracts of Papers of the American Chemical Society* 230:U1371-U1372). Structures have been deposited in the Protein Data Bank under ID codes 3EL7 (Src-3) (SEQ ID NO:4) and 3EL8 (Src-5) (SEQ ID NO:4).

TABLE 2

X-ray crystallographic data collection and refinement statistics.

| Data Collection | | |
|---|---|---|
| Structure | Src-3 | Src-5 |
| Space Group | P21 | P1 |
| Unit Cell Dimensions | a = 42.4 Å, b = 63.1 Å, c = 56.1 Å | a = 42.4 Å, b = 63.7 Å, c = 73.8 Å $\alpha$ = 101.0°, $\beta$ = 90.2°, $\gamma$ = 90.1° |

TABLE 2-continued

X-ray crystallographic data collection and refinement statistics.

| | $\alpha = 90.0°, \beta = 91.9°,$ $\gamma = 90.0°$ | |
|---|---|---|
| Numbers of molecules/asymmetric unit | 1 | 2 |
| X-ray Source | ALS 5.0.1 | ALS 5.0.3 |
| Wavelength (Å) | 0.9774 | 0.9774 |
| Resolution (Å) | 30-2.80 | 50-2.30 |
| Total Reflections | 42531 | 117,900 |
| Unique Reflections | 7,350 | 31,919 |
| I/s | 11.97(4.55) | 12.50(2.79) |
| Completeness (%) | 99.4(99.1) | 96.1(82.1) |
| Rsym (%) | 10.6(31.6) | 8.5(31.2) |
| Model Refinement | | |
| Resolution (Å) | 30-2.8 | 50-2.3 |
| Number of Reflections Rwork/Rfree | 6970/366 | 29,310/1535 |
| Rwork/Rfree | 22.0/28.9 | 22.1/26.5 |
| Rmsd from ideality in Bond length (Å) | 0.007 | 0.007 |
| Rmsd from ideality in Angles (°) | 1.3 | 1.3 |
| Number of Protein Atoms In Model | 2036 | 4180 |
| Number of Drug atoms In model | 36 | 33 |
| Number of waters | 59 | 176 |
| Favored/Allowed/Outliers in the Ramachandran Plot (%) | 92.2/7.8/0.0 | 96.1/3.7/0.2 |

Numbers in parentheses refer to the outer shell (2.80 Å-2.86 Å) for Src-3 and (2.30 Å-2.38 Å) for Src-5.

Chemical Synthesis.

Starting materials were commercially available. Reactions were monitored by thin layer chromatography (TLC), and compounds were characterized by liquid chromatography-mass spectrometry (LC-MS) and nuclear magnetic resonance (NMR) spectroscopy. Compounds 1-4 were synthesized starting from 3-nitrophenyl acetic acid, and Cmpd 5 was synthesized starting from 4-nitrophenyl boronic acid based on established routes for preparing pyrazolopyrimidines as known in the art (Bishop et al., 1999, *J American Chemical Society* 121:627-631; Bishop et al., 1998, *Curr Biol* 8:257-266; Blethrow et al., 2004, *Curr Protoc Mol Biol Chapter* 18, Unit 18 11; Apsel et al., 2008, Nat. Chem. Biol. 4:691-699; Dar et al., 2008, Chem. Biol. 20:1015-1022) with modifications as described herein.

Example 4

2-(1-methoxy-2-(3-nitrophenyl)ethylidene)malononitrile 2-(1-methoxy-2-(3-nitrophenyl)ethylidene)malononitrile, a compound useful in the synthesis of compounds described herein, is conveniently synthesized by a variety of routes known in the art, including that provided in Scheme 3 following.

Scheme 3

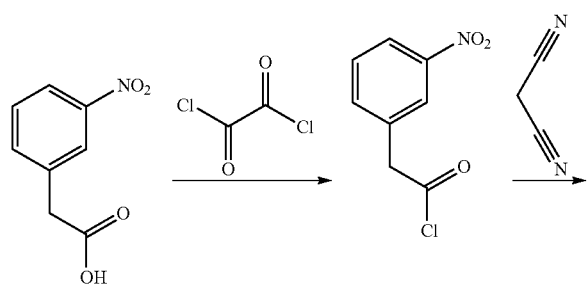

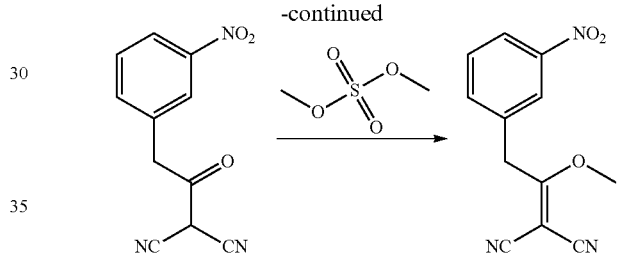

2-(3-nitrophenyl)acetyl chloride

To a solution of 3-nitrophenyl acetic acid (5 g, 27.6 mmol; Sigma-Aldrich) was added oxalyl chloride (12 mL, 138 mmol) and DMF (0.1 mL) in 40 mL $CH_2Cl_2$. The reaction mixture was stirred for 6 hours at room temperature yielding a clear yellow solution. Solvent was removed in vacuo to afford a yellow solid of the acid chloride, which was washed with $CH_2Cl_2$ three times and carried on directly to the next step.

2-(2-(3-nitrophenyl)acetyl)malononitrile

The acid chloride was dissolved in 10 mL of THF and added dropwise to a reaction flask containing an ice-cold solution of malononitrile (2.7 g, 41 mmol) and NaH (3.5 g of a 60% paraffin oil emulsion, 88.3 mmol) in THF. The reaction was stirred for 4 hours and warmed to room temperature, after which 25 mL of 2N HCl was added. The aqueous layer was extracted three times with EtOAc. The organic extracts were combined and concentrated in vacuo.

2-(1-methoxy-2-(3-nitrophenyl)ethylidene)malononitrile

The crude material containing 2-(2-(3-nitrophenyl)acetyl)malononitrile was dissolved in $H_2O$ (7 mL) and 1,4-dioxane (42 mL), to which $NaHCO_3$ (11.5 g, 138 mmol) and dimethyl sulfate (10.5 mL, 110 mmol) were added. The reaction mixture was heated to 80° C. and left stirring for 12 hours. The reaction mixture was diluted with EtOAc (100 mL) and brine (100 mL). The aqueous portion was extracted with EtOAc (3×100 mL). The combined organic fractions were dried over $MgSO_4$, filtered, and concentrated in vacuo. The recovered solid was purified by silica gel chromatography (100% chloroform). Fractions containing the desired enol ether were pooled, concentrated, and dissolved in hot MeOH. The solution was cooled and fine white crystals formed overnight, which were recovered by filtration and washed with ice cold MeOH to afford 2-(1-methoxy-2-(3-nitrophenyl)ethylidene) malononitrile. $^1$H NMR (400 MHz, DMSO): δ 7.78 (1H, d), 7.72 (t, 1H), 8.22 (d, 1H), 8.25 (s, 1H), 4.36 (s, 2H), 4.04 (s, 3H).

Example 5

1-(3-((4-amino-1-methyl-1H-pyrazolo[3,4-d]pyrimidin-3-yl)methyl)phenyl)-3-(3-(trifluoromethyl)phenyl)urea (Cmpd 1)

2-(1-methoxy-2-(3-nitrophenyl)ethylidene)malononitrile (0.4 g; 1.6 mmol) was combined with methylhydrazine (0.09 mL; 1.6 mmol; Sigma-Aldrich) in 10 mL of THF for 1 hour on a ice-bath. The product was concentrated in vacuo and recrystallized from MeOH to yield 3-(3-nitrobenzyl)-5-amino-1-methyl-1H-pyrazole-4-carbonitrile (ESI-MS m/z [M+H]+ found 258.1, calculated 258.09). The crystallized product (0.2 g; 0.8 mmol) was combined with formamide (1.5 mL) and heated to 160° C. overnight. $H_2O$ was added to the cooled reaction and the precipitate was filtered and dried to yield 3-(3-nitrobenzyl)-1-methyl-1H-pyrazolo[3,4-d]pyrimidin-4-amine (ESI-MS m/z [M+H]+ found 285.1, calculated 285.1). This precipitated intermediate (0.09 g; 0.33 mmol) was then mixed with excess Zinc dust, 5 mL THF, 0.4 mL HOAc for 12 hours under Argon at room temperature. Afterwards the reaction was filtered through Celite®, extracted with EtOAc and concentrated in vacuo to yield 3-(3-aminobenzyl)-1-methyl-1H-pyrazolo[3,4-d]pyrimidin-4-amine (ESI-MS m/z [M+H]+ found 255.3, calculated 255.13).). To the reduced precursor, molar equivalents of 3-(trifluoromethyl)phenyl isocyanate (Sigma-Aldrich) were added drop wise in ice-cold $CH_2Cl_2$. The reaction proceeded until completion as judged by TLC, was concentrated in vacuo, resuspended in 50:50 $H_2O$-$CH_3CN$, and purified on a $C_{18}$ column in $CH_3CN/H_2O/0.1\%$ TFA (1-100% gradient) to yield final Cmpd 1 1-(3-((4-amino-1-methyl-1H-pyrazolo[3,4-d]pyrimidin-3-yl)methyl)phenyl)-3-(3-(trifluoromethyl)phenyl)urea (ESI-MS m/z [M+H]+ found 442.1, calculated 442.15; $^1$H NMR (400 MHz, DMSO): δ 9.31 (s, 1H), 9.05 (s, 1H), 8.43 (s, 1H), 8.03 (s, 1H), 7.56 (d, J=8 Hz, 1H), 7.50 (t, J=8 Hz, 1H), 7.37 (s, 1H), 7.36 (d, J=8 HZ, 1H), 7.30 (d, J=8 Hz, 1H), 7.21 (t, J=8 Hz, 1H), 6.88 (d, J=8 Hz, 1H), 4.40 (s, 2H), 3.93 (s, 1H). $^{13}$C NMR (400 MHz, DMSO): δ 33.48, 34.34, 98.15, 116.47 (d), 115.05, 117.11, 117.98, 119.13, 122.29, 122.91, 124.73 (q), 129.33, 130.00 (q), 130.32, 139.24, 140.15, 141.21, 146.00, 149.49, 152.37, 153.00, 153.76, 159.48 (q)).

Example 6

1-(3-((4-amino-1-isopropyl-1H-pyrazolo[3,4-d]pyrimidin-3-yl)methyl)phenyl)-3-(3-(trifluoromethyl) phenyl)urea (Cmpd 2)

A specific synthetic strategy for Cmpd 2 is depicted in Scheme 4 following.

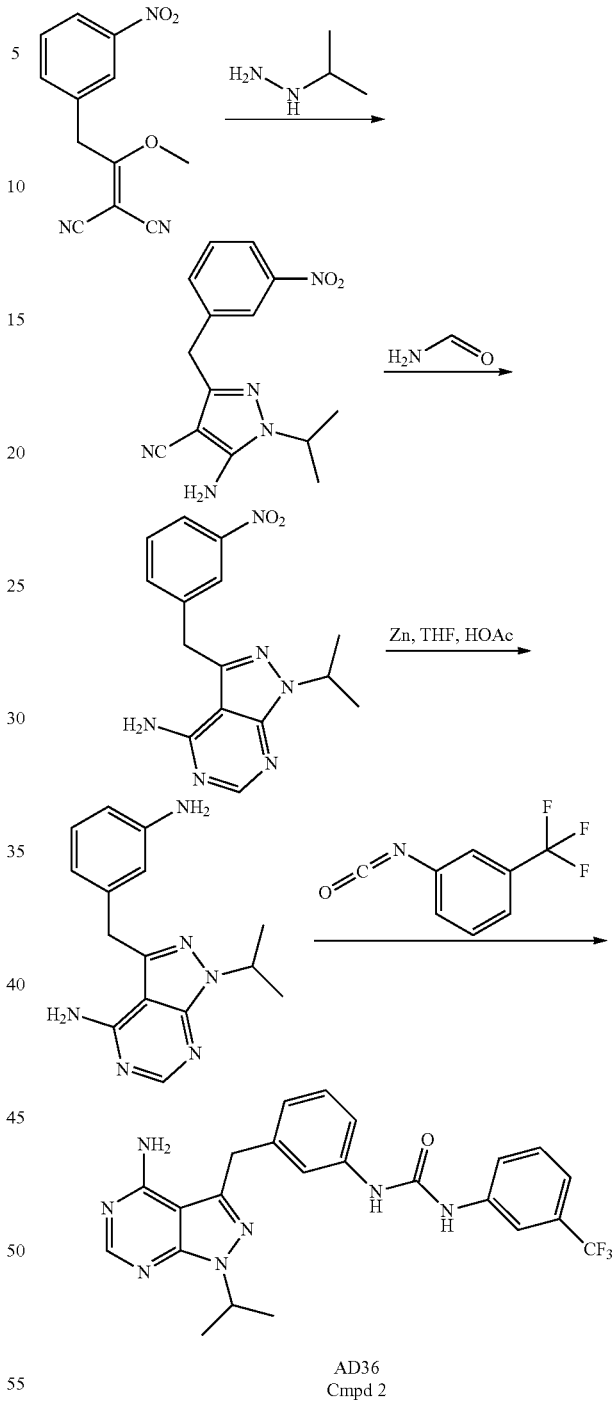

Scheme 4

AD36
Cmpd 2

Reagent 2-(1-methoxy-2-(3-nitrophenyl)ethylidene)malononitrile (1.2 g; 4.7 mmol) was combined with isopropylhydrazine-HCl (0.57 g; 5.2 mmol; Sigma-Aldrich), 1.4 mL triethylamine in 50 mL EtOH for at 2 hours at RT. The reaction was concentrated in vacuo, suspended in brine and extracted with chloroform. The organic layer was dried over $MgSO_4$. Following, the organic suspension was filtered, concentrated in vacuo, and purified on silica gel in 1% MeOH: $CHCl_3$ to yield 3-(3-nitrobenzyl)-5-amino-1-isopropyl-1H-pyrazole-4-carbonitrile (ESI-MS m/z [M+H]+ found 286.4, calculated 286.12). The product was combined with formamide (1.5 mL) and heated to 160° C. overnight. H$_2$0 was added to the cooled reaction and the precipitate was filtered and dried to yield 3-(3-nitrobenzyl)-1-isopropyl-1H-pyrazolo[3,4-d]pyrimidin-4-amine (ESI-MS m/z [M+H]+ found 313.4, calculated 313.13). This precipitated intermediate was then mixed with excess Zinc dust, 5 mL THF, 0.4 mL HOAc for 12 hours under Argon at room temperature. Afterwards the reaction was filtered through Celite®, extracted with EtOAc and concentrated in vacuo to yield 3-(3-aminobenzyl)-1-isopropyl-1H-pyrazolo[3,4-d]pyrimidin-4-amine ESI-MS m/z [M+H]+ found 283.11, calculated 282.16. To the reduced precursor, molar equivalents of 3-(trifluoromethyl)phenyl isocyanate (Sigma-Aldrich) were added drop wise in ice-cold CH$_2$Cl$_2$. The reaction proceeded until completion as judged by TLC, was concentrated in vacuo, resuspended in 50:50 H$_2$0-CH$_3$CN, and purified on a C$_{18}$ column in CH$_3$CN/H$_2$0/0.1% TFA (1-100% gradient) to yield Cmpd 2 1-(3-((4-amino-1-isopropyl-1H-pyrazolo[3,4-d]pyrimidin-3-yl)methyl)phenyl)-3-(3-(trifluoromethyl)phenyl)urea (ESI-MS m/z [M+H]+ found 470.5, calculated 470.18; $^1$H NMR (400 MHz, DMSO): δ 9.25 (1H, s), 8.97 (s, 1H), 8.36 (s, 1H), 8.05 (s, 1H), 7.48-7.54 (m, 2H), 7.41 (s, 1H), 7.30 (d, J=8 Hz, 2H), 7.20 (t, J=8 Hz, 1H0, 6.88 (d, J=8 Hz, 1H), 5.03 (septet, J=8 Hz, 1H), 1.48 (s, 6H), $^{13}$C NMR (400 MHz, DMSO): δ 22.15, 33.44, 49.21, 98.32, 116.48 (d), 117.03, 118.92, 122.16, 122.67, 124.70 (q), 129.33, 129.98 (q), 130.47 (q), 139.50, 140.07, 141.15, 145.31, 150.15, 151.77, 152.94, 154.32, 159.10 (q)).

Example 7

1-(3-((4-amino-1-cyclopentyl-1H-pyrazolo[3,4-d]pyrimidin-3-yl)methyl)phenyl)-3-(3-(trifluoromethyl)phenyl)urea (Cmpd 3)

Reagent 2-(1-methoxy-2-(3-nitrophenyl)ethylidene)malononitrile (0.3 g; 1.3 mmol) was combined with hydrazine monohydrate (0.07 mL; 1.4 mmol; Sigma-Aldrich) in 5 mL EtOH for 1 hour at RT. The reaction was concentrated in vacuo to yield 3-(3-nitrobenzyl)-5-amino-1H-pyrazole-4-carbonitrile (0.3 g; 1.3 mmol; ESI-MS m/z [M+H]+ found 244.5, calculated 244.1, $^1$H NMR (400 MHz, DMSO): δ 11.77 (s, 1H), 8.09 (d, J=8 Hz, 1H), 8.08 (s, 1H), 7.69 (d, J=8 Hz, 1H), 7.60 (m, 1H), 6.33 (s, 2H), 3.96 (s, 2H)), which was subsequently combined with formamide (6 mL) and heated to 180° C. overnight. H$_2$O was added to the cooled reaction and the precipitate was filtered and dried to yield 3-(3-nitrobenzyl)-1H-pyrazolo[3,4-d]pyrimidin-4-amine (0.26 g; 0.96 mmol; ESI-MS m/z [M+H]+ found 271.4, calculated 271.09; $^1$H NMR (400 MHz, DMSO): δ 8.18 (s, 1H), 8.10 (s, 1H), 8.06 (d, J=8 Hz, 1H), 7.69 (d, J=8 Hz, 1H), 7.58 (m, 1H), 7.22 (br, 2H), 4.51 (s, 2H)). The recovered intermediate (0.05 g; 0.18 mmol) was combined with bromocyclopentane (0.1 mL; 0.38 mmol), 0.125 g K$_2$CO$_3$, in 1 mL DMF and refluxed under argon for 2 hours. The reaction was filtered to remove solid K$_2$CO$_3$, and the filtrate was combined with brine and the organic product was extracted in CH$_2$Cl$_2$ to yield 3-(3-nitrobenzyl)-1-cyclopentyl-1H-pyrazolo[3,4-d]pyrimidin-4-amine (ESI-MS m/z [M+H]+ found 339.5, calculated 339.15; $^1$H NMR (400 MHz, CDCl$_3$): δ 8.30 (s, 1H), 8.12 (m, 2H), 7.51 (m, 2H), 5.25 (pen, 8 Hz, 1H), 5.06 (br, 2H), 4.42 (s, 2H), 2.14 (m, 4H), 1.97 (m, 2H), 1.73 (m, 2H)). Reduction of this material was carried out as per Cmpd 1 to yield 3-(3-aminobenzyl)-1-cyclopentyl-1H-pyrazolo[3,4-d]pyrimidin-4-amine (ESI-MS m/z [M+H]+ found 309.5, calculated 309.17). The reduced precursor was coupled to 3-(trifluoromethyl)phenyl isocyanate and purified as described for Cmpd 1 to yield Cmpd 3 1-(3-((4-amino-1-cyclopentyl-1H-pyrazolo[3,4-d]pyrimidin-3-yl)methyl)phenyl)-3-(3-(trifluoromethyl)phenyl)urea (ESI-MS m/z [M+H]+ found 496.4, calculated 496.2; $^1$H NMR (400 MHz, DMSO): δ 9.22 (s, 1H), 8.93 (s, 1H), 8.34 (s, 1H), 8.06 (s, 1H), 7.50-7.60, (m, 2H), 7.43 (s, 1H), 7.18-7.22 (m, 3H), 6.90 (d, J=8 Hz, 1H), 5.20 (pentet, J=7 Hz, 1H), 4.40 (s, 2H), 1.98-2.13 (m, 4H), 1.85-1.95 (m, 2H), 1.62-1.73 (m, 2H); $^{13}$C NMR (400 MHz, DMSO): δ 24.76, 32.33, 33.48, 57.62, 98.34, 114.48, 117.01, 118.17, 118.46, 118.89, 122.13, 122.34, 122.66, 129.97 (q), 139.53, 140.11, 141.16, 145.37, 150.60, 152.32, 152.94, 154.38, 159.00 (q)).

Example 8

1-(3-((1-tert-butyl-4-amino-1H-pyrazolo[3,4-d]pyrimidin-3-yl)methyl)phenyl)-3-(3-(trifluoromethyl)phenyl)urea (Cmpd 4)

Reagent 2-(1-methoxy-2-(3-nitrophenyl)ethylidene)malononitrile (1.2 g; 4.7 mmol) was combined with tert-butylhydrazine-HCl (0.57 g; 5.2 mmol; Sigma-Aldrich), 1.4 mL triethylamine in 50 mL EtOH for at 2 hours at 80° C. The reaction was concentrated in vacuo, resuspended in brine and extracted with chloroform. The organic layer was dried over MgSO$_4$. Following, the organic suspension was filtered, concentrated in vacuo, and purified on silica gel in 1% MeOH:CHCl$_3$ to yield 3-(3-nitrobenzyl)-1-tert-butyl-5-amino-1H-pyrazole-4-carbonitrile (ESI-MS m/z [M–CH$_3$]+ found 285.5, calculated 285.14; $^1$H NMR (400 MHz, DMSO): δ8.11 (s, 1H), 8.08-8.12 (m, 1H), 7.69 (d, J=8 Hz, 1H), 7.59-7.64 (m, 1H), 3.96 (s, 2H), 3.34 (br, 2H), 1.52 (s, 9H)). This product was combined with formamide as per Cmpd 1 to yield 3-(3-nitrobenzyl)-1-tert-butyl-1H-pyrazolo[3,4-d]pyrimidin-4-amine (ESI-MS m/z [M+H]+ found 327.4, calculated 327.15; $^1$H NMR (400 MHz, DMSO): δ 8.22 (s, 1H), 8.14 (s, 1H), 8.07 (d, J=8 Hz, 1H), 7.67 (d, J=8 Hz, 1H), 7.59 (d, J=8 Hz, 1H), 7.22 (br, 2H), 4.52 (s, 2H), 1.70 (s, 9H)). Reduction of this material was completed as per Cmpd 1 to yield 3-(3-aminobenzyl)-1-tert-butyl-1H-pyrazolo[3,4-d]pyrimidin-4-amine (ESI-MS m/z [M+H]+ found 297.13, calculated 297.17). The reduced precursor was coupled to 3-(trifluoromethyl)phenyl isocyanate and purified as described for Cmpd 1 to yield Cmpd 4 1-(3-((1-tert-butyl-4-amino-1H-pyrazolo[3,4-d]pyrimidin-3-yl)methyl)phenyl)-3-(3-(trifluoromethyl)phenyl)urea (ESI-MS m/z [M+H]+ found 484.5, calculated 484.2; $^1$H NMR (400 MHz, DMSO): δ 9.25 (s, 1H), 8.96 (s, 1H), 8.32 (s, 1H), 8.06 (s, 1H), 7.46-7.55 (m, 2H), 7.40 (s, 1H), 7.29 (d, J=8 Hz, 2H), 7.20 (t, J=8 Hz, 1H), 6.89 (d, J=8 Hz, 1H), 4.39 (s, 2H), 1.73 (s, 9H). $^{13}$C NMR (400 MHz, DMSO): δ 29.25, 33.40, 60.74, 99.58, 116.43 (d), 116.95, 118.86, 122.13, 122.64, 124.69 (q), 129.29, 129.98 (q), 130.32, 139.60, 140.06, 141.16, 143.31, 149.70, 152.69, 152.92, 154.81, 159.12 (q)).

Example 9

1-(4-(4-amino-1-isopropyl-1H-pyrazolo[3,4-d]pyrimidin-3-yl)phenyl)-3-(3-(trifluoromethyl)phenyl)urea (Cmpd 5)

A synthetic strategy for Cmpd 5 is depicted in Scheme 5 following.

Scheme 5

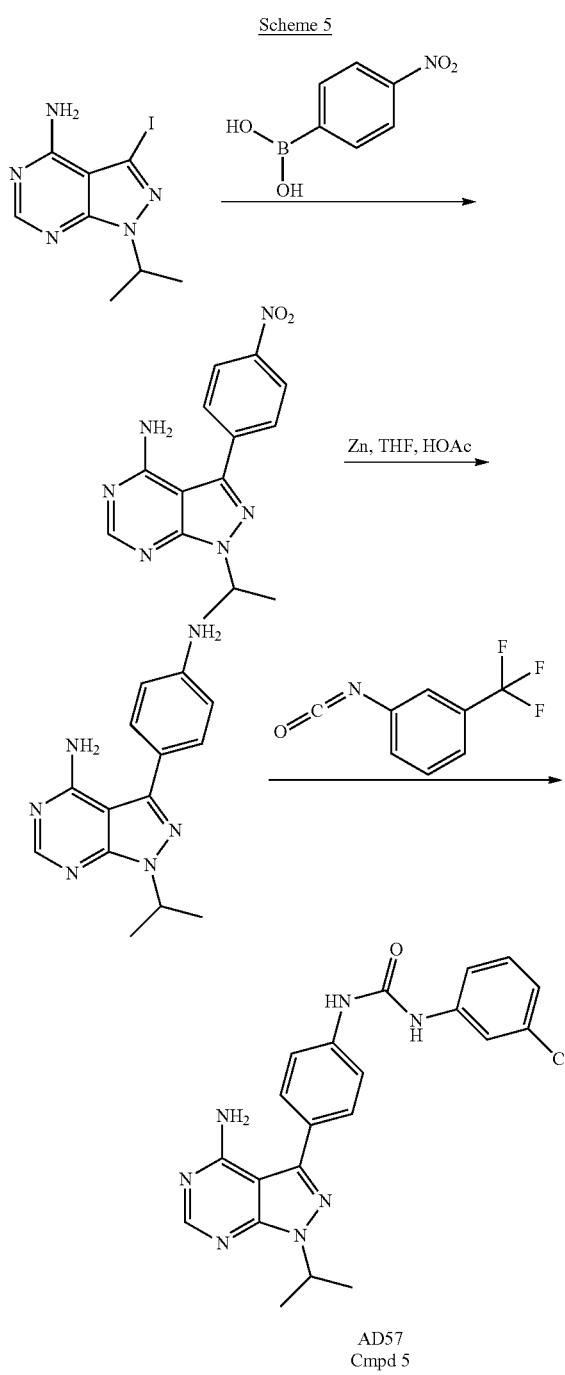

AD57
Cmpd 5

With reference to Scheme 5, 4-nitrophenyl boronic acid (100 mg, 0.330 mmol; Sigma-Aldrich), was coupled to 3-iodo-1-isopropyl-1H-pyrazolo[3,4-d]pyrimidin-4-amine (140 mg, 0.8248 mmol; Apsel et al., 2008) via the Suzuki reaction in 6 mL 1,2 methoxy ethane, 1 mL of saturated sodium carbonate, 1.65 mL EtOH, and 200 mg of polymer-bound tetrakis Palladium. The reaction was stirred under argon for 12 hours at room temperature, filtered through Whatman paper to remove Palladium, mixed with brine, extracted in chloroform and the product was subsequently purified on silica in EtOAc and concentrated in vacuo. The purified solid 1-isopropyl-3-(4-nitrophenyl)-1H-pyrazolo[3,4-d]pyrimidin-4-amine (ESI-MS m/z [M+H]+ found 299.1, calculated 299.1; 100 mg, 0.336 mmol) was combined with Zinc dust, 5 mL THF, 0.4 mL HOAc for 12 hours at room temperature under Argon. Then the reaction mixture was filtered through Celite®, extracted with EtOAc and concentrated in vacuo to yield 3-(4-aminophenyl)-1-isopropyl-1H-pyrazolo[3,4-d]pyrimidin-4-amine (ESI-MS m/z [M+H]+ found 269.1, calculated 269.1). To this reduced product, molar equivalents of 3-(trifluoromethyl)phenyl isocyanate (Sigma-Aldrich) were added dropwise in ice-cold $CH_2Cl_2$. The reaction proceeded until completion as judged by TLC, was concentrated in vacuo, resuspended in 50:50 $H_2O$-$CH_3CN$, and purified on a C18 column in $CH_3CN/H_2O/0.1\%$ TFA (1-100% gradient) to yield Cmpd 5 1-(4-(4-amino-1-isopropyl-1H-pyrazolo[3,4-d]pyrimidin-3-yl)phenyl)-3-(3-(trifluoromethyl)phenyl)urea (ESI-MS m/z [M+H]+ found 455.2, calculated 455.2; $^1$H NMR (400 MHz, DMSO): δ 9.48 (s, 1H), 9.42 (s, 1H), 8.39 (s, 1H), 8.07 (s, 1H), 7.70 (d, J=8 Hz, 2H), 7.60 (d, J=8 Hz, 2H), 7.60-7.64 (m, 1H), 7.53 (t, J=8 Hz, 1H), 7.33 (d, J=8 Hz, 1H), 5.10 (septet, J=6.8 Hz, 1H), 1.51 (d, J=6 Hz, 6H), 3.10 (q, J=4 Hz, 1.5H, trace triethylamine), 1.18 (t, J=8 Hz, 2H, trace triethylamine). $^{13}$C NMR (400 MHz, DMSO): δ 9.08 (trace triethylamine), 22.23, 46.20 (trace triethylamine), 49.17, 97.40, 115.45, 116.0 (d), 119.20, 122.34, 124.70 (q), 126.19, 129.35, 130.00 (q), 130.40, 140.85, 141.09, 145.20, 151.70, 152.35, 153.00, 155.72, 159.41 (q)).

Example 10

N-(3-((4-amino-1-benzyl-1H-pyrazolo[3,4-d]pyrimidin-3-yl)methyl)phenyl)-3-(trifluoromethyl)benzamide (BB5)

A synthetic strategy for Cmpd BB5 is depicted in Scheme 6 following.

Scheme 6

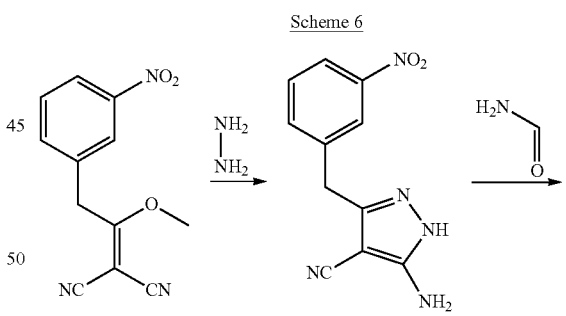

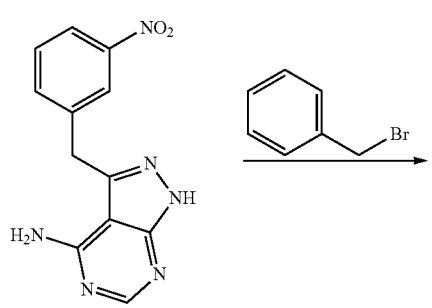

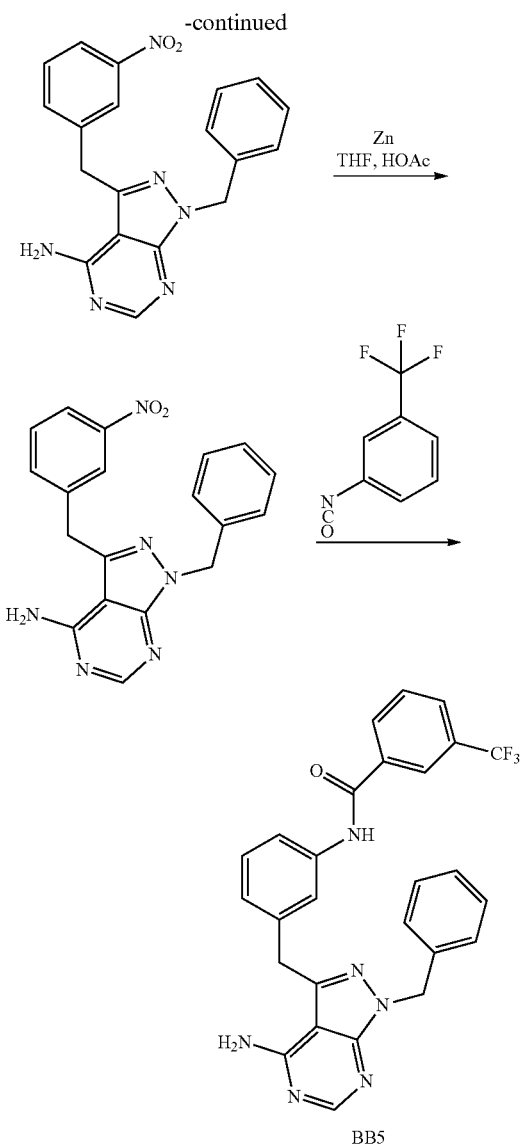

Reagent 2-(1-methoxy-2-(3-nitrophenyl)ethylidene)malononitrile (0.97 g; 4.0 mmol) was combined with hydrazine (0.3 mL; 6.0 mmol; Sigma-Aldrich) in 10 mL EtOH for 90 minutes at room temperature. Afterwards the reaction was concentrated in vacuo, suspended in brine and extracted with chloroform (3×50 mL). The organic layer was dried over MgSO₄, then filtered, and concentrated in vacuo to afford 3-(3-nitrobenzyl)-5-amino-1H-pyrazole-4-carbonitrile (ESI-MS m/z [M+H]+ found 244.5, calculated 244.1). The product was combined with formamide (1.5 mL) and heated to 160° C. overnight. H₂0 was added to the cooled reaction and the precipitate was filtered and dried to afford 3-(3-nitrobenzyl)-1H-pyrazolo[3,4-d]pyrimidin-4-amine (ESI-MS m/z [M+H]+ found 271.4, calculated 271.1). This recovered solid (50 mg, 0.19 mmol) was then added to a solution containing benzyl bromide (0.1 mL, 0.28 mmol), K₂CO₃ (0.125 g), DMF (1.0 mL). The reaction mixture was purged with Argon and stirred overnight at 80° C. The reaction was filtered to remove solid K₂CO₃, and the filtrate was combined with brine and the organic product was extracted in CH₂Cl₂ (3×50 mL) to afford 3-(3-nitrobenzyl)-1-benzyl-1H-pyrazolo[3,4-d]pyrimidin-4-amine (ESI-MS m/z [M+H]+ found 361.4, calculated 361.1).

This precipitated intermediate was then mixed with excess Zinc dust, 5 mL THF, 0.4 mL HOAc for 12 hours under Argon at room temperature. Afterwards the reaction was filtered through Celite®, extracted with EtOAc and concentrated in vacuo to afford 3-(3-aminobenzyl)-1-benzyl-1H-pyrazolo[3,4-d]pyrimidin-4-amine (ESI-MS m/z [M+H]+ found 331.5, calculated 331.2). To this reduced precursor, molar equivalents of 3-(trifluoromethyl) benzoyl chloride (Sigma-Aldrich) were added drop wise in ice-cold CH₂Cl₂. The reaction proceeded until completion as judged by TLC, was concentrated in vacuo, resuspended in 50:50 H₂0-CH₃CN, and purified on a C₁₈ column in CH₃CN/H₂0/0.1% TFA (1-100% gradient) to yield final Cmpd BB5 N-(3-((4-amino-1-benzyl-1H-pyrazolo[3,4-d]pyrimidin-3-yl)methyl)phenyl)-3-(trifluoromethyl)benzamide (ESI-MS m/z [M+H]+ found 503.4, calculated 503.2).

Example 11

1-(3-((4-amino-1-benzyl-1H-pyrazolo[3,4-d]pyrimidin-3-yl)methyl)phenyl)-3-(3-(trifluoromethyl)phenyl)urea (BB6)

To 3-(3-aminobenzyl)-1-benzyl-1H-pyrazolo[3,4-d]pyrimidin-4-amine, molar equivalents of 3-(trifluoromethyl)phenyl isocyanate (Sigma-Aldrich) were added drop wise in ice-cold CH₂Cl₂. The reaction proceeded until completion as judged by TLC, was concentrated in vacuo, resuspended in 50:50 H₂0-CH₃CN, and purified on a C18 column in CH₃CN/H₂0/0.1% TFA (1-100% gradient) to yield final Cmpd BB6 1-(3-((4-amino-1-benzyl-1H-pyrazolo[3,4-d]pyrimidin-3-yl)methyl)phenyl)-3-(3-(trifluoromethyl)phenyl)urea (ESI-MS m/z [M+H]+ found 518.4, calculated 518.2).

Example 12

1-(4-(4-amino-1-methyl-1H-pyrazolo[3,4-d]pyrimidin-3-yl)phenyl)-3-(3-(trifluoromethyl)phenyl)urea (AD59)

A synthetic strategy for Cmpd AD59 is depicted in Scheme 7 following.

Scheme 7

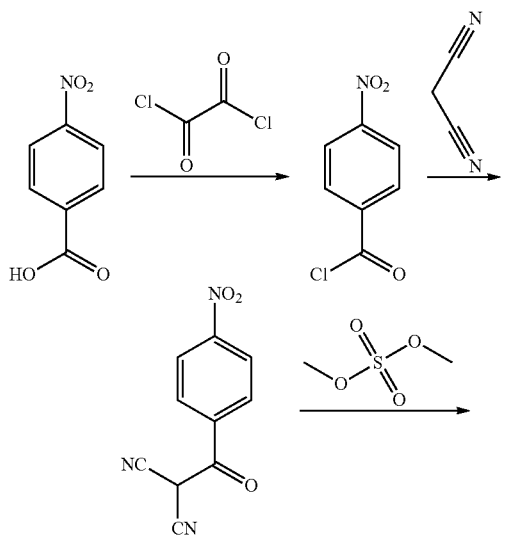

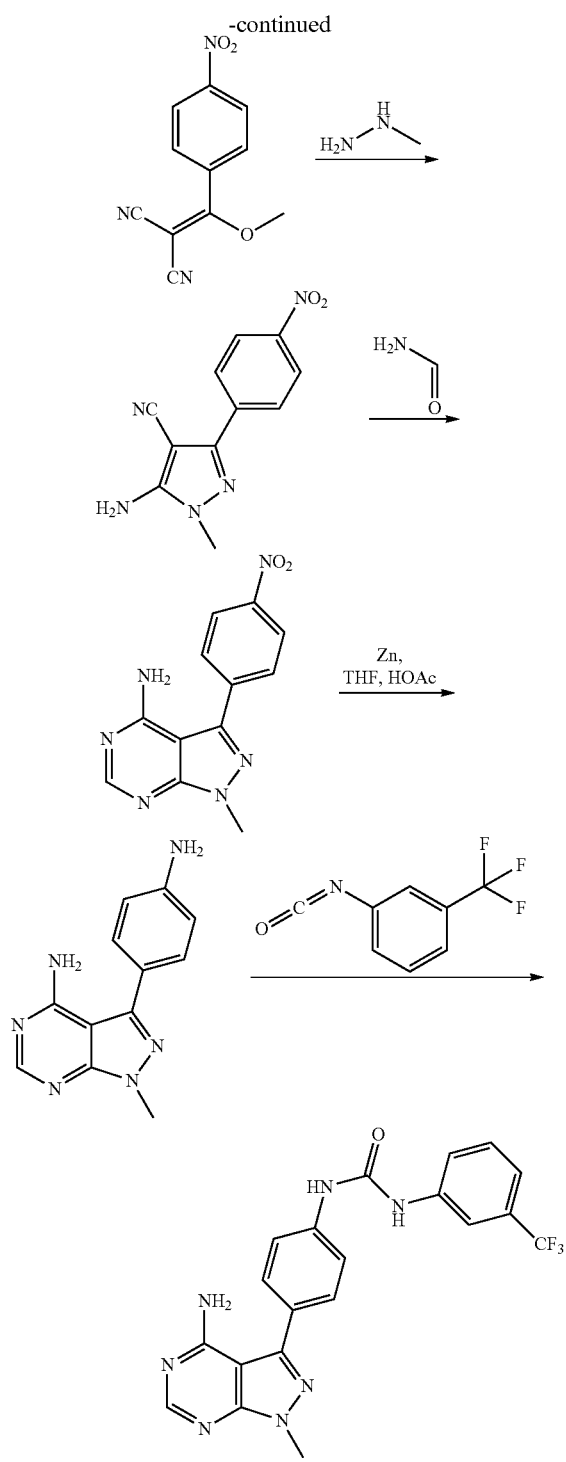

4-nitrobenzoic acid (5 g, 29.9 mmol; Sigma-Aldrich) was combined with oxalyl chloride (13.1 mL, 149.5) and DMF (0.1 mL) in 50 mL of dichloromethane and stirred for 2 hours at room temperature to yield a clear yellow solution. The reaction mixture was concentrated in vacuo and washed twice with dichloromethane to yield a bright yellow solid. The solid was dissolved in dry THF and added drop-wise to a round bottom flask containing a cooled solution of malononitrile (2.96 g, 44.9 mmol) and NaH (8.45 g of a 60% oil emulsion; 95.7 mmol) in THF. The reaction was allowed to warm slowly to room temperature and left for 2 hours. Following, 25 mL of 2N HCl and 50 mL of brine were added and the organic layer was extracted 3 times using EtOAc. The combined organic extracts were dried over $Na_2SO_4$, filtered, and concentrated in vacuo. This brown solid was dissolved in 50 mL of $H_2O$/dioxane (1:8), $NaHCO_3$ (20.1 g, 239 mmol), and dimethyl sulfate (14.2 mL, 150 mmol). The solution was heated to 80° C. for four hours. After cooling, brine was added, and the organic layer was extracted three times using EtOAc. The combined extracts were dried, concentrated in vacuo, and purified on silica in EtOAc-hexanes (50-100% gradient). The pure yellow solid, containing 2-(methoxy(4-nitrophenyl)methylene)malononitrile (100 mg, 0.436 mmol) was added dropwise to monomethylhydrazine (20.1 mg, 0.436 mmol) in ice-cold THF. After 2 hours the reaction was complete as judged by TLC, giving 5-amino-1-methyl-3-(4-nitrophenyl)-1H-pyrazole-4-carbonitrile (ESI-MS m/z [M+H]+ found 243.9, calculated 244.1), which was concentrated in vacuo, suspended in 2 mL of formamide and heated to 165° C. for 12 hours. Following, the solution was cooled, 8 mL of $H_2O$ was added, and a brown solid was collected by filtration. The purified solid 1-methyl-3-(4-nitrophenyl)-1H-pyrazolo[3,4-d]pyrimidin-4-amine (ESI-MS m/z [M+H]+ found 270.9, calculated 271.1; 60 mg, 0.222 mmol) was combined with Zinc dust (0.4 g), 10 mL THF, 0.25 mL HOAc for 12 hours at room temperature. Afterwards, the reaction mixture was filtered through Celite®, extracted with EtOAc and concentrated in vacuo to yield 3-(4-aminophenyl)-1-methyl-1H-pyrazolo[3,4-d]pyrimidin-4-amine (ESI-MS m/z [M+H]+ found 241.0, calculated 241.1). To this reduced product, molar equivalents of 3-(trifluoromethyl)phenyl isocyanate (Sigma-Aldrich) were added dropwise in ice-cold $CH_2Cl_2$. The reaction proceeded until completion as judged by TLC, was concentrated in vacuo, resuspended in 50:50 $H_2O$-$CH_3CN$, and purified on a C18 column in $CH_3CN$/$H_2O$/0.1% TFA (1-100% gradient) to afford Cmpd AD59 1-(4-(4-amino-1-methyl-1H-pyrazolo[3,4-d]pyrimidin-3-yl)phenyl)-3-(3-(trifluoromethyl)phenyl)urea (ESI-MS m/z [M+H]+ found 428.0, calculated 428.1).

Example 13

1-(4-(4-amino-1-cyclopentyl-1H-pyrazolo[3,4-d]pyrimidin-3-yl)phenyl)-3-(3-(trifluoromethyl)phenyl)urea (AD60)

A synthetic strategy for Cmpd AD60 is depicted in Scheme 8 following.

Scheme 8

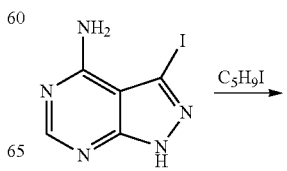

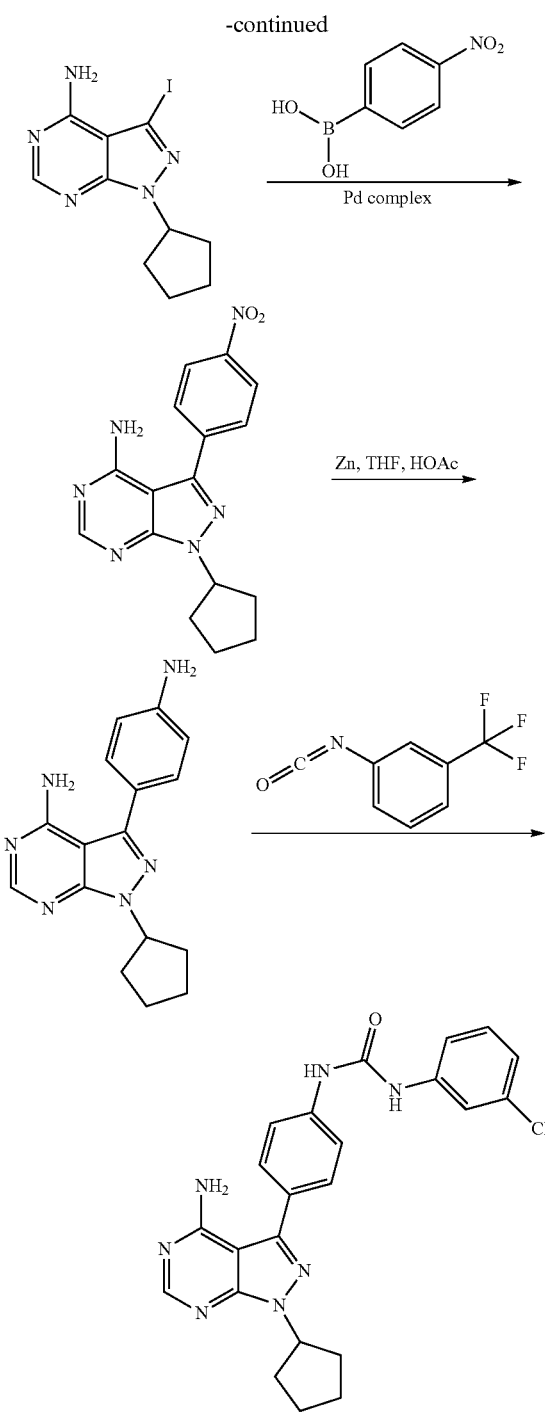

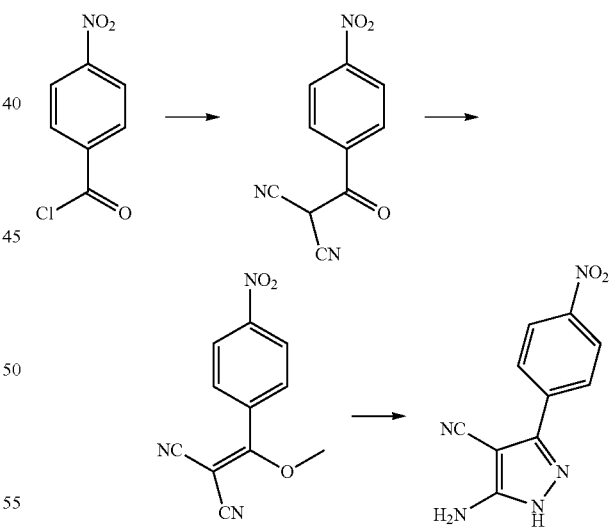

5-amino-3-(4-nitrophenyl)-1H-pyrazole-4-carbonitrile coupled to 1-cyclopentyl-3-iodo-1H-pyrazolo[3,4-d]pyrimidin-4-amine (150 mg, 0.456 mmol) via the Suzuki reaction in 6 mL 1,2 methoxy ethane, 1 mL of saturated sodium carbonate, 1.65 mL EtOH, and 200 mg of polymer-bound tetrakis palladium. The reaction was stirred under argon for 12 hours at room temperature, filtered through Whatman paper to remove palladium, mixed with brine, extracted in chloroform and the product was subsequently purified on silica in EtOAc and concentrated in vacuo. The purified solid 1-cyclopentyl-3-(4-nitrophenyl)-1H-pyrazolo[3,4-d]pyrimidin-4-amine (ESI-MS m/z [M+H]+ found 325.0, calculated 325.1; 100 mg, 0.31 mmol) was combined with Zinc dust (605 mg, 9.25 mmol), 10 mL THF, 0.35 mL HOAc for 12 hours at room temperature under Argon. The reaction was filtered through Celite®, extracted with EtOAc and concentrated in vacuo to yield 3-(4-aminophenyl)-1-cyclopentyl-1H-pyrazolo[3,4-d]pyrimidin-4-amine (ESI-MS m/z [M+H]+ found 295.0, calculated 295.2). To this reduced product, molar equivalents of 3-(trifluoromethyl)phenyl isocyanate (Sigma-Aldrich) were added dropwise in ice-cold CH2Cl2. The reaction proceeded until completion as judged by TLC, was concentrated in vacuo, resuspended in 50:50 H20-CH3CN, and purified on a C18 column in CH3CN/H20/0.1% TFA (1-100% gradient) to yield AD60 1-(4-(4-amino-1-cyclopentyl-1H-pyrazolo[3,4-d]pyrimidin-3-yl)phenyl)-3-(3-(trifluoromethyl)phenyl)urea (ESI-MS m/z [M+H]+ found 482.2, calculated 482.0).

Example 14

1-(4-(4-amino-1-(3-hydroxypropyl)-1H-pyrazolo[3,4-d]pyrimidin-3-yl)phenyl)-3-(3-(trifluoromethyl)phenyl)urea (AD64)

Step 1

Reagent 3-iodo-1H-pyrazolo[3,4-d]pyrimidin-4-amine) (0.5 g; 1.9 mmol; Apsel et al., 2008, Id.) was combined with cyclopentyl iodide (0.24 mL; 2.1 mmol), 1.06 g K2CO3, in 20 mL DMF and heated to 45° C. under argon for 2 hours. The reaction was filtered to remove solid K₂CO₃, and the filtrate was combined with brine and the organic product was extracted in CH₂Cl₂ (3×50 mL). The combined organic layer was concentrated in vacuo and purified by silica gel chromatography (MeOH/Chloroform; 5:95) to afford 1-cyclopentyl-3-iodo-1H-pyrazolo[3,4-d]pyrimidin-4-amine (ESI-MS m/z [M+H]+ found 330.0, calculated 330.0). 4-nitrophenyl boronic acid (190 mg, 1.1 mmol; Sigma-Aldrich), was A 1000 mL round bottom flask was pre-cooled in an ice-water bath, to which a solution of malononitrile (10.2 g, 0.154 mol) was mixed into a suspension of sodium hydride (6.72 g, 0.28 mol) in THF (100 mL). To this mixture, 4-nitrobenzoyl chloride (26 g, 0.14 mol; Sigma-Aldrich) was added slowly. After 20 minutes, the reaction was removed from the ice-water bath and left stirring for 2 hours. Dimethyl sulfate (16 mL, 0.168 mol) was then added with a syringe. The reaction vessel was placed into an oil bath at 90° C. and almost immediately afterwards a yellow solid began to form. The reaction was left at 90° C. for 2 hours. The reaction mixture was removed from the oil bath and allowed to cool to room temperature. Afterwards, hydrazine (7.5 mL, 0.154 mol) was added, and the reaction was left stirring for 60 minutes. 200 mL of brine and 100 mL of 2N HCl were added and separated from the organic layer. The aqueous phase was extracted two additional times with CH$_2$Cl$_2$. The organic phases were combined and concentrated in vacuo to yield a bright yellow solid. The solid was suspended in 100 mL EtOH, refluxed for 30 minutes, and the insoluble solid was collected by filtration, washed with room temperature EtOH, and dried to yield 5-amino-3-(4-nitrophenyl)-1H-pyrazole-4-carbonitrile (9.1 g, 28% yield).

Step 2

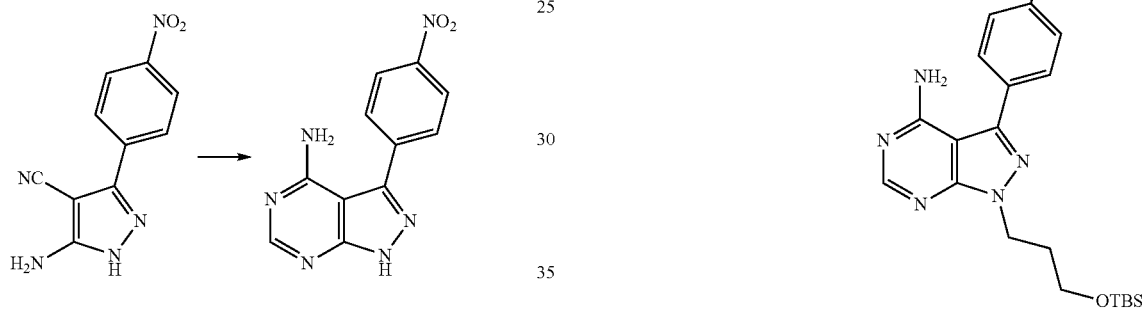

3-(4-nitrophenyl)-1H-pyrazolo[3,4-d]pyrimidin-4-amine

A solution of formamide (30 mL) and 5-amino-3-(4-nitrophenyl)-1H-pyrazole-4-carbonitrile (7.25 g, 32 mmol) was heated to 160° C. overnight under an argon atmosphere. The reaction was cooled, and 25 mL of H$_2$O was added. The resulting solid was recovered by filtration and rinsed with cold H$_2$O to afford 3-(4-nitrophenyl)-1H-pyrazolo[3,4-d]pyrimidin-4-amine (5.9 g, 72% yield). ESI-MS m/z [M+H]+ found 257.5, calculated 257.2.

Step 3

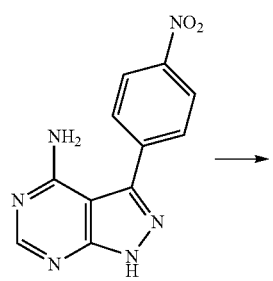

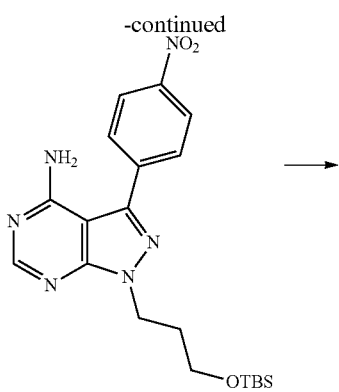

3-(-t-butyldimethylsilyloxy)-protected 3-(4-amino-3-(4-aminophenyl)-1H-pyrazolo[3,4-d]pyrimidin-1-yl)propan-1-ol A solution of 3-(4-nitrophenyl)-1H-pyrazolo[3,4-d]pyrimidin-4-amine (0.5 g, 1.95 mmol) and K$_2$CO$_3$ (1.08 g, 7.8 mmol) in DMF (20 mL) was brought to 80° C. under an argon atmosphere. 3-(-t-butyldimethylsilyloxy)propyl bromide (0.54 mL, 2.34 mmol) was added with a syringe. The reaction mixture was left stirring for 3 hours. The reaction mixture was cooled and then filtered. The filtrate was concentrated in vacuo, but not to dryness. 14 mL of 0.1 sodium citrate was added causing an orange solid to form, which was collected by filtration to afford TBS-protected 3-(4-amino-3-(4-nitrophenyl)-1H-pyrazolo[3,4-d]pyrimidin-1-yl)propan-1-ol (0.79 g, 94% yield). ESI-MS m/z [M+H]+ found 429.6, calculated 429.6.

The orange solid (400 mg, 0.93 mmol) was combined with zinc dust (1.8 g, 28 mmol), 10 mL THF, and 1 mL HOAc for 12 hours at room temperature under an argon atmosphere. Following, the reaction mixture was filtered through Celite®, extracted with EtOAc, and concentrated in vacuo to afford TBS-protected 3-(4-amino-3-(4-aminophenyl)-1H-pyrazolo[3,4-d]pyrimidin-1-yl)propan-1-ol. ESI-MS m/z [M+H]+ found 399.7, calculated 399.6).

Step 4

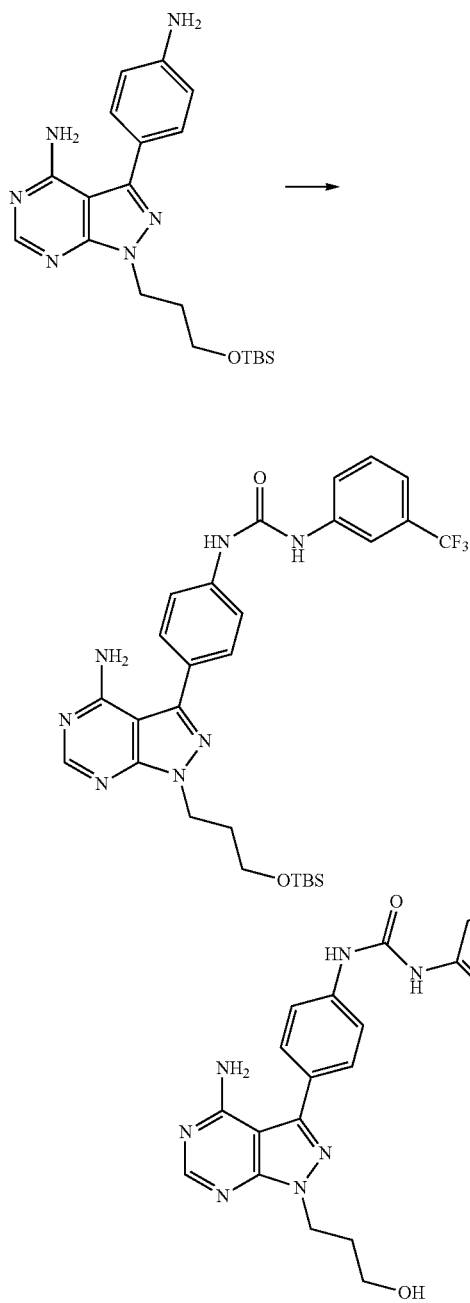

A solution of TBS-protected 3-(4-amino-3-(4-aminophenyl)-1H-pyrazolo[3,4-d]pyrimidin-1-yl)propan-1-ol (0.2 g, 0.51 mmol) in CH$_2$Cl$_2$ (10 mL) was cooled in an ice-water bath. To this, 3-(trifluoromethyl)phenyl isocyanate (0.072 mL, 0.5 mmol) diluted in CH$_2$Cl$_2$ (5 mL) was added dropwise. The reaction was allowed to warm to room temperature and left stirring for 12 hours. Formation of the urea intermediate was judged by TLC and LC-MS (ESI-MS m/z [M+H]+ found 586.8, calculated 587.7). Then 2N HCl (3 mL) was added into the reaction mixture. After 1 hour, water (25 mL) was added, and organic phases were extracted (2×50 mL CH$_2$Cl$_2$). Organic phases were concentrated in vacuo and purified using silica gel column chromatography (EtOAc, 100%) to afford final compound AD64. ESI-MS m/z [M+H]+ found 472.6, calculated 472.4.

Example 15

N-(4-(4-amino-1-(3-hydroxypropyl)-1H-pyrazolo[3,4-d]pyrimidin-3-yl)phenyl)-3-(trifluoromethyl)benzamide (AD65)

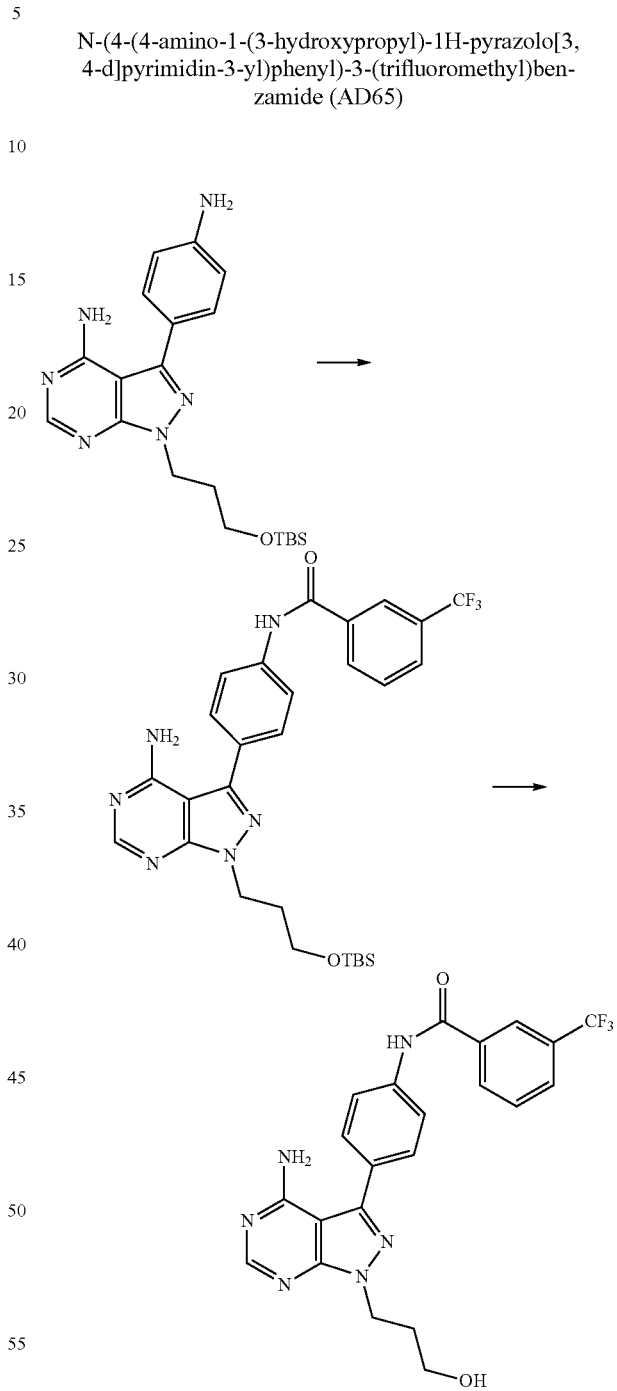

A solution of TBS-protected 3-(4-amino-3-(4-aminophenyl)-1H-pyrazolo[3,4-d]pyrimidin-1-yl)propan-1-ol (0.2 g, 0.51 mmol) in CH$_2$Cl$_2$ (10 mL) was cooled in an ice-water bath. To this, 3-(trifluoromethyl)benzoyl chloride (0.074 mL, 0.5 mmol; Sigma-Aldrich) diluted in CH$_2$Cl$_2$ (5 mL) was added dropwise. The reaction was allowed to warm to room temperature and left stirring for 3 hours. Formation of the benzamide intermediate was judged by TLC and LC-MS (ESI-MS m/z [M+H]+ found 571.7, calculated 571.2). Afterwards, 2N HCl (3 mL) was added directly to the reaction mixture and stirred for 1 hour. Water (25 mL) was added, and organic phases were extracted (2×CH$_2$Cl$_2$). Organic phases were concentrated in vacuo and purified using silica gel column chromatography (EtOAc, 100%) to afford final compound AD65. ESI-MS m/z [M+H]+ found 457.6, calculated 457.2.

Example 16

1-(4-(4-amino-1-((S)-tetrahydrofuran-3-yl)-1H-pyrazolo[3,4-d]pyrimidin-3-yl)phenyl)-3-(3-(trifluoromethyl)phenyl)urea (AD66)

Step 1

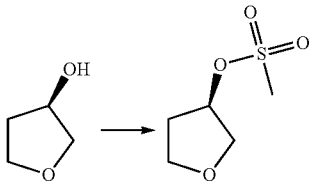

(R)-tetrahydrofuran-3-yl methanesulfonate

A solution of (R)-tetrahydrofuran-3-ol (1.1 g, 12.5 mmol) and triethylamine (13.6 mL, 97.5 mmol) in CH$_2$Cl$_2$ was cooled in an ice-water bath. To this, methanesulfonyl chloride (3.0 mL, 39 mmol) diluted in CH$_2$Cl$_2$ (10 mL) was added dropwise. The reaction was left stirring for 12 hours at room temperature. Water was added, and organic phases extracted in CH$_2$Cl$_2$ (3×50 mL), which were subsequently dried onto silica and purified by silica gel chromatography (50% EtOAc:Hexanes to 100% EtOAc gradient) to afford (R)-tetrahydrofuran-3-yl methanesulfonate (0.97 g, brown oil, 47% yield).

Step 2

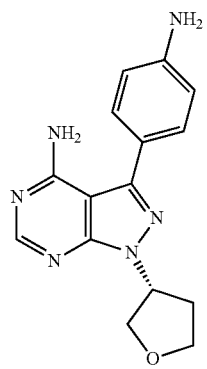

3-(4-aminophenyl)-1-((S)-tetrahydrofuran-3-yl)-1H-pyrazolo[3,4-d]pyrimidin-4-amine A solution of 3-(4-nitrophenyl)-1H-pyrazolo[3,4-d]pyrimidin-4-amine (0.5 g, 1.95 mmol), K$_2$CO$_3$ (1.08 g, 7.8 mmol), and (R)-tetrahydrofuran-3-yl methanesulfonate (0.389 g, 2.34 mmol) in DMF (20 mL) was brought to 80° C. under an argon atmosphere. The reaction mixture was left stirring for 3 hours, then cooled and filtered. The filtrate was concentrated in vacuo, but not to dryness. 20 mL of 0.1 sodium citrate was added causing a solid to form, which was collected by filtration to afford 1-((S)-tetrahydrofuran-3-yl)-3-(4-nitrophenyl)-1H-pyrazolo[3,4-d]pyrimidin-4-amine. ESI-MS m/z [M+H]+ found 327.6, calculated 327.3.

The resulting solid (250 mg, 0.77 mmol) was combined with zinc dust (1.5 g, 23 mmol), 30 mL THF, and 0.9 mL HOAc for 12 hours at room temperature under an argon atmosphere. Following, the reaction mixture was filtered through Celite® and concentrated in vacuo to afford 3-(4-aminophenyl)-1-((S)-tetrahydrofuran-3-yl)-1H-pyrazolo[3,4-d]pyrimidin-4-amine. ESI-MS m/z [M+H]+ found 297.2, calculated 297.1).

Step 3

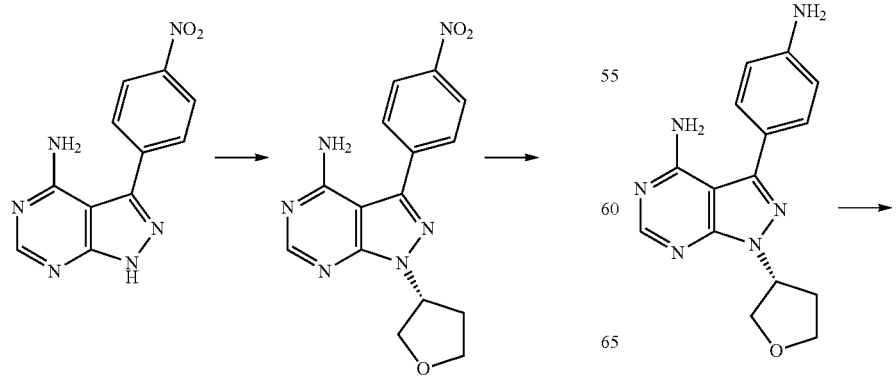

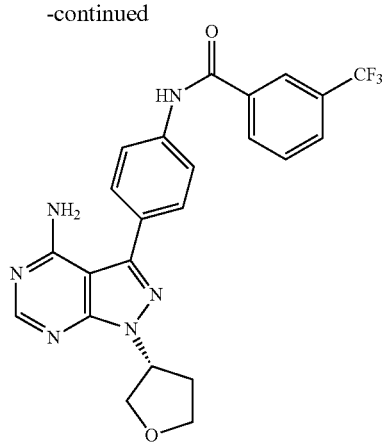

A solution of 3-(4-aminophenyl)-1-((S)-tetrahydrofuran-3-yl)-1H-pyrazolo[3,4-d]pyrimidin-4-amine (0.1 g, 0.34 mmol) in CH$_2$Cl$_2$ (10 mL) was cooled in an ice-water bath. To this, 3-(trifluoromethyl)benzoyl chloride (0.050 mL, 0.34 mmol) diluted in CH$_2$Cl$_2$ (5 mL) was added dropwise. The reaction was allowed to warm to room temperature and left stirring for 12 hours. The reaction proceeded until completion as judged by TLC and LC-MS, was concentrated in vacuo, resuspended in 50:50 H$_2$O—CH$_3$CN, and purified on a C18 column in CH$_3$CN/H$_2$O/0.1% TFA (1-100% gradient) to afford AD67. ESI-MS m/z [M+H]+ found 469.4, calculated 469.2.

Example 18

N-(4-(4-amino-1-((R)-tetrahydrofuran-3-yl)-1H-pyrazolo[3,4-d]pyrimidin-3-yl)phenyl)-3-(trifluoromethyl)benzamide (AD68)

Step 1

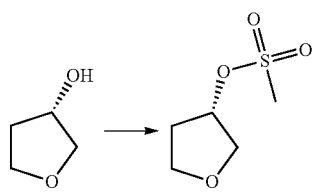

(S)-tetrahydrofuran-3-yl methanesulfonate

A solution of (S)-tetrahydrofuran-3-ol (1.0 g, 11 mmol) and triethylamine (9.4 mL, 86 mmol) in CH$_2$Cl$_2$ (20 mL) was cooled in an ice-water bath. To this, methanesulfonyl chloride (3.0 mL, 39 mmol) diluted in CH$_2$Cl$_2$ (10 mL) was added dropwise. The reaction was left stirring for 12 hours at room temperature. Water was added, and organic phases extracted in CH$_2$Cl$_2$ (3×50 mL), which were subsequently dried onto silica and purified by silica gel chromatography (50% EtOAc: Hexanes to 100% EtOAc gradient) to afford (S)-tetrahydrofuran-3-yl methanesulfonate (1.52 g, brown oil, 83% yield).

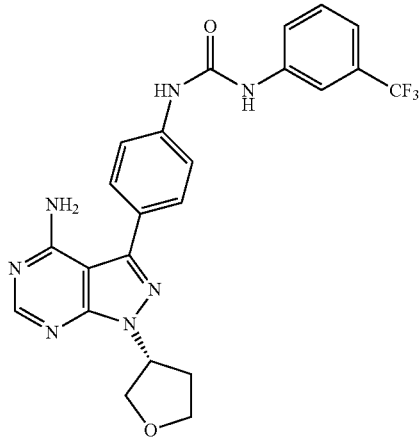

A solution of 3-(4-aminophenyl)-1-((S)-tetrahydrofuran-3-yl)-1H-pyrazolo[3,4-d]pyrimidin-4-amine (0.1 g, 0.34 mmol) in CH$_2$Cl$_2$ (10 mL) was cooled in an ice-water bath. To this, 3-(trifluoromethyl)phenyl isocyanate (0.047 mL, 0.34 mmol) diluted in CH$_2$Cl$_2$ (5 mL) was added dropwise. The reaction was allowed to warm to room temperature and left stirring for 12 hours. Reaction completion was judged by TLC and LC-MS. The reaction mixture was filtered, dried onto silica, and purified using silica gel column chromatography (50% EtOAc:Hexanes to 100% EtOAc gradient) to afford final compound AD66. ESI-MS m/z [M+H]+ found 484.4, calculated 484.2.

Example 17

N-(4-(4-amino-1-((S)-tetrahydrofuran-3-yl)-1H-pyrazolo[3,4-d]pyrimidin-3-yl)phenyl)-3-(trifluoromethyl)benzamide (AD67)

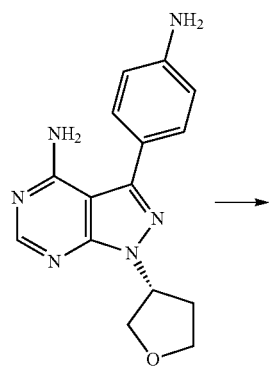

Step 2

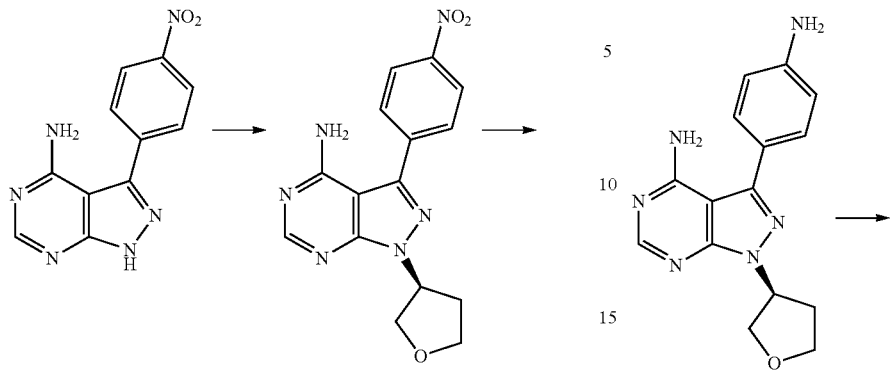

Step 3

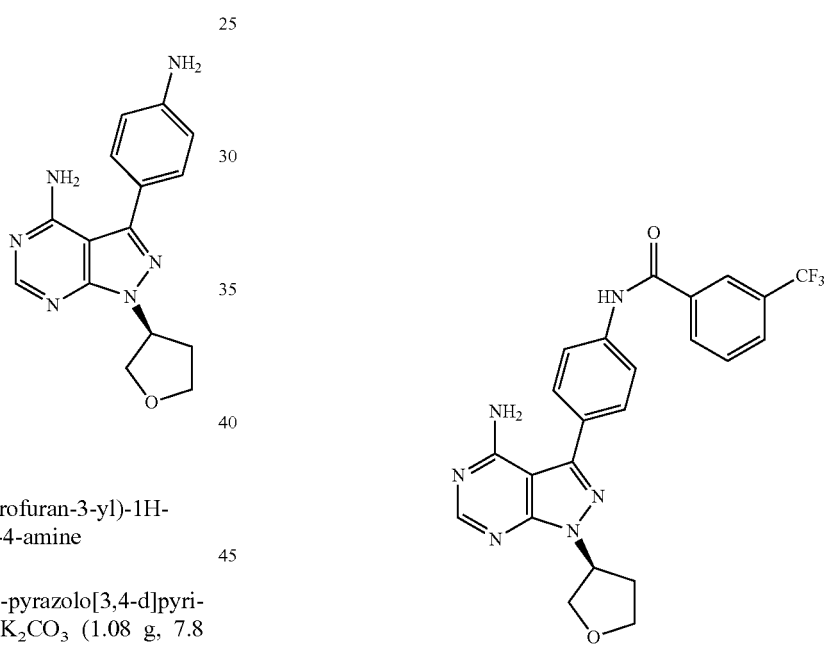

3-(4-aminophenyl)-1-((R)-tetrahydrofuran-3-yl)-1H-pyrazolo[3,4-d]pyrimidin-4-amine A solution of 3-(4-nitrophenyl)-1H-pyrazolo[3,4-d]pyrimidin-4-amine (0.5 g, 1.95 mmol), $K_2CO_3$ (1.08 g, 7.8 mmol), and (S)-tetrahydrofuran-3-yl methanesulfonate (0.389 g, 2.34 mmol) in DMF (20 mL) was brought to 80° C. under an argon atmosphere. The reaction mixture was left stirring for 3 hours, then cooled and filtered. The filtrate was concentrated in vacuo, but not to dryness. 20 mL of 0.1 sodium citrate was added causing a solid to form, which was collected by filtration to afford 1-((R)-tetrahydrofuran-3-yl)-3-(4-nitrophenyl)-1H-pyrazolo[3,4-d]pyrimidin-4-amine. ESI-MS m/z [M+H]+ found 327.6, calculated 327.3.

The resulting solid (250 mg, 0.77 mmol) was combined with zinc dust (1.5 g, 23 mmol), 30 mL THF, and 0.9 mL HOAc for 12 hours at room temperature under an argon atmosphere. Following, the reaction mixture was filtered through Celite® and concentrated in vacuo to afford 3-(4-aminophenyl)-1-((R)-tetrahydrofuran-3-yl)-1H-pyrazolo[3,4-d]pyrimidin-4-amine. ESI-MS m/z [M+H]+ found 297.5, calculated 297.1).

A solution of 3-(4-aminophenyl)-1-((R)-tetrahydrofuran-3-yl)-1H-pyrazolo[3,4-d]pyrimidin-4-amine (0.075 g, 0.25 mmol) in $CH_2Cl_2$ (10 mL) was cooled in an ice-water bath. To this, 3-(trifluoromethyl)benzoyl chloride (0.035 mL, 0.25 mmol) diluted in $CH_2Cl_2$ (5 mL) was added dropwise. The reaction was allowed to warm to room temperature and left stirring for 12 hours. The reaction proceeded until completion as judged by TLC and LC-MS, was concentrated in vacuo, resuspended in 50:50 $H_2O$—$CH_3CN$, and purified on a C18 column in $CH_3CN/H_2O/0.1\%$ TFA (1-100% gradient) to afford AD68. ESI-MS m/z [M+H]+ found 469.4, calculated 469.2.

81

Example 19

1-(4-(4-amino-1-((R)-tetrahydrofuran-3-yl)-1H-pyrazolo[3,4-d]pyrimidin-3-yl)phenyl)-3-(3-(trifluoromethyl)phenyl)urea (AD69)

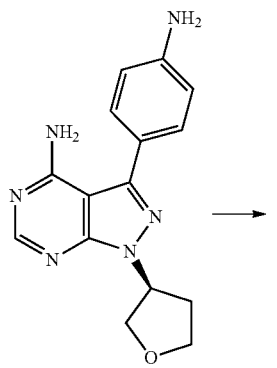

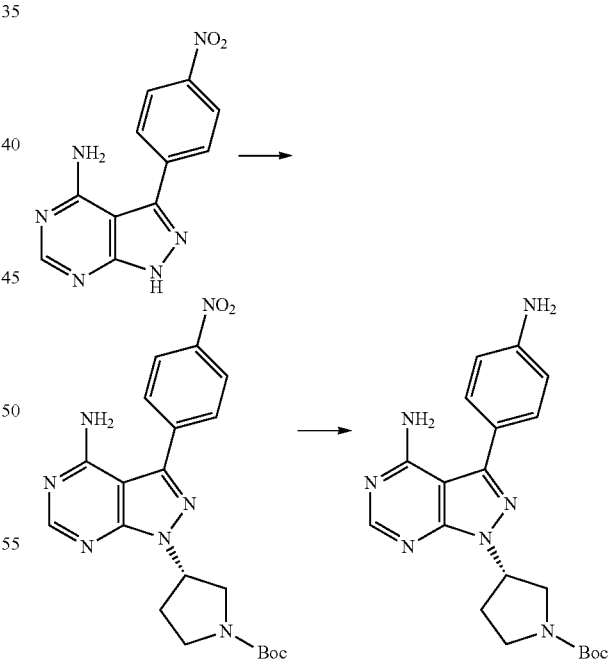

A solution of 3-(4-aminophenyl)-1-((R)-tetrahydrofuran-3-yl)-1H-pyrazolo[3,4-d]pyrimidin-4-amine (0.075 g, 0.25 mmol) in CH$_2$Cl$_2$ (10 mL) was cooled in an ice-water bath. To this, 3-(trifluoromethyl)phenyl isocyanate (0.035 mL, 0.25 mmol) diluted in CH$_2$Cl$_2$ (5 mL) was added dropwise. The reaction was allowed to warm to room temperature and left stirring for 12 hours. The reaction proceeded until completion as judged by TLC and LC-MS, was concentrated in vacuo, resuspended in 50:50 H$_2$O—CH$_3$CN, and purified on a C18 column in CH$_3$CN/H$_2$O/0.1% TFA (1-100% gradient) to afford AD69. ESI-MS m/z [M+H]+ found 484.4, calculated 484.4.

82

Example 20

N-(4-(4-amino-1-((S)-pyrrolidin-3-yl)-1H-pyrazolo[3,4-d]pyrimidin-3-yl)phenyl)-3-(trifluoromethyl)benzamide (AD070)

Step 1

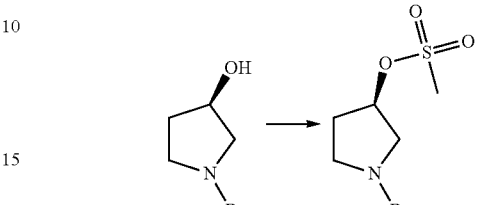

(R)-1-(tert-butoxycarbonyl)pyrrolidin-3-yl methanesulfonate

A solution of (R)-tert-butyl 3-hydroxypyrrolidine-1-carboxylate (1.0 g, 5.3 mmol) and triethylamine (2.77 mL, 20 mmol) in CH$_2$Cl$_2$ (20 mL) was cooled in an ice-water bath. To this, methanesulfonyl chloride (1.15 mL, 15 mmol) diluted in CH$_2$Cl$_2$ (10 mL) was added dropwise. The reaction was left stirring for 12 hours at room temperature. Water was added, and organic phases extracted in CH$_2$Cl$_2$ (3×50 mL), which were subsequently dried onto silica and purified by silica gel chromatography (50% EtOAc:Hexanes to 100% EtOAc gradient) to afford (R)-1-(tert-butoxycarbonyl)pyrrolidin-3-yl methanesulfonate (1.53 g, brown oil, 100% yield).

Step 2

(S)-tert-butyl 3-(4-amino-3-(4-aminophenyl)-1H-pyrazolo[3,4-d]pyrimidin-1-yl)pyrrolidine-1-carboxylate A solution of 3-(4-nitrophenyl)-1H-pyrazolo[3,4-d]pyrimidin-4-amine (0.5 g, 1.95 mmol), K$_2$CO$_3$ (1.08 g, 7.8 mmol), and (R)-1-(tert-butoxycarbonyl)pyrrolidin-3-yl methanesulfonate (0.62 g, 2.34 mmol) in DMF (20 mL) was brought to 80° C. under an argon atmosphere. The reaction mixture was left stirring for 6 hours, then cooled and filtered. The filtrate was concentrated in vacuo, but not to dryness. 20 mL of 0.1 sodium citrate was added causing a solid to form, which was collected by filtration to afford (S)-tert-butyl 3-(4-amino-3-(4-nitrophenyl)-1H-pyrazolo[3,4-d]pyrimidin-1-yl)pyrrolidine-1-carboxylate (0.43 g, 52% yield). ESI-MS m/z [M+H]+ found 426.7, calculated 426.2.

The resulting solid (330 mg, 0.78 mmol) was combined with zinc dust (1.5 g, 23 mmol), 30 mL THF, and 0.9 mL HOAc for 12 hours at room temperature under an argon atmosphere. Following, the reaction mixture was filtered through Celite®, mixed with water, and extracted with EtOAc. The organic phases were concentrated in vacuo to afford (S)-tert-butyl 3-(4-amino-3-(4-aminophenyl)-1H-pyrazolo[3,4-d]pyrimidin-1-yl)pyrrolidine-1-carboxylate. ESI-MS m/z [M+H]+ found 396.5, calculated 396.5).

Step 3

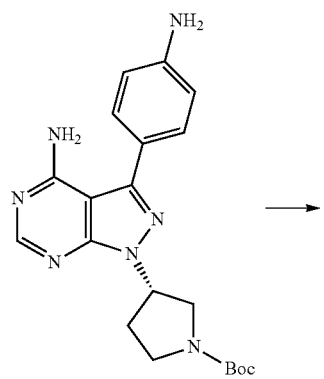

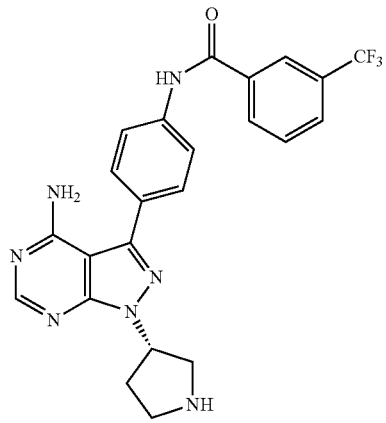

A solution of (S)-tert-butyl 3-(4-amino-3-(4-aminophenyl)-1H-pyrazolo[3,4-d]pyrimidin-1-yl)pyrrolidine-1-carboxylate (0.075 g, 0.17 mmol) in CH$_2$Cl$_2$ (10 mL) was cooled in an ice-water bath. To this, 3-(trifluoromethyl)benzoyl chloride (0.025 mL, 0.17 mmol) diluted in CH$_2$Cl$_2$ (5 mL) was added dropwise. The reaction was allowed to warm to room temperature and left stirring for 4 hours, yielding the benzamide derivative (ESI-MS m/z [M+H]+ found 568.5, calculated 568.6). Boc-deprotection was completed through the addition of formic acid (5 mL) and concentrated HCl (0.5 mL) added dropwise directly to the reaction mixture. The reaction mixture was left stirring for 12 hours and then was concentrated in vacuo, resuspended in 50:50 H$_2$O—CH$_3$CN, and purified on a C18 column in CH$_3$CN/H$_2$O/0.1% TFA (1-100% gradient) to afford AD70. ESI-MS m/z [M+H]+ found 468.5, calculated 468.2.

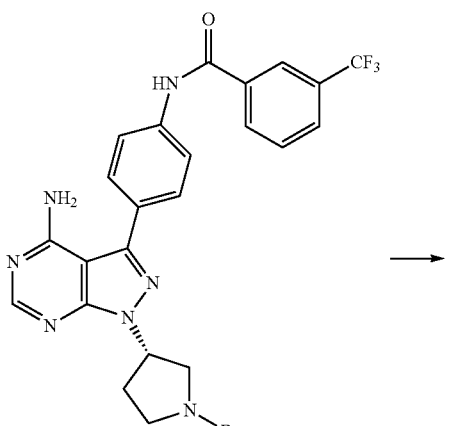

Example 21a 1-(4-(4-amino-1-((S)-pyrrolidin-3-yl)-1H-pyrazolo [3,4-d]pyrimidin-3-yl)phenyl)-3-(3-(trifluoromethyl) phenyl)urea (AD71a)

Example 21b (S)-3-(4-amino-3-(4-aminophenyl)-1H-pyrazolo[3,4-d]pyrimidin-1-yl)-N-(3-(trifluoromethyl)phenyl) pyrrolidine-1-carboxamide (AD71b)

Example 21c (S)-3-(4-amino-3-(4-(3-(3-(trifluoromethyl)phenyl)ureido)phenyl)-1H-pyrazolo[3,4-d]pyrimidin-1-yl)-N-(3-(trifluoromethyl)phenyl)pyrrolidine-1-carboxamide (AD71c)

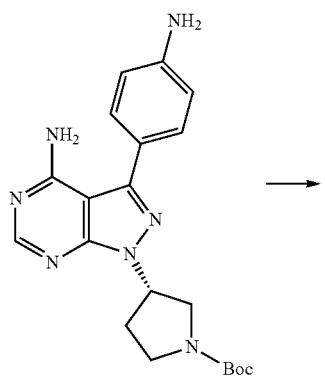

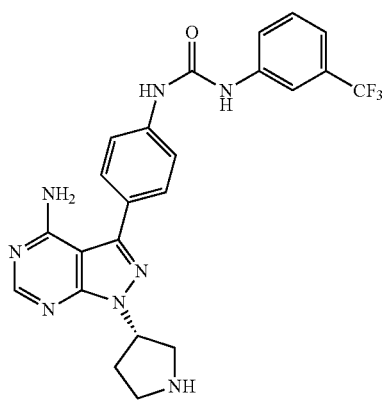
AD71a

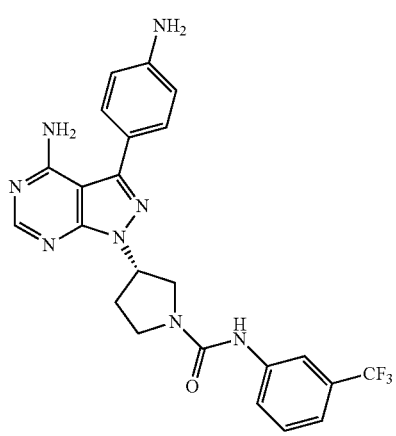
AD71b

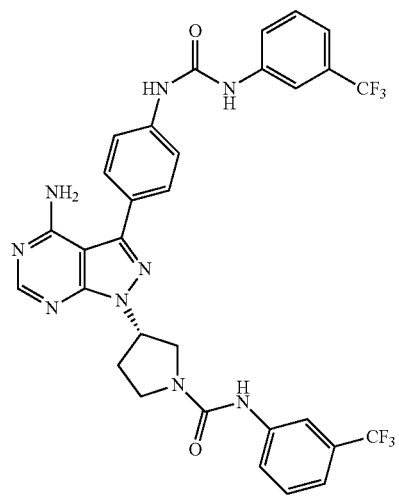
AD71c

A solution of (S)-tert-butyl 3-(4-amino-3-(4-aminophenyl)-1H-pyrazolo[3,4-d]pyrimidin-1-yl)pyrrolidine-1-carboxylate (0.080 g, 0.17 mmol) in CH$_2$Cl$_2$ (10 mL) was cooled in an ice-water bath. To this, 3-(trifluoromethyl)phenyl isocyanate (0.026 mL, 0.19 mmol) diluted in CH$_2$Cl$_2$ (5 mL) was added dropwise. The reaction was allowed to warm to room temperature and left stirring for 6 hours. After, formic acid (5 mL) and concentrated HCl (0.5 mL) were added dropwise directly to the reaction mixture. Three major species were observed by LC-MS corresponding to AD71a, AD71b, and AD71c. The reaction mixture was left stirring for 12 hours and then was concentrated in vacuo, resuspended in 50:50 H$_2$O—CH$_3$CN, and purified on a C$_{18}$ column in CH$_3$CN/H$_2$O/0.1% TFA (1-100% gradient) to afford AD71a (ESI-MS m/z [M+H]+ found 483.5, calculated 483.2), AD71b (ESI-MS m/z [M+H]+ found 483.5, calculated 483.2), and AD71c (ESI-MS m/z [M+H]+ found 670.5, calculated 670.2).

Example 22

N-(4-(4-amino-1-((R)-pyrrolidin-3-yl)-1H-pyrazolo[3,4-d]pyrimidin-3-yl)phenyl)-3-(trifluoromethyl)benzamide (AD72)

Step 1

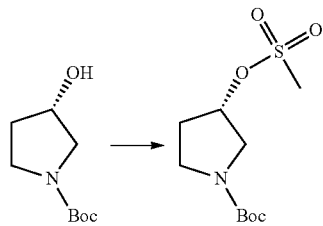 [SMILES: CC(C)(C)OC(=O)N1CC[C@H](O)C1 ; CC(C)(C)OC(=O)N1CC[C@H](OS(C)(=O)=O)C1]

(S)-1-(tert-butoxycarbonyl)pyrrolidin-3-yl methanesulfonate

A solution of (S)-tert-butyl 3-hydroxypyrrolidine-1-carboxylate (1.0 g, 5.3 mmol) and triethylamine (2.77 mL, 20 mmol) in CH$_2$Cl$_2$ (20 mL) was cooled in an ice-water bath. To this, methanesulfonyl chloride (1.15 mL, 15 mmol) diluted in CH$_2$Cl$_2$ (10 mL) was added dropwise. The reaction was left stirring for 12 hours at room temperature. Water was added, and organic phases extracted in CH$_2$Cl$_2$ (3×50 mL), which were subsequently dried onto silica and purified by silica gel chromatography (50% EtOAc:Hexanes to 100% EtOAc gradient) to afford (S)-1-(tert-butoxycarbonyl)pyrrolidin-3-yl methanesulfonate (0.97 g, brown oil, 70% yield).

Step 2

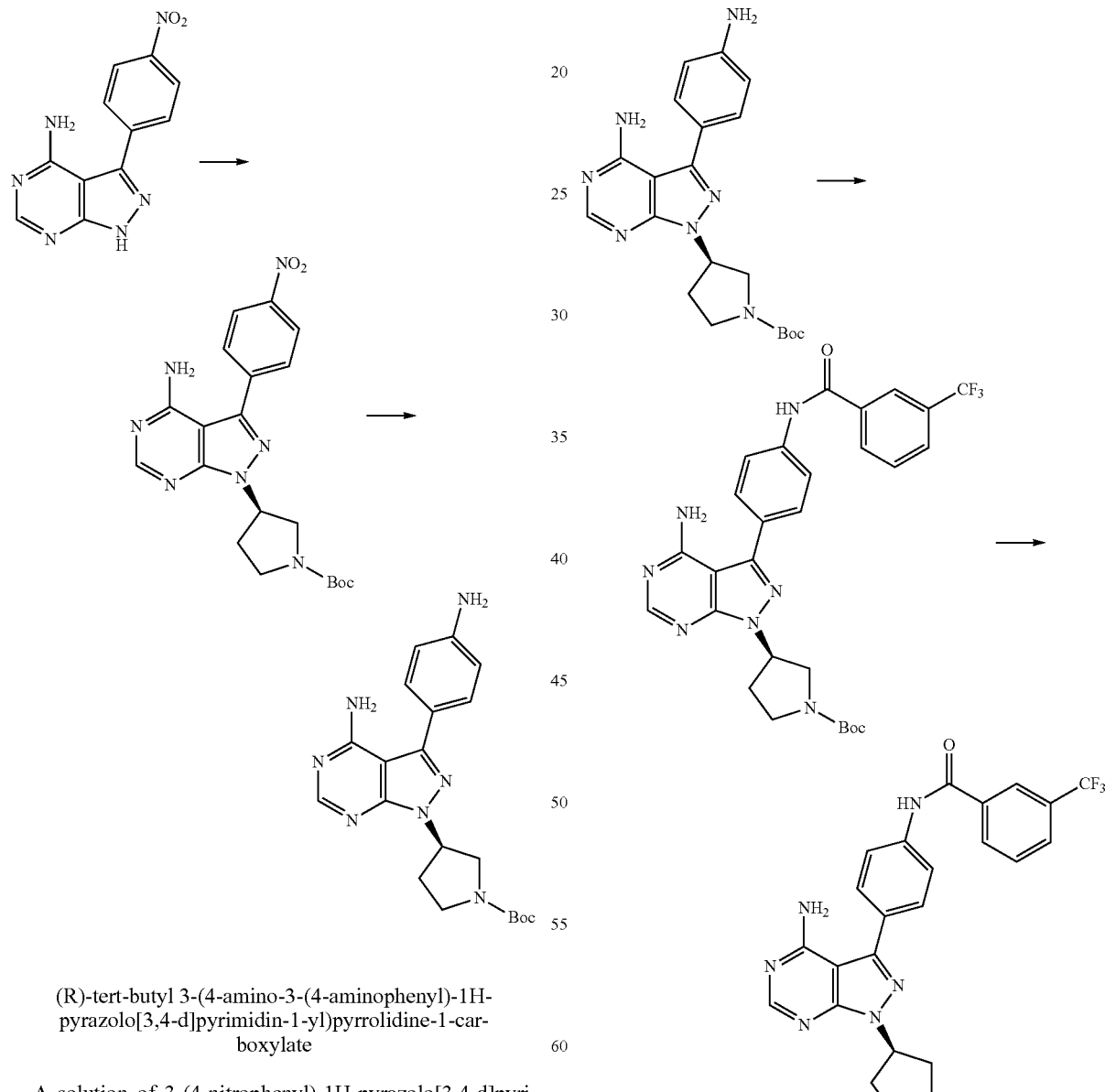

(R)-tert-butyl 3-(4-amino-3-(4-aminophenyl)-1H-pyrazolo[3,4-d]pyrimidin-1-yl)pyrrolidine-1-carboxylate A solution of 3-(4-nitrophenyl)-1H-pyrazolo[3,4-d]pyrimidin-4-amine (0.5 g, 1.95 mmol), K$_2$CO$_3$ (1.08 g, 7.8 mmol), and (S)-1-(tert-butoxycarbonyl)pyrrolidin-3-yl methanesulfonate (0.62 g, 2.34 mmol) in DMF (20 mL) was brought to 80° C. under an argon atmosphere. The reaction mixture was left stirring for 2 hours, then cooled and filtered. The filtrate was concentrated in vacuo, but not to dryness. 20 mL of 0.1 sodium citrate was added causing a solid to form, which was collected by filtration to afford (R)-tert-butyl 3-(4-amino-3-(4-nitrophenyl)-1H-pyrazolo[3,4-d]pyrimidin-1-yl)pyrrolidine-1-carboxylate (0.38 g, 46% yield). ESI-MS m/z [M+H]+ found 426.5, calculated 426.2.

The resulting solid (300 mg, 0.70 mmol) was combined with zinc dust (1.4 g, 21 mmol), 30 mL THF, and 0.8 mL HOAc for 12 hours at room temperature under an argon atmosphere. Following, the reaction mixture was filtered through Celite® and concentrated in vacuo to afford (R)-tert-butyl 3-(4-amino-3-(4-aminophenyl)-1H-pyrazolo[3,4-d]pyrimidin-1-yl)pyrrolidine-1-carboxylate. ESI-MS m/z [M+H]+ found 396.5, calculated 396.5.

Step 3

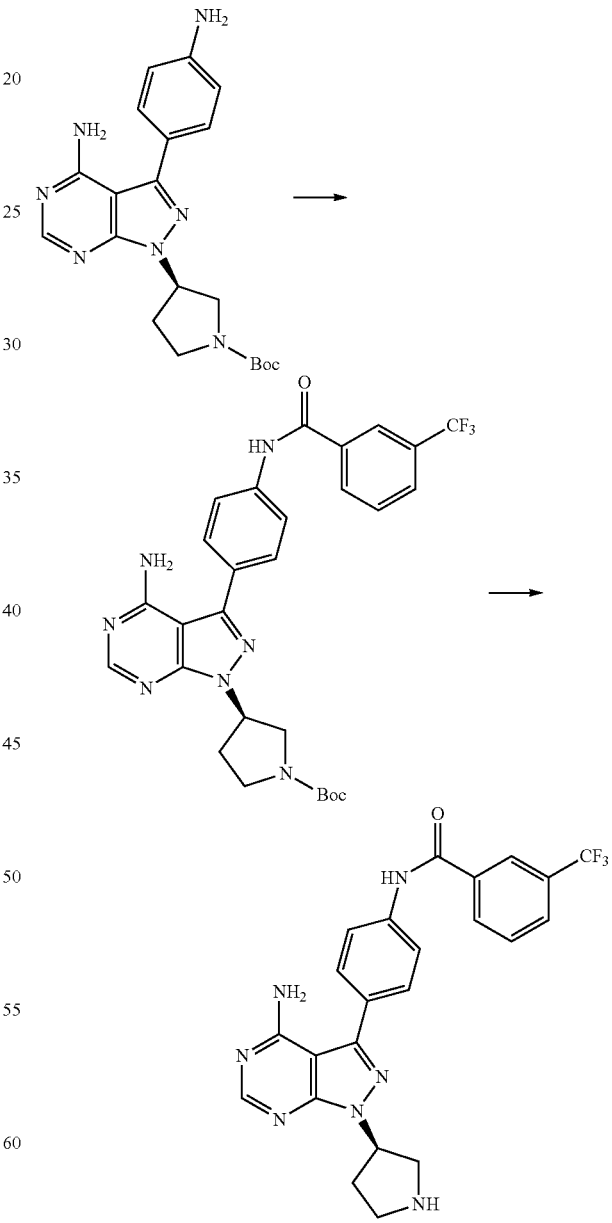

A solution of (R)-tert-butyl 3-(4-amino-3-(4-aminophenyl)-1H-pyrazolo[3,4-d]pyrimidin-1-yl)pyrrolidine-1-carboxylate (0.055 g, 0.14 mmol) in CH$_2$Cl$_2$ (10 mL) was cooled in an ice-water bath. To this, 3-(trifluoromethyl)benzoyl chloride (0.021 mL, 0.14 mmol) diluted in $CH_2Cl_2$ (5 mL) was added dropwise. The reaction was allowed to warm to room temperature and left stirring for 4 hours, yielding the benzamide derivative. Boc-deprotection was completed through the addition of formic acid (5 mL) and concentrated HCl (0.5 mL) added dropwise directly to the reaction mixture. The reaction mixture was left stirring for 12 hours and then was concentrated in vacuo, resuspended in 50:50 $H_2O$—$CH_3CN$, and purified on a C18 column in $CH_3CN/H_2O/0.1\%$ TFA (1-100% gradient) to afford AD72. ESI-MS m/z [M+H]+ found 468.5, calculated 468.2.

Example 23a 1-(4-(4-amino-1-((R)-pyrrolidin-3-yl)-1H-pyrazolo[3,4-d]pyrimidin-3-yl)phenyl)-3-(3-(trifluoromethyl)phenyl)urea (AD73a)

Example 23b (R)-3-(4-amino-3-(4-aminophenyl)-1H-pyrazolo[3,4-d]pyrimidin-1-yl)-N-(3-(trifluoromethyl)phenyl)pyrrolidine-1-carboxamide (AD73b)

Example 23c (R)-3-(4-amino-3-(4-(3-(3-(trifluoromethyl)phenyl)ureido)phenyl)-1H-pyrazolo[3,4-d]pyrimidin-1-yl)-N-(3-(trifluoromethyl)phenyl)pyrrolidine-1-carboxamide (AD73c)

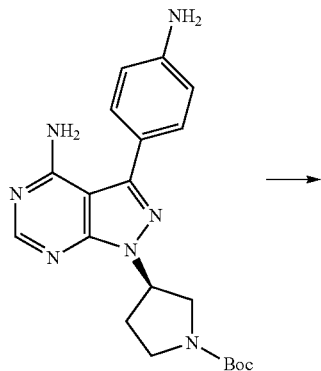

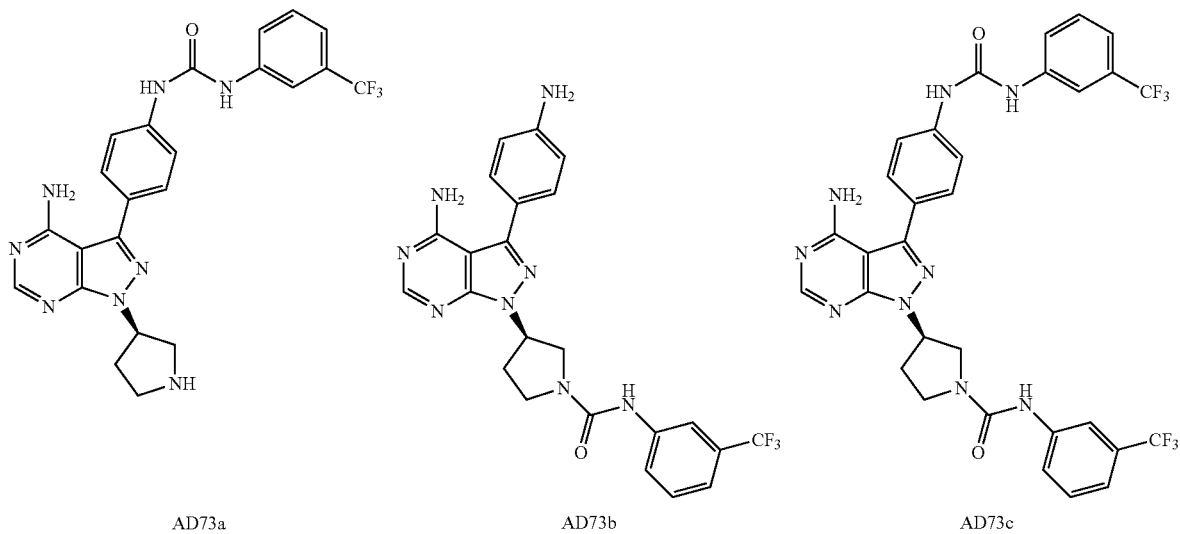

AD73a      AD73b      AD73c

A solution of (R)-tert-butyl 3-(4-amino-3-(4-aminophenyl)-1H-pyrazolo[3,4-d]pyrimidin-1-yl)pyrrolidine-1-carboxylate (0.090 g, 0.23 mmol) in $CH_2Cl_2$ (10 mL) was cooled in an ice-water bath. To this, 3-(trifluoromethyl)phenyl isocyanate (0.032 mL, 0.23 mmol) diluted in $CH_2Cl_2$ (5 mL) was added dropwise. The reaction was allowed to warm to room temperature and left stirring for 6 hours. After, formic acid (5 mL) and concentrated HCl (0.5 mL) were added dropwise directly to the reaction mixture. Three major species were observed by LC-MS corresponding to AD73a, AD73b, and AD73c. The reaction mixture was left stirring for 12 hours and then was concentrated in vacuo, resuspended in 50:50 $H_2O$—$CH_3CN$, and purified on a C18 column in $CH_3CN$/$H_2O$/0.1% TFA (1-100% gradient) to afford AD73a (ESI-MS m/z [M+H]+ found 483.5, calculated 483.2), AD73b (ESI-MS m/z [M+H]+ found 483.5, calculated 483.2), and AD73c (ESI-MS m/z [M+H]+ found 670.5, calculated 670.2).

Example 24

(S)-tert-butyl 3-(4-amino-3-(4-(3-(3-(trifluoromethyl)phenyl)ureido)phenyl)-1H-pyrazolo[3,4-d]pyrimidin-1-yl)pyrrolidine-1-carboxylate (AD78)

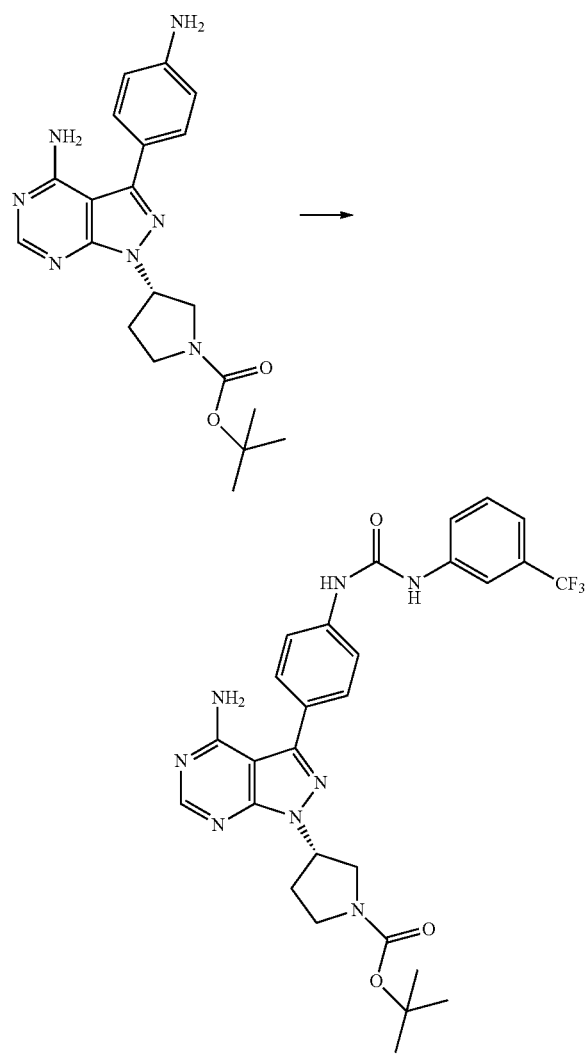

A solution of (S)-tert-butyl 3-(4-amino-3-(4-aminophenyl)-1H-pyrazolo[3,4-d]pyrimidin-1-yl)pyrrolidine-1-carboxylate (0.035 g, 0.09 mmol) in $CH_2Cl_2$ (10 mL) was cooled in an ice-water bath. To this, 3-(trifluoromethyl)phenyl isocyanate (0.012 mL, 0.09 mmol) diluted in $CH_2Cl_2$ (5 mL) was added dropwise. The reaction was allowed to warm to room temperature and left stirring for 6 hours. The reaction proceeded until completion as judged by TLC and LC-MS, was concentrated in vacuo, resuspended in 50:50 $H_2O$—$CH_3CN$, and purified on a C18 column in $CH_3CN$/$H_2O$/0.1% TFA (1-100% gradient) to afford AD78. ESI-MS m/z [M+H]+ found 583.5, calculated 583.2.

Example 25

(R)-tert-butyl 3-(4-amino-3-(4-(3-(3-(trifluoromethyl)phenyl)ureido)phenyl)-1H-pyrazolo[3,4-d]pyrimidin-1-yl)pyrrolidine-1-carboxylate (AD79)

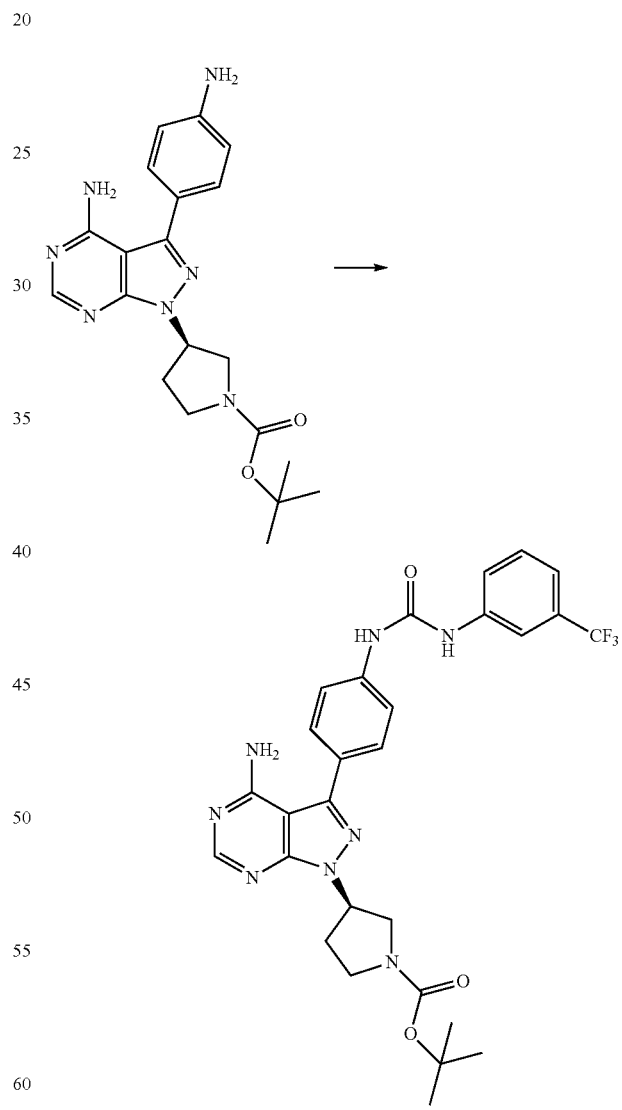

A solution of (R)-tert-butyl 3-(4-amino-3-(4-aminophenyl)-1H-pyrazolo[3,4-d]pyrimidin-1-yl)pyrrolidine-1-carboxylate (0.100 g, 0.25 mmol) in $CH_2Cl_2$ (10 mL) was cooled in an ice-water bath. To this, 3-(trifluoromethyl)phenyl isocyanate (0.035 mL, 0.25 mmol) diluted in $CH_2Cl_2$ (5 mL) was added dropwise. The reaction was allowed to warm to room temperature and left stirring for 6 hours. The reaction proceeded until completion as judged by TLC and LC-MS, was concentrated in vacuo, resuspended in 50:50 $H_2O$—$CH_3CN$, and purified on a C18 column in $CH_3CN/H_2O/0.1\%$ TFA (1-100% gradient) to afford AD79. ESI-MS m/z [M+H]+ found 583.5, calculated 583.2.

Example 26

Cell Based Assays: Inhibition of Bcr-Abl and T315I Bcr-Abl

The ability of AD57 to inhibit Bcr-Abl and T315I Bcr-Abl was examined in a cell based assay. The Bcr-Abl oncogene was transduced into BaF3 cells, rendering them IL-3-independent. "IL-3" refers to interleukin 3 which in human maps to gene locus 5q31.1, as known in the art. Recombinant IL-3 is available commercially. BaF3 is a hematopoietic cell line that is normally dependent on IL-3 for growth and proliferation. However, through expression of activated Bcr-Abl, the cells become transformed to an IL-3 independent state. In this assay, cell proliferation is directly correlated to the activity of Bcr-Abl. Wild-type Bcr-Abl, T315I Bcr-Abl, and parental BaF3 cells were treated with AD57 (Cmpd 5) at the indicated concentrations for two days. The parental BaF3 cells, but not the Bcr-Abl transduced cells, were grown in the presence of recombinant IL-3 during the time course of this experiment. After the two day treatment, cell proliferation was quantified using the dye Resazurin, which is converted into a fluorescently detectable form only when metabolized by living cells.

Figure 7A:
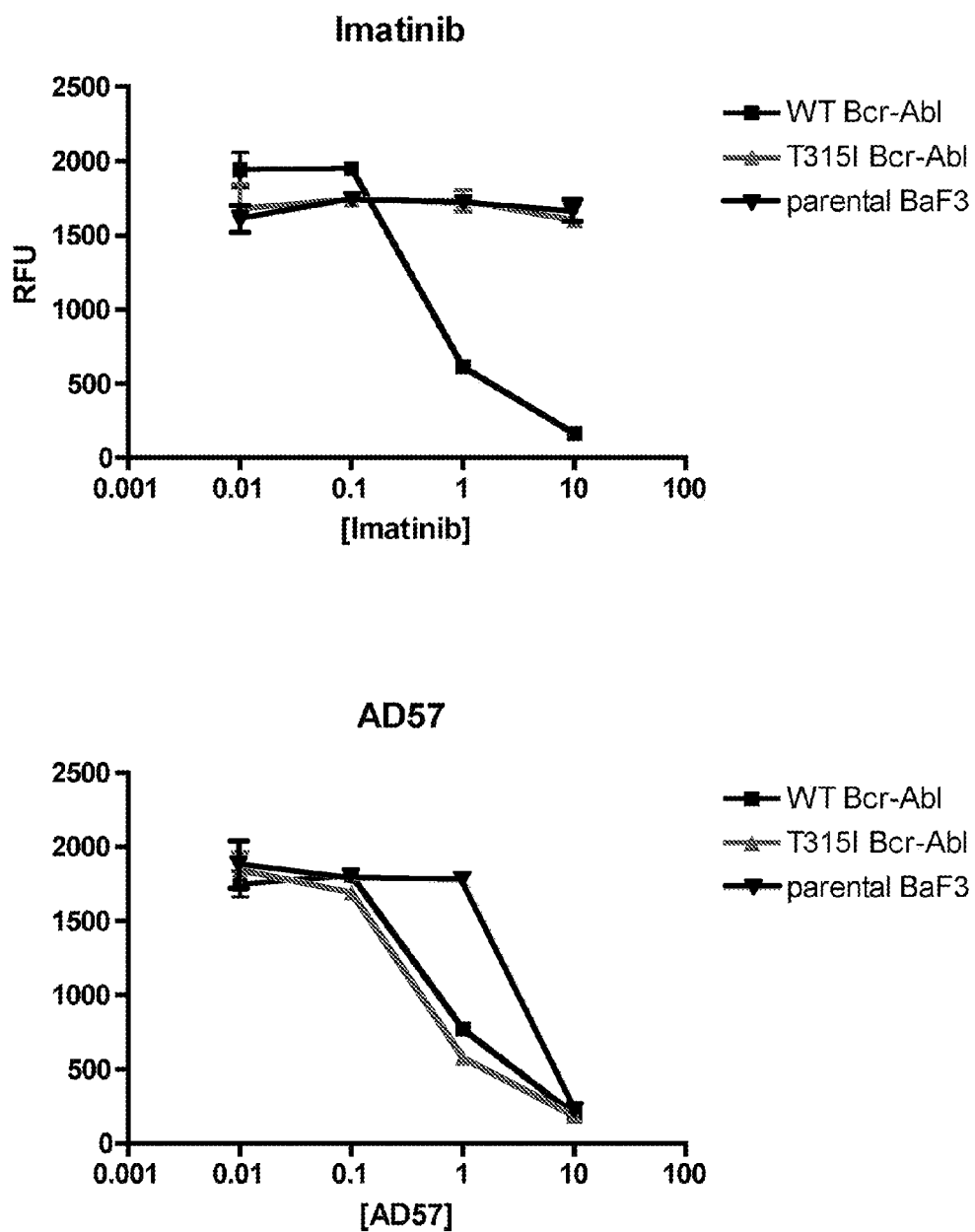
FIG. 7. Cell-based assays to test the ability of AD57 to inhibit Bcr-ABL and T3151 Bcr-Abl in BaF3 cells. A-C. Cell proliferation was quantified by incubation with Resazurin for the indicated time period after 2 or 3 days of drug exposure.
Figure 7B:
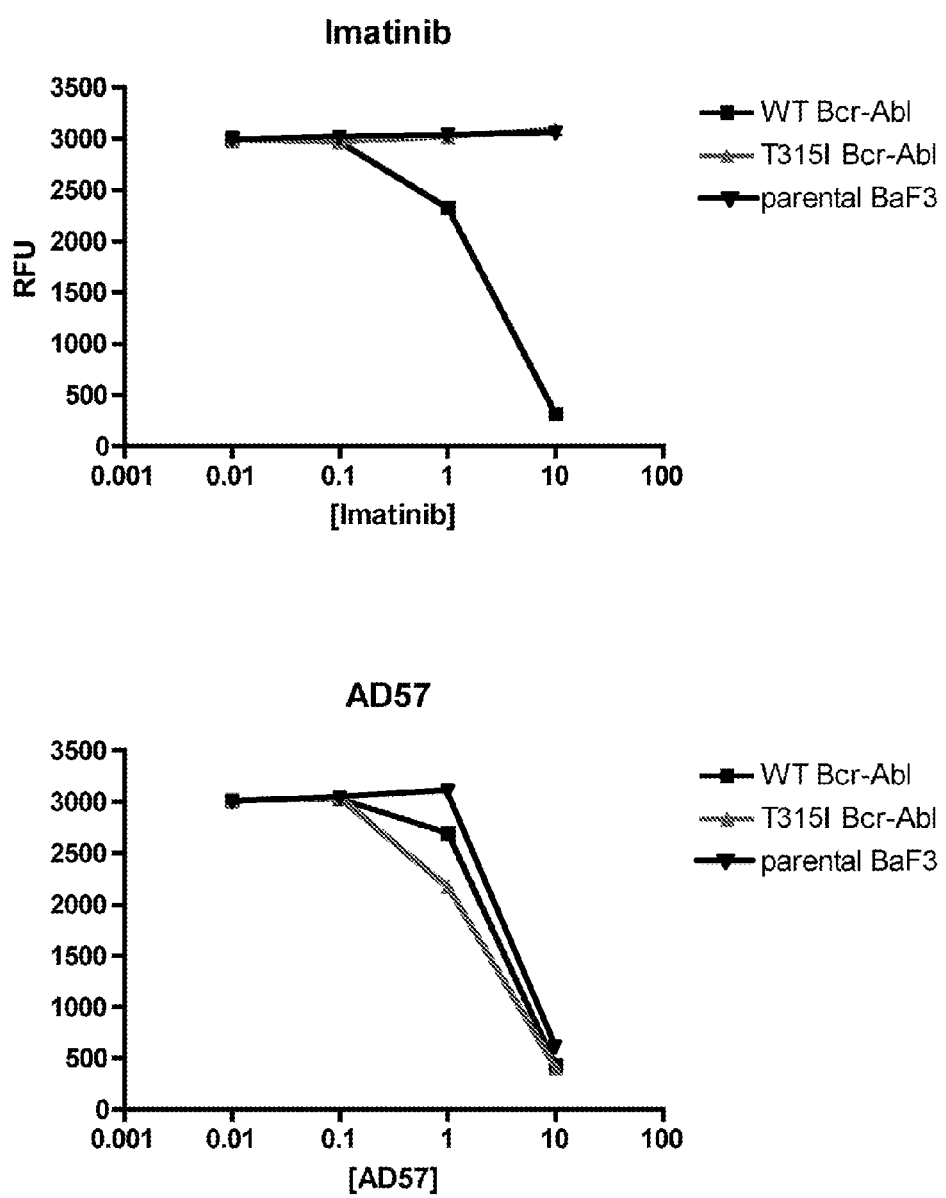
Figure 7C:
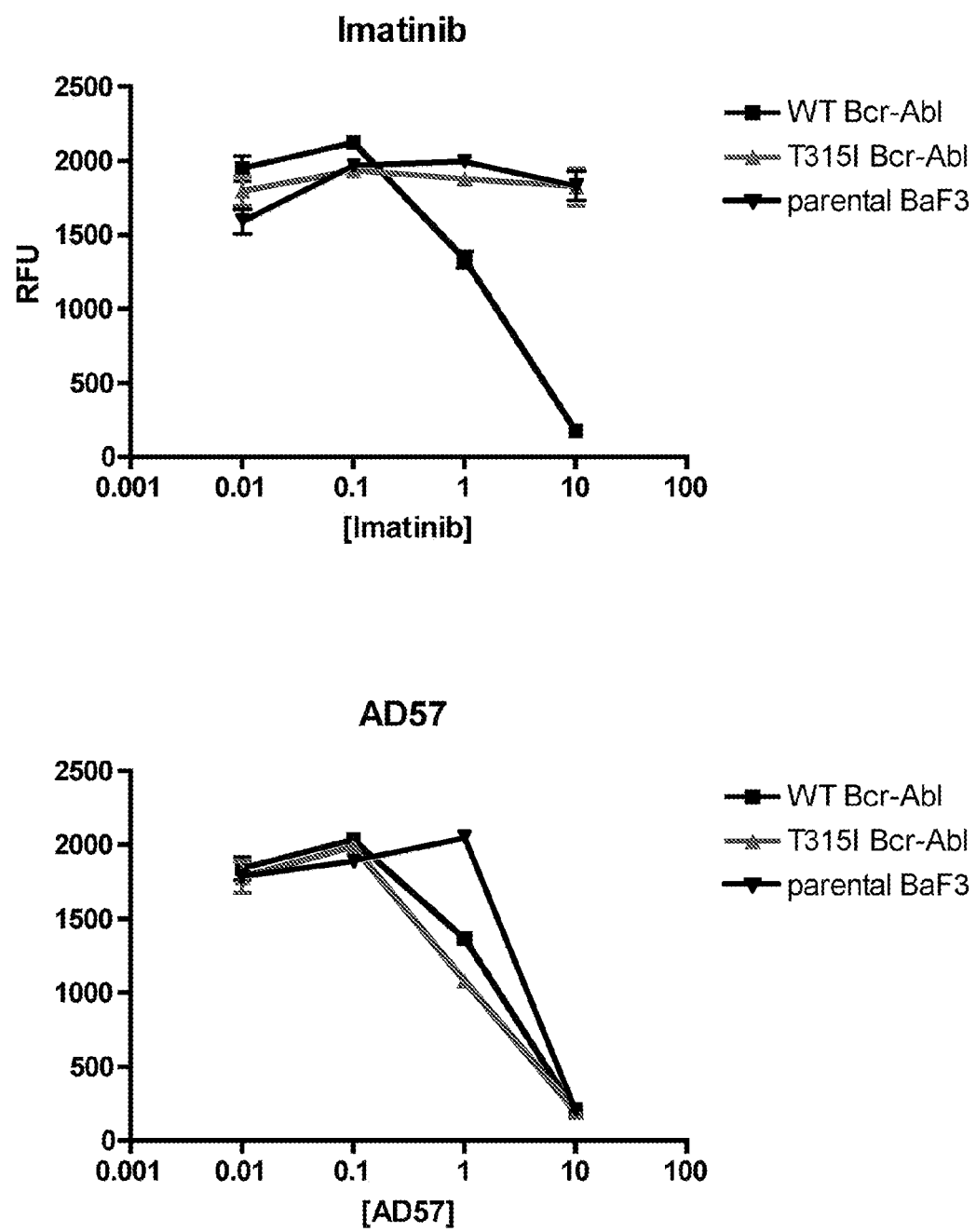

FIG. 7 A-C shows that AD57 (Cmpd 5) equally inhibits the growth of Bcr-Abl and T315I Bcr-Abl cells. According to the crystal structure of AD57 (Cmpd 5) in complex with Src, the ability of AD57 (Cmpd 5) to equally inhibit WT and T315I Bcr-Abl is likely mediated through its unique ability to recognize the DFG-out conformation of the kinase, but in a manner that renders the drug insensitive to mutations at the Thr315 position. Notably, the effects of AD57 (Cmpd 5) on WT and T315I Bcr-Abl differ with respect to Imatinib, which effectively inhibits Bcr-Abl, but not the T315I mutant. This result suggests that AD57 (Cmpd 5) will be effective in inhibiting the growth of cancer cells that are dependent of Bcr-Abl, and will not be rendered ineffective by the emergence of drug-resistant clones, including the highly prevalent T315I Bcr-Abl mutant. Cancers that have been treated by Imatinib include CML, gastrointestinal stromal tumors, hypereoinophilic syndrome, and Ph-positive acute lymphoblastic leukemia. Resistance to Imatinib in these cancers has been linked to mutations at the position that is analogous T315I, including T6701 in c-Kit (SEQ ID NO:3) and T674I in PDGFR (SEQ ID NO:10). Since AD57 (Cmpd 5) inhibits T315I Bcr-Abl, it is plausible that the inhibitor will be effective against Bcr-Abl, c-Kit, PDGFR, and their Imatinib-resistant forms in these cancers.

It is possible to inhibit the growth of BaF3 cells transduced with Bcr-Abl through non-specific inhibition mediated toxicity. Therefore, the effects of the inhibitors on the growth of parental BaF3 cells have also been measured. AD57 (Cmpd 5) preferentially inhibits Bcr-Abl transformed BaF3 cells, but not parental BaF3 cells (especially comparing the growth of cells at 1 mM inhibitor). This suggests that the primary target of AD57 (Cmpd 5) in the BaF3-Bcr-Abl cells is indeed Bcr-Abl. This result also suggests that the effects of AD57 (Cmpd 5) on Bcr-Abl transduced BaF3 cells is not mediated through a generally toxic mechanism.

Example 27

Developing a DFG-Out Binder for c-Src

Figure 5:
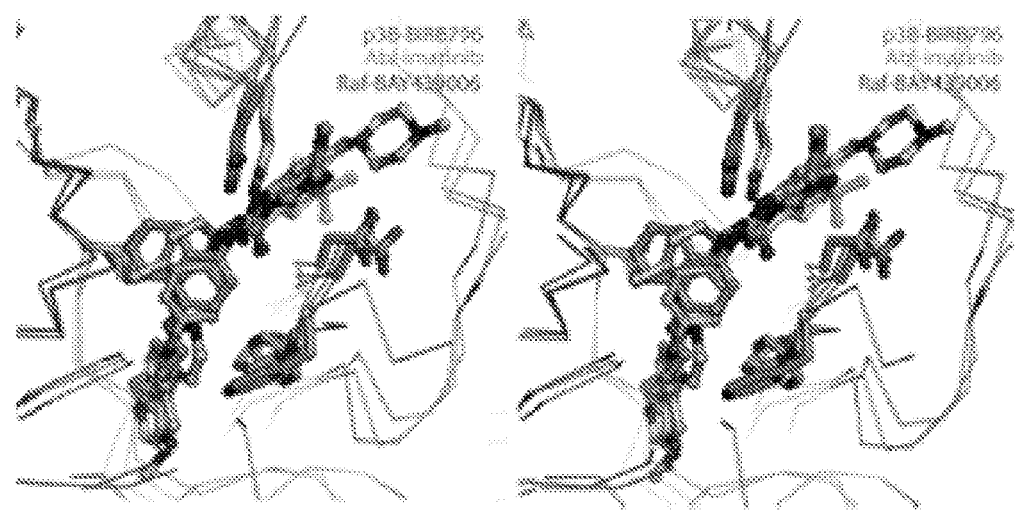
FIG. 5. Three different Type II inhibitors follow a nearly identical path within the active site of three different kinases.

An approach pioneered by Liu, Gray, and co-workers was applied, whereby type II (DFG-out) kinase inhibitors can be created by fusing a so-called hinge binding element of a type-I kinase inhibitor to an element capable of binding in the pocket created by the characteristic DFG movement in type II inhibitor bound structures (Liu and Gray, 2006, Id.; Okram et al., 2006, Id.) The hinge-binding element from the well-characterized pyrazolopyrimidine PP1 was chosen for that purpose, because it has been examined at both the structural and functional level and was first identified as a selective c-Src family tyrosine kinase inhibitor (Hanke et al., 1996, *J Biol Chem* 271:695-701; Liu et al., 1999, *Chem Biol* 6:671-678; Schindler et al., 1999, *Mol Cell* 3:639-648). In order to select the DFG-out binding element for the design, the co-crystal structures of Abl, Raf and p38 were examined in complex with Imatinib, BAY43-9006, and BIRB796, respectively; three chemically distinct type II inhibitors with three different kinase targets (Pargellis et al., 2002, Id.; Schindler et al., 2000, Id.; Wan et al., 2004, Id.). Each inhibitor follows nearly the identical path within the active site pocket, despite their chemical uniqueness (FIG. 5). A key feature of the observed binding modes is the interaction with a portion of the activation segment termed the DFG motif and a highly conserved glutamic acid residue within helix αC, which are mediated through the amide/urea linker and hydrophobic portions of the inhibitors. Movement of the Asp residue out and the Phe residue in (hence 'DFG-out') by a flip of approximately 180 degrees relative to their position in the active state creates the cavity that is filled by these inhibitors. The extended portions of each inhibitor are remarkably similar, and their interactions with the kinase are mediated through highly conserved residues within the ATP pocket, suggesting that the general inhibitor features could be applied to other kinases.

Figure 1B:
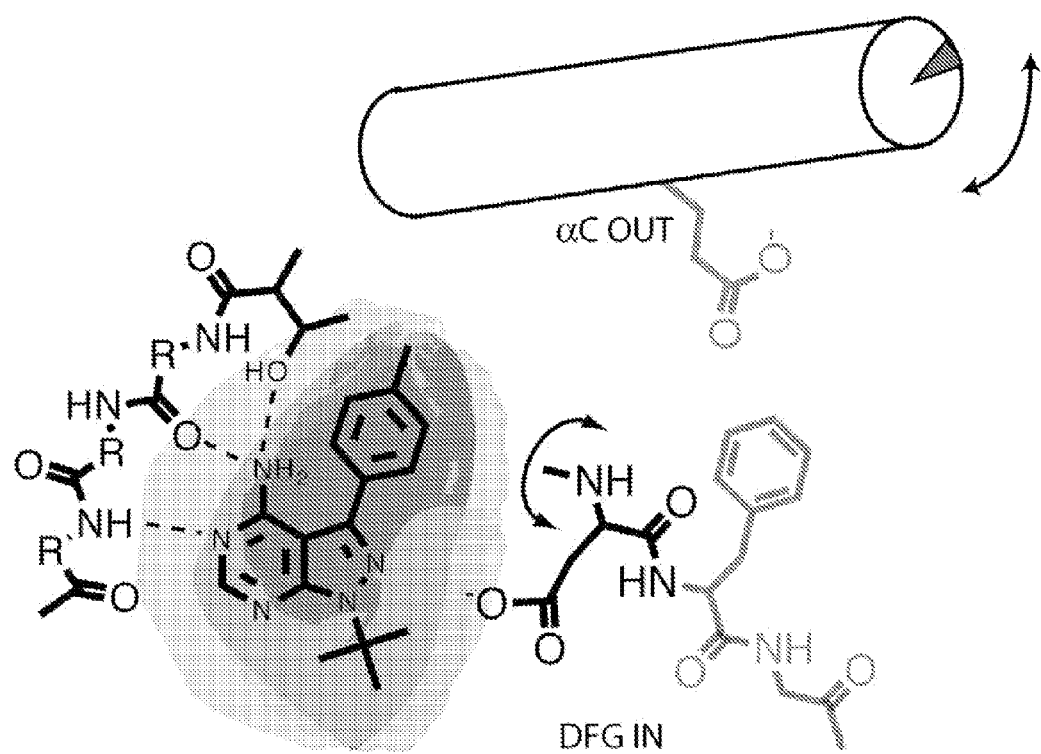
Figure 1C:
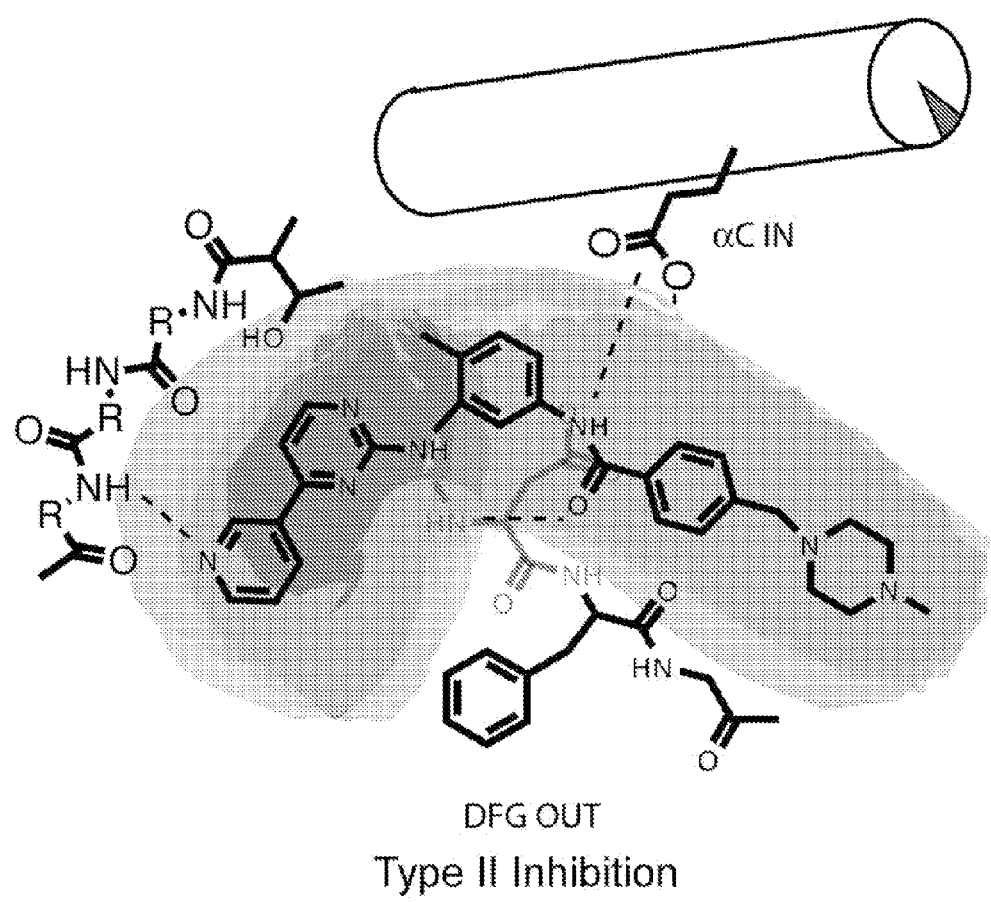

It was hypothesized that derivatization on the phenyl ring in PP1 with a m-trifluoromethyl phenylurea group would create an inhibitor that could engage the DFG-out pocket. The pyrazolopyrimidine core of PP1 occupies the portion of the active site within which the adenosine ring of ATP normally sits, forming key hydrogen bonds with the backbone of the kinase hinge region (FIG. 1B). A panel of molecules were synthesized searching for an inhibitor with tight (nM) binding affinity for c-Src.

Figure 2:
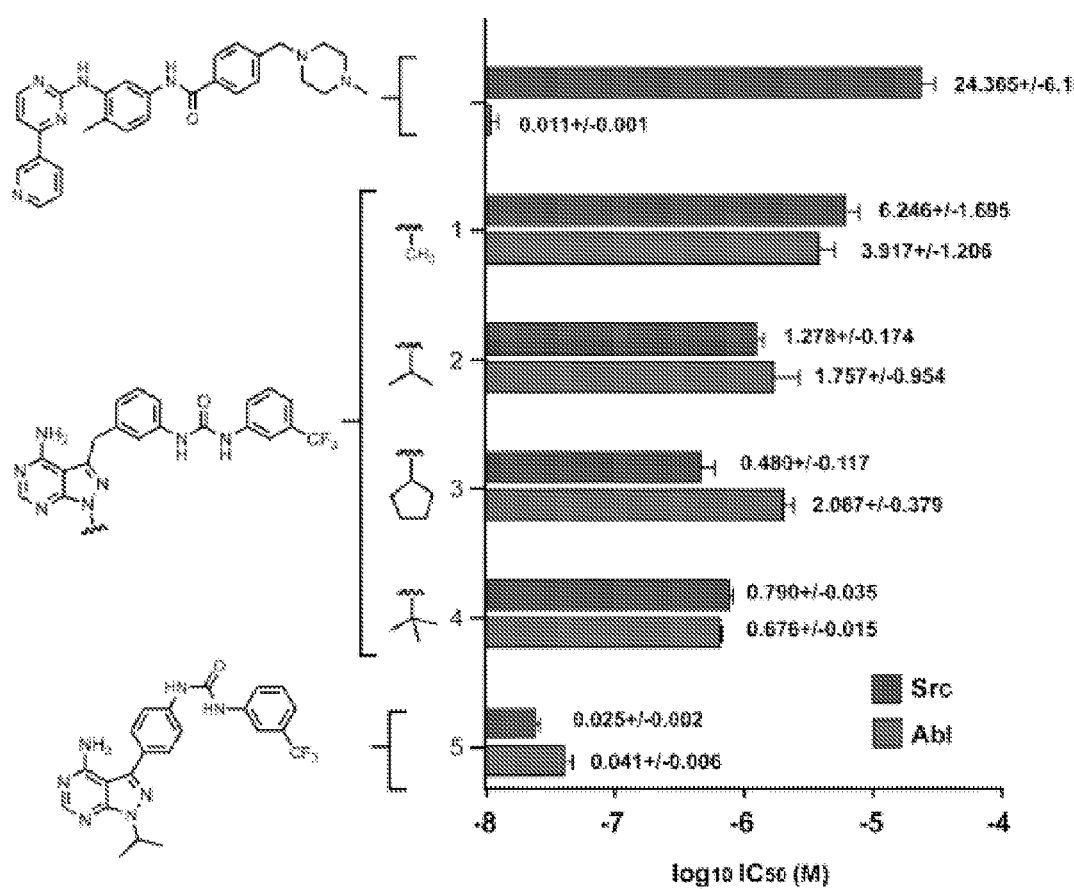
FIG. 2. $IC_{50}$ values of Imatinib, and compounds 1-5 for both c-Src and Abl.

The modelling suggested that addition of a methylene group between the pyrazolopyrimidine core and the phenyl ring would provide flexibility in guiding the m-trifluoromethyl phenyl urea substitution into the DFG pocket. Therefore, compounds 1-4 were synthesized, in which the phenyl group of PP1 has been replaced with a benzyl functionality and the N1 position of the pyrazole ring has been varied with different alkyl groups (FIG. 2 middle). Cmpd 5 was created to provide a direct link between the pyrazolopyrimidine core and the derivatized phenyl (FIG. 2 bottom). Each molecule was prepared based on previously established routes for generating pyrazolopyrimidines (Bishop et al., 1999, Id.; Bishop et al., 1998, Id.; Blethrow et al., 2004, Id.) with the exception that the urea linker was appended through inclusion of a nitro group in the starting material, which in the final synthetic steps was reduced and coupled to m-trifluoromethyl phenyl isocyanate to generate the type II analogues.

Example 28

Inhibition of Src and Abl In Vitro

To ascertain the potency of the designed compounds, their ability to inhibit kinase domain fragments of c-Src and Abl that were expressed and purified identically from bacteria in their unphosphorylated forms was examined. The half maximal inhibitory concentrations ($IC_{50}$) was measured utilizing an in vitro assay in which the kinase catalyses phosphorylation of a synthetic peptide substrate in the presence of 100 mM ATP and varying amounts of inhibitor (FIG. 2). From this analysis, the $IC_{50}$ values for Imatinib were 24,370 and 11 nM for c-Src and Abl, respectively. These values are in close agreement to published values and highlight the inherent selectivity of Imatinib for Abl with respect to c-Src (Seeliger et al., 2007, Id.).

Cmpd 1 was found to inhibit c-Src with an $IC_{50}$ of approximately 6.2 µM, whereas a control compound in which the urea linker was placed at the para position of the benzyl ring lacked any detectable inhibitory activity (data not shown). In measuring the $IC_{50}$ values for 1-4, an interesting correlation between the size of the alkyl group substitutions and selectivity for c-Src and Abl was observed (FIG. 2). The methyl derivative 1 was the weakest inhibitor against both c-Src and Abl, followed by the isopropyl 2 and t-butyl 3 compounds which gained moderate potency, with the optimal derivative appearing to be the cyclopentyl substitution 4, with an $IC_{50}$ of 480 nM for c-Src (FIG. 2). Curiously, while most compounds in this set equally inhibited both c-Src and Abl, the cyclopentyl derivative showed a reproducible selectivity towards c-Src over Abl of approximately 5 fold. Although small, this modest degree of selectivity appeared significant in comparison to the yet smaller $IC_{50}$ value differences between c-Src and Abl for compounds 1, 2, and 4. Cmpd 5 was the most potent inhibitor that we identified, with $IC_{50}$ values of 25 and 41 nM for c-Src and Abl, respectively (FIG. 2). Interestingly, the potency of 5 approaches that of Imatinib for Abl, but without any significant discrimination against c-Src. In this test of compounds two interesting features were identified: Cmpd 3 with unexpected selectivity for c-Src, and Cmpd 5 with extremely high potency for both c-Src and Abl. In order to investigate whether the designed mode of binding was achieved co-crystal structures of c-Src bound to inhibitors 3 and 5 were determined.

Example 29

Binding Mode Revealed by Co-Crystallography

Figure 3:
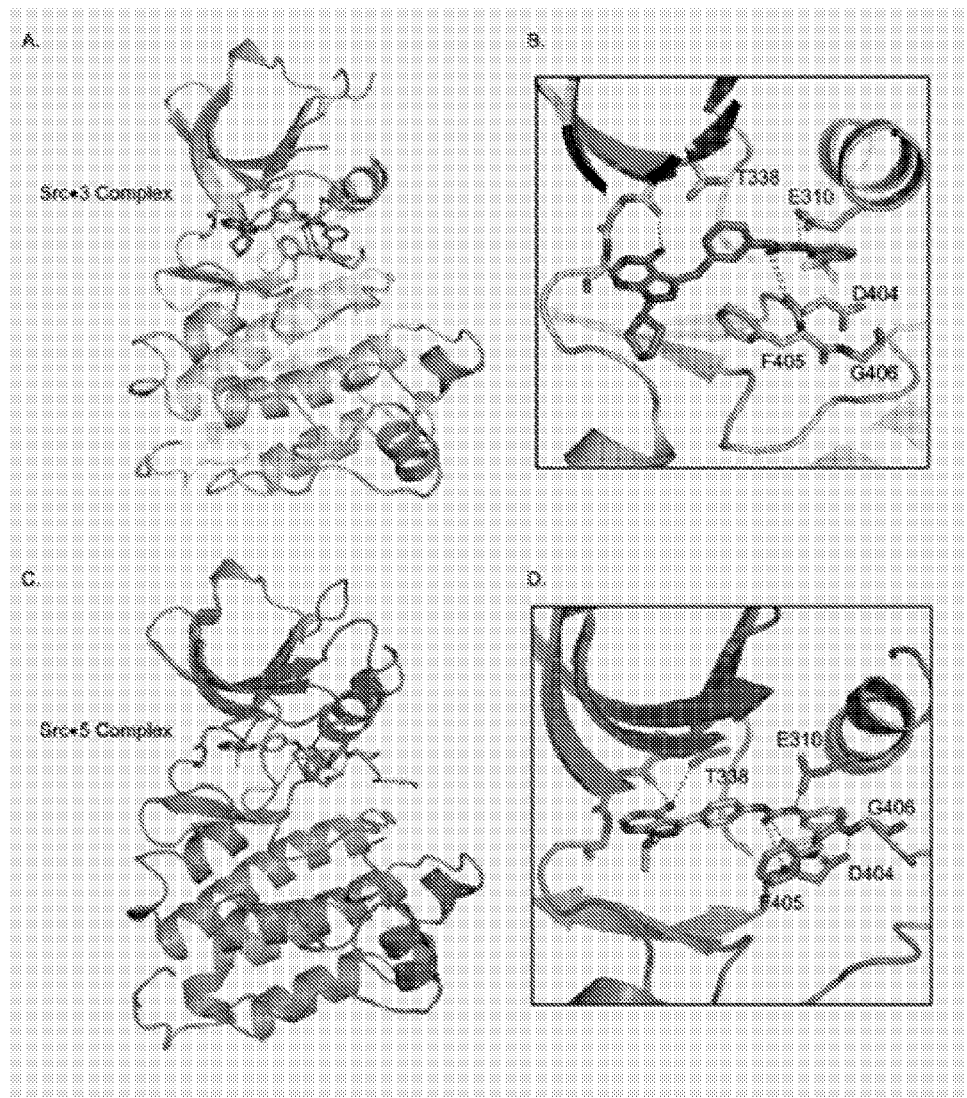
FIG. 3. Crystal structures of compounds 3 and 5 bound to c-Src. A. Illustration of c-Src in complex with 3. B. Magnification of the active site of c-Src in complex with 3. C. Illustration of c-Src in complex with 5. D. Magnification of the active site of c-Src in complex with 5.

Purified c-Src kinase domain in complex with 3 and 5 yielded crystals that diffracted to 2.8 and 2.3 Angstrom, respectively. Both structures were determined by molecular replacement, finding a single copy of c-Src within the asymmetric unit of the $P2_1$ crystal form for the c-Src-3 complex and two copies of c-Src in the P1 crystal form of the c-Src-5 complex. Interestingly, only one kinase molecule within the c-Src-5 complex appeared to contain inhibitor. This feature was observed previously in the co-crystal structure of c-Src with Imatinib, where only one kinase within the asymmetric unit was found to be in a drug complex despite molar equivalents of the protein and inhibitor at a concentration well above their binding constant (Seeliger et al., 2007, Id.). The structures of c-Src in complex with 3 and 5 are shown in FIG. 3, with corresponding magnification of the active site.

As shown, the pyrazolopyrimidine core for both inhibitors lie deep within the adenosine pocket that is lined by the hinge region of the kinase. In comparison to PP1, the plane of the pyrazolopyrimidine rings of both 3 and 5 deviate slightly with respect to each other. As a result of the altered geometry, both 3 and 5 only form a single hydrogen bond to the main chain carbonyl of Glu339. Cmpd 3 is shifted away from the side chain hydroxyl of the Thr338 gatekeeper, and as a result does not foam the hydrogen bond seen in PP1 or in 5 with this residue. Both the benzyl group of 3 and the phenyl group in 5 lie juxtaposed to the gatekeeper; both of which are twisted out of plane relative to the pyrazolopyrimidine ring. In both 3 and 5, the urea extension forms the designed hydrogen bond with the side chain of Glu310 within helix aC, while the m-trifluoromethyl phenyl portion of both compounds lie within a pocket lined by residues Leu317, Leu322, Val402, Met314, His384. As a result of occupying this space, Asp404 and Phe405 are flipped near 180 degrees relative to their active state positions. In the c-Src-5 complex, the side chain carbonyl of Asp404 forms a hydrogen bond to the main chain amide of Gly406 (FIG. 3B). The precise configuration has not been observed in crystal structures of DFG-out kinases, but has been hypothesized to occur during the DFG flip as revealed in molecular dynamic simulations (Levinson et al., 2006, Id.). Interestingly, the configuration of the aspartic acid side chain through to the glycine amide is strikingly similar to the structure of a beta bend (Fersht, 1999, *Structure and Mechanism in Protein Science: a guide to enzyme catalysis and protein folding*, New York: W.H. Freeman and Co.) In a classic beta bend, a nine atom turn along the main chain separates a carbonyl acceptor from an amide donor, and often contains a —$CH_2$-glycine between the donor-acceptor pairs. Here the side chain of Asp404 appears to supply both the carbonyl acceptor and intervening —$CH_2$-group. In both structures of c-Src described here, the configuration of the DFG triad and the position of Glu310 of helix aC adopt conformations that deviate from what was previously observed in either apo c-Src or the PP1-bound form of the closely related enzyme HCK (Schindler et al., 1999, Id.; Xu et al., 1997, *Nature* 385:595-602). Rather 3 and 5 recognize the DFG-out configuration of c-Src that is similarly engaged by Imatinib.

In their hybrid design approach, the set of type II inhibitors that were successfully developed for Abl by Liu, Gray, and co-workers started from four different type I scaffolds (Okram et al., 2006, Id.). It is noteworthy to mention that each of the designed inhibitors was tested against a panel of protein kinases including c-Src. Interestingly, each type II variant exhibited decreased affinity for c-Src relative to the starting scaffolds, whereas they gained potency and selectivity for Abl. While these experiments suggested that a hybrid design approach is feasible, it also hinted at the restricted effectiveness of new type II inhibitors towards certain kinases.

One of the more significant differences between the c-Src complexes and the Abl-Imatinib structure is in the path of the P-loop (FIG. 4A); the region defined by the "GXGXXG motif" of kinases within the b1-b2 linker and that forms the top shelf of the ATP pocket. Notably, in the Abl-Imatinib complex, the P-loop tightly encloses the drug binding site in large part through residue Tyr253, which folds back onto the lip of the pyrimidine core. In the c-Src-Imatinib complex, the region occupied by Tyr253 of Abl is left unoccupied, whereas in the c-Src-3 complex, the cyclopentyl group of the inhibitor itself fills this space. Since the overall binding conformation of compounds 1-4 are less sensitive to the influence of substitutions at the R-1 position on the pyrazole ring this series of inhibitors could be a reliable measure of engaging the Tyr253 pocket through varying steric bulk of the inhibitor. Indeed, the structure and activity of compounds 1-4 could be explained based on the potential role of the Tyr253 region as an affinity pocket, since there is a distinct structure activity relationship when this substituent is varied.

Figure 4:
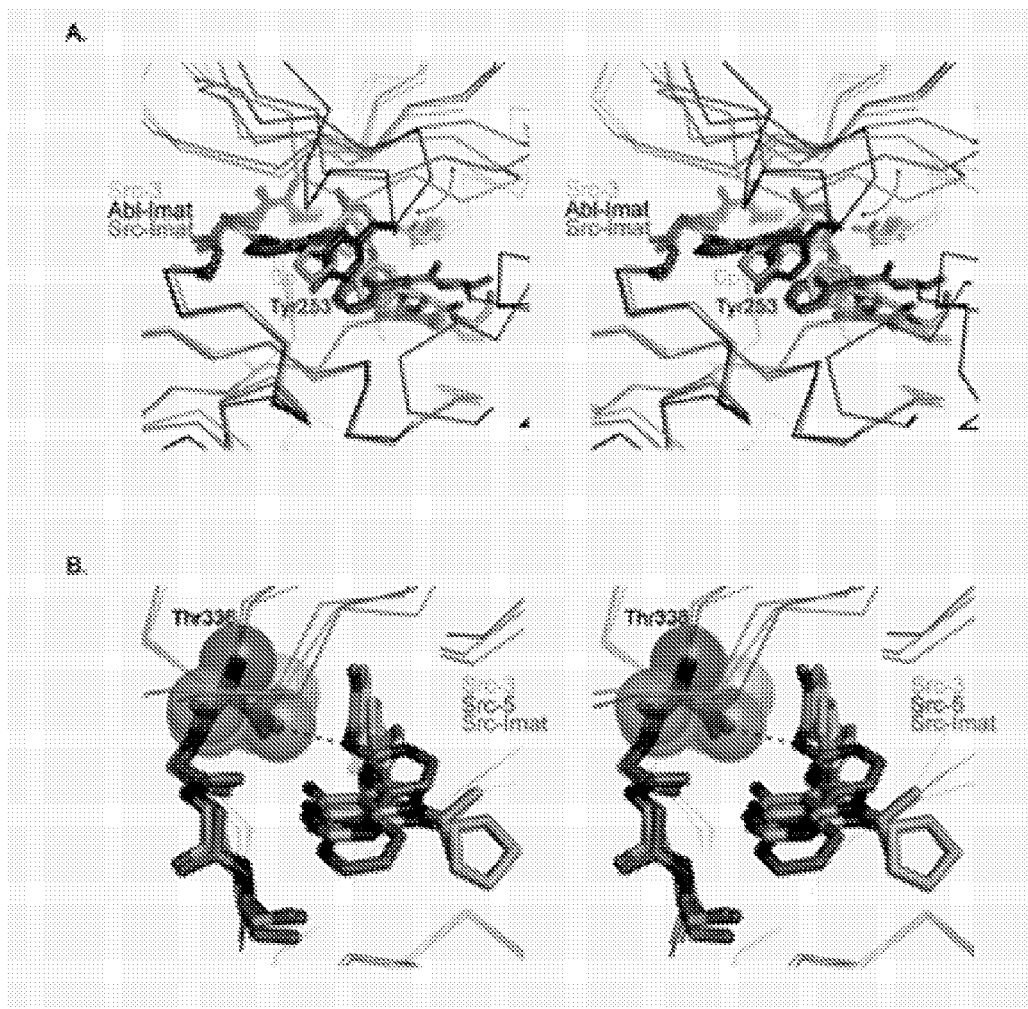
FIG. 4. Structural differences in the binding of 3, 5, and Imatinib to c-Src. A. stereo figure of a structural superposition of 3 in complex with c-Src and Imatinib in complex with Abl (PDB 1IEP) or c-Src (PDB 2OIQ). B. Stereo figure of 3, 5, and Imatinib in complex with c-Src.

Interestingly, one other distinguishing feature between the 3-, 5-, and Imatinib complexes with c-Src is in the approach of these inhibitors towards the gatekeeper pocket (FIG. 4B). Notably, the benzyl group of 3 and the phenyl ring of 5 are rotated away from Thr338 relative to o-methyl-phenylamino portion of Imatinib in a rank order that reflects the relative affinity of the drugs for c-Src. This extra distance from the gatekeeper Thr suggests compounds 1-5 may bind to mutant kinases such as the clinically relevant Imatinib resistant Abl Thr315Ile kinase (Shah et al., 2002, *Cancer Cell* 2:117-125). It can be concluded that the relative energy differences between favoured and disfavoured conformational states of particular kinases can be overcome by small molecules.

What is claimed is:

1. A compound having the formula:

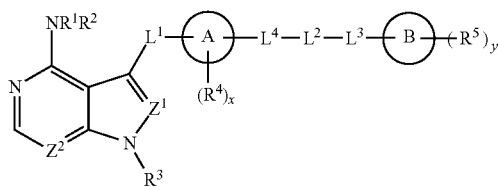

IV wherein
- x is an integer from 0 to 4;
- y is an integer from 0 to 5;
- ring A is arylene or heteroarylene;
- ring B is aryl or heteroaryl;
- $Z^1$ is —N= or —C($R^{22}$)=;
- $Z^2$ is —N= or —C($R^{23}$)=;
- $R^1$ and $R^2$ are independently hydrogen, substituted or unsubstituted alkyl, or substituted or unsubstituted heteroalkyl;
- $R^3$ is independently —CN, —$CF_3$, —S(O)$_n R^6$, —N(O)$_m$, —$NR^7 R^8$, —C(O)$R^9$, —$NR^{10}$—C(O)$R^{11}$, —$NR^{12}$—C(O)—$OR^{13}$, —C(O)$NR^{14} R^{15}$, —$NR^{16}$S(O)$_2 R^{17}$, —S(O)$_2 NR^{18} R^{18'}$, —$OR^{19}$, halomethyl, unsubstituted heteroalkyl, unsubstituted cycloalkyl, unsubstituted aryl, or unsubstituted heteroaryl;
- $R^{22}$ and $R^{23}$ are independently —CN, —$CF_3$, —S(O)$_n R^6$, —N(O)$_m$, —$NR^7 R^8$, —C(O)$R^9$, —$NR^{10}$—C(O)$R^{11}$, —$NR^{12}$—C(O)—$OR^{13}$, —C(O)$NR^{14} R^{15}$, —$NR^{16}$S(O)$_2 R^{17}$, —S(O)$_2 NR^{18} R^{18'}$, —$OR^{19}$, halomethyl, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
- $R^4$ and $R^5$ are independently halogen, —CN, —$CF_3$, —S(O)$_n R^6$, —N(O)$_m$, —$NR^7 R^8$, —C(O)$R^9$, —$NR^{10}$—C(O)$R^{11}$, —$NR^{12}$—C(O)—$OR^{13}$, —C(O)$NR^{14} R^{15}$, —$NR^{16}$S(O)$_2 R^{17}$, —S(O)$_2 NR^{18} R^{18'}$, —$OR^{19}$, halomethyl, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
- n is an integer from 0 to 2;
- m is an integer from 1 to 2;
- $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{18'}$, and $R^{19}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
- $L^1$ is a bond, substituted or unsubstituted alkylene or substituted or unsubstituted heteroalkylene;

L² is —C(O)—;
L³ is —NH—; and
L⁴ is —NH—.

2. The compound of claim 1, wherein ring A is phenylene, and ring B is phenyl.

3. The compound of claim 1, wherein $R^1$ and $R^2$ are hydrogen.

4. The compound of claim 1, wherein $R^3$ is unsubstituted alkyl.

5. The compound of claim 1, wherein $R^3$ is methyl, ethyl or isopropyl.

6. The compound of claim 1, wherein $R^5$ is —CF₃.

7. The compound of claim 1 having the formula:

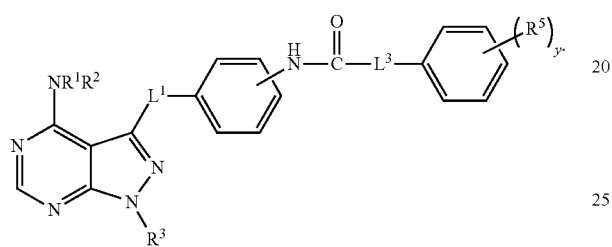

II

8. The compound of claim 7, wherein
$R^1$ and $R^2$ are hydrogen;
$R^3$ is methyl, ethyl, or isopropyl;
$R^5$ is independently —CF₃ or halogen;
$R^{20}$ is hydrogen;
$L^1$ is a bond or methylene;
$L^3$ is —N($R^{20}$)—; and
y is 1 or 2.

9. A compound of claim 1 having the formula

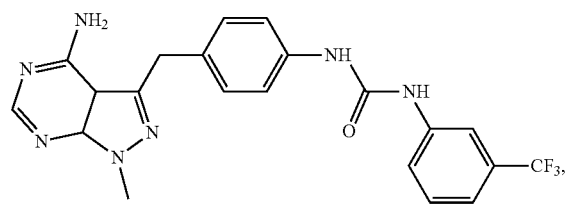

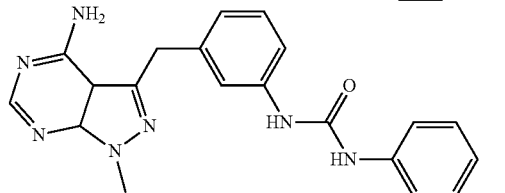

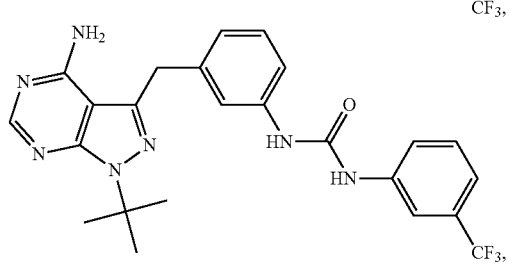

-continued

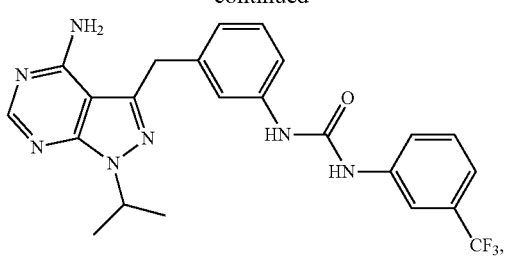

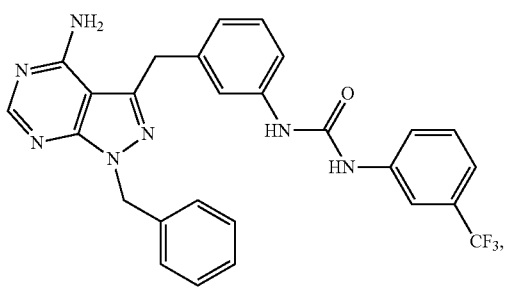

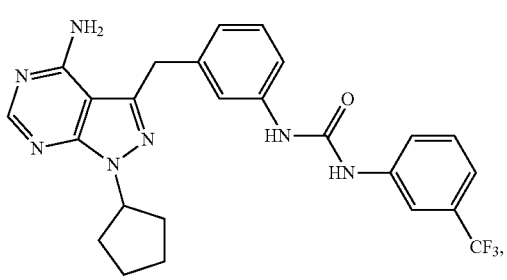

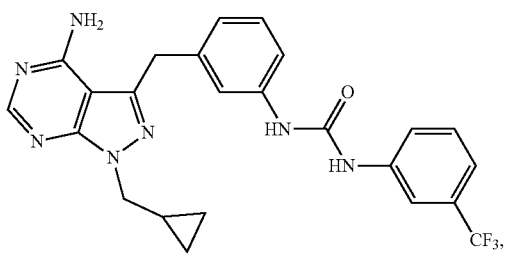

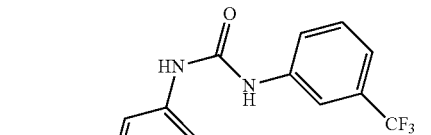

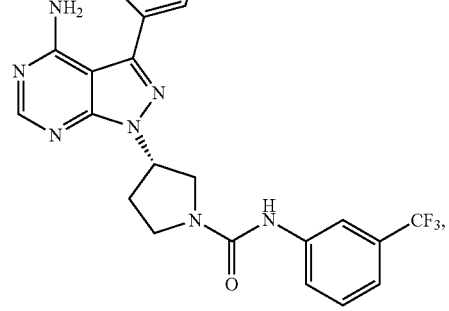

137
-continued
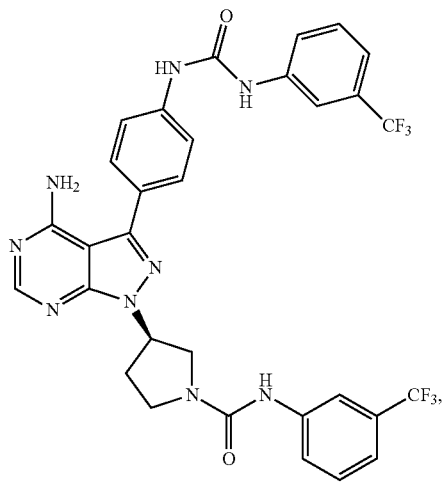
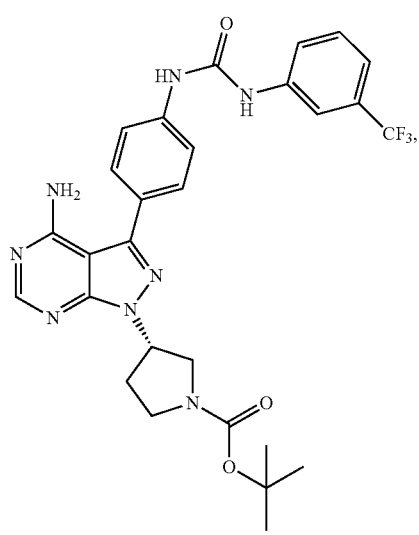
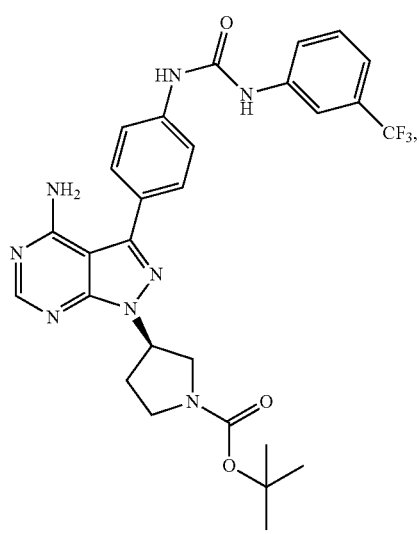 [SMILES: CC(C)(C)OC(=O)N1CC[C@@H](n2nc(-c3ccc(NC(=O)Nc4cccc(C(F)(F)F)c4)cc3)c3c(N)ncnc32)C1]
138
-continued
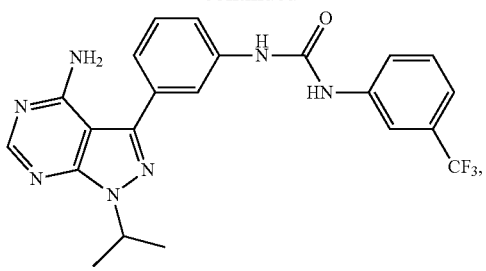
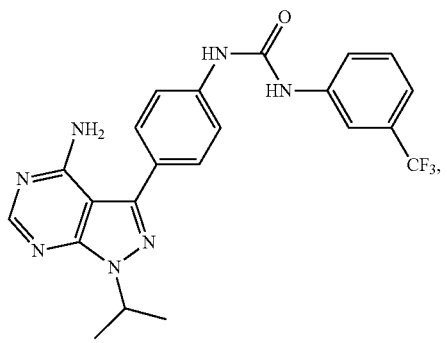
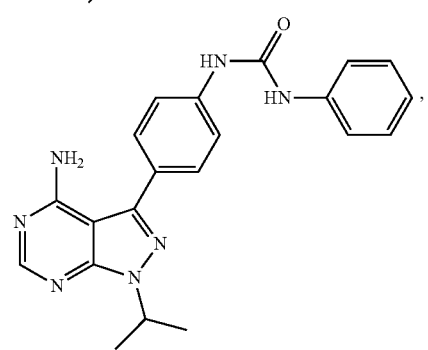
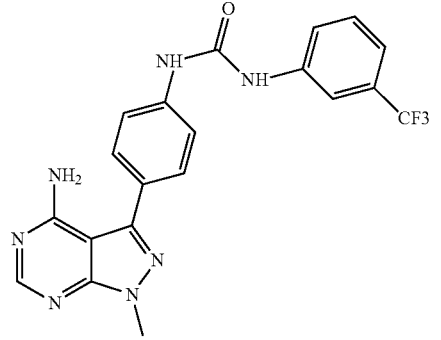 or
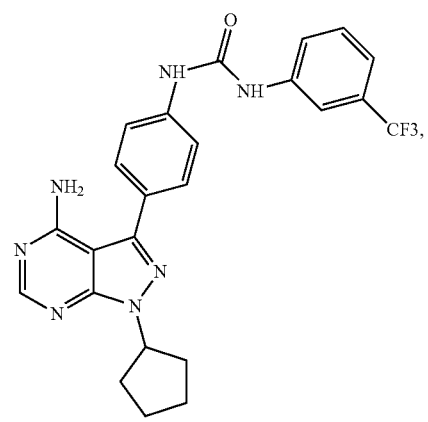

-continued

10. The compound of claim 1, wherein L¹ is a bond.

* * * * *

UNITED STATES PATENT AND TRADEMARK OFFICE
CERTIFICATE OF CORRECTION

PATENT NO.         : 8,697,709 B2
APPLICATION NO.    : 13/124657
DATED              : April 15, 2014
INVENTOR(S)        : Dar et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 134 days.

Signed and Sealed this
Twenty-ninth Day of September, 2015

Michelle K. Lee
*Director of the United States Patent and Trademark Office*

SEQUENCE LISTING

```
<160> NUMBER OF SEQ ID NOS: 12

<210> SEQ ID NO 1
<211> LENGTH: 2031
<212> TYPE: PRT
<213> ORGANISM: Homo sapiens

<400> SEQUENCE: 1

Met Val Asp Pro Val Gly Phe Ala Glu Ala Trp Lys Ala Gln Phe Pro
1               5                   10                  15

Asp Ser Glu Pro Pro Arg Met Glu Leu Arg Ser Val Gly Asp Ile Glu
            20                  25                  30

Gln Glu Leu Glu Arg Cys Lys Ala Ser Ile Arg Arg Leu Glu Gln Glu
        35                  40                  45

Val Asn Gln Glu Arg Phe Arg Met Ile Tyr Leu Gln Thr Leu Leu Ala
    50                  55                  60

Lys Glu Lys Lys Ser Tyr Asp Arg Gln Arg Trp Gly Phe Arg Arg Ala
65                  70                  75                  80

Ala Gln Ala Pro Asp Gly Ala Ser Glu Pro Arg Ala Ser Ala Ser Arg
            85                  90                  95

Pro Gln Pro Ala Pro Ala Asp Gly Ala Asp Pro Pro Pro Ala Glu Glu
            100                 105                 110

Pro Glu Ala Arg Pro Asp Gly Glu Gly Ser Pro Gly Lys Ala Arg Pro
            115                 120                 125

Gly Thr Ala Arg Arg Pro Gly Ala Ala Ala Ser Gly Glu Arg Asp Asp
    130                 135                 140

Arg Gly Pro Pro Ala Ser Val Ala Ala Leu Arg Ser Asn Phe Glu Arg
145                 150                 155                 160

Ile Arg Lys Gly His Gly Gln Pro Gly Ala Asp Ala Glu Lys Pro Phe
            165                 170                 175

Tyr Val Asn Val Glu Phe His His Glu Arg Gly Leu Val Lys Val Asn
            180                 185                 190

Asp Lys Glu Val Ser Asp Arg Ile Ser Ser Leu Gly Ser Gln Ala Met
            195                 200                 205

Gln Met Glu Arg Lys Lys Ser Gln His Gly Ala Gly Ser Ser Val Gly
        210                 215                 220

Asp Ala Ser Arg Pro Pro Tyr Arg Gly Arg Ser Ser Glu Ser Ser Cys
225                 230                 235                 240

Gly Val Asp Gly Asp Tyr Glu Asp Ala Glu Leu Asn Pro Arg Phe Leu
            245                 250                 255

Lys Asp Asn Leu Ile Asp Ala Asn Gly Gly Ser Arg Pro Pro Trp Pro
            260                 265                 270

Pro Leu Glu Tyr Gln Pro Tyr Gln Ser Ile Tyr Val Gly Gly Met Met
        275                 280                 285

Glu Gly Glu Gly Lys Gly Pro Leu Leu Arg Ser Gln Ser Thr Ser Glu
        290                 295                 300
```

```
Gln Glu Lys Arg Leu Thr Trp Pro Arg Arg Ser Tyr Ser Pro Arg Ser
305                 310                 315                 320

Phe Glu Asp Cys Gly Gly Tyr Thr Pro Asp Cys Ser Ser Asn Glu
            325                 330                 335

Asn Leu Thr Ser Ser Glu Glu Asp Phe Ser Ser Gly Gln Ser Ser Arg
                340                 345                 350

Val Ser Pro Ser Pro Thr Thr Tyr Arg Met Phe Arg Asp Lys Ser Arg
            355                 360                 365

Ser Pro Ser Gln Asn Ser Gln Gln Ser Phe Asp Ser Ser Pro Pro
    370                 375                 380

Thr Pro Gln Cys His Lys Arg His Arg His Cys Pro Val Val Val Ser
385                 390                 395                 400

Glu Ala Thr Ile Val Gly Val Arg Lys Thr Gly Gln Ile Trp Pro Asn
                405                 410                 415

Asp Gly Glu Gly Ala Phe His Gly Asp Ala Asp Gly Ser Phe Gly Thr
            420                 425                 430

Pro Pro Gly Tyr Gly Cys Ala Ala Asp Arg Ala Glu Glu Gln Arg Arg
            435                 440                 445

His Gln Asp Gly Leu Pro Tyr Ile Asp Asp Ser Pro Ser Ser Ser Pro
    450                 455                 460

His Leu Ser Ser Lys Gly Arg Gly Ser Arg Asp Ala Leu Val Ser Gly
465                 470                 475                 480

Ala Leu Glu Ser Thr Lys Ala Ser Glu Leu Asp Leu Glu Lys Gly Leu
                485                 490                 495

Glu Met Arg Lys Trp Val Leu Ser Gly Ile Leu Ala Ser Glu Glu Thr
            500                 505                 510

Tyr Leu Ser His Leu Glu Ala Leu Leu Leu Pro Met Lys Pro Leu Lys
    515                 520                 525

Ala Ala Ala Thr Thr Ser Gln Pro Val Leu Thr Ser Gln Gln Ile Glu
    530                 535                 540

Thr Ile Phe Phe Lys Val Pro Glu Leu Tyr Glu Ile His Lys Glu Phe
545                 550                 555                 560

Tyr Asp Gly Leu Phe Pro Arg Val Gln Gln Trp Ser His Gln Gln Arg
                565                 570                 575

Val Gly Asp Leu Phe Gln Lys Leu Ala Ser Gln Leu Gly Val Tyr Arg
            580                 585                 590

Ala Phe Val Asp Asn Tyr Gly Val Ala Met Glu Met Ala Glu Lys Cys
    595                 600                 605

Cys Gln Ala Asn Ala Gln Phe Ala Glu Ile Ser Glu Asn Leu Arg Ala
    610                 615                 620

Arg Ser Asn Lys Asp Ala Lys Asp Pro Thr Thr Lys Asn Ser Leu Glu
625                 630                 635                 640

Thr Leu Leu Tyr Lys Pro Val Asp Arg Val Thr Arg Ser Thr Leu Val
                645                 650                 655

Leu His Asp Leu Leu Lys His Thr Pro Ala Ser His Pro Asp His Pro
            660                 665                 670

Leu Leu Gln Asp Ala Leu Arg Ile Ser Gln Asn Phe Leu Ser Ser Ile
    675                 680                 685

Asn Glu Glu Ile Thr Pro Arg Arg Gln Ser Met Thr Val Lys Lys Gly
    690                 695                 700

Glu His Arg Gln Leu Leu Lys Asp Ser Phe Met Val Glu Leu Val Glu
705                 710                 715                 720

Gly Ala Arg Lys Leu Arg His Val Phe Leu Phe Thr Glu Leu Leu Leu
                725                 730                 735
```

-continued

Cys Thr Lys Leu Lys Lys Gln Ser Gly Gly Lys Thr Gln Tyr Asp
         740                 745                 750

Cys Lys Trp Tyr Ile Pro Leu Thr Asp Leu Ser Phe Gln Met Val Asp
         755                 760                 765

Glu Leu Glu Ala Val Pro Asn Ile Pro Leu Val Pro Asp Glu Glu Leu
         770                 775                 780

Asp Ala Leu Lys Ile Lys Ile Ser Gln Ile Lys Ser Asp Ile Gln Arg
785                 790                 795                 800

Glu Lys Arg Ala Asn Lys Gly Ser Lys Ala Thr Glu Arg Leu Lys Lys
             805                 810                 815

Lys Leu Ser Glu Gln Glu Ser Leu Leu Leu Met Ser Pro Ser Met
             820                 825                 830

Ala Phe Arg Val His Ser Arg Asn Gly Lys Ser Tyr Thr Phe Leu Ile
         835                 840                 845

Ser Ser Asp Tyr Glu Arg Ala Glu Trp Arg Glu Asn Ile Arg Glu Gln
850                 855                 860

Gln Lys Lys Cys Phe Arg Ser Phe Ser Leu Thr Ser Val Glu Leu Gln
865                 870                 875                 880

Met Leu Thr Asn Ser Cys Val Lys Leu Gln Thr Val His Ser Ile Pro
             885                 890                 895

Leu Thr Ile Asn Lys Glu Asp Asp Glu Ser Pro Gly Leu Tyr Gly Phe
             900                 905                 910

Leu Asn Val Ile Val His Ser Ala Thr Gly Phe Lys Gln Ser Ser Lys
         915                 920                 925

Ala Leu Gln Arg Pro Val Ala Ser Asp Phe Glu Pro Gln Gly Leu Ser
930                 935                 940

Glu Ala Ala Arg Trp Asn Ser Lys Glu Asn Leu Leu Ala Gly Pro Ser
945                 950                 955                 960

Glu Asn Asp Pro Asn Leu Phe Val Ala Leu Tyr Asp Phe Val Ala Ser
             965                 970                 975

Gly Asp Asn Thr Leu Ser Ile Thr Lys Gly Glu Lys Leu Arg Val Leu
             980                 985                 990

Gly Tyr Asn His Asn Gly Glu Trp Cys Glu Ala Gln Thr Lys Asn Gly
         995                 1000                1005

Gln Gly Trp Val Pro Ser Asn Tyr Ile Thr Pro Val Asn Ser Leu
    1010                1015                1020

Glu Lys His Ser Trp Tyr His Gly Pro Val Ser Arg Asn Ala Ala
    1025                1030                1035

Glu Tyr Leu Leu Ser Ser Gly Ile Asn Gly Ser Phe Leu Val Arg
    1040                1045                1050

Glu Ser Glu Ser Ser Pro Gly Gln Arg Ser Ile Ser Leu Arg Tyr
    1055                1060                1065

Glu Gly Arg Val Tyr His Tyr Arg Ile Asn Thr Ala Ser Asp Gly
    1070                1075                1080

Lys Leu Tyr Val Ser Ser Glu Ser Arg Phe Asn Thr Leu Ala Glu
    1085                1090                1095

Leu Val His His His Ser Thr Val Ala Asp Gly Leu Ile Thr Thr
    1100                1105                1110

Leu His Tyr Pro Ala Pro Lys Arg Asn Lys Pro Thr Val Tyr Gly
    1115                1120                1125

Val Ser Pro Asn Tyr Asp Lys Trp Glu Met Glu Arg Thr Asp Ile
    1130                1135                1140

Thr Met Lys His Lys Leu Gly Gly Gly Gln Tyr Gly Glu Val Tyr

```
                1145                1150                1155

Glu Gly Val Trp Lys Lys Tyr Ser Leu Thr Val Ala Val Lys Thr
        1160                1165                1170

Leu Lys Glu Asp Thr Met Glu Val Glu Glu Phe Leu Lys Glu Ala
    1175                1180                1185

Ala Val Met Lys Glu Ile Lys His Pro Asn Leu Val Gln Leu Leu
    1190                1195                1200

Gly Val Cys Thr Arg Glu Pro Pro Phe Tyr Ile Ile Thr Glu Phe
    1205                1210                1215

Met Thr Tyr Gly Asn Leu Leu Asp Tyr Leu Arg Glu Cys Asn Arg
    1220                1225                1230

Gln Glu Val Asn Ala Val Val Leu Leu Tyr Met Ala Thr Gln Ile
    1235                1240                1245

Ser Ser Ala Met Glu Tyr Leu Glu Lys Lys Asn Phe Ile His Arg
    1250                1255                1260

Asp Leu Ala Ala Arg Asn Cys Leu Val Gly Glu Asn His Leu Val
    1265                1270                1275

Lys Val Ala Asp Phe Gly Leu Ser Arg Leu Met Thr Gly Asp Thr
    1280                1285                1290

Tyr Thr Ala His Ala Gly Ala Lys Phe Pro Ile Lys Trp Thr Ala
    1295                1300                1305

Pro Glu Ser Leu Ala Tyr Asn Lys Phe Ser Ile Lys Ser Asp Val
    1310                1315                1320

Trp Ala Phe Gly Val Leu Leu Trp Glu Ile Ala Thr Tyr Gly Met
    1325                1330                1335

Ser Pro Tyr Pro Gly Ile Asp Leu Ser Gln Val Tyr Glu Leu Leu
    1340                1345                1350

Glu Lys Asp Tyr Arg Met Glu Arg Pro Glu Gly Cys Pro Glu Lys
    1355                1360                1365

Val Tyr Glu Leu Met Arg Ala Cys Trp Gln Trp Asn Pro Ser Asp
    1370                1375                1380

Arg Pro Ser Phe Ala Glu Ile His Gln Ala Phe Glu Thr Met Phe
    1385                1390                1395

Gln Glu Ser Ser Ile Ser Asp Glu Val Glu Lys Glu Leu Gly Lys
    1400                1405                1410

Gln Gly Val Arg Gly Ala Val Ser Thr Leu Leu Gln Ala Pro Glu
    1415                1420                1425

Leu Pro Thr Lys Thr Arg Thr Ser Arg Arg Ala Ala Glu His Arg
    1430                1435                1440

Asp Thr Thr Asp Val Pro Glu Met Pro His Ser Lys Gly Gln Gly
    1445                1450                1455

Glu Ser Asp Pro Leu Asp His Glu Pro Ala Val Ser Pro Leu Leu
    1460                1465                1470

Pro Arg Lys Glu Arg Gly Pro Pro Glu Gly Gly Leu Asn Glu Asp
    1475                1480                1485

Glu Arg Leu Leu Pro Lys Asp Lys Lys Thr Asn Leu Phe Ser Ala
    1490                1495                1500

Leu Ile Lys Lys Lys Lys Lys Thr Ala Pro Thr Pro Pro Lys Arg
    1505                1510                1515

Ser Ser Ser Phe Arg Glu Met Asp Gly Gln Pro Glu Arg Arg Gly
    1520                1525                1530

Ala Gly Glu Glu Glu Gly Arg Asp Ile Ser Asn Gly Ala Leu Ala
    1535                1540                1545
```

-continued

```
Phe Thr Pro Leu Asp Thr Ala Asp Pro Ala Lys Ser Pro Lys Pro
    1550                1555                1560

Ser Asn Gly Ala Gly Val Pro Asn Gly Ala Leu Arg Glu Ser Gly
    1565                1570                1575

Gly Ser Gly Phe Arg Ser Pro His Leu Trp Lys Lys Ser Ser Thr
    1580                1585                1590

Leu Thr Ser Ser Arg Leu Ala Thr Gly Glu Glu Glu Gly Gly Gly
    1595                1600                1605

Ser Ser Ser Lys Arg Phe Leu Arg Ser Cys Ser Ala Ser Cys Val
    1610                1615                1620

Pro His Gly Ala Lys Asp Thr Glu Trp Arg Ser Val Thr Leu Pro
    1625                1630                1635

Arg Asp Leu Gln Ser Thr Gly Arg Gln Phe Asp Ser Ser Thr Phe
    1640                1645                1650

Gly Gly His Lys Ser Glu Lys Pro Ala Leu Pro Arg Lys Arg Ala
    1655                1660                1665

Gly Glu Asn Arg Ser Asp Gln Val Thr Arg Gly Thr Val Thr Pro
    1670                1675                1680

Pro Pro Arg Leu Val Lys Lys Asn Glu Glu Ala Ala Asp Glu Val
    1685                1690                1695

Phe Lys Asp Ile Met Glu Ser Ser Pro Gly Ser Ser Pro Pro Asn
    1700                1705                1710

Leu Thr Pro Lys Pro Leu Arg Arg Gln Val Thr Val Ala Pro Ala
    1715                1720                1725

Ser Gly Leu Pro His Lys Glu Glu Ala Trp Lys Gly Ser Ala Leu
    1730                1735                1740

Gly Thr Pro Ala Ala Ala Glu Pro Val Thr Pro Thr Ser Lys Ala
    1745                1750                1755

Gly Ser Gly Ala Pro Gly Gly Thr Ser Lys Gly Pro Ala Glu Glu
    1760                1765                1770

Ser Arg Val Arg Arg His Lys His Ser Ser Glu Ser Pro Gly Arg
    1775                1780                1785

Asp Lys Gly Lys Leu Ser Arg Leu Lys Pro Ala Pro Pro Pro Pro
    1790                1795                1800

Pro Ala Ala Ser Ala Gly Lys Ala Gly Gly Lys Pro Ser Gln Ser
    1805                1810                1815

Pro Asp Gln Glu Ala Ala Gly Glu Ala Val Leu Gly Ala Lys Thr
    1820                1825                1830

Lys Ala Thr Ser Leu Val Asp Ala Val Asn Ser Asp Ala Ala Lys
    1835                1840                1845

Pro Ser Gln Pro Gly Glu Gly Leu Lys Lys Pro Val Leu Pro Ala
    1850                1855                1860

Thr Pro Lys Pro Gln Ser Ala Lys Pro Ser Gly Thr Pro Ile Ser
    1865                1870                1875

Pro Ala Pro Val Pro Ser Thr Leu Pro Ser Ala Ser Ser Ala Leu
    1880                1885                1890

Ala Gly Asp Gln Pro Ser Ser Thr Ala Phe Ile Pro Leu Ile Ser
    1895                1900                1905

Thr Arg Val Ser Leu Arg Lys Thr Arg Gln Pro Pro Glu Arg Ile
    1910                1915                1920

Ala Ser Gly Ala Ile Thr Lys Gly Val Val Leu Asp Ser Thr Glu
    1925                1930                1935

Ala Leu Cys Leu Ala Ile Ser Arg Asn Ser Glu Gln Met Ala Ser
    1940                1945                1950
```

```
His Ser Ala Val Leu Glu Ala Gly Lys Asn Leu Tyr Ser Phe Cys
    1955                1960                1965

Val Ser Tyr Val Asp Ser Ile Gln Gln Met Arg Asn Lys Phe Ala
    1970                1975                1980

Phe Arg Glu Ala Ile Asn Lys Leu Glu Asn Asn Leu Arg Glu Leu
    1985                1990                1995

Gln Ile Cys Pro Ala Thr Ala Gly Ser Gly Pro Ala Ala Thr Gln
    2000                2005                2010

Asp Phe Ser Lys Leu Leu Ser Ser Val Lys Glu Ile Ser Asp Ile
    2015                2020                2025

Val Gln Arg
    2030

<210> SEQ ID NO 2
<211> LENGTH: 533
<212> TYPE: PRT
<213> ORGANISM: Gallus gallus

<400> SEQUENCE: 2

Met Gly Ser Ser Lys Ser Lys Pro Lys Asp Pro Ser Gln Arg Arg Arg
1               5                   10                  15

Ser Leu Glu Pro Pro Asp Ser Thr His His Gly Gly Phe Pro Ala Ser
            20                  25                  30

Gln Thr Pro Asn Lys Thr Ala Ala Pro Asp Thr His Arg Thr Pro Ser
        35                  40                  45

Arg Ser Phe Gly Thr Val Ala Thr Glu Pro Lys Leu Phe Gly Gly Phe
    50                  55                  60

Asn Thr Ser Asp Thr Val Thr Ser Pro Gln Arg Ala Gly Ala Leu Ala
65                  70                  75                  80

Gly Gly Val Thr Thr Phe Val Ala Leu Tyr Asp Tyr Glu Ser Arg Thr
                85                  90                  95

Glu Thr Asp Leu Ser Phe Lys Lys Gly Glu Arg Leu Gln Ile Val Asn
            100                 105                 110

Asn Thr Glu Gly Asp Trp Trp Leu Ala His Ser Leu Thr Thr Gly Gln
        115                 120                 125

Thr Gly Tyr Ile Pro Ser Asn Tyr Val Ala Pro Ser Asp Ser Ile Gln
    130                 135                 140

Ala Glu Glu Trp Tyr Phe Gly Lys Ile Thr Arg Arg Glu Ser Glu Arg
145                 150                 155                 160

Leu Leu Leu Asn Pro Glu Asn Pro Arg Gly Thr Phe Leu Val Arg Glu
                165                 170                 175

Ser Glu Thr Thr Lys Gly Ala Tyr Cys Leu Ser Val Ser Asp Phe Asp
            180                 185                 190

Asn Ala Lys Gly Leu Asn Val Lys His Tyr Lys Ile Arg Lys Leu Asp
        195                 200                 205

Ser Gly Gly Phe Tyr Ile Thr Ser Arg Thr Gln Phe Ser Ser Leu Gln
    210                 215                 220

Gln Leu Val Ala Tyr Tyr Ser Lys His Ala Asp Gly Leu Cys His Arg
225                 230                 235                 240

Leu Thr Asn Val Cys Pro Thr Ser Lys Pro Gln Thr Gln Gly Leu Ala
                245                 250                 255

Lys Asp Ala Trp Glu Ile Pro Arg Glu Ser Leu Arg Leu Glu Val Lys
            260                 265                 270

Leu Gly Gln Gly Cys Phe Gly Glu Val Trp Met Gly Thr Trp Asn Gly
        275                 280                 285
```

```
Thr Thr Arg Val Ala Ile Lys Thr Leu Lys Pro Gly Thr Met Ser Pro
    290                 295                 300

Glu Ala Phe Leu Gln Glu Ala Gln Val Met Lys Lys Leu Arg His Glu
305                 310                 315                 320

Lys Leu Val Gln Leu Tyr Ala Val Val Ser Glu Glu Pro Ile Tyr Ile
                325                 330                 335

Val Thr Glu Tyr Met Ser Lys Gly Ser Leu Leu Asp Phe Leu Lys Gly
            340                 345                 350

Glu Met Gly Lys Tyr Leu Arg Leu Pro Gln Leu Val Asp Met Ala Ala
        355                 360                 365

Gln Ile Ala Ser Gly Met Ala Tyr Val Glu Arg Met Asn Tyr Val His
    370                 375                 380

Arg Asp Leu Arg Ala Ala Asn Ile Leu Val Gly Glu Asn Leu Val Cys
385                 390                 395                 400

Lys Val Ala Asp Phe Gly Leu Ala Arg Leu Ile Glu Asp Asn Glu Tyr
                405                 410                 415

Thr Ala Arg Gln Gly Ala Lys Phe Pro Ile Lys Trp Thr Ala Pro Glu
            420                 425                 430

Ala Ala Leu Tyr Gly Arg Phe Thr Ile Lys Ser Asp Val Trp Ser Phe
        435                 440                 445

Gly Ile Leu Leu Thr Glu Leu Thr Thr Lys Gly Arg Val Pro Tyr Pro
    450                 455                 460

Gly Met Val Asn Arg Glu Val Leu Asp Gln Val Glu Arg Gly Tyr Arg
465                 470                 475                 480

Met Pro Cys Pro Pro Glu Cys Pro Glu Ser Leu His Asp Leu Met Cys
                485                 490                 495

Gln Cys Trp Arg Lys Asp Pro Glu Glu Arg Pro Thr Phe Glu Tyr Leu
            500                 505                 510

Gln Ala Phe Leu Glu Asp Tyr Phe Thr Ser Thr Glu Pro Gln Tyr Gln
        515                 520                 525

Pro Gly Glu Asn Leu
    530

<210> SEQ ID NO 3
<211> LENGTH: 976
<212> TYPE: PRT
<213> ORGANISM: Homo sapiens

<400> SEQUENCE: 3

Met Arg Gly Ala Arg Gly Ala Trp Asp Phe Leu Cys Val Leu Leu Leu
1                   5                  10                  15

Leu Leu Arg Val Gln Thr Gly Ser Ser Gln Pro Ser Val Ser Pro Gly
                20                  25                  30

Glu Pro Ser Pro Pro Ser Ile His Pro Gly Lys Ser Asp Leu Ile Val
            35                  40                  45

Arg Val Gly Asp Glu Ile Arg Leu Leu Cys Thr Asp Pro Gly Phe Val
        50                  55                  60

Lys Trp Thr Phe Glu Ile Leu Asp Glu Thr Asn Glu Asn Lys Gln Asn
65                  70                  75                  80

Glu Trp Ile Thr Glu Lys Ala Glu Ala Thr Asn Thr Gly Lys Tyr Thr
                85                  90                  95

Cys Thr Asn Lys His Gly Leu Ser Asn Ser Ile Tyr Val Phe Val Arg
                100                 105                 110

Asp Pro Ala Lys Leu Phe Leu Val Asp Arg Ser Leu Tyr Gly Lys Glu
            115                 120                 125
```

```
Asp Asn Asp Thr Leu Val Arg Cys Pro Leu Thr Asp Pro Glu Val Thr
        130                 135                 140

Asn Tyr Ser Leu Lys Gly Cys Gln Gly Lys Pro Leu Pro Lys Asp Leu
145                 150                 155                 160

Arg Phe Ile Pro Asp Pro Lys Ala Gly Ile Met Ile Lys Ser Val Lys
                165                 170                 175

Arg Ala Tyr His Arg Leu Cys Leu His Cys Ser Val Asp Gln Glu Gly
                180                 185                 190

Lys Ser Val Leu Ser Glu Lys Phe Ile Leu Lys Val Arg Pro Ala Phe
            195                 200                 205

Lys Ala Val Pro Val Val Ser Val Ser Lys Ala Ser Tyr Leu Leu Arg
        210                 215                 220

Glu Gly Glu Glu Phe Thr Val Thr Cys Thr Ile Lys Asp Val Ser Ser
225                 230                 235                 240

Ser Val Tyr Ser Thr Trp Lys Arg Glu Asn Ser Gln Thr Lys Leu Gln
                245                 250                 255

Glu Lys Tyr Asn Ser Trp His His Gly Asp Phe Asn Tyr Glu Arg Gln
            260                 265                 270

Ala Thr Leu Thr Ile Ser Ser Ala Arg Val Asn Asp Ser Gly Val Phe
        275                 280                 285

Met Cys Tyr Ala Asn Asn Thr Phe Gly Ser Ala Asn Val Thr Thr Thr
    290                 295                 300

Leu Glu Val Val Asp Lys Gly Phe Ile Asn Ile Phe Pro Met Ile Asn
305                 310                 315                 320

Thr Thr Val Phe Val Asn Asp Gly Glu Asn Val Asp Leu Ile Val Glu
                325                 330                 335

Tyr Glu Ala Phe Pro Lys Pro Glu His Gln Gln Trp Ile Tyr Met Asn
            340                 345                 350

Arg Thr Phe Thr Asp Lys Trp Glu Asp Tyr Pro Lys Ser Glu Asn Glu
        355                 360                 365

Ser Asn Ile Arg Tyr Val Ser Glu Leu His Leu Thr Arg Leu Lys Gly
    370                 375                 380

Thr Glu Gly Gly Thr Tyr Thr Phe Leu Val Ser Asn Ser Asp Val Asn
385                 390                 395                 400

Ala Ala Ile Ala Phe Asn Val Tyr Val Asn Thr Lys Pro Glu Ile Leu
                405                 410                 415

Thr Tyr Asp Arg Leu Val Asn Gly Met Leu Gln Cys Val Ala Ala Gly
            420                 425                 430

Phe Pro Glu Pro Thr Ile Asp Trp Tyr Phe Cys Pro Gly Thr Glu Gln
        435                 440                 445

Arg Cys Ser Ala Ser Val Leu Pro Val Asp Val Gln Thr Leu Asn Ser
    450                 455                 460

Ser Gly Pro Pro Phe Gly Lys Leu Val Val Gln Ser Ser Ile Asp Ser
465                 470                 475                 480

Ser Ala Phe Lys His Asn Gly Thr Val Glu Cys Lys Ala Tyr Asn Asp
                485                 490                 495

Val Gly Lys Thr Ser Ala Tyr Phe Asn Phe Ala Phe Lys Gly Asn Asn
            500                 505                 510

Lys Glu Gln Ile His Pro His Thr Leu Phe Thr Pro Leu Leu Ile Gly
        515                 520                 525

Phe Val Ile Val Ala Gly Met Met Cys Ile Ile Val Met Ile Leu Thr
    530                 535                 540

Tyr Lys Tyr Leu Gln Lys Pro Met Tyr Glu Val Gln Trp Lys Val Val
```

-continued

```
            545                 550                 555                 560
Glu Glu Ile Asn Gly Asn Asn Tyr Val Tyr Ile Asp Pro Thr Gln Leu
                    565                 570                 575

Pro Tyr Asp His Lys Trp Glu Phe Pro Arg Asn Arg Leu Ser Phe Gly
            580                 585                 590

Lys Thr Leu Gly Ala Gly Ala Phe Gly Lys Val Val Glu Ala Thr Ala
            595                 600                 605

Tyr Gly Leu Ile Lys Ser Asp Ala Ala Met Thr Val Ala Val Lys Met
            610                 615                 620

Leu Lys Pro Ser Ala His Leu Thr Glu Arg Glu Ala Leu Met Ser Glu
625                 630                 635                 640

Leu Lys Val Leu Ser Tyr Leu Gly Asn His Met Asn Ile Val Asn Leu
                    645                 650                 655

Leu Gly Ala Cys Thr Ile Gly Gly Pro Thr Leu Val Ile Thr Glu Tyr
                    660                 665                 670

Cys Cys Tyr Gly Asp Leu Leu Asn Phe Leu Arg Arg Lys Arg Asp Ser
            675                 680                 685

Phe Ile Cys Ser Lys Gln Glu Asp His Ala Glu Ala Ala Leu Tyr Lys
            690                 695                 700

Asn Leu Leu His Ser Lys Glu Ser Ser Cys Ser Asp Ser Thr Asn Glu
705                 710                 715                 720

Tyr Met Asp Met Lys Pro Gly Val Ser Tyr Val Val Pro Thr Lys Ala
                    725                 730                 735

Asp Lys Arg Arg Ser Val Arg Ile Gly Ser Tyr Ile Glu Arg Asp Val
                    740                 745                 750

Thr Pro Ala Ile Met Glu Asp Asp Glu Leu Ala Leu Asp Leu Glu Asp
            755                 760                 765

Leu Leu Ser Phe Ser Tyr Gln Val Ala Lys Gly Met Ala Phe Leu Ala
            770                 775                 780

Ser Lys Asn Cys Ile His Arg Asp Leu Ala Ala Arg Asn Ile Leu Leu
785                 790                 795                 800

Thr His Gly Arg Ile Thr Lys Ile Cys Asp Phe Gly Leu Ala Arg Asp
                    805                 810                 815

Ile Lys Asn Asp Ser Asn Tyr Val Val Lys Gly Asn Ala Arg Leu Pro
            820                 825                 830

Val Lys Trp Met Ala Pro Glu Ser Ile Phe Asn Cys Val Tyr Thr Phe
            835                 840                 845

Glu Ser Asp Val Trp Ser Tyr Gly Ile Phe Leu Trp Glu Leu Phe Ser
850                 855                 860

Leu Gly Ser Ser Pro Tyr Pro Gly Met Pro Val Asp Ser Lys Phe Tyr
865                 870                 875                 880

Lys Met Ile Lys Glu Gly Phe Arg Met Leu Ser Pro Glu His Ala Pro
                    885                 890                 895

Ala Glu Met Tyr Asp Ile Met Lys Thr Cys Trp Asp Ala Asp Pro Leu
            900                 905                 910

Lys Arg Pro Thr Phe Lys Gln Ile Val Gln Leu Ile Glu Lys Gln Ile
            915                 920                 925

Ser Glu Ser Thr Asn His Ile Tyr Ser Asn Leu Ala Asn Cys Ser Pro
            930                 935                 940

Asn Arg Gln Lys Pro Val Val Asp His Ser Val Arg Ile Asn Ser Val
945                 950                 955                 960

Gly Ser Thr Ala Ser Ser Ser Gln Pro Leu Leu Val His Asp Asp Val
                    965                 970                 975
```

<210> SEQ ID NO 4
<211> LENGTH: 286
<212> TYPE: PRT
<213> ORGANISM: Gallus gallus

<400> SEQUENCE: 4

| Gly | His | Met | Gln | Thr | Gln | Gly | Leu | Ala | Lys | Asp | Ala | Trp | Glu | Ile | Pro |
|---|---|---|---|---|---|---|---|---|---|---|---|---|---|---|---|
| 1 | | | | 5 | | | | | 10 | | | | | 15 | |

| Arg | Glu | Ser | Leu | Arg | Leu | Glu | Val | Lys | Leu | Gly | Gln | Gly | Cys | Phe | Gly |
|---|---|---|---|---|---|---|---|---|---|---|---|---|---|---|---|
| | | | 20 | | | | | 25 | | | | | 30 | | |

| Glu | Val | Trp | Met | Gly | Thr | Trp | Asn | Gly | Thr | Thr | Arg | Val | Ala | Ile | Lys |
|---|---|---|---|---|---|---|---|---|---|---|---|---|---|---|---|
| | | 35 | | | | | 40 | | | | | 45 | | | |

| Thr | Leu | Lys | Pro | Gly | Thr | Met | Ser | Pro | Glu | Ala | Phe | Leu | Gln | Glu | Ala |
|---|---|---|---|---|---|---|---|---|---|---|---|---|---|---|---|
| | 50 | | | | | 55 | | | | | 60 | | | | |

| Gln | Val | Met | Lys | Lys | Leu | Arg | His | Glu | Lys | Leu | Val | Gln | Leu | Tyr | Ala |
|---|---|---|---|---|---|---|---|---|---|---|---|---|---|---|---|
| 65 | | | | | 70 | | | | | 75 | | | | | 80 |

| Val | Val | Ser | Glu | Glu | Pro | Ile | Tyr | Ile | Val | Thr | Glu | Tyr | Met | Ser | Lys |
|---|---|---|---|---|---|---|---|---|---|---|---|---|---|---|---|
| | | | | 85 | | | | | 90 | | | | | 95 | |

| Gly | Ser | Leu | Leu | Asp | Phe | Leu | Lys | Gly | Glu | Met | Gly | Lys | Tyr | Leu | Arg |
|---|---|---|---|---|---|---|---|---|---|---|---|---|---|---|---|
| | | | 100 | | | | | 105 | | | | | 110 | | |

| Leu | Pro | Gln | Leu | Val | Asp | Met | Ala | Ala | Gln | Ile | Ala | Ser | Gly | Met | Ala |
|---|---|---|---|---|---|---|---|---|---|---|---|---|---|---|---|
| | | 115 | | | | | 120 | | | | | 125 | | | |

| Tyr | Val | Glu | Arg | Met | Asn | Tyr | Val | His | Arg | Asp | Leu | Arg | Ala | Ala | Asn |
|---|---|---|---|---|---|---|---|---|---|---|---|---|---|---|---|
| | 130 | | | | | 135 | | | | | 140 | | | | |

| Ile | Leu | Val | Gly | Glu | Asn | Leu | Val | Cys | Lys | Val | Ala | Asp | Phe | Gly | Leu |
|---|---|---|---|---|---|---|---|---|---|---|---|---|---|---|---|
| 145 | | | | | 150 | | | | | 155 | | | | | 160 |

| Ala | Arg | Leu | Ile | Glu | Asp | Asn | Glu | Tyr | Thr | Ala | Arg | Gln | Gly | Ala | Lys |
|---|---|---|---|---|---|---|---|---|---|---|---|---|---|---|---|
| | | | | 165 | | | | | 170 | | | | | 175 | |

| Phe | Pro | Ile | Lys | Trp | Thr | Ala | Pro | Glu | Ala | Ala | Leu | Tyr | Gly | Arg | Phe |
|---|---|---|---|---|---|---|---|---|---|---|---|---|---|---|---|
| | | | 180 | | | | | 185 | | | | | 190 | | |

| Thr | Ile | Lys | Ser | Asp | Val | Trp | Ser | Phe | Gly | Ile | Leu | Leu | Thr | Glu | Leu |
|---|---|---|---|---|---|---|---|---|---|---|---|---|---|---|---|
| | | 195 | | | | | 200 | | | | | 205 | | | |

| Thr | Thr | Lys | Gly | Arg | Val | Pro | Tyr | Pro | Gly | Met | Val | Asn | Arg | Glu | Val |
|---|---|---|---|---|---|---|---|---|---|---|---|---|---|---|---|
| | 210 | | | | | 215 | | | | | 220 | | | | |

| Leu | Asp | Gln | Val | Glu | Arg | Gly | Tyr | Arg | Met | Pro | Cys | Pro | Glu | Cys |
|---|---|---|---|---|---|---|---|---|---|---|---|---|---|---|
| 225 | | | | | 230 | | | | | 235 | | | | | 240 |

| Pro | Glu | Ser | Leu | His | Asp | Leu | Met | Cys | Gln | Cys | Trp | Arg | Lys | Asp | Pro |
|---|---|---|---|---|---|---|---|---|---|---|---|---|---|---|---|
| | | | | 245 | | | | | 250 | | | | | 255 | |

| Glu | Glu | Arg | Pro | Thr | Phe | Glu | Tyr | Leu | Gln | Ala | Phe | Leu | Glu | Asp | Tyr |
|---|---|---|---|---|---|---|---|---|---|---|---|---|---|---|---|
| | | | 260 | | | | | 265 | | | | | 270 | | |

| Phe | Thr | Ser | Thr | Glu | Pro | Gln | Tyr | Gln | Pro | Gly | Glu | Asn | Leu |
|---|---|---|---|---|---|---|---|---|---|---|---|---|---|
| | | 275 | | | | | 280 | | | | | 285 | |

<210> SEQ ID NO 5
<211> LENGTH: 293
<212> TYPE: PRT
<213> ORGANISM: Mus musculus

<400> SEQUENCE: 5

| Gly | Ala | Met | Asp | Pro | Ser | Ser | Pro | Asn | Tyr | Asp | Lys | Trp | Glu | Met | Glu |
|---|---|---|---|---|---|---|---|---|---|---|---|---|---|---|---|
| 1 | | | | 5 | | | | | 10 | | | | | 15 | |

| Arg | Thr | Asp | Ile | Thr | Met | Lys | His | Lys | Leu | Gly | Gly | Gly | Gln | Tyr | Gly |
|---|---|---|---|---|---|---|---|---|---|---|---|---|---|---|---|
| | | | 20 | | | | | 25 | | | | | 30 | | |

| Glu | Val | Tyr | Glu | Gly | Val | Trp | Lys | Lys | Tyr | Ser | Leu | Thr | Val | Ala | Val |
|---|---|---|---|---|---|---|---|---|---|---|---|---|---|---|---|
| | | 35 | | | | | 40 | | | | | 45 | | | |

Lys Thr Leu Lys Glu Asp Thr Met Glu Val Glu Glu Phe Leu Lys Glu

```
                        50                  55                  60
Ala Ala Val Met Lys Glu Ile Lys His Pro Asn Leu Val Gln Leu Leu
 65                  70                  75                  80

Gly Val Cys Thr Arg Glu Pro Pro Phe Tyr Ile Ile Thr Glu Phe Met
                 85                  90                  95

Thr Tyr Gly Asn Leu Leu Asp Tyr Leu Arg Glu Cys Asn Arg Gln Glu
             100                 105                 110

Val Ser Ala Val Val Leu Leu Tyr Met Ala Thr Gln Ile Ser Ser Ala
         115                 120                 125

Met Glu Tyr Leu Glu Lys Lys Asn Phe Ile His Arg Asp Leu Ala Ala
     130                 135                 140

Arg Asn Cys Leu Val Gly Glu Asn His Leu Val Lys Val Ala Asp Phe
145                 150                 155                 160

Gly Leu Ser Arg Leu Met Thr Gly Asp Thr Tyr Thr Ala His Ala Gly
                165                 170                 175

Ala Lys Phe Pro Ile Lys Trp Thr Ala Pro Glu Ser Leu Ala Tyr Asn
            180                 185                 190

Lys Phe Ser Ile Lys Ser Asp Val Trp Ala Phe Gly Val Leu Leu Trp
        195                 200                 205

Glu Ile Ala Thr Tyr Gly Met Ser Pro Tyr Pro Gly Ile Asp Leu Ser
    210                 215                 220

Gln Val Tyr Glu Leu Leu Glu Lys Asp Tyr Arg Met Glu Arg Pro Glu
225                 230                 235                 240

Gly Cys Pro Glu Lys Val Tyr Glu Leu Met Arg Ala Cys Trp Gln Trp
                245                 250                 255

Asn Pro Ser Asp Arg Pro Ser Phe Ala Glu Ile His Gln Ala Phe Glu
            260                 265                 270

Thr Met Phe Gln Glu Ser Ser Ile Ser Asp Glu Val Glu Lys Glu Leu
        275                 280                 285

Gly Lys Arg Gly Thr
    290

<210> SEQ ID NO 6
<211> LENGTH: 450
<212> TYPE: PRT
<213> ORGANISM: Homo sapiens

<400> SEQUENCE: 6

Met Ser Ala Ile Gln Ala Ala Trp Pro Ser Gly Thr Glu Cys Ile Ala
 1               5                  10                  15

Lys Tyr Asn Phe His Gly Thr Ala Glu Gln Asp Leu Pro Phe Cys Lys
             20                  25                  30

Gly Asp Val Leu Thr Ile Val Ala Val Thr Lys Asp Pro Asn Trp Tyr
         35                  40                  45

Lys Ala Lys Asn Lys Val Gly Arg Glu Gly Ile Ile Pro Ala Asn Tyr
     50                  55                  60

Val Gln Lys Arg Glu Gly Val Lys Ala Gly Thr Lys Leu Ser Leu Met
 65                  70                  75                  80

Pro Trp Phe His Gly Lys Ile Thr Arg Glu Gln Ala Glu Arg Leu Leu
                 85                  90                  95

Tyr Pro Pro Glu Thr Gly Leu Phe Leu Val Arg Glu Ser Thr Asn Tyr
             100                 105                 110

Pro Gly Asp Tyr Thr Leu Cys Val Ser Cys Asp Gly Lys Val Glu His
         115                 120                 125

Tyr Arg Ile Met Tyr His Ala Ser Lys Leu Ser Ile Asp Glu Glu Val
```

```
              130                 135                 140
Tyr Phe Glu Asn Leu Met Gln Leu Val Glu His Tyr Thr Ser Asp Ala
145                 150                 155                 160

Asp Gly Leu Cys Thr Arg Leu Ile Lys Pro Lys Val Met Glu Gly Thr
                165                 170                 175

Val Ala Ala Gln Asp Glu Phe Tyr Arg Ser Gly Trp Ala Leu Asn Met
                180                 185                 190

Lys Glu Leu Lys Leu Leu Gln Thr Ile Gly Lys Gly Glu Phe Gly Asp
                195                 200                 205

Val Met Leu Gly Asp Tyr Arg Gly Asn Lys Val Ala Val Lys Cys Ile
210                 215                 220

Lys Asn Asp Ala Thr Ala Gln Ala Phe Leu Ala Glu Ala Ser Val Met
225                 230                 235                 240

Thr Gln Leu Arg His Ser Asn Leu Val Gln Leu Leu Gly Val Ile Val
                245                 250                 255

Glu Glu Lys Gly Gly Leu Tyr Ile Val Thr Glu Tyr Met Ala Lys Gly
                260                 265                 270

Ser Leu Val Asp Tyr Leu Arg Ser Arg Gly Arg Ser Val Leu Gly Gly
                275                 280                 285

Asp Cys Leu Leu Lys Phe Ser Leu Asp Val Cys Glu Ala Met Glu Tyr
                290                 295                 300

Leu Glu Gly Asn Asn Phe Val His Arg Asp Leu Ala Ala Arg Asn Val
305                 310                 315                 320

Leu Val Ser Glu Asp Asn Val Ala Lys Val Ser Asp Phe Gly Leu Thr
                325                 330                 335

Lys Glu Ala Ser Ser Thr Gln Asp Thr Gly Lys Leu Pro Val Lys Trp
                340                 345                 350

Thr Ala Pro Glu Ala Leu Arg Glu Lys Lys Phe Ser Thr Lys Ser Asp
                355                 360                 365

Val Trp Ser Phe Gly Ile Leu Leu Trp Glu Ile Tyr Ser Phe Gly Arg
370                 375                 380

Val Pro Tyr Pro Arg Ile Pro Leu Lys Asp Val Val Pro Arg Val Glu
385                 390                 395                 400

Lys Gly Tyr Lys Met Asp Ala Pro Asp Gly Cys Pro Pro Ala Val Tyr
                405                 410                 415

Glu Val Met Lys Asn Cys Trp His Leu Asp Ala Ala Met Arg Pro Ser
                420                 425                 430

Phe Leu Gln Leu Arg Glu Gln Leu Glu His Ile Lys Thr His Glu Leu
                435                 440                 445

His Leu
    450

<210> SEQ ID NO 7
<211> LENGTH: 6
<212> TYPE: PRT
<213> ORGANISM: Artificial
<220> FEATURE:
<223> OTHER INFORMATION: Artificial sequence

<400> SEQUENCE: 7

His His His His His His
1               5

<210> SEQ ID NO 8
<211> LENGTH: 11
<212> TYPE: PRT
<213> ORGANISM: Artificial
```

```
<220> FEATURE:
<223> OTHER INFORMATION: Artificial sequence

<400> SEQUENCE: 8

Glu Ala Ile Tyr Ala Ala Pro Phe Lys Lys Lys
1               5                   10

<210> SEQ ID NO 9
<211> LENGTH: 9
<212> TYPE: PRT
<213> ORGANISM: Artificial
<220> FEATURE:
<223> OTHER INFORMATION: Artificial sequence

<400> SEQUENCE: 9

Glu Ile Tyr Gly Glu Phe Lys Lys Lys
1               5

<210> SEQ ID NO 10
<211> LENGTH: 1089
<212> TYPE: PRT
<213> ORGANISM: Homo sapiens

<400> SEQUENCE: 10

Met Gly Thr Ser His Pro Ala Phe Leu Val Leu Gly Cys Leu Leu Thr
1               5                   10                  15

Gly Leu Ser Leu Ile Leu Cys Gln Leu Ser Leu Pro Ser Ile Leu Pro
                20                  25                  30

Asn Glu Asn Glu Lys Val Val Gln Leu Asn Ser Ser Phe Ser Leu Arg
            35                  40                  45

Cys Phe Gly Glu Ser Glu Val Ser Trp Gln Tyr Pro Met Ser Glu Glu
        50                  55                  60

Glu Ser Ser Asp Val Glu Ile Arg Asn Glu Glu Asn Asn Ser Gly Leu
65                  70                  75                  80

Phe Val Thr Val Leu Glu Val Ser Ser Ala Ser Ala Ala His Thr Gly
                85                  90                  95

Leu Tyr Thr Cys Tyr Tyr Asn His Thr Gln Thr Glu Glu Asn Glu Leu
            100                 105                 110

Glu Gly Arg His Ile Tyr Ile Tyr Val Pro Asp Pro Asp Val Ala Phe
        115                 120                 125

Val Pro Leu Gly Met Thr Asp Tyr Leu Val Ile Val Glu Asp Asp Asp
    130                 135                 140

Ser Ala Ile Ile Pro Cys Arg Thr Thr Asp Pro Glu Thr Pro Val Thr
145                 150                 155                 160

Leu His Asn Ser Glu Gly Val Val Pro Ala Ser Tyr Asp Ser Arg Gln
                165                 170                 175

Gly Phe Asn Gly Thr Phe Thr Val Gly Pro Tyr Ile Cys Glu Ala Thr
            180                 185                 190

Val Lys Gly Lys Lys Phe Gln Thr Ile Pro Phe Asn Val Tyr Ala Leu
        195                 200                 205

Lys Ala Thr Ser Glu Leu Asp Leu Glu Met Glu Ala Leu Lys Thr Val
    210                 215                 220

Tyr Lys Ser Gly Glu Thr Ile Val Val Thr Cys Ala Val Phe Asn Asn
225                 230                 235                 240

Glu Val Val Asp Leu Gln Trp Thr Tyr Pro Gly Glu Val Lys Gly Lys
                245                 250                 255

Gly Ile Thr Met Leu Glu Glu Ile Lys Val Pro Ser Ile Lys Leu Val
            260                 265                 270
```

```
Tyr Thr Leu Thr Val Pro Glu Ala Thr Val Lys Asp Ser Gly Asp Tyr
            275                 280                 285

Glu Cys Ala Ala Arg Gln Ala Thr Arg Glu Val Lys Glu Met Lys Lys
290                 295                 300

Val Thr Ile Ser Val His Glu Lys Gly Phe Ile Glu Ile Lys Pro Thr
305                 310                 315                 320

Phe Ser Gln Leu Glu Ala Val Asn Leu His Glu Val Lys His Phe Val
                325                 330                 335

Val Glu Val Arg Ala Tyr Pro Pro Arg Ile Ser Trp Leu Lys Asn
                340                 345                 350

Asn Leu Thr Leu Ile Glu Asn Leu Thr Glu Ile Thr Thr Asp Val Glu
            355                 360                 365

Lys Ile Gln Glu Ile Arg Tyr Arg Ser Lys Leu Lys Leu Ile Arg Ala
370                 375                 380

Lys Glu Glu Asp Ser Gly His Tyr Thr Ile Val Ala Gln Asn Glu Asp
385                 390                 395                 400

Ala Val Lys Ser Tyr Thr Phe Glu Leu Leu Thr Gln Val Pro Ser Ser
                405                 410                 415

Ile Leu Asp Leu Val Asp Asp His His Gly Ser Thr Gly Gly Gln Thr
                420                 425                 430

Val Arg Cys Thr Ala Glu Gly Thr Pro Leu Pro Asp Ile Glu Trp Met
            435                 440                 445

Ile Cys Lys Asp Ile Lys Lys Cys Asn Asn Glu Thr Ser Trp Thr Ile
            450                 455                 460

Leu Ala Asn Asn Val Ser Asn Ile Ile Thr Glu Ile His Ser Arg Asp
465                 470                 475                 480

Arg Ser Thr Val Glu Gly Arg Val Thr Phe Ala Lys Val Glu Glu Thr
                485                 490                 495

Ile Ala Val Arg Cys Leu Ala Lys Asn Leu Leu Gly Ala Glu Asn Arg
                500                 505                 510

Glu Leu Lys Leu Val Ala Pro Thr Leu Arg Ser Glu Leu Thr Val Ala
            515                 520                 525

Ala Ala Val Leu Val Leu Leu Val Ile Val Ile Ile Ser Leu Ile Val
            530                 535                 540

Leu Val Val Ile Trp Lys Gln Lys Pro Arg Tyr Glu Ile Arg Trp Arg
545                 550                 555                 560

Val Ile Glu Ser Ile Ser Pro Asp Gly His Glu Tyr Ile Tyr Val Asp
                565                 570                 575

Pro Met Gln Leu Pro Tyr Asp Ser Arg Trp Glu Phe Pro Arg Asp Gly
                580                 585                 590

Leu Val Leu Gly Arg Val Leu Gly Ser Gly Ala Phe Gly Lys Val Val
                595                 600                 605

Glu Gly Thr Ala Tyr Gly Leu Ser Arg Ser Gln Pro Val Met Lys Val
            610                 615                 620

Ala Val Lys Met Leu Lys Pro Thr Ala Arg Ser Ser Glu Lys Gln Ala
625                 630                 635                 640

Leu Met Ser Glu Leu Lys Ile Met Thr His Leu Gly Pro His Leu Asn
                645                 650                 655

Ile Val Asn Leu Leu Gly Ala Cys Thr Lys Ser Gly Pro Ile Tyr Ile
                660                 665                 670

Ile Thr Glu Tyr Cys Phe Tyr Gly Asp Leu Val Asn Tyr Leu His Lys
            675                 680                 685

Asn Arg Asp Ser Phe Leu Ser His His Pro Glu Lys Pro Lys Lys Glu
690                 695                 700
```

Leu Asp Ile Phe Gly Leu Asn Pro Ala Asp Glu Ser Thr Arg Ser Tyr
705                 710                 715                 720

Val Ile Leu Ser Phe Glu Asn Gly Asp Tyr Met Asp Met Lys Gln
            725                 730                 735

Ala Asp Thr Thr Gln Tyr Val Pro Met Leu Glu Arg Lys Glu Val Ser
        740                 745                 750

Lys Tyr Ser Asp Ile Gln Arg Ser Leu Tyr Asp Arg Pro Ala Ser Tyr
            755                 760                 765

Lys Lys Lys Ser Met Leu Asp Ser Glu Val Lys Asn Leu Leu Ser Asp
        770                 775                 780

Asp Asn Ser Glu Gly Leu Thr Leu Leu Asp Leu Leu Ser Phe Thr Tyr
785                 790                 795                 800

Gln Val Ala Arg Gly Met Glu Phe Leu Ala Ser Lys Asn Cys Val His
                805                 810                 815

Arg Asp Leu Ala Ala Arg Asn Val Leu Leu Ala Gln Gly Lys Ile Val
            820                 825                 830

Lys Ile Cys Asp Phe Gly Leu Ala Arg Asp Ile Met His Asp Ser Asn
        835                 840                 845

Tyr Val Ser Lys Gly Ser Thr Phe Leu Pro Val Lys Trp Met Ala Pro
850                 855                 860

Glu Ser Ile Phe Asp Asn Leu Tyr Thr Thr Leu Ser Asp Val Trp Ser
865                 870                 875                 880

Tyr Gly Ile Leu Leu Trp Glu Ile Phe Ser Leu Gly Gly Thr Pro Tyr
                885                 890                 895

Pro Gly Met Met Val Asp Ser Thr Phe Tyr Asn Lys Ile Lys Ser Gly
            900                 905                 910

Tyr Arg Met Ala Lys Pro Asp His Ala Thr Ser Glu Val Tyr Glu Ile
        915                 920                 925

Met Val Lys Cys Trp Asn Ser Glu Pro Glu Lys Arg Pro Ser Phe Tyr
930                 935                 940

His Leu Ser Glu Ile Val Glu Asn Leu Leu Pro Gly Gln Tyr Lys Lys
945                 950                 955                 960

Ser Tyr Glu Lys Ile His Leu Asp Phe Leu Lys Ser Asp His Pro Ala
                965                 970                 975

Val Ala Arg Met Arg Val Asp Ser Asp Asn Ala Tyr Ile Gly Val Thr
            980                 985                 990

Tyr Lys Asn Glu Glu Asp Lys Leu Lys Asp Trp Glu Gly Gly Leu Asp
        995                 1000                1005

Glu Gln Arg Leu Ser Ala Asp Ser Gly Tyr Ile Ile Pro Leu Pro
    1010                1015                1020

Asp Ile Asp Pro Val Pro Glu Glu Asp Leu Gly Lys Arg Asn
    1025                1030                1035

Arg His Ser Ser Gln Thr Ser Glu Glu Ser Ala Ile Glu Thr Gly
    1040                1045                1050

Ser Ser Ser Ser Thr Phe Ile Lys Arg Glu Asp Glu Thr Ile Glu
    1055                1060                1065

Asp Ile Asp Met Met Asp Asp Ile Gly Ile Asp Ser Ser Asp Leu
    1070                1075                1080

Val Glu Asp Ser Phe Leu
    1085

<210> SEQ ID NO 11
<211> LENGTH: 1130
<212> TYPE: PRT

-continued

<213> ORGANISM: Homo sapiens

<400> SEQUENCE: 11

```
Met Leu Glu Ile Cys Leu Lys Leu Val Gly Cys Lys Ser Lys Gly
1               5                   10                  15

Leu Ser Ser Ser Ser Cys Tyr Leu Glu Ala Leu Gln Arg Pro
            20                  25                  30

Val Ala Ser Asp Phe Glu Pro Gln Gly Leu Ser Glu Ala Ala Arg Trp
            35                  40                  45

Asn Ser Lys Glu Asn Leu Leu Ala Gly Pro Ser Glu Asn Asp Pro Asn
        50                  55                  60

Leu Phe Val Ala Leu Tyr Asp Phe Val Ala Ser Gly Asp Asn Thr Leu
65                  70                  75                  80

Ser Ile Thr Lys Gly Glu Lys Leu Arg Val Leu Gly Tyr Asn His Asn
                85                  90                  95

Gly Glu Trp Cys Glu Ala Gln Thr Lys Asn Gly Gln Gly Trp Val Pro
            100                 105                 110

Ser Asn Tyr Ile Thr Pro Val Asn Ser Leu Glu Lys His Ser Trp Tyr
            115                 120                 125

His Gly Pro Val Ser Arg Asn Ala Ala Glu Tyr Leu Leu Ser Ser Gly
            130                 135                 140

Ile Asn Gly Ser Phe Leu Val Arg Glu Ser Glu Ser Ser Pro Gly Gln
145                 150                 155                 160

Arg Ser Ile Ser Leu Arg Tyr Glu Gly Arg Val Tyr His Tyr Arg Ile
                165                 170                 175

Asn Thr Ala Ser Asp Gly Lys Leu Tyr Val Ser Ser Glu Ser Arg Phe
            180                 185                 190

Asn Thr Leu Ala Glu Leu Val His His Ser Thr Val Ala Asp Gly
            195                 200                 205

Leu Ile Thr Thr Leu His Tyr Pro Ala Pro Lys Arg Asn Lys Pro Thr
            210                 215                 220

Val Tyr Gly Val Ser Pro Asn Tyr Asp Lys Trp Glu Met Glu Arg Thr
225                 230                 235                 240

Asp Ile Thr Met Lys His Lys Leu Gly Gly Gly Gln Tyr Gly Glu Val
                245                 250                 255

Tyr Glu Gly Val Trp Lys Lys Tyr Ser Leu Thr Val Ala Val Lys Thr
            260                 265                 270

Leu Lys Glu Asp Thr Met Glu Val Glu Glu Phe Leu Lys Glu Ala Ala
            275                 280                 285

Val Met Lys Glu Ile Lys His Pro Asn Leu Val Gln Leu Leu Gly Val
            290                 295                 300

Cys Thr Arg Glu Pro Pro Phe Tyr Ile Ile Thr Glu Phe Met Thr Tyr
305                 310                 315                 320

Gly Asn Leu Leu Asp Tyr Leu Arg Glu Cys Asn Arg Gln Glu Val Asn
                325                 330                 335

Ala Val Val Leu Leu Tyr Met Ala Thr Gln Ile Ser Ser Ala Met Glu
            340                 345                 350

Tyr Leu Glu Lys Lys Asn Phe Ile His Arg Asp Leu Ala Ala Arg Asn
            355                 360                 365

Cys Leu Val Gly Glu Asn His Leu Val Lys Val Ala Asp Phe Gly Leu
            370                 375                 380

Ser Arg Leu Met Thr Gly Asp Thr Tyr Thr Ala His Ala Gly Ala Lys
385                 390                 395                 400

Phe Pro Ile Lys Trp Thr Ala Pro Glu Ser Leu Ala Tyr Asn Lys Phe
```

```
                   405                 410                 415
Ser Ile Lys Ser Asp Val Trp Ala Phe Gly Val Leu Leu Trp Glu Ile
                420                 425                 430

Ala Thr Tyr Gly Met Ser Pro Tyr Pro Gly Ile Asp Leu Ser Gln Val
                435                 440                 445

Tyr Glu Leu Leu Glu Lys Asp Tyr Arg Met Glu Arg Pro Glu Gly Cys
            450                 455                 460

Pro Glu Lys Val Tyr Glu Leu Met Arg Ala Cys Trp Gln Trp Asn Pro
465                 470                 475                 480

Ser Asp Arg Pro Ser Phe Ala Glu Ile His Gln Ala Phe Glu Thr Met
                485                 490                 495

Phe Gln Glu Ser Ser Ile Ser Asp Glu Val Glu Lys Glu Leu Gly Lys
            500                 505                 510

Gln Gly Val Arg Gly Ala Val Ser Thr Leu Leu Gln Ala Pro Glu Leu
            515                 520                 525

Pro Thr Lys Thr Arg Thr Ser Arg Arg Ala Ala Glu His Arg Asp Thr
        530                 535                 540

Thr Asp Val Pro Glu Met Pro His Ser Lys Gly Gln Gly Glu Ser Asp
545                 550                 555                 560

Pro Leu Asp His Glu Pro Ala Val Ser Pro Leu Leu Pro Arg Lys Glu
                565                 570                 575

Arg Gly Pro Pro Glu Gly Gly Leu Asn Glu Asp Glu Arg Leu Leu Pro
            580                 585                 590

Lys Asp Lys Lys Thr Asn Leu Phe Ser Ala Leu Ile Lys Lys Lys Lys
        595                 600                 605

Lys Thr Ala Pro Thr Pro Pro Lys Arg Ser Ser Phe Arg Glu Met
        610                 615                 620

Asp Gly Gln Pro Glu Arg Arg Gly Ala Gly Glu Glu Gly Arg Asp
625                 630                 635                 640

Ile Ser Asn Gly Ala Leu Ala Phe Thr Pro Leu Asp Thr Ala Asp Pro
                645                 650                 655

Ala Lys Ser Pro Lys Pro Ser Asn Gly Ala Gly Val Pro Asn Gly Ala
                660                 665                 670

Leu Arg Glu Ser Gly Gly Ser Gly Phe Arg Ser Pro His Leu Trp Lys
            675                 680                 685

Lys Ser Ser Thr Leu Thr Ser Ser Arg Leu Ala Thr Gly Glu Glu Glu
        690                 695                 700

Gly Gly Gly Ser Ser Lys Arg Phe Leu Arg Ser Cys Ser Ala Ser
705                 710                 715                 720

Cys Val Pro His Gly Ala Lys Asp Thr Glu Trp Arg Ser Val Thr Leu
                725                 730                 735

Pro Arg Asp Leu Gln Ser Thr Gly Arg Gln Phe Asp Ser Ser Thr Phe
            740                 745                 750

Gly Gly His Lys Ser Glu Lys Pro Ala Leu Pro Arg Lys Arg Ala Gly
            755                 760                 765

Glu Asn Arg Ser Asp Gln Val Thr Arg Gly Thr Val Thr Pro Pro Pro
        770                 775                 780

Arg Leu Val Lys Lys Asn Glu Glu Ala Ala Asp Glu Val Phe Lys Asp
785                 790                 795                 800

Ile Met Glu Ser Ser Pro Gly Ser Ser Pro Pro Asn Leu Thr Pro Lys
                805                 810                 815

Pro Leu Arg Arg Gln Val Thr Val Ala Pro Ala Ser Gly Leu Pro His
            820                 825                 830
```

```
Lys Glu Glu Ala Gly Lys Gly Ser Ala Leu Gly Thr Pro Ala Ala Ala
        835                 840                 845

Glu Pro Val Thr Pro Thr Ser Lys Ala Gly Ser Gly Ala Pro Gly Gly
    850                 855                 860

Thr Ser Lys Gly Pro Ala Glu Glu Ser Arg Val Arg Arg His Lys His
865                 870                 875                 880

Ser Ser Glu Ser Pro Gly Arg Asp Lys Gly Lys Leu Ser Arg Leu Lys
            885                 890                 895

Pro Ala Pro Pro Pro Pro Ala Ala Ser Ala Gly Lys Ala Gly Gly
        900                 905                 910

Lys Pro Ser Gln Ser Pro Ser Gln Glu Ala Ala Gly Glu Ala Val Leu
        915                 920                 925

Gly Ala Lys Thr Lys Ala Thr Ser Leu Val Asp Ala Val Asn Ser Asp
    930                 935                 940

Ala Ala Lys Pro Ser Gln Pro Gly Glu Gly Leu Lys Lys Pro Val Leu
945                 950                 955                 960

Pro Ala Thr Pro Lys Pro Gln Ser Ala Lys Pro Ser Gly Thr Pro Ile
            965                 970                 975

Ser Pro Ala Pro Val Pro Ser Thr Leu Pro Ser Ala Ser Ser Ala Leu
        980                 985                 990

Ala Gly Asp Gln Pro Ser Ser Thr Ala Phe Ile Pro Leu Ile Ser Thr
    995                 1000                1005

Arg Val Ser Leu Arg Lys Thr Arg Gln Pro Pro Glu Arg Ile Ala
    1010                1015                1020

Ser Gly Ala Ile Thr Lys Gly Val Val Leu Asp Ser Thr Glu Ala
    1025                1030                1035

Leu Cys Leu Ala Ile Ser Arg Asn Ser Glu Gln Met Ala Ser His
    1040                1045                1050

Ser Ala Val Leu Glu Ala Gly Lys Asn Leu Tyr Thr Phe Cys Val
    1055                1060                1065

Ser Tyr Val Asp Ser Ile Gln Gln Met Arg Asn Lys Phe Ala Phe
    1070                1075                1080

Arg Glu Ala Ile Asn Lys Leu Glu Asn Asn Leu Arg Glu Leu Gln
    1085                1090                1095

Ile Cys Pro Ala Thr Ala Gly Ser Gly Pro Ala Ala Thr Gln Asp
    1100                1105                1110

Phe Ser Lys Leu Leu Ser Ser Val Lys Glu Ile Ser Asp Ile Val
    1115                1120                1125

Gln Arg
    1130

<210> SEQ ID NO 12
<211> LENGTH: 283
<212> TYPE: PRT
<213> ORGANISM: Homo sapiens

<400> SEQUENCE: 12

Gln Thr Gln Gly Leu Ala Lys Asp Ala Trp Glu Ile Pro Arg Glu Ser
1               5                   10                  15

Leu Arg Leu Glu Val Lys Leu Gly Gln Gly Cys Phe Gly Glu Val Trp
            20                  25                  30

Met Gly Thr Trp Asn Gly Thr Thr Arg Val Ala Ile Lys Thr Leu Lys
        35                  40                  45

Pro Gly Thr Met Ser Pro Glu Ala Phe Leu Gln Glu Ala Gln Val Met
    50                  55                  60
```

```
Lys Lys Leu Arg His Glu Lys Leu Val Gln Leu Tyr Ala Val Val Ser
65              70                  75                  80
Glu Glu Pro Ile Tyr Ile Val Thr Glu Tyr Met Asn Lys Gly Ser Leu
                85                  90                  95
Leu Asp Phe Leu Lys Gly Glu Thr Gly Lys Tyr Leu Arg Leu Pro Gln
                100                 105                 110
Leu Val Asp Met Ser Ala Gln Ile Ala Ser Gly Met Ala Tyr Val Glu
                115                 120                 125
Arg Met Asn Tyr Val His Arg Asp Leu Arg Ala Ala Asn Ile Leu Val
        130                 135                 140
Gly Glu Asn Leu Val Cys Lys Val Ala Asp Phe Gly Leu Ala Arg Leu
145                 150                 155                 160
Ile Glu Asp Asn Glu Trp Thr Ala Arg Gln Gly Ala Lys Phe Pro Ile
                165                 170                 175
Lys Trp Thr Ala Pro Glu Ala Ala Leu Tyr Gly Arg Phe Thr Ile Lys
                180                 185                 190
Ser Asp Val Trp Ser Phe Gly Ile Leu Leu Thr Glu Leu Thr Thr Lys
        195                 200                 205
Gly Arg Val Pro Tyr Pro Gly Met Val Asn Arg Glu Val Leu Asp Gln
210                 215                 220
Val Glu Arg Gly Tyr Arg Met Pro Cys Pro Pro Glu Cys Pro Glu Ser
225                 230                 235                 240
Leu His Asp Leu Met Cys Gln Cys Trp Arg Lys Glu Pro Glu Glu Arg
                245                 250                 255
Pro Thr Phe Glu Tyr Leu Gln Ala Phe Leu Glu Asp Tyr Phe Thr Ser
                260                 265                 270
Thr Glu Pro Gln Tyr Gln Pro Gly Glu Asn Leu
        275                 280
```